(12) United States Patent
Masui et al.

(10) Patent No.: US 7,935,706 B2
(45) Date of Patent: May 3, 2011

(54) NITROGEN-CONTAINING HETEROCYCLE DERIVATIVES SUBSTITUTED WITH CYCLIC GROUP

(75) Inventors: Moriyasu Masui, Osaka (JP); Makoto Adachi, Takarazuka (JP); Hidenori Mikamiyama, Osaka (JP); Akira Matsumura, Osaka (JP); Naoki Tsuno, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 175 days.

(21) Appl. No.: 12/278,412

(22) PCT Filed: Feb. 21, 2007

(86) PCT No.: PCT/JP2007/053166
§ 371 (c)(1),
(2), (4) Date: Aug. 6, 2008

(87) PCT Pub. No.: WO2007/099828
PCT Pub. Date: Sep. 7, 2007

(65) Prior Publication Data
US 2009/0062261 A1 Mar. 5, 2009

(30) Foreign Application Priority Data

Feb. 23, 2006 (JP) .................. 2006-046740
May 30, 2006 (JP) .................. 2006-149750
Nov. 27, 2006 (JP) .................. 2006-318360

(51) Int. Cl.
*A61K 31/497* (2006.01)
(52) U.S. Cl. ............... 514/255.05; 544/359; 548/217
(58) Field of Classification Search .......... 544/359; 548/217
See application file for complete search history.

(56) References Cited

U.S. PATENT DOCUMENTS

| | | | |
|---|---|---|---|
| 3,407,199 A | 10/1968 | Pachter | |
| 3,538,089 A | 11/1970 | Schmidt et al. | |
| 4,455,422 A | 6/1984 | Banno et al. | |
| 4,960,778 A | 10/1990 | Lesieur et al. | |
| 5,283,242 A | 2/1994 | Ellingboe | |
| 5,576,318 A | 11/1996 | Bietti et al. | |
| 5,948,784 A | 9/1999 | Fujiwara et al. | |
| 6,352,981 B1 | 3/2002 | Treiber et al. | |
| 2005/0124627 A1 | 6/2005 | Schadt et al. | |

FOREIGN PATENT DOCUMENTS

| | | |
|---|---|---|
| CH | 460 016 | 7/1968 |
| CH | 460 017 | 7/1968 |
| DE | 102 48 067 A1 | 4/2004 |
| DE | 102 48 925 A1 | 4/2004 |
| EP | 0 296 560 A2 | 12/1988 |
| EP | 0 367 141 A2 | 5/1990 |
| EP | 0 903 349 A2 | 3/1999 |
| EP | 1 484 327 A1 | 12/2004 |
| EP | 1 251 128 B1 | 12/2006 |
| JP | 2-169569 A | 6/1990 |
| JP | 2003-212868 A | 7/2003 |
| WO | WO 86/00899 A1 | 2/1986 |
| WO | WO 99/61426 A1 | 12/1999 |
| WO | WO 01/32634 A1 | 5/2001 |
| WO | WO 01/56974 A2 | 8/2001 |
| WO | WO 01/07436 A2 | 12/2001 |
| WO | WO 02/16349 A1 | 2/2002 |
| WO | WO 02/34718 A1 | 5/2002 |
| WO | WO 02/40466 A2 | 5/2002 |
| WO | WO 02/051806 A1 | 7/2002 |
| WO | WO 02/068409 A1 | 9/2002 |
| WO | WO 02/080928 A1 | 10/2002 |
| WO | WO 03/010159 A1 | 2/2003 |
| WO | WO 03/053366 A2 | 7/2003 |
| WO | WO 03/057688 A2 | 7/2003 |

(Continued)

OTHER PUBLICATIONS

West, Anthony R., Solid State Chemistry and its Applications, Wiley, New York, 1988, pp. 358 and 365.*
International Search Report of PCT/JP2007/053166.
Caroti et al. "Synthesis, Antilipidemic and Platelet Antiaggregatory Activity of 2-Aminobenzimidazole Amide Derivatives". II Farmaco, vol. 44(3), 1989, pp. 227-225.
Šukalović et al. "Synthesis, dopamine $D_2$ receptor binding studies and docking analysis of 5-[3-(4-arylpiperazin-1-yl)propyl]-1H-benzimidazole, 5-[2-(4-arylpiperazin-1-yl)ethoxy]-1H-benzimidazole and their analogs". European Journal of Medicinal Chemistry, vol. 40, 2005, pp. 481-493.

(Continued)

*Primary Examiner* — James O Wilson
*Assistant Examiner* — Brian McDowell
(74) *Attorney, Agent, or Firm* — Hamre, Schumann, Mueller & Larson, P.C.

(57) ABSTRACT

It was found out that the nitrogen-containing heterocyclic derivative represented by the formula (I) specifically binds to a receptor of NR1/NR2B, and is used as a NR2B receptor antagonist.

A compound represented by:

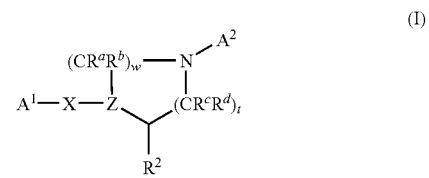

(I)

wherein Z is N or $CR^1$, $A^1$ is a nitrogen-containing aromatic monocyclic group which is optionally substituted, a nitrogen-containing aromatic fused cyclic group which is optionally substituted etc., $A^2$ is an aromatic hydrocarbon cyclic group or an aromatic heterocyclic group, each optionally having a substituent, $R^1$, $R^2$, $R^a$, $R^b$, $R^c$ and $R^d$ are each independently hydrogen, hydroxy, etc., w is 2 or 3, t is 1 or 2, X is —$(CR^3R^4)$m-, —$CO(CR^3R^4)$n-, —$CONR^5(CR^3R^4)$n- etc., m is an integer of 1 to 4, n is an integer of 0 to 4, $R^3$ and $R^4$ are each independently hydrogen, halogen, hydroxy etc., and $R^5$ is hydrogen or lower alkyl,
or a pharmaceutically acceptable salt, or a solvate thereof.

6 Claims, No Drawings

FOREIGN PATENT DOCUMENTS

| WO | WO 2004/046124 A1 | 6/2004 |
|---|---|---|
| WO | WO 2004/087145 A2 | 10/2004 |
| WO | WO 2004/100956 A1 | 11/2004 |
| WO | WO 2004/103954 A1 | 12/2004 |
| WO | WO 2005/019215 A1 | 3/2005 |
| WO | WO 2005/080317 A2 | 9/2005 |
| WO | WO 2006/008133 A2 | 1/2006 |
| WO | WO 2006/010964 A1 | 2/2006 |
| WO | WO 2006/010966 A1 | 2/2006 |
| WO | WO 2006/010967 A1 | 2/2006 |
| WO | WO 2006/010968 A1 | 2/2006 |
| WO | WO 2006/010969 A1 | 2/2006 |
| WO | WO 03/028728 A1 | 4/2006 |
| WO | WO 2006/055187 A1 | 5/2006 |
| WO | WO 2006/058338 A2 | 6/2006 |
| WO | WO 2006/058753 A1 | 6/2006 |
| WO | WO 2006/090272 A1 | 8/2006 |
| WO | WO 2006/090273 A2 | 8/2006 |

OTHER PUBLICATIONS

Yous et al. "Lipid-lowering properties of 6-benzoyl-2(3H)-benzothiazolone and structurally related compounds". Journal of Enzyme Inhibition and Medicinal Chemistry, vol. 20(6), Dec. 2005, pp. 525-532.

Abadi. "Phenylpiperazinylmethylheterocycle Derivatives: Synthesis and Dopamine Receptor Binding Profiles". Arch. Pharm. Pharm. Med. Chem, vol. 337, 2004, pp. 383-390.

Tomić et al. "Pharmacological evaluation of selected arylpiperazines with atypical antipsychotic potential". Bioorganic & Medicinal Chemistry Letters, vol. 14, 2004, pp. 4263-4266.

Keiser et al. "Evaluation of quinolone derivatives for antitrypanosomal activity." Tropical Medicine and International Health, vol. 6(5), May 2001, pp. 369-389.

Roglic et al. "Introduction of a methyl group in α- or β-position of 1-heteroarylethyl-4-phenyl-piperazines affects their dopaminergic/serotonergic properties". Arch. Pharm. Pharm. Med. Chem., vol. 334, 2001, pp. 375-380.

Shankhar et al. "Optically active antifungal azoles: synthesis and antifungal activity of (2R,3S)-2-(2,4-difluorophenyl)-3-(5-{2-[4-aryl-piperazin-1-yl]-ethyl}-tetrazol-2-yl/1-yl)-1-[1,2,4]-triazol-1-yl-butan-2-ol". Bioorganic & Medicinal Chemistry Letters, vol. 12, 2004, pp. 2225-2238.

Loren et al. "The Banert Cascade: A synthetic Sequence to Polyfunctional NH-1,2,3-Triazoles". Synthesis, 2005 No. 9, pp. 1514-1520.

Krasavin et al. "Synthesis and Practical Use of 1H-1,2,3-Benzotriazole-5-carboxaldehyde for Reductive Amination", Synthetic Communications, vol. 35, 2005, 2587-2595.

Prauda et al. "Unexpected Formation of 1,2-Dihydro-2-azolyl- and azubylisoquino-lines by the reduction of the Corresponding Isoquinolunuim Salts with Sodium Borohydride in Methanol". J. Heterocyclic Chem, vol. 41, Nov.-Dec. 2004, pp. 915-929.

Cecchetti et al. (1,4-Benzothiazinyloxy) alkylpiperazine Derivatives as Potentiqal Antihypertensive Agents:. Bioorganic & Medicinal Chemistry Letters, vol. 10, 2000, pp. 465-468.

Borza et al. "Benzimidazole-2-carboxamides as novel NR2B selective NMDA receptor antagonists". Bioorganic & Medicinal Chemistry Letters, vol. 16, 2006, pp. 4638-4640.

Borza et al. "Kynurenic acid amides as novel NR2B selective NMDA receptor antagonists". Bioorganic & Medicinal Chemistry Letters, vol. 17, 2007, pp. 406-409.

Borza et al. "Selective MR1/2B N-Mehtyl-D-aspartate Receptor Antagonists among Indole-2-carboxamides and Benzimidazole-2-carboxamides". J. Med. Chem, vol. 50, 2007, pp. 901-914.

Broza et al. "New Benzoyl ureqa derivatives as a novel NR2B selective NMDA receptor antagonists". Pharmazie, vol. 61(9), 2006, 799-800.

Bonte et al., "Amino ketone and amino alcohol derivatives of benzoxazolinone: synthesis, adrenergic and antihypertensive properties", European Journal of Medical Chemistry, vol. 25, No. 4, May 1, 1990, pp. 361-368.

\* cited by examiner

NITROGEN-CONTAINING HETEROCYCLE DERIVATIVES SUBSTITUTED WITH CYCLIC GROUP

TECHNICAL FIELD

The present invention relates to a nitrogen-containing heterocycle derivative useful as a drug such as an analgesic and the like, which exhibits the specific antagonism to a glutamic acid receptor of a central nervous cell, particularly, an NR1/NR2B receptor which is one kind of NMDA receptors and, preferably, has little side effect on the motion function (e.g.: abnormal sensation) and mental symptom (e.g.: schizophrenia).

BACKGROUND ART

An amino acid such as L-glutamic acid and L-aspartic acid is important as a neurotransmitter in a central nervous system for activating a nerve cell. However, excessive accumulation of these excitatory amino acids outside a cell is thought to cause loss of nerve and motion functions seen in various cerebro-neurological diseases such as Parkinson's disease, senile dementia, Huntington's chorea, and epilepsy, as well as at anoxia, ischemia, hypoglycemia state, or head or spinal cord damage.

It is known that the activity of the excitatory amino acid on a central nervous cell acts via a glutamic acid receptor present on a nerve cell, and a glutamic acid receptor antagonist is thought to be useful as a remedy for the aforementioned diseases and symptoms, and for example, as an anti-epileptic drug, a preventive for ischemic brain injury, or a drug for anti-Parkinsonism.

The NMDA receptor which is one kind of glutamic acid receptors is composed of two subunits of NR1 and NR2, and there are further 4 kinds (NR2A, 2B, 2C, 2D) of subfamilies in the NR2 subunit. It is said that the NR1/NR2A receptor is exclusively involved in memory formation or learning acquisition, and the NR1/NR2B receptor is involved in transmission of neurodegenerative cell death or pain at ischemia. Therefore, a drug exhibiting high affinity for the NR1/NR2B receptor has a high possibility that it becames an effective analgesic having little side effect.

Compounds similar to the present compounds are described in the Patent Literature 1 to 20 and non-Patent Literature 1, but the compound related to the present invention is described in none of them.
[Patent Literature 1]
International Publication WO 03/057688
[Patent Literature 2]
International Publication WO 02/068409
[Patent Literature 3]
International Publication WO 02/080928
[Patent Literature 4]
International Publication WO 02/40466
[Patent Literature 5]
Japanese Patent Application Laid-Open (JP-A) No. 11-147872
[Patent Literature 6]
JP-A No. 1-079151
[Patent Literature 7]
JP-A No. 2-169569
[Patent Literature 8]
International Publication WO 2003/076420
[Patent Literature 9]
International Publication WO 2003/010159
[Patent Literature 10]
International Publication WO 2006/010968
[Patent Literature 11]
International Publication WO 2006/010964
[Patent Literature 12]
International Publication WO 2003/053366
[Patent Literature 13]
International Publication WO 03/084948
[Patent Literature 14]
International Publication WO 2002/051806
[Patent Literature 15]
International Publication WO 2001/007436
[Patent Literature 16]
International Publication WO 86/00899
[Patent Literature 17]
Switzerland Patent Application Publication No. $CH_{460016}$
[Patent Literature 18]
Switzerland Patent Application Publication No. $CH_{460017}$
[Patent Literature 19]
U.S. Pat. No. 3,538,089
[Non-Patent Literature 1]
Farmaco 1989, vol. 44, No. 5, p. 227-255

DISCLOSURE OF THE INVENTION

Problems to be Solved in the Invention

An object of the present invention is to provide a NMDA receptor antagonist which is highly active and, more preferably, exhibits high affinity for a subtype, particularly a NR1/NR2B receptor, particularly an analgesic for cancer pain or the like.

Means to Solve the Problems

The present invention provides the following.
(1) A compound represented by the formula (I):

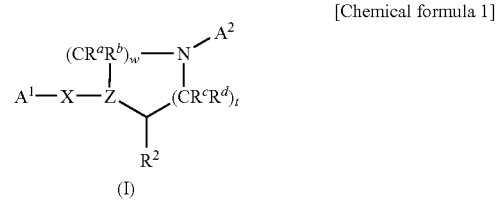

[Chemical formula 1]

(I)

wherein Z is N or $CR^1$;
$A^1$ is a nitrogen-containing aromatic monocyclic group which is optionally substituted, or a nitrogen-containing aromatic fused cyclic group which is optionally substituted,
the nitrogen-containing aromatic monocyclic group or the nitrogen-containing aromatic fused cyclic group satisfies at least one of the following conditions:
i) the group has at least one group selected from optionally substituted hydroxy, optionally protected amino and optionally substituted aminooxy, and
ii) the group contains —NH— in the ring;
$A^2$ is an aromatic hydrocarbon cyclic group which is optionally substituted, or an aromatic heterocyclic group which is optionally substituted;
$R^1$ and $R^2$ are each independently hydrogen, hydroxy or lower alkyl, or $R^1$ and $R^2$ may be taken together to form a single bond;

$R^a$, $R^b$, $R^c$ and $R^d$ are each independently hydrogen or lower alkyl and, when there are a plurality of $R^a$s, a plurality of $R^b$s, a plurality of $R^c$s or a plurality of $R^d$s, they may be different from each other;

w is 2 or 3;

t is 0 or 2;

X is:
—$(CR^3R^4)m$-,
—$CO(CR^3R^4)n$-,
—$(CR^3R^4)mCO$—,
—$CONR^5(CR^3R^4)n$-,
—$NR^5CO(CR^3R^4)n$-,
—$(CR^3R^4)mNR^5CO$—,
—$NR^5CONR^6(CR^3R^4)n$-,
—$C(=N—OR^7)(CR^3R^4)n$-,
—$(CR^8R^9)rO(CR^3R^4)n$-,
—$(CR^8R^9)rS(CR^3R^4)n$-,
—$(CR^8R^9)rSO(CR^3R^4)n$-,
—$(CR^8R^9)rSO_2(CR^3R^4)n$-,
—$CR^9=N—O(CR^3R^4)n$-,
—$C(=O)O(CR^3R^4)n$-,
—$(CR^3R^4)mC(=N—OR^7)$—,
—$CH(OR^8)(CR^3R^4)n$-,
—$(CR^3R^4)mCH(OR^8)$—,
—$NR^5COCO(CR^3R^4)n$-,
—$(CR^3R^4)mNR^5COCO$—,
—$COCONR^5(CR^3R^4)n$-,
—$NR^5COCH(OR^8)(CR^3R^4)n$-,
—$CH(OR^8)(CR^3R^4)nNR^5CO$—,
—$NR^r(CR^3R^4)mCO$—,
-$A^3$-$(CR^3R^4)n$-,
—$(CR^3R^4)m$-$A^3$-,
-$A^3$-$CR^{10}=CR^{11}(CR^3R^4)n$-,
—$CR^{10}=CR^{11}(CR^3R^4)n$-$A^3$-,
-$A^3$-$NR^6(CR^3R^4)n$-,
—$(CR^3R^4)nNR^6$-$A^3$- or
—$NR^6(CR^3R^4)m$-$A^3$-, further, X may be
—$CONR^5(CR^3R^4)m$—$NR^6$—,
—$(CR^3R^4)mCONR^5$—,
—$(CR^3R^4)mNR^5CONR^6$—,
—$CO(CR^3R^4)mNR^5$—, or
-$A^3$-$(CR^3R^4)mNR^6$— when Z is $CR^1$;

m is an integer of 1 to 4;

n and r are an integer of 0 to 4;

$A^3$ is an aromatic hydrocarbon cyclic group which is optionally substituted, an aromatic heterocyclic group which is optionally substituted, or a non-aromatic heterocyclic group which is optionally substituted;

$R^3$ and $R^4$ are each independently hydrogen, halogen, hydroxy, optionally substituted lower alkyl, or optionally substituted lower alkoxy, when there are plurality of $R^3$s and $R^4$s, respectively, they may be different from each other;

$R^5$, $R^6$, $R^7$, $R^8$, $R^9$, $R^{10}$ and $R^{11}$ are each independently hydrogen or lower alkyl, and when m or n is 1 or more, $R^1$ may be taken together with $R^3$ on $CR^3R^4$ adjacent to a carbon atom to which $R^1$ binds, to form a single bond, or a pharmaceutically acceptable salt, or a solvate thereof.

(1') A compound represented by the formula (I):

[Chemical formula 1]

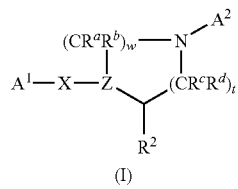

(I)

wherein Z is N or $CR^1$;

$A^1$ is a nitrogen-containing aromatic monocyclic group which is optionally substituted, or a nitrogen-containing aromatic fused cyclic group which is optionally substituted, the nitrogen-containing aromatic monocyclic group or the nitrogen-containing aromatic fused cyclic group satisfies at least one of the following conditions:

i) the group has at least one group selected from optionally protected hydroxy, optionally protected amino and optionally substituted aminooxy, and ii) the group contains —NH— in the ring;

$A^2$ is an aromatic hydrocarbon cyclic group which is optionally substituted or an aromatic heterocyclic group which is optionally substituted;

$R^1$ and $R^2$ are each independently hydrogen, hydroxy or lower alkyl, or $R^1$ and $R^2$ may be taken together to form a single bond;

$R^a$, $R^b$, $R^c$ and $R^d$ are each independently hydrogen or lower alkyl and, when there are a plurality of $R^a$s, a plurality of $R^b$s, a plurality of $R^c$s or a plurality of $R^d$s, they may be different, respectively;

w is 2 or 3;

t is 1 or 2;

X is —$(CR^3R^4)m$-, —$CO(CR^3R^4)n$-, —$(CR^3R^4)nCO$—, —$CONR^5(CR^3R^4)n$-, —$CONR^5(CR^3R^4)m$— $NR^6$—, —$(CR^3R^4)nCONR^5$—, —$NR^5CO(CR^3R^4)n$-, —$(CR^3R^4)n$ $NR^5CO$—, —$NR^5CONR^6(CR^3R^4)n$-, —$(CR^3R^4)nNR^5CONR^6$—, —$C(=N—OR^7)(CR^3R^4)n$-, —$(CR^8R^9)rO(CR^3R^4)n$-, —$(CR^8R^9)rS(CR^3R^4)n$-, —$(CR^8R^9)rSO(CR^3R^4)n$-, —$(CR^8R^9)rSO_2(CR^3R^4)n$-, —$CR^9=N—O(CR^3R^4)n$-, —$C(=O)O(CR^3R^4)n$-, —$(CR^3R^4)nC(=N—OR^7)$—, —$CH(OR^3)(CR^3R^4)n$-, —$(CR^3R^4)nCH(OR^8)$—, —$NR^5COCO(CR^3R^4)n$-, —$(CR^3R^4)nNR^5COCO$—, $COCONR^5(CR^3R^4)n$-, —$NR^5COCH(OR^8)(CR^3R^4)n$-, —$CH(OR^8)(CR^3R^4)n$ $NR^5CO$—, -$A^3$-$(CR^3R^4)n$-, —$(CR^3R^4)n$-$A^3$-, -$A^3$-$CR^{10}=CR^{11}(CR^3R^4)n$-, —$CR^{10}=CR^{11}(CR^3R^4)n$-$A^3$-, -$A^3$-$(CR^3R^4)nNR^6$—, $A^3$-$NR^6(CR^3R^4)n$-, —$(CR^3R^4)n$ $NR^6$-$A^3$- or —$NR^6(CR^3R^4)n$-$A^3$-;

m is an integer of 1 to 4;

n and r are an integer of 0 to 4;

$A^3$ is an aromatic hydrocarbon cyclic group which is optionally substituted, an aromatic heterocyclic group which is optionally substituted, or a non-aromatic heterocyclic group which is optionally substituted;

$R^3$ and $R^4$ are each independently, hydrogen, halogen, hydroxy, optionally substituted lower alkyl, or optionally substituted lower alkoxy and, where there are a plurality of $R^3$s and $R^4$s, respectively, they may be different from each other;

$R^5$, $R^6$, $R^7$, $R^8$, $R^9$, $R^{10}$ and $R^{11}$ are each independently hydrogen or lower alkyl;

when m or n is 1 or more, $R^1$ may be take together with $R^3$ on $CR^3R^4$ adjacent to a carbon atom to which $R^1$ binds to form a single bond, or a pharmaceutically acceptable salt, or a solvate thereof.

(1″) a compound represented by the formula (I):

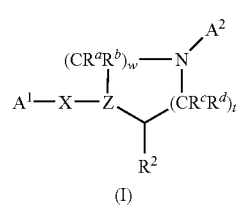

[Chemical formula 2]

(I)

wherein Z is N or $CR^1$;

$A^1$ is a nitrogen-containing aromatic monocyclic group having at least one of optionally protected hydroxy, optionally protected amino or optionally substituted aminooxy, and further optionally substituted with other group or a nitrogen-containing aromatic fused cyclic group having at least one of optionally protected hydroxy, optionally protected amino or optionally substituted aminooxy, and further optionally substituted with other group, or a nitrogen-containing aromatic monocyclic group containing —NH— in the ring, in which other ring constituting atoms may be substituted with a substituent other than optionally protected hydroxy, optionally protected amino, and optionally substituted aminooxy or a nitrogen-containing aromatic fused cyclic group containing —NH— in the ring, in which other ring constituting atoms may be substituted with a substituent other than optionally protected hydroxy, optionally protected amino, and optionally substituted aminooxy;

$A^2$ is an aromatic hydrocarbon group which is optionally substituted, or an aromatic heterocyclic group which is optionally substituted;

$R^1$ and $R^2$ are each independently hydrogen, hydroxy or lower alkyl, or $R^1$ and $R^2$ may be taken together to form a single bond;

$R^a$, $R^b$, $R^c$ and $R^d$ are each indepentyl hydrogen or lower alkyl and, when there are a plurality of $R^a$s, a plurality of $R^b$s, a plurality of $R^c$s, or a plurality of $R^d$s, they may be different respectively;

w is 2 or 3;

t is 1 or 2;

X is —$(CR^3R^4)m$-, —$CO(CR^3R^4)n$-, —$(CR^3R^4)nCO$—, —$CONR^5(CR^3R^4)n$-, —$(CR^3R^4)nCONR^5$—, —$NR^5CO(CR^3R^4)n$-, —$(CR^3R^4)nNR^5CO$—, —$NR^5CONR^6(CR^3R^4)n$-, —$(CR^3R^4)nNR^5CONR^6$—, —$C(=N-OR^7)(CR^3R^4)n$-, —$(CR^3R^4)nC(=N-OR^7)$—, —$CH(OR^8)(CR^3R^4)n$-, —$(CR^3R^4)nCH(OR^8)$—, —$NR^5COCO(CR^3R^4)n$-, —$(CR^3R^4)nNR^5COCO$—, —$COCONR^5(CR^3R^4)n$-, $NR^5COCH(OR^8)(CR^3R^4)n$-, —$CH(OR^8)(CR^3R^4)nNR^5CO$—, -$A^3$-$(CR^3R^4)n$-, —$(CR^3R^4)n$-$A^3$-, -$A^3$-$CR^{10}=CR^{11}(CR^3R^4)n$-, —$CR^{10}=CR^{11}(CR^3R^4)n$-$A^3$-, -$A^3$-$(CR^3R^4)nNR^6$— or —$NR^6(CR^3R^4)n$-$A^3$-;

m is an integer of 1 to 4;

n is an integer of 0 to 4;

$A^3$ is:

[Chemical formula 3]

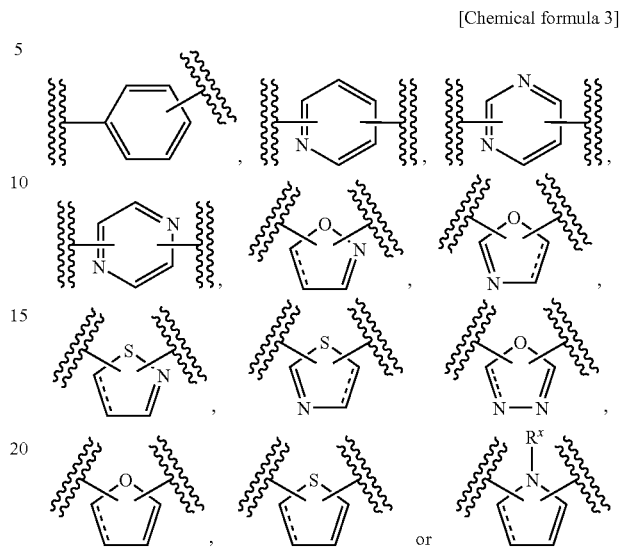

, or wherein a broken line indicates the presence or the absence of a bond and $R^x$ is hydrogen or lower alkyl;

$R^3$ and $R^4$ are each independently hydrogen, halogen, hydroxy, optionally substituted lower alkyl, or optionally substituted lower alkoxy and, when there are a plurality of $R^3$s and $R^4$s, they may be different each other;

$R^5$, $R^6$, $R^7$, $R^8$, $R^9$, $R^{10}$ and $R^{11'''}$ are each independently hydrogen or lower alkyl;

when m or n is 1 or more, $R^1$ may be taken together with $R^3$ on $CR^3R^4$ adjacent to carbon atom to which $R^1$ binds, to form a single bond, or pharmaceutically acceptable salt, or a solvate thereof.

(1‴) A compound represented by the formula (I′):

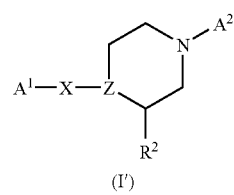

[Chemical formula 4]

(I′)

wherein Z is N or $CR^1$;

$A^1$ is a nitrogen-containing aromatic monocyclic group having at least one of optionally protected hydroxy, optionally protected amino or optionally substituted aminooxy, and further optionally substituted with other group or a nitrogen-containing aromatic fused cyclic group having at least one of optionally protected hydroxy, optionally protected amino or optionally substituted aminooxy, and further optionally substituted with other group, or a nitrogen-containing aromatic monocyclic group containing —NH— in the ring, in which other ring constituting atoms may be substituted with a substituent other than optionally protected hydroxy, optionally protected amino and optionally substituted aminooxy or a nitrogen-containing aromatic fused cyclic group containing —NH— in the ring, in which other ring constituting atoms may be substituted with a substituent other than optionally protected hydroxy, optionally protected amino and optionally substituted aminooxy;

A² is an aromatic hydrocarbon cyclic group which is optionally substituted, or an aromatic heterocyclic group which is optionally substituted;

R¹ and R² are each independently hydrogen, hydroxy or lower alkyl, or R¹ and R² may be taken together to form a single bond;

X is —(CR³R⁴)m-, —CO(CR³R⁴)n-, —(CR³R⁴)nCO—, —CONR⁵(CR³R⁴)n-, —(CR³R⁴)nCONR⁵—, —NR⁵CO(CR³R⁴)n-, —(CR³R⁴)nNR⁵CO—, NR⁵CONR⁶(CR³R⁴)n-, —(CR³R⁴)nNR⁵CONR⁶—, C(=N—OR⁷)(CR³R⁴)n-, —(CR³R⁴)nC(=N—OR⁷)—, —CH(OR⁸)(CR³R⁴)n-, (CR³R⁴)nCH(OR⁸)—, —NR⁵COCO(CR³R⁴)n-, —(CR³R⁴)nNR⁵COCO—, —COCONR⁵(CR³R⁴)n-, —NR⁵COCH(OR⁸)(CR³R⁴)n, CH(OR⁸)(CR³R⁴)nNR⁵CO—, -A³-(CR³R⁴)n-, —(CR³R⁴)n-A³-, -A³-CR¹⁰=CR¹¹(CR³R⁴)n-, —CR¹⁰=CR¹¹(CR³R⁴)n-A³-, -A³-(CR³R⁴)nNR⁶— or —NR⁶(CR³R⁴)n-A³-;

m is an integer of 1 to 4;
n is an integer of 0 to 4;
A³ is:

[Chemical formula 5]

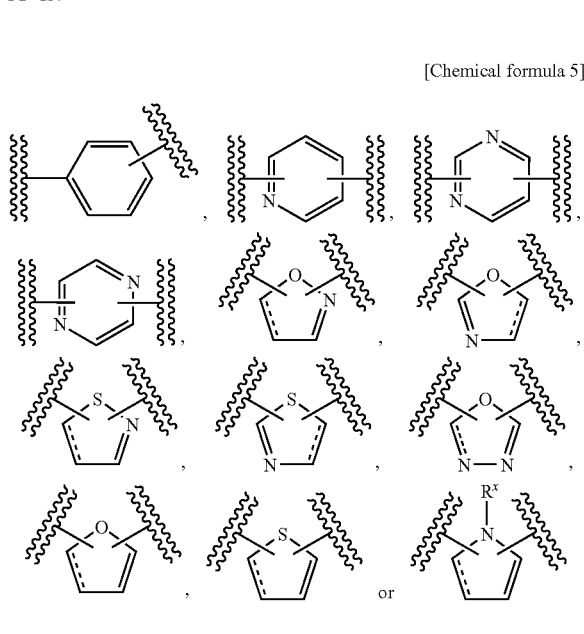

wherein a broken line indicates the presence or the absence of a bond and R^x is hydrogen or lower alkyl;

R³ and R⁴ are each independently hydrogen, halogen, hydroxy, optionally substituted lower alkyl or optionally substituted lower alkoxy and, when there are a plurality of R³s and R⁴s, they may be different from each other, R⁵, R⁶, R⁷, R⁸, R⁹, R¹⁰ and R¹¹ are each independently hydrogen or lower alkyl;

when m or n is 1 or more, R¹ may be taken together with R³ on CR³R⁴ adjacent to carbon atom to which R¹ binds, to form a single bond, or a pharmaceutically acceptable salt, or a solvate thereof.

(2) The compound according to (1), (1') or (1"), wherein w is 2 or 3, and t is 1, or a pharmaceutically acceptable salt, or a solvate thereof.

(3) The compound according to (1), (1'), or (1") (1''') or (2), wherein X is —(CR³R⁴)m-, —CO(CR³R⁴)n-, —CONR⁵(CR³R⁴)n-, —(CR³R⁴)mCONR⁵—, —NR⁵CO(CR³R⁴)n-, —(CR³R⁴)mNR⁵CO—, —NR⁵CONR⁶(CR³R⁴)n-, —C(=N—OR⁷)(CR³R⁴)n-, —CH(OR⁸)(CR³R⁴)n-, —NR⁵COCO(CR³R⁴)n-, —NR⁵COCH(OR⁸)(CR³R⁴)n-, —NR⁵(CR³R⁴)mCO—, -A³-(CR³R⁴)n-, -A³-CR¹⁰=CR¹¹(CR³R⁴)n- or -A³-(CR³R⁴)nNR⁶—, or a pharmaceutically acceptable salt, or a solvate thereof.

(4) The compound according to (1), (1'), (1"), (1'''), (2) or (3), wherein A¹ is pyridyl substituted with at least hydroxy, quinolyl substituted with at least hydroxy, benzoxazolyl substituted with at least hydroxy, benzimidazolyl substituted with at least hydroxy, pyridyl substituted with at least optionally protected amino, imidazolyl in which ring constituting atoms other than —NH— may be substituted, pyrrolyl in which ring constituting atoms other than —NH— may be substituted, pyrazolyl in which ring constituting atoms other than —NH— may be substituted, benzopyrazolyl in which ring constituting atoms other than —NH— may be substituted, benzimidazolyl in which ring constituting atoms other than —NH— may be substituted, or indolyl in which ring constituting atoms other than —NH— may be substituted, or a pharmaceutically acceptable salt, or a solvate thereof (5) The compound according to (1), (1'), (1"), (1'''), (2) or (3), wherein A¹ is:

[Chemical formula 6]

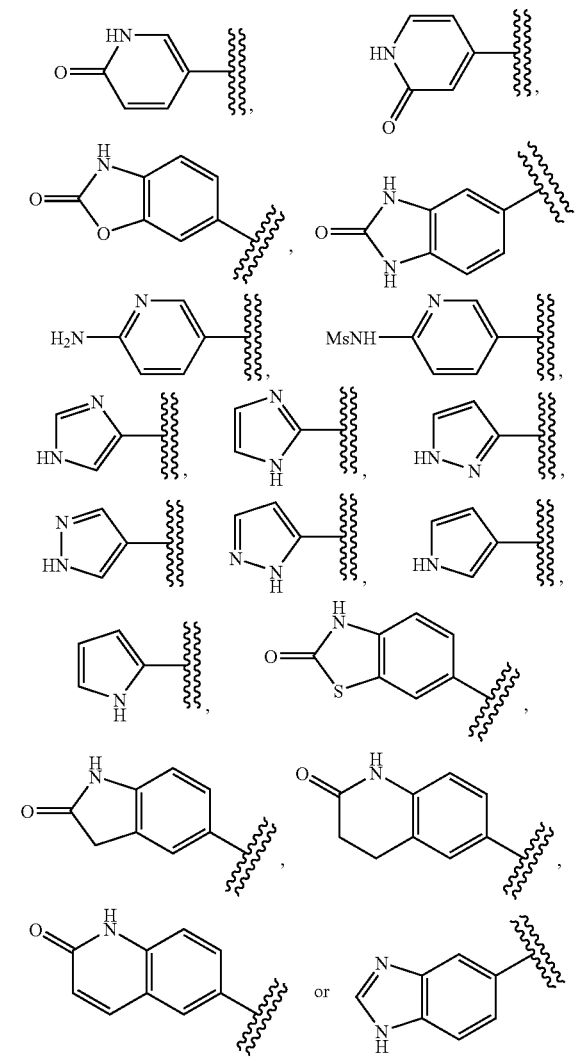

or a pharmaceutically acceptable salt, or a solvate thereof.

(6) The compound according to any one of (1) to (5), (1'), (1") and (1'''), wherein X is CO(CHR³)n-, —CONH(CHR³)n-, —NHCO(CHR³)n-, —NHCONH(CHR³)n-, —NH-COCO(CHR³)n- or —NR⁵(CR³R⁴)mCO— or a pharmaceutically acceptable salt, or a solvate thereof (7) The compound according to any one of (1) to (5), (1'), (1") and (1'''), wherein X is —CO(CHR³)₂—, CONHCHR³—, —CONH(CHR³)₂—, NHCOCHR³—, —NHCO(CHR³)₂—, —NHCONH—, —NHCOCO— or NHCH₂CO— or a pharmaceutically acceptable salt, or a solvate thereof.

(8) The compound according to any one of (1) to (7), (1'), (1") and (1'''), wherein Z is CR¹, R¹ and R² are each independently hydrogen or hydroxy, or R¹ and R² are taken together to form a single bond and, when m or n is 1 or more, R¹ is taken together with R³ on CR³R⁴ adjacent to a carbon atom to which R¹ binds, to form a single bond, or a pharmaceutically acceptable salt, or a solvate thereof.

(9) The compound according to any one of (1) to (7), (1'), (1") and (1'''), wherein Z is N, or a pharmaceutically acceptable salt, or a solvate thereof.

(10) The compound according to any one of (1) to (9), (1'), (1") and (1'''), wherein A² is phenyl optionally substituted with one or more groups selected from halogen, cyano, lower alkyl, halogeno lower alkyl, lower alkoxy and halogeno lower alkoxy or pyridyl optionally substituted with one or more groups selected from halogen, cyano, lower alkyl, halogeno lower alkyl, lower alkoxy and halogeno lower alkoxy, or a pharmaceutically acceptable salt, or a solvate thereof.

(11) The compound according to any one of (1) to (10), (I'), (1") and (1'''), wherein A² is para-substituted phenyl, meta and para-di-substituted phenyl or meta and para-tri-substituted phenyl (3,4,5-tri-substituted phenyl), or a pharmaceutically acceptable salt, or a solvate thereof.

(12) A pharmaceutical composition containing the compound according to any one of (1) to (11), (1'), (1") and (1'''), or a pharmaceutically acceptable salt, or a solvate thereof.

(13) The pharmaceutical composition according to (12), which has the NMDA receptor antagonism.

(14) The pharmaceutical composition according to (13), which has the NR1/NR2B receptor antagonism.

(15) A method of alleviating pain, or a method of treating migraine, cerebral stroke, head trauma, Alzheimer's diseases, Parkinson's disease, tinnitus, epilepsia, Huntington's disease, motion disorder or alcoholism, comprising administering the compound as defined in any one of (1) to (11), (1'), (1") and (1''').

(16) Use of the compound as defined in any one of (1) to (11), (1'), (1") and (1'''), for producing an analgesic, or a remedy for migraine, cerebral stroke, head trauma, Alzheimer's diseases, Parkinson's disease, tinnitus, epilepsia, Huntington's disease, motion disorder or alcoholism.

EFFECT OF THE INVENTION

The present compound is not only used in treating neurodegeneration such as cerebral stroke and cerebral trauma, but also is useful as an analgesic (e.g. cancer pain analgesic) having little side effect.

BEST MODE FOR CARRYING OUT THE INVENTION

Herein, the "optionally protected hydroxy" includes, for example, hydroxy optionally protected with a protecting group selected from lower alkyl (methyl, tert-butyl etc.), aryl lower alkyl (triphenylmethyl, benzyl etc.); tri lower alkylsilyl (trimethylsilyl, tert-butyldimethylsilyl, triethylsilyl, triisopropylsilyl etc.), lower alkyldiarylsilyl (tert-butyldiphenylsilyl etc.), triaryl lower alkylsilyl (tribenzylsilyl etc.), lower alkoxy lower alkyl (methoxymethyl, 1-ethoxyethyl, 1-methyl-1-methoxymethyl etc.), lower alkoxy lower alkoxy lower alkyl (methoxyethoxymethyl etc.), lower alkylthio lower alkyl (methylthiomethyl etc.), tetrahydropyranyl (tetrahydropyran-2-yl, 4-methoxytetrahydropyran-4-yl etc.), tetrahydrothiopyranyl (tetrahydrothiopyran-2-yl etc.), tetrahydrofuranyl (tetrahydrofuran-2-yl etc.), tetrahydrothiofuranyl (tetrahydrothiofuran-2-yl etc.), aryl lower alkoxy lower alkyl (benzyloxymethyl etc.), lower alkylsulfonyl, arylsulfonyl, lower alkylarylsulfonyl (p-toluenesulfonyl etc.) and acyl. A preferable protecting group is lower alkyl, aryl lower alkyl or lower alkylsulfonyl.

The "optionally protected amino" includes, for example, amino optionally protected with a protecting group selected from lower alkoxycarbonyl (tert-butyloxycarbonyl etc.), lower alkenyloxycarbonyl (vinyloxycarbonyl, allyloxycarbonyl etc.), halogeno lower alkoxycarbonyl (2-iodinated ethoxycarbonyl, 2,2,2-trichloroethoxycarbonyl etc.), aryl lower alkoxycarbonyl (benzyloxycarbonyl, p-methoxybenzyloxycarbonyl, o-nitrobenzyloxycarbonyl, p-nitrobenzyloxycarbonyl, phenyloxycarbonyl etc.), tri lower alkylsilyl (trimethylsilyl, triethylsilyl, tert-butyldimethylsilyl etc.), diazo, acyl (formyl, acetyl, pivaloyl, benzoyl etc.), halogeno acyl (trifluoroacetyl etc.), lower alkylsulfonyl (methanesulfonyl etc.), halogeno lower alkylsulfonyl (trifluoroethanesulfonyl etc.), arylsulfonyl, lower alkylarylsulfonyl (toluenesulfonyl, 4-tert-butylbenzenesulfonyl etc.), aryl lower alkyl (triphenylmethyl etc.). A preferable protecting group is acyl or lower alkylsulfonyl.

Examples of a substituent of the "optionally substituted aminooxy" include lower alkyl and acyl.

The "nitrogen-containing aromatic monocyclic group" includes a 5- to 6-membered aromatic cyclic group having at least one N in the ring and, further, optionally having O or S, such as:

[Chemical formula 7]

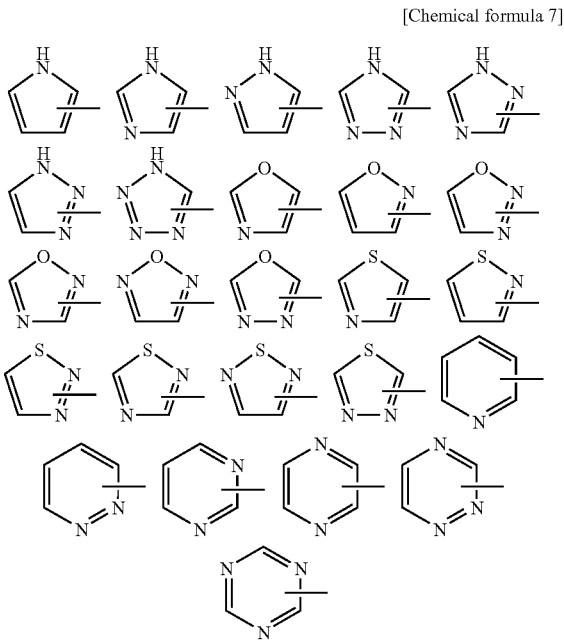

The "nitrogen-containing aromatic fused cyclic group" includes:

a) a group in which one or two aromatic ring(s) or non-aromatic ring(s) (preferably, benzene ring or aromatic hetero ring" is (are) fused to a 5- to 6-membered aromatic cyclic group having at least one N in the ring and, further, optionally having O or S, and b) a group in which one or two benzene ring(s) or aromatic hetero ring(s) is (are) fused to a 5- to 7-membered non-aromatic cyclic group having at least one N in the ring and, further, optionally having O or S, preferably a).

Examples include:

[Chemical formula 8]

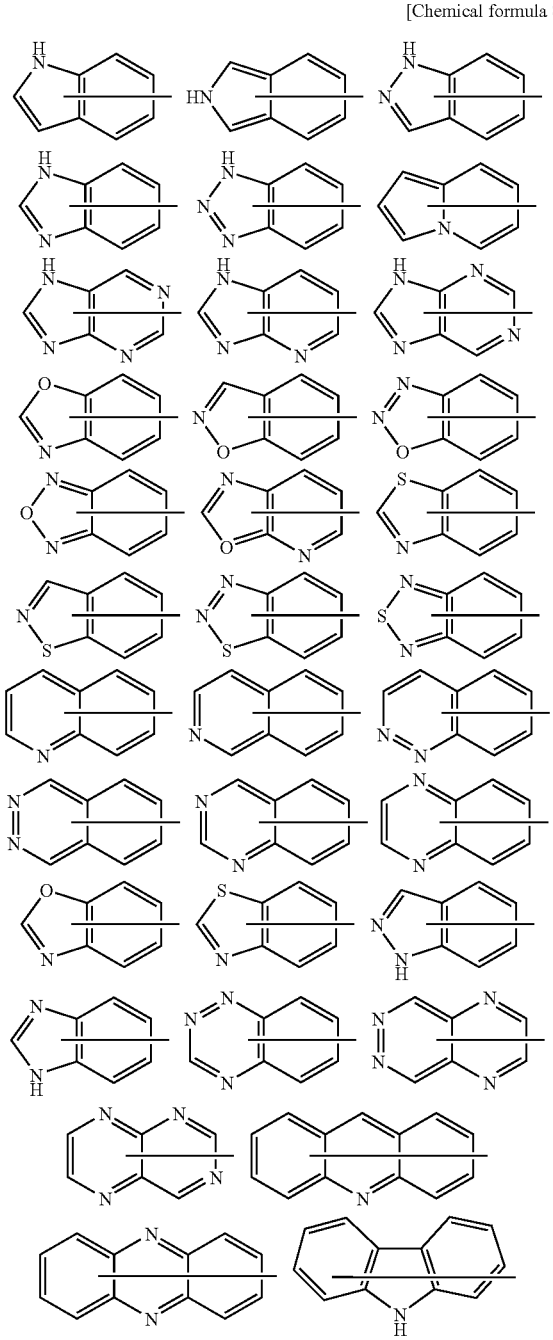

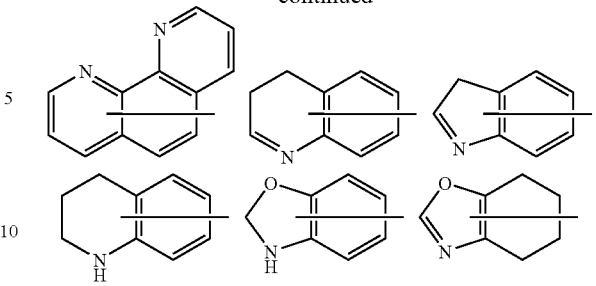

-continued

A bond may be present on any ring.

The "nitrogen-containing aromatic monocyclic group which is optionally substituted, or nitrogen-containing aromatic fused cyclic group which is optionally substituted", and the "nitrogen-containing aromatic monocyclic group or the nitrogen-containing aromatic fused cyclic group having at least one of optionally protected hydroxy, optionally protected amino or optionally substituted aminooxy and, further optionally substituted with other group" satisfying the condition of "i) having at least one group selected from optionally protected hydroxy, optionally protected amino and optionally substituted aminooxy" includes the "nitrogen-containing aromatic monocyclic group" having at least one group selected from optionally protected hydroxy, optionally protected amino and optionally substituted aminooxy on the ring and, further, optionally substituted with one or more groups selected from Substituent group α, and the "nitrogen-containing aromatic fused cyclic group" having at least one group selected from optionally protected hydroxy, optionally protected amino and optionally substituted aminooxy on the ring and, further, optionally substituted with one or more groups selected from Substituent group α.

Herein, the Substituent group α is a group consisting of halogen, lower alkyl, halogeno lower alkyl, lower alkoxy, halogeno lower alkoxy, acyl, acyloxy, lower alkylamino, carboxy, lower alkoxycarbonyl, cyano and nitro.

The "pyridyl substituted with at least hydroxy", the "quinolyl substituted with at least hydroxy", the "benzoxazolyl substituted with at least hydroxy" and the "benzimidazolyl substituted with at least hydroxy" include pyridyl, quinolyl, benzoxazolyl and benzimidazolyl having at least one hydroxy as a substituent and, optionally substituted with 1 or more groups selected from Substituent group α, respectively. Examples are 6-hydroxypyridin-3-yl, 2-hydroxypyridin-3-yl, 6-hydroxy-4-methyl-pyridin-3-yl, 4-acetyl-2-hydroxy-benzoxazol-6-yl.

The "pyridyl substituted with at least optionally protected amino" includes pyridyl having at least one amino or protected amino as a substituent and, further, optionally substituted with 1 or more groups selected from Substituent group α.

The "nitrogen-containing aromatic monocyclic group which is optionally substituted, or the nitrogen-containing aromatic fused cyclic group which is optionally substituted" and the "nitrogen-containing aromatic monocyclic group or the nitrogen-containing aromatic fused cyclic group containing —NH— in the ring, and in which other ring constituting atoms may be substituted with a substituent other than optionally protected hydroxy, optionally protected amino and optionally substituted aminooxy" satisfying the condition of "ii) containing —NH— in the ring" includes groups containing a —NH— group in the ring among the "nitrogen-containing aromatic monocyclic group" and the "nitrogen-containing aromatic fused cyclic group".

Examples are as follows:

[Chemical formula 9]

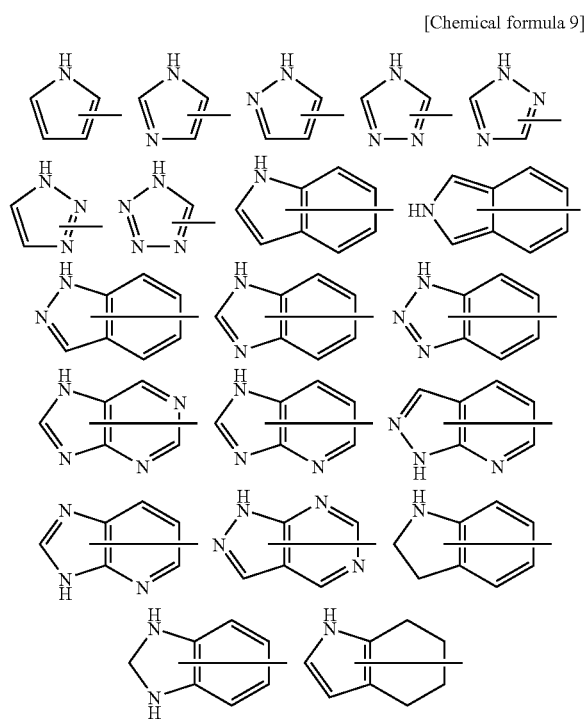

A bond may be present on any ring, and arbitrary ring constituting atoms other than —NH— may be substituted with one or more groups selected from Substituent group β.

Herein, Substituent group β is halogen, lower alkyl, halogeno lower alkyl, acyl, carboxy, lower alkoxycarbonyl, cyano and nitro.

The "imidazolyl in which ring constituting atoms other than —NH— may be substituted", the "pyrrolyl in which ring constituting atoms other than —NH— may be substituted", the "pyrazolyl in which ring constituting atoms other than —NH— may be substituted", the "benzpyrazolyl in which ring constituting atoms other than —NH— may be substituted", the "benzimidazolyl in which ring constituting atoms other than —NH— may be substituted" and the "indolyl in which ring constituting atoms other than —NH— may be substituted" include imidazolyl, pyrrolyl, pyrazolyl, benzpyrazolyl, benzimidazolyl and indolyl in which arbitrary ring constituting atoms other than —NH— may be substituted with 1 or more groups selected from Substituent group β, respectively.

The "aromatic hydrocarbon cyclic group" includes phenyl, naphthyl, phenanthryl and the like.

Examples of a substituent of the "aromatic hydrocarbon cyclic group which is optionally substituted" include halogen, hydroxy, lower alkyl, halogeno lower alkyl, lower alkoxy, halogeno lower alkoxy, lower alkylsulfonyloxy, halogeno lower alkylsulfonyloxy, acyl, acyloxy, amino, lower alkylamino, acylamino, nitro, cyano, carboxy, lower alkoxycarbonyl, carbamoyl, lower alkylcarbamoyl, aromatic hydrocarbon cyclic group optionally substituted with 1 or more groups selected from Substituent group γ, arylthio optionally substituted with one or more groups selected from Substituent group γ, aryloxy optionally substituted with one or more groups selected from Substituent group γ, arylamino optionally substituted with one or more groups selected from Substituent group γ, arylsulfonyloxy optionally substituted with one or more groups selected from Substituent group γ.

Herein, the Substituent group γ is a group consisting of halogen, hydroxy, lower alkyl, halogeno lower alkyl, lower alkoxy, halogeno lower alkoxy, acyl, acyloxy, amino, lower alkylamino, acylamino, carboxy, lower alkoxycarbonyl, cyano and nitro.

A preferable example of the "aromatic hydrocarbon cyclic group which is optionally substituted" is phenyl substituted at a para-position or phenyl substituted at a meta-position and a para-position, and a substituent is preferably halogen and/or halogeno lower alkyl.

An aryl part of the "arylsulfonyl", the "arylsulfonyloxy", the "aryloxy", the "arylthio", the "arylamino", the "aryl lower alkyl", the "lower alkyldiarylsilyl", the "triaryl lower alkylsilyl", the "aryl lower alkoxy lower alkyl", the "lower alkylarylsulfonyl", or the "aryl lower alkoxycarbonyl" is the same as that of the "aromatic hydrocarbon cyclic group". Preferable is phenyl.

The "aromatic heterocyclic group" includes a 5- to 6-membered aromatic monocyclic group containing 1 to 4 hetero atom(s) selected from the group consisting of N, O and S (e.g. pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl), and an aromatic fused cyclic group (e.g. indolyl, isoindolyl, indolizidinyl, benzimidazolyl, benzpyrazolyl, indazolyl, cinnolinyl, phthalazinyl, benzoxazolyl, benzisoxazolyl, benzoxadiazolyl, benzothiazolyl, benzisothiazolyl, benzthiadiazolyl, benzofuryl, isobenzofuryl, benzothienyl, benzotriazolyl, imidazopyridyl, triazolopyridyl, imidathiazolyl, pyrazinopyridazinyl, quinazolinyl, quinolyl, isoquinolyl, quinoxalinyl, purinyl, pteridinyl, naphthyridinyl and pyrazinopyridazinyl etc.).

The "non-aromatic heterocyclic group" include a 5 to 6-membered aromatic monocyclic group containing 1 to 4 hetero atom(s) selected from the group consisting of N, O and S (e.g. thiranyl, oxylanyl, azetidinyl, pyrrolidinyl, pyrrolinyl, imidazolidinyl, imidazolinyl, pyrazohdinyl, pyrazolinyl, tetrahydrofuryl, dihydrofuryl, oxazolinyl, oxazolidinyl, isoxazolinyl, isoxazolidinyl, oxadiazolinyl, oxathiolanyl, dioxolanyl, dioxolyl, tetrahydrothienyl, dihydrothienyl, thiazolinyl, thiazolidinyl, isothiazolinyl, isothiazolidinyl, tetrahydropyranyl, thianyl, piperidinyl, dioxanyl, piperadinyl, morpholinyl, morpholino, thiomorpholinyl, thiomorpholino, dihydropyridyl etc.).

Particularly, the "aromatic hydrocarbon cyclic group", the "aromatic heterocyclic group" and the "non-aromatic heterocyclic group" in $A^3$ include a divalent group of the "aromatic hydrocarbon cyclic group", the "aromatic heterocyclic group" and the "non-aromatic heterocyclic group". A bond may be present at any possible position and, specifically, examples include the following groups:

[Chemical formula 10]

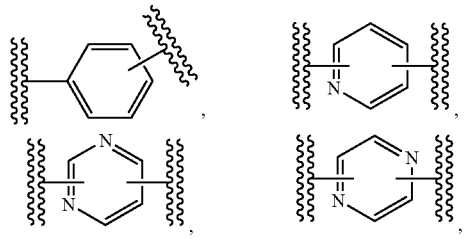

-continued

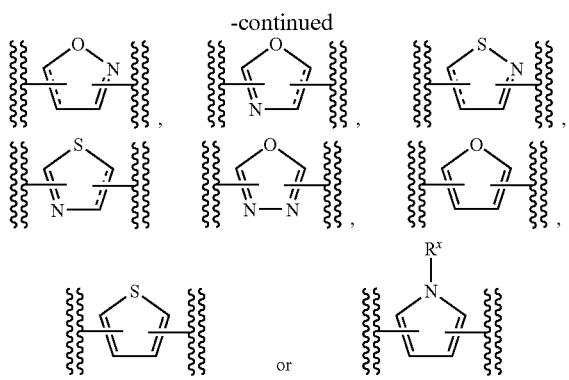

wherein a broken line indicates the presence or the absence of the bond, and $R^x$ is hydrogen or lower alkyl A substituent of the "aromatic heterocyclic group which is optionally substituted" and the "non-aromatic heterocyclic group which is optionally substituted" is the same as that of the "aromatic hydrocarbon cyclic group which is optionally substituted".

A preferable example of the "aromatic heterocyclic group which is optionally substituted" in $A^2$ is optionally substituted pyridyl, and examples of a preferable substituent include halogen, halogeno lower alkyl, lower alkoxy, halogeno lower alkoxy and the like.

The "halogen" includes F, Cl, Br and I.

A lower alkyl part and a halogen part of the "halogeno lower alkyl", the "halogeno lower alkoxy", the "halogeno lower alkoxycarbonyl", the "halogenoacyl", "halogeno lower alkylsulfonyl", and the "halogeno lower alkylsulfonyloxy" are the same as the "halogen".

The "lower alkyl" includes a linear or branched alkyl of a carbon number of 1 to 10, preferably a carbon number of 1 to 6, further preferably a carbon number of 1 to 3, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl. Particularly preferable is methyl or ethyl.

Examples of a substituent of the "optionally substituted lower alkyl" include halogen, hydroxy, lower alkoxy, halogeno lower alkoxy, acyl, acyloxy, amino, lower alkylamino, acylamino, carboxy, lower alkoxycarbonyl, cyano, nitro and the like, and a preferable example of substituted lower alkyl is trihalogeno lower alkyl and the like.

A lower alkyl part of the "halogeno lower alkyl", the "lower alkoxy lower alkyl", the "lower alkoxy lower alkoxy lower alkyl", the "lower alkylthio lower alkyl", the "aryl lower alkoxy lower alkyl", the "lower alkoxy", the "halogeno lower alkoxy", the "lower alkoxycarbonyl", the "halogeno lower alkoxycarbonyl", the "aryl lower alkoxycarbonyl", the "lower alkylcarbamoyl", the "lower alkylsulfonyl", the "lower alkylarylsulfonyl", the "lower alkylsulfonyloxy", "halogeno lower alkylsulfonyl", the "halogeno lower alkylsulfonyloxy", the "lower alkylamino", the "aryl lower alkyl", the "tri lower alkkylsilyl", the "lower alkyldiarylsilyl", and the "triaryl lower alkylsilyl" is the same as the "lower alkyl".

A substituent of the "optionally substituted lower alkoxy" is the same as the substituent of the "optionally substituted lower alkyl".

The "lower alkenyl" includes a linear or branched alkenyl of a carbon number of 2 to 10, preferably a carbon number of 2 to 8, further preferably a carbon number of 3 to 6, having one or more double bonds at an arbitrary position. Specifically, examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

A lower alkenyl part of the "lower alkenyloxycarbonyl" is the same as the "lower alkenyl".

The "acyl" includes aliphatic acyl and aroyl of a carbon number of 1 to 7. Specifically, examples include formyl, acetyl, propionyl, butyryl, isobutyryl, valeryl, pivaloyl, hexanoyl, acryloyl, propionyl, methacryloyl, crotonolyl and benzoyl.

An acyl part of the "acyloxy", the "acylamino" and the "halogeno acyl" is the same as the "acyl".

The case that "$R^1$ and $R^2$ are taken together to form a single bond" means that

[Chemical formula 11]

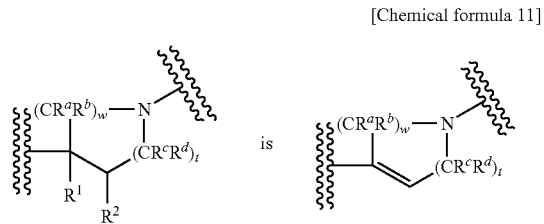

The case that "when m or n is 1 or more, $R^1$ is taken together with $R^3$ on $CR^3R^4$ adjacent to a carbon atom to which $R^1$ binds" means that

[Chemical formula 12]

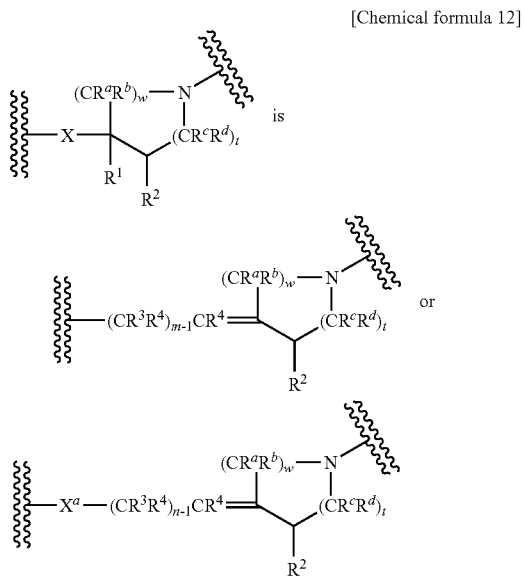

wherein $X^a$ is —CO—, —CONR$^5$—, —NR$^5$CO—, —NR$^5$CONR$^6$—, —C(=N—OR)—, —(CR$^8$R$^9$)rO—, —(CR$^8$R$^9$)rS—, —(CR$^8$R$^9$)rSO—, —(CR$^8$R$^9$)rSO$_2$—, —CR$^9$=N—O—, —C(=O)O—, —CH(OR$^8$)—, —NR$^5$COCO—, —COCONR$^5$—, —NR$^5$COCH(OR$^8$)—, -A$^3$-, -A$^3$NR$^6$— or -A$^3$-CR$^{10}$=CR$^{11}$—, and other symbols are as defined above.

The present compound (I) is not limited to a specified isomer, but includes all possible isomers and racemates. For example, a tautomer is included as follows.

[Chemical formula 13]

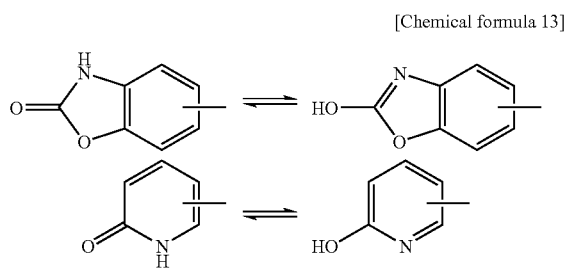

A general method of synthesizing the present compound will be shown below, but the method is not limited to the present synthesizing method.

A Method: Synthesis of (I-a) from (II)

A compound represented by the general formula (I-a) can be synthesized by condensing ketone represented by the general formula (II) and an organophosphorus compound represented by the general formula (III) or (IV) in the presence of a base:

[Chemical formula 14]

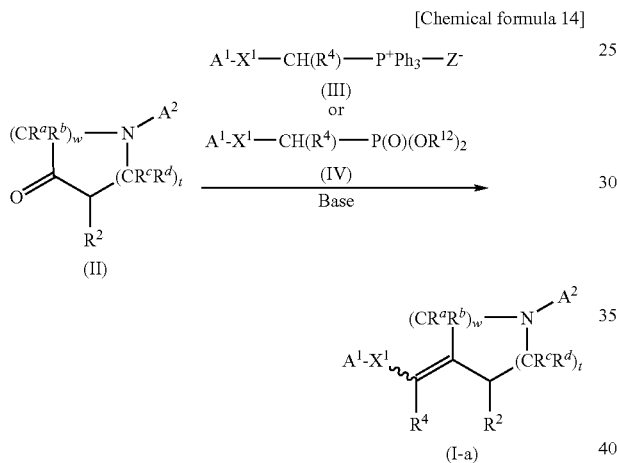

wherein $X^1$ is optionally substituted lower alkenylene, or $-A^3-(CR^3R^4)s$, s is an integer of 0 to 3, Z is a chlorine atom or a bromine atom, a wave line indicates a cis or trans form, and other respective symbols are as defined above.

The ketone represented by the general formula (II) can be synthesized by the method described in Reference Examples 8 to 9 described later, and a method similar thereto. And, the organophosphorus compound represented by the general formula (III) and (IV) can be synthesized by the method described in New Experimental Chemistry Course 14, MARUZEN Co., Ltd (1977), or a method similar thereto.

The organophosphorus compound represented by the general formula (III) or (IV) can be used at 1 to 5 mole equivalent based on the compound represented by the general formula (II).

Examples of a reaction solvent include tetrahydrofuran, diethyl ether, acetonitrile, N,N-dimethylformamide, dimethyl sulfoxide, liquid ammonia and the like.

Examples of the base include lithium hydroxide, sodium hydroxide, potassium hydroxide, sodium hydride, potassium hydride, sodium methoxide, potassium tert-butoxide, n-butyllithium, lithiumhexamethyldisilazide, sodium hexamethyldisilazide, potassium hexamethyldisilazide, sodium amide and the like. The base can be used at 1.0 to 5 mole equivalent based on the compound represented by the general formula (II).

An example of a reaction temperature is −70 to 100° C.

An example of a reaction time is 0.5 to 72 hours.

The resulting compound represented by the general formula (I-a) can be isolated and purified by the known means (e.g. chromatography, recrystallization etc.).

B Method: Synthesis of (I-b) from (I-a)

A compound represented by the general formula (I-b) can be synthesized by reducing a compound represented by the general formula (I-a) with hydrogen in the presence of a metal catalyst:

[Chemical formula 15]

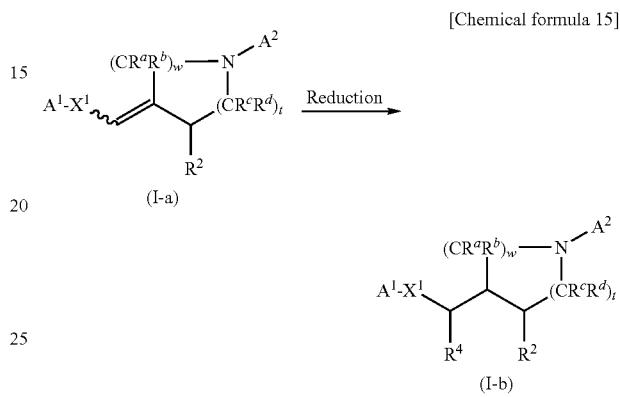

wherein each symbol is as defined above.

Examples of the reaction solvent include methanol, ethanol, ethyl acetate, tetrahydrofuran, N,N-dimethylformamide and the like.

Examples of the metal catalyst include 5% palladium-carbon, 10% palladium-carbon, platinum oxide, chlorotris(triphenylphosphine)rhodium (I). The metal catalyst can be used at 0.01 to 0.5 weight percent based on the compound represented by the general formula (I-a).

An example of a hydrogen pressure is 1 to 50 atm.

An example of a reaction temperature is 20° C. to a refluxing temperature of a solvent.

An example of a reaction time is 0.5 to 72 hours.

The resulting compound represented by the general formula (I-b) can be isolated and purified by the known means (e.g. chromatography, recrystallization etc.).

C Method: Synthesis of (I-c) from (II)

A compound represented by the general formula (I-c) can be synthesized by reacting the ketone represented by the general formula (II) with an organometallic compound represented by the general formula (V):

[Chemical formula 16]

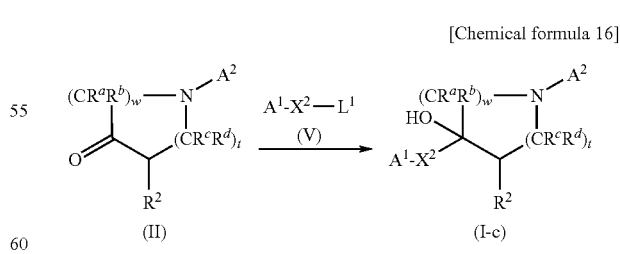

wherein X2 is optionally substituted lower alkenylene, or $-A^3-(CR^3R^4)n$, $L^1$ is lithium, MgCl, MgBr or MgI, and other respective symbols are as defied above.

The compound represented by the general formula (V) can be used at 1 to 3 mole equivalent based on the ketone represented by the general formula (II).

An example of a reaction solvent is diethyl ether, tetrahydrofuran and the like.

An example of a reaction temperature is −70 to 50° C.

An example of a reaction time is 0.5 to 24 hours.

The resulting compound represented by the general formula (I-c) can be isolated and purified by the known method (e.g. chromatography, recrystallization etc.).

D Method: Synthesis of (I-d) from Compound (VI):

[Chemical formula 17]

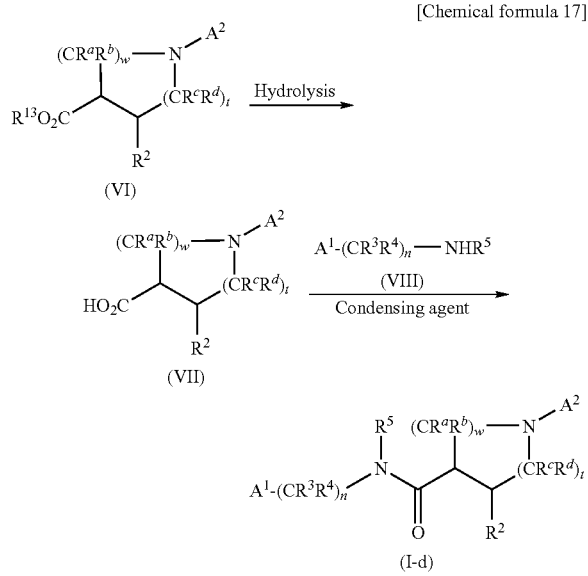

wherein $R^{13}$ is $C_{1-4}$ alkyl, and other respective symbols are as defined above.

Compounds represented by the general formulas (VI) and (VII) can be synthesized by the method described in Reference Example 11 described later, and a method similar thereto.

Synthesis of (VII) from (VI)

Carboxylic acid represented by the general formula (VII) can be synthesized by hydrolyzing the compound represented by the general formula (VI).

Lithium hydroxide, sodium hydroxide or potassium hydroxide can be used at 1 to 5 mole equivalent based on the compound represented by the general formula (VI).

Examples of a reaction solvent include methanol, ethanol, propanol, isopropanol, butanol, water and the like, and they can be used alone or in combination.

An example of a reaction temperature is 0° C. to a refluxing temperature of a solvent.

An example of a reaction time is 0.5 to 24 hours.

The resulting compound represented by the general formula (VII) can be isolated and purified by the known method (e.g. chromatography, recrystallization etc.).

Synthesis of (I-d) from (VII)

An amide compound represented by the general formula (I-d) can be synthesized by condensing carboxylic acid represented by the general formula (VII) and an amine compound represented by the general formula (VIII) in the presence of a condensing agent.

The compound represented by the general formula (VIII) can be used at 0.5 to 2 mole equivalent based on the compound represented by the general formula (VII).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (VII). 1-Hydroxybenzotriazole may be used as a condensation assistant at 0.5 to 2 mole equivalent.

Examples of the base include triethylamine, N-methylmorpholine, 4-dimethylaminopyridine and the like, and these can be used alone, or in combination. The base can be used at 0.05 to 2 mole equivalent based on the compound represented by the general formula (VII).

An example of a reaction temperature is 0 to 100° C.

An example of a reaction time is 0.5 to 72 hours.

The resulting compound represented by the general formula (I-d) can be isolated and purified by the known means (e.g. chromatography, recrystallization etc.).

E Method: Synthesis of (I-e) from Compound (VII):

[Chemical formula 18]

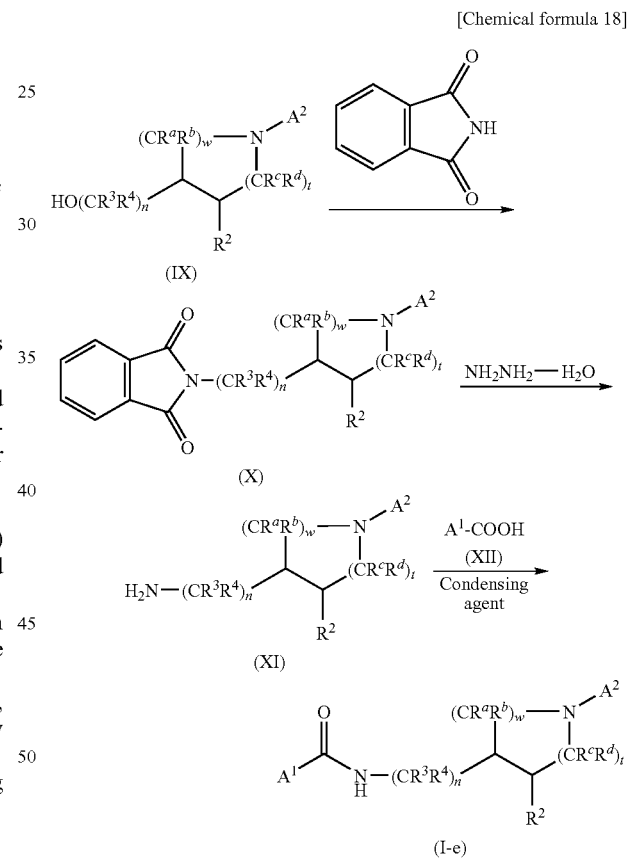

wherein respective symbols are as defined above.

An alcohol represented by the general formula (IX) can be synthesized by the method described in Reference Examples 1 to 7 described later, and a method similar thereto.

Synthesis of (X) from (IX)

A compound represented by the general formula (X) can be synthesized by condensing the alcohol represented by the general formula (IX) and phthalimide in the presence of an azo compound and a trivalent phosphorus compound.

The phthalimide can be used at 1 to 3 mole equivalent based on the compound represented by the general formula (IX).

Examples of a reaction solvent include tetrahydrofuran, diethyl ether, acetonitrile and the like.

Examples of the azo compound include diethyl azodicarboxylate, diisopropyl azodicarboxylate and the like, and the azo compound can be used at 1 to 3 mole equivalent based on the compound represented by the general formula (IX).

Examples of the trivalent phosphorus compound include triphenylphosphine, tributylphosphine and the like, and the trivalent phosphorus compound can be used at 1 to 3 mole equivalent based on the compound represented by the general formula (IX).

An example of a reaction temperature is 0° C. to a refluxing temperature of a solvent.

An example of a reaction time is 0.5 to 72 hours.

The resulting compound represented by the general formula (X) can be isolated and purified by the known means (e.g. chromatography, recrystallization etc.).

Synthesis of (XI) from (X)

An amine compound represented by the general formula (XI) can be synthesized by treating the compound represented by the general formula (XI) with hydrazine hydrate.

The hydrazine hydrate can be used at 1.0 to 5 mole equivalent based on the compound represented by the general formula (X).

Examples of the reaction solvent include methanol, ethanol, dichloromethane, N,N-dimethylformamide and the like.

An example of a reaction temperature is 0 to 100° C.

An example of a reaction time is 0.5 to 24 hours.

The resulting compound represented by the general formula (XI) can be isolated and purified by the known means (e.g. chromatography, recrystallization etc.).

Synthesis of (I-e) from (XI)

An amide compound represented by the general formula (I-e) can be synthesized by condensing the amine compound represented by the general formula (XII) with carboxylic acid represented by the general formula (X) in the presence of a condensing agent.

The compound represented by the general formula (X) can be used at 0.5 to 2 mole equivalent based on the compound represented by the general formula (XII).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, ethyl chlorocarbonate, isobutyl chlorocarbonate, thionyl chloride, oxalyl chloride and the like, and the condensing agent can be used at 0.5 to 2 mole equivalent based on the compound represented by the general formula (XII). 1-Hydroxybenzotriazole may be used as a condensation assistant at 0.5 to 2 mole equivalent.

Examples of the base include triethylamine, N-methylmorpholine, 4-dimethylaminopyridine and the like, and they may be used alone, or in combination. The base can be used at 0.05 to 2 mole equivalent based on the compound represented by the general formula (XI).

An example of a reaction temperature is 0 to 100° C.

An example of a reaction time is 0.5 to 72 hours.

The resulting compound represented by the general formula (I-e) can be isolated and purified by the known means (e.g. chromatography, recrystallization etc.).

F Method: Synthesis of (I-f) from Compound (XI)

A compound represented by the general formula (I-f) can be synthesized by reacting the amine represented by the general formula (XI) with isocyanate represented by the general formula (XIII) or carbamate represented by (XIV):

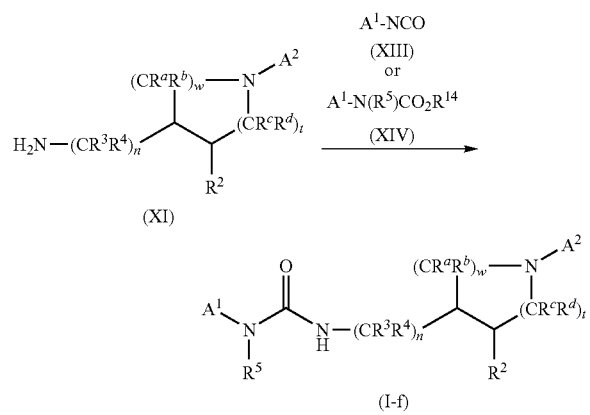

[Chemical formula 19]

wherein $R^{14}$ is phenyl, or 4-nitrophenyl, and other respective symbols are as defined above.

The compound represented by the general formula (XIII) or (XIV) can be used at 0.5 to 3 mole equivalent based on the compound represented by the general formula (XI).

Examples of a reaction solvent include methylene chloride, 1,2-dichloroethane, toluene, acetonitrile, tetrahydrofuran and the like.

If necessary, amine such as triethylamine, diisopropylethylamine and the like can be used at 0.05 to 2 mole equivalent based on the compound represented by the general formula (XII).

An example of a reaction temperature is 0 to 100° C.

An example of a reaction time is 0.5 to 72 hours.

The resulting compound represented by the general formula (I-f) can be isolated and purified by the known means (e.g. chromatography, recrystallization etc.).

G Method: Synthesis of (I-g) from Compound (II):

[Chemical formula 20]

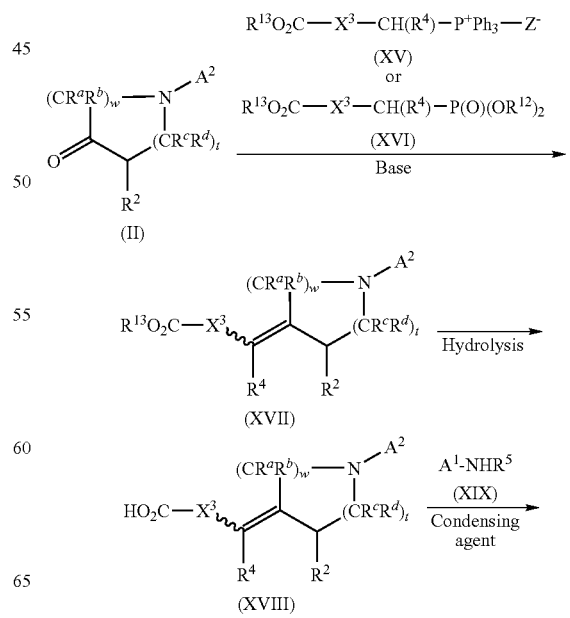

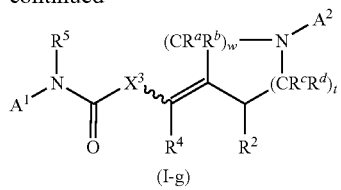

(I-g)

wherein $X^3$ is $(CR^3R^4)s$; other respective symbols are as defined above.

Synthesis of (XVII) from (II)

A compound represented by the general formula (XVII) can be synthesized by condensing the ketone represented by the general formula (II) with an organophosphorus compound represented by the general formula (XV) or (XVI) in the presence of a base.

The organophosphorus compound represented by the general formula (XV) or (XVI) can be used at 1 to 5 mole equivalent based on the compound represented by the general formula (II).

Examples of a reaction solvent include tetrahyrofuran, diethyl ether, acetonitrile, N,N-dimethylformamide, dimethyl sulfoxide, liquid ammonia and the like.

Examples of the base include lithium hydroxide, sodium hydroxide, potassium hydroxide, sodium hydride, potassium hydride, sodium methoxide, potassium tert-butoxide, n-butyllithium, lithiumhexamethyldisilazide, sodium hexaethyldisilazide, potassium hexamethyldisilazide, sodium amide and the like. The base can be used at 1.0 to 5 mole equivalent based on the compound represented by the general formula (II).

An example of a reaction temperature is −70 to 100° C.

An example of a reaction time is 0.5 to 72 hours.

The resulting compound represented by the general formula (XVII) can be isolated and purified by the known means (e.g. chromatography, recrystallization etc.).

Synthesis of (XVIII) from (XVII)

Carboxylic acid represented by the general formula (XVIII) can be synthesized by hydrolyzing the compound represented by the general formula (XVII).

Lithium hydroxide, sodium hydroxide, potassium hydroxide or the like can be used at 1.0 to 5 mole equivalent based on the compound represented by the general formula (XVII).

Examples of a reaction solvent include methanol, ethanol, propanol, isopropanol, butanol, water and the like, and these can be used alone, or in combination.

An example of a reaction temperature is 0° C. to a refluxing temperature of a solvent.

An example of a reaction time is 0.5 to 24 hours.

The resulting compound represented by the general formula (XVIII) can be isolated and purified by the known means (e.g. chromatography, recrystallization etc.).

Synthesis of (I-g) from (XVIII)

An amide compound represented by the general formula (I-g) can be synthesized by condensing carboxylic acid represented by the general formula (XVIII) with an amine compound represented by the general formula (XIX) in the presence of a condensing agent.

The compound represented by the general formula (XIX) can be used at 0.5 to 2 mole equivalent based on the compound represented by the general formula (XVIII).

Examples of the reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XVIII). 1-Hydroxybenzotriazole may be used as a condensation assistant at 0.5 to 2 mole equivalent.

Examples of the base include triethylamine, N-methylmorpholine, 4-dimethylaminopyridine and the like, and these can be used alone, or in combination. The base can be used at 0.05 to 2 mole equivalent based on the compound represented by the general formula (XVIII).

An example of a reaction temperature is 0 to 100° C.

An example of a reaction time is 0.5 to 72 hours.

The resulting compound represented by the general formula (I-g) can be isolated and purified by the known means (e.g. chromatography, recrystallization etc.).

H Method: Synthesis of (I-h) from Compound (XVII):

[Chemical formula 21]

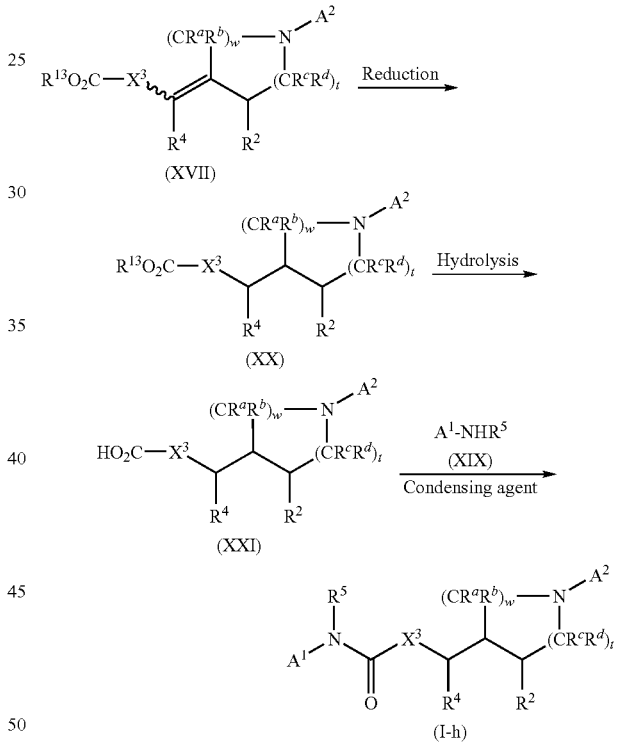

wherein respective symbols are as defined above.

Synthesis of (XX) from (XVII)

A compound represented by the general formula (XX) can be synthesized by reducing the compound represented by the general formula (XVII) with hydrogen in the presence of a metal catalyst.

Examples of a reaction solvent include methanol, ethanol, ethyl acetate, tetrahydrofuran, N,N-dimethylformamide and the like.

Examples of the metal catalyst include 5% palladium-carbon, 10% palladium-carbon, platinum oxide, chlorotris (triphenylphosphine)rhodium (I) and the like, and the metal catalyst can be used at 0.01 to 0.5 weight percent based on the compound represented by the general formula (VXII).

An example of a hydrogen pressure is 1 atm to 50 atm.

An example of a reaction temperature is 20° C. to a refluxing temperature of a solvent.

An example of a reaction time is 0.5 to 72 hours.

The resulting compound represented by the general formula (XX) can be isolated and purified by the known means (e.g. chromatography, recrystallization etc.).

Synthesis of (XXI) from (XX)

Carboxylic acid represented by the general formula (XXI) can be synthesized by hydrolyzing the compound represented by the general formula (XXI).

Lithium hydroxide, sodium hydroxide, potassium hydroxide, and the like can be used at 1.0 to 5 mole equivalent based on the compound represented by the general formula (XX).

Examples of a reaction solvent include methanol, ethanol, propanol, isopropanol, butanol, water and the like, and these can be used alone, or in combination.

An example of a reaction temperature is 0° C. to a refluxing temperature of a solvent.

An example of a reaction time is 0.5 to 24 hours.

The resulting compound represented by the general formula (XXI) can be isolated and purified by the known means (e.g. chromatography, recrystallization etc.).

Synthesis of (I-h) from (XXI)

An amide compound represented by the general formula (I-h) can be synthesized by condensing carboxylic acid represented by the general formula (XXI) with an amine compound represented by the general formula (XIX) in the presence of a condensing agent.

The compound represented by the general formula (XIX) can be used at 0.5 to 2 mole equivalent based on the compound represented by the general formula (XXI).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonylimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXI). 1-Hydroxybenzotriazole may be used as a condensation assistant at 0.5 to 2 mole equivalent.

Examples of the base include triethylamine, N-methylmorpholine, 4-dimethylaminopyridine and the like, and these can be used alone or in combination. The base can be used at 0.05 to 2 mole equivalent based on the compound represented by the general formula (XXI).

An example of a reaction temperature is 0 to 100° C.

An example of a reaction time is 0.5 to 72 hours.

The resulting compound represented by the general formula (I-h) can be isolated and purified by the known means (e.g. chromatography, recrystallization etc.).

I Method: Synthesis of (I-i) from Compound (XVII-a) or (XX-a):

[Chemical formula 22]

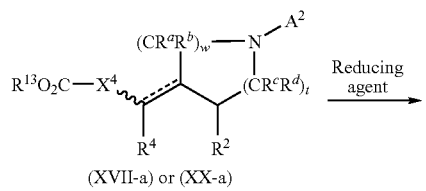

(XVII-a) or (XX-a)

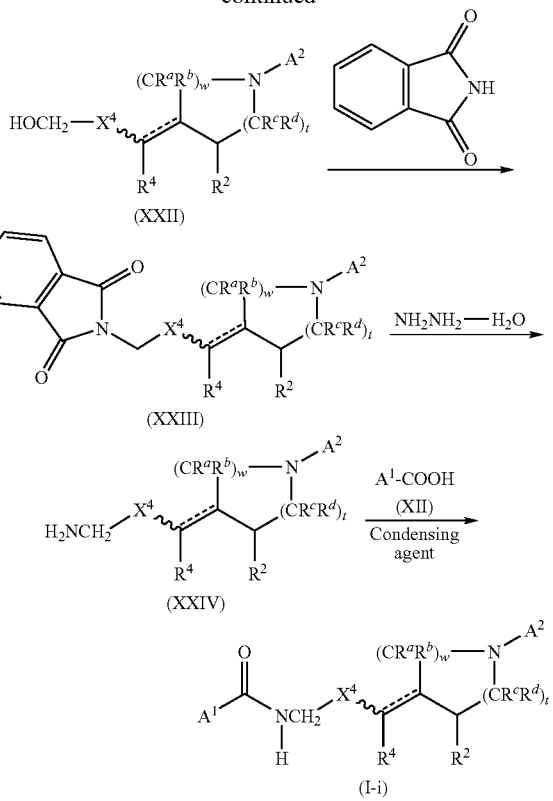

wherein X4 is $(CR^3R^4)_v$, v is an integer of 0 to 2, a broken line indicates the presence or the absence of a bond, and other symbols are as defined above.

Synthesis of (XXII) from (XVII-a) or (XX-a)

An alcohol represented by the general formula (XXII) can be synthesized by reducing a compound represented by the general formula (XVII-a) or (XX-a) in the presence of a reducing agent.

Examples of a reaction solvent include diethyl ether, tetrahydrofuran, toluene, ethanol and the like, and these can be used alone, or in combination.

Examples of the reducing agent include sodium borohydride, lithium borohydride, lithium aluminum borohydride, diisobutyl aluminum hydride and the like, and the reducing agent can be used at 0.5 to 6 mole equivalent based on the compound represented by the general formula (XVII-a) or (XX-a).

An example of a reaction temperature is 0° C. to a refluxing temperature of a solvent.

An example of a reaction time is 0.5 to 72 hours.

The resulting compound represented by the general formula (XXII) can be isolated and purified by the known means (e.g. chromatography, recrystallization etc.).

Synthesis of (XXIII) from (XXII)

A compound represented by the general formula (XXIII) can be synthesized by condensing an alcohol represented by the general formula (XXII) with phthalimide in the presence of an azo compound and a trivalent phosphorus compound.

The phthalimide can be used at 1 to 3 mole equivalent based on the compound represented by the general formula (XXII).

Examples of a reaction solvent include tetrahydrofuran, diethyl ether, acetonitrile and the like.

Examples of the azo compound include diethyl azodicarboxylate, diisopropyl azo dicarboxylate, and the like, and the azo compound can be used at 1 to 3 mole equivalent based on the compound represented by the general formula (XXII).

Examples of the trivalent phosphorous compound include triphenylphosphine, tributylphosphine and the like, and the trivalent phosphorus compound can be used at 1 to 3 mole equivalent based on the compound represented by the general formula (XXII).

An example of a reaction temperature is 0° C. to a refluxing temperature of a solvent.

An example of a reaction time is 0.5 to 72 hours.

The resulting compound represented by the general formula (XXIII) can be isolated and purified by the known means (e.g. chromatography, recrystallization etc.).

Synthesis of (XXIV) from (XXIII)

An amine compound represented by the general formula (XXIV) can be synthesized by treating the compound represented by the general formula (XXIII) with hydrazine hydrate.

The hydrazine hydrate can be used at 1.0 to 5 mole equivalent based on the compound represented by the general formula (XXIII).

Examples of a reaction solvent include methanol, ethanol, dichloromethane, N,N-dimethylformamide and the like.

An example of a reaction temperature is 0 to 100° C.

An example of a reaction time is 0.6 to 24 hours.

The resulting compound represented by the general formula (XXIV) can be isolated and purified by the known means (e.g. chromatography, recrystallization etc.).

Synthesis of (I-i) from (XXIV)

An amide compound represented by the general formula (I-i) can be synthesized by condensing the amine compound represented by the general formula (XXIV) with carboxylic acid represented by the general formula (XII) in the presence of a condensing agent.

The compound represented by the general formula (XII) can be used at 0.5 to 2 mole equivalent based on the compound represented by the general formula (XXIV).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarobodiimide hydrochloride, ethyl chlorocarbonate, isobutyl chlorocarbonate, thionyl chloride, oxalyl chloride and the like, and the condensing agent can be used at 0.5 to 2 mole equivalent based on the compound represented by the general formula (XXIV). 1-Hydroxybenzotriazole may be used as a condensation assistant at 0.5 to 2 mole equivalent.

Examples of the base include triethylamine, N-methylmorpholine, 4-dimethylaminopyridine and the like, and these can be used alone, or in combination. The base can be used at 0.05 to 2 mole equivalent based on the compound represented by the general formula (XXIV).

An example of a reaction temperature is 0 to 100° C.

An example of a reaction time is 0.5 to 72 hours.

The resulting compound represented by the general formula (I-i) can be isolated and purified by the known means (e.g. chromatography, recrystallization etc.).

J Method: Synthesis of (I-j) from Compound (XXIV)

A compound represented by the general formula (I-j) can be synthesized by reacting amine represented by the general formula (XXIV) with isocyanate represented by the general formula (XIII) or carbamate represented by (XIV):

[Chemical formula 23]

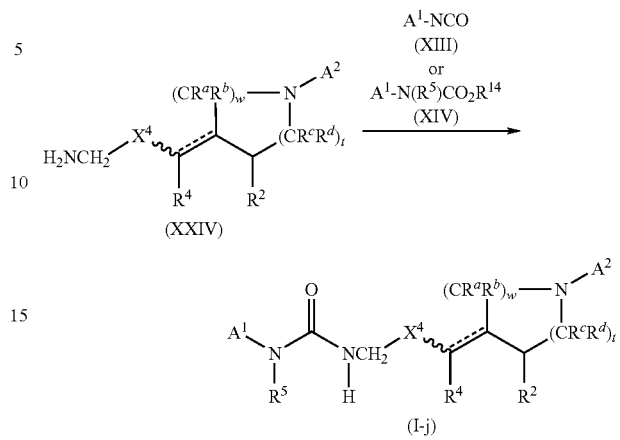

wherein respective symbols are as defined above.

The compound represented by the general formula (XIII) or (XIV) can be used at 0.5 to 3 mole equivalent based on the compound represented by the general formula (XXIV).

Examples of a reaction solvent include methylene chloride, 1,2-dichloroethane, toluene, acetonitrile, tetrahydrofuran and the like.

If necessary, amine such as triethylamine, diisopropylethylamine and the like can be used at 0.05 to 2 mole equivalent based on the compound represented by the general formula (XXV).

An example of a reaction temperature is 0 to 100° C.

An example of a reaction time is 0.5 to 72 hours.

The resulting compound represented by the general formula (I-j) can be isolated and purified by the known means (e.g. chromatography, recrystallization etc.).

K Method: Synthesis of (I-k) from Compound (XXII):

[Chemical formula 24]

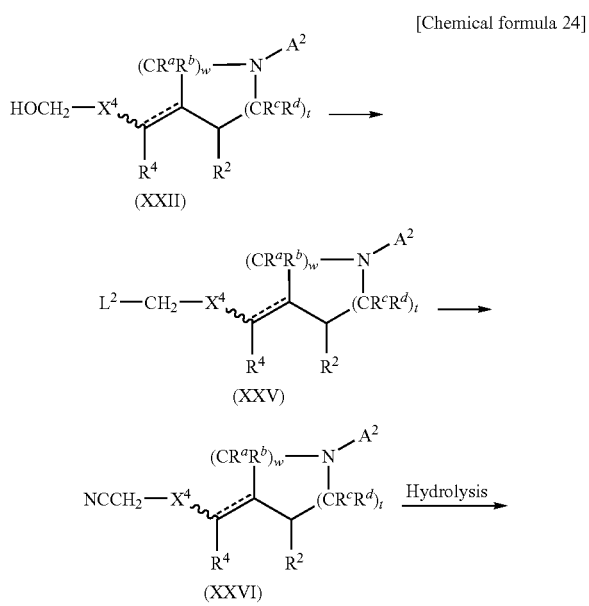

-continued

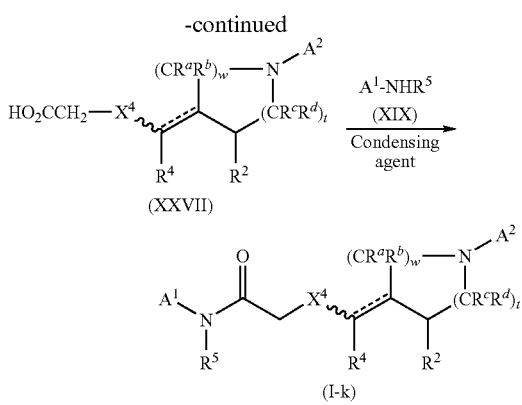

wherein $L^2$ is a halogen atom, $C_{1-4}$ alkylsulfonyloxy, $C_{6-9}$ alylsulfonyloxy, and other respective symbols are as defined above.

Synthesis of (XXV) from (XXII)

A compound represented by the general formula (XXV) can be synthesized by reacting the compound represented by the general formula (XXII) with a halogenating agent, alkylsulfonyl chloride or arylsulfonyl chloride.

Examples of a reaction solvent include acetonitrile, methylene chloride, tetrahydrofuran, toluene, N,N-dimethylformamide and the like.

Examples of the halogenating agent include carbon tetrachloridehtriphenhylphosphine, carbon tetrabromide/triphenylphosphine, and carbon tetrachloride or carbon tetrabromide can be used at 0.5 to 4 mole equivalent, and triphenylphosphine can be used at 0.5 to 2 mole equivalent based on the compound represented by the general formula (XXII).

Examples of the alkylsulfonyl chloride and the arylsulfonyl chloride include methanesulfonyl chloride benzenesulfonyl chloride, toluenesulfonyl chloride and the like, and it can be used at 0.5 to 2 mole equivalent based on the compound represented by the general formula (XXX). Thereupon, as the base, triethylamine or the like can be used at 1 to 6 mole equivalent based on the compound represented by the general formula (XXII).

An example of a reaction temperature is 20° C. to a refluxing temperature of a solvent.

An example of a reaction time is 0.5 to 72 hours.

The resulting compound represented by the general formula (XXV) can be isolated and purified by the known means (e.g. chromatography, recrystallization etc.).

Synthesis of (XXVI) from (XXV)

A cyan compound represented by the general formula (XXVI) can be synthesized by reacting the compound represented by the general formula (XXV) with a cyanidating agent.

Examples of a reaction solvent include methylene chloride, tetrahydrofuran, N,N-dimethylformamide, dimethyl sulfoxide and the like, and these can be used alone, or in combination.

Examples of the cyanidating agent include sodium cyanide, potassium cyanide, tetrabutylammonium cyanide, tetramethylammonium cyanide and the like, and the cyanidating agent can be used at 1 to 3 mole equivalent based on the compound represented by the general formula (XXV).

An example of a reaction temperature is 0 to 100° C.

An example of a reaction time is 0.5 to 72 hours.

The resulting compound represented by the general formula (XXVI) can be isolated and purified by the known means (e.g. chromatography, recrystallization etc.).

Synthesis of (XXVII) from (XXVI)

Carboxylic acid represented by the general formula (XXVII) can be synthesized by hydrolyzing the compound represented by the general formula (XXVI).

Sodium hydroxide, potassium hydroxide or the like can be used at 1.0 to 5 mole equivalent based on the compound represented by the general formula (XXVI).

Examples of a reaction solvent include methanol, ethanol, propanol, isopropanol, butanol, water and the like, and these can be used alone, or in combination.

An example of a reaction temperature is 0° C. to a refluxing temperature of a solvent.

An example of a reaction time is 0.5 to 48 hours.

The resulting compound represented by the general formula (XXVII) can be isolated and purified by the known means (e.g. chromatography, recrystallization etc.).

Synthesis of (I-k) from (XXVII)

An amide compound represented by the general formula (I-k) can be synthesized by condensing carboxylic acid represented by the general formula (XXVII) with an amine compound represented by the general formula (XIX) in the presence of a condensing agent.

The compound represented by the general formula (XIX) can be used at 0.5 to 2 mole based on the compound represented by the general formula (XXVII).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonyldimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXVII). 1-Hydroxybenzotriazole or the like may be used as a condensation assistant at 0.5 to 2 mole equivalent.

Examples of a base include triethylamine, N-methylmorpholine, 4-dimethyl aminopyridine and the like, and they can be used alone, or by mixing. The base can be used at 0.05 to 2 mole equivalent based on the compound represented by the general formula (XXVII).

An example of a reaction temperature is 0 to 100° C.

An example of a reaction time is 0.5 to 72 hours.

The resulting compound represented by the general formula (I-k) can be isolated and purified by the known means (e.g. chromatography, recrystallization etc.).

L Method: Synthesis of (I-l) from Compound (XXII):

[Chemical formula 25]

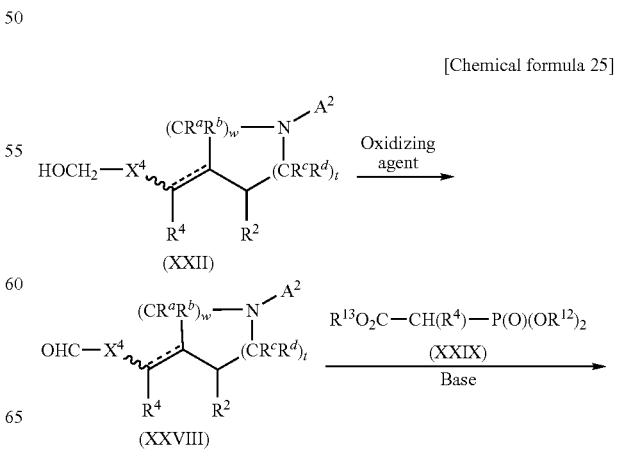

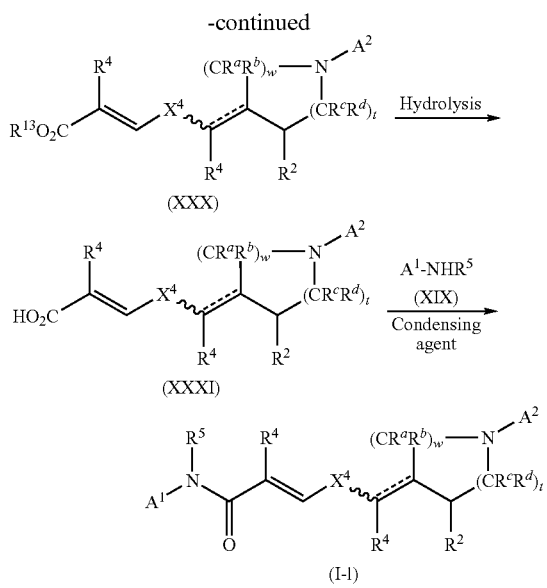

wherein respective symbols are as defined above.

Synthesis of (XXVIII) from (XXII)

A compound represented by the general formula (XXVIII) can be synthesized by reacting the compound represented by the general formula (XXII) with an oxidizing agent.

Examples of a reaction solvent include ethyl acetate, methylene chloride, dimethyl sulphoxide and the like.

Examples of the oxidizing agent include 1-hydroxy-1,2-benziodooxol-3(1H)-one 1-oxide, 1,1-dihydro-1,1,1-triacetoxy-1,2-benziodooxol-3(1H)-one and the like, and the oxidizing agent can be used at 1 to 5 mole equivalent based on the compound represented by the general formula (XXII).

An example of a reaction temperature is 0 to 50° C.

An example of a reaction time is 0.5 to 24 hours.

The resulting compound represented by the general formula (XXVIII) can be isolated and purified by the known means (e.g. chromatography, recrystallization etc).

Synthesis of (XXX) from (XXVIII)

A compound represented by the general formula (XXX) can be synthesized by condensing the compound represented by the general formula (XXVIII) with an organophosphorus compound represented by the general formula (XXIX) in the presence of a base.

The organophosphorus compound represented by the general formula (XXIX) can be used at 1 to 5 mole equivalent based on the compound represented by the general formula (XXVIII).

Examples of a reaction solvent include tetrahydrofuran, diethyl ether, acetonitrile, N,N-dimethylformamide, dimethyl sulfoxide, liquid ammonia and the like.

Examples of the base include lithium hydroxide, sodium hydroxide, potassium hydroxide, sodium hydride, potassium hydride, sodium methoxide, potassium tert-butoxide, n-butyllithium, lithiumhexamethyldisilazide, sodium hexamethyldisilazide, potassium hexamethyldisilazide, sodium amide and the like. The base can be used at 1.0 to 5 mole equivalent based on the compound represented by the general formula (XXVIII).

An example of a reaction temperature is −70 to 100° C.

An example of a reaction time is 0.5 to 72 hours.

The resulting compound represented by the general formula (XXX) can be isolated and purified by the known means (e.g. chromatography, recrystallization etc.).

Synthesis of (XXXI) from (XXX)

Carboxylic acid represented by the general formula (XXXI) can be synthesized by hydrolyzing the compound represented by the general formula (XXX).

Lithium hydroxide, sodium hydroxide, potassium hydroxide or the like can be used at 1.0 to 5 mole equivalent based on the compound represented by the general formula (XXX).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The resulting compound represented by the general formula (XXXI) can be isolated and purified by the known means (e.g. chromatography, recrystallization etc.).

Synthesis of (I-l) from (XXXI)

An amide compound represented by the general formula (I-l) can be synthesized by condensing the carboxylic acid represented by the general formula (XXXI) with an amine compound represented by the general formula (XIX) in the presence of a condensing agent.

The compound represented by the general formula (XIX) can be used at 0.5 to 2 mole equivalent based on the compound represented by the general formula (XXXI).

Examples of a reaction solvent include methylene chloride, tetrahydrofuran, N,N-dimethylformamide and the like.

Examples of a condensing agent include dicyclohexylcarbodiimide, 1-(3-dimethylaminopropyl)-3-ethylcarbodiimide hydrochloride, N,N'-carbonyl diimidazole, ethyl chlorocarbonate, isobutyl chlorocarbonate, thionyl chloride, oxalyl chloride and the like, and the condensing agent can be used at 0.5 to 2 mole equivalent. 1-Hydroxybenzotriazole or the like may be used as a condensation assistant at 0.5 to 2 mole equivalent.

Examples of a base include triethylamine, N-morpholine, 4-dimethylaminopyridine and the like, and these can be used alone, or mixing. The base can be used at 0.05 to 2 mole equivalent based on the compound represented by the general formula (XXXI).

An example of a reaction temperature is 0 to 100° C.

An example of a reaction time is 0.5 to 72 hours.

The resulting compound represented by the general formula (I-1) can be isolated and purified by the known means (e.g. chromatography, recrystallization etc.).

M method: Synthesis of (I-m) from Compound (XXXII):

[Chemical formula 26]

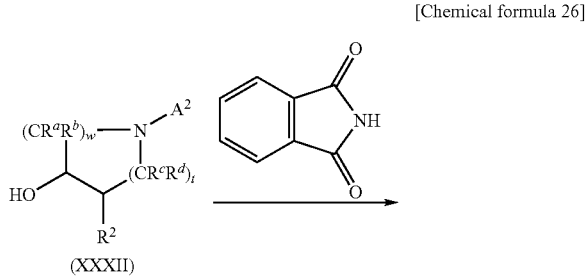

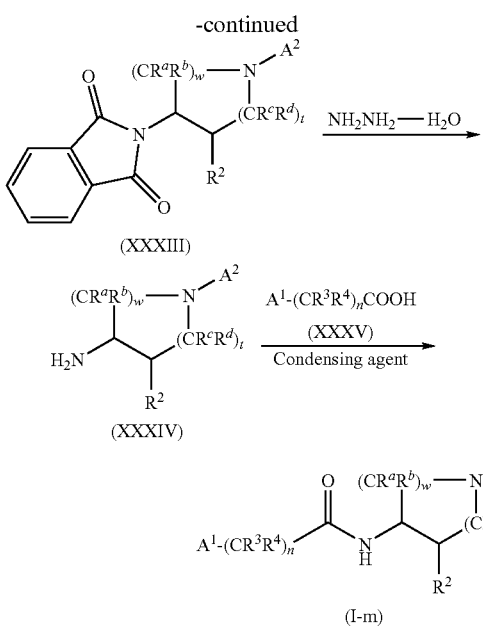

wherein respecting symbols are as defined above.

A compound represented by the general formula (XXXII) can be synthesized by the method described in Reference Examples 4 to 7 described later, and a method similar thereto.

Synthesis of (XXXIII) from (XXXII)

A compound represented by the general formula (XXXIII) can be synthesized by condensing an alcohol represented by the general formula (XXXII) with phthalimide in the presence of an azo compound and a trivalent phosphorus compound.

Phthalimide can be used at 1 to 3 mole equivalent based on the compound represented by the general formula (XXXII).

Examples of a reaction solvent include tetrahydrofuran, diethyl ether, acetonitrile and the like.

Examples of the azo compound include diethyl azo dicarboxylate, diisopropyl azo dicarboxylate and the like, and the azo compound can be used at 1 to 3 mole equivalent based on the compound represented by the general formula (XXXII).

Examples of the trivalent phosphorus compound include triphenylphosphine, tributylphosphine and the like, and the trivalent phosphorus compound can be used at 1 to 3 mole equivalent based on the compound represented by the general formula (XXXII).

An example of a reaction temperature is 0° C. to a refluxing temperature of a solvent.

An example of a reaction time is 0.5 to 72 hours.

The resulting compound represented by the general formula (XXXIII) can be isolated and purified by the known means (e.g. chromatography, recrystallization etc.).

Synthesis of (XXXIV) from (XXXIII)

An amine compound represented by the general formula (XXXIV) can be synthesized by treating the compound represented by the general formula (XXXIII) with a hydrazine hydrate.

The hydrazine hydrate can be used at 1.0 to 5 mole equivalent based on the compound represented by the general formula (XXXIII).

Example of a reaction solvent include methanol, ethanol, dichloromethane, N,N-dimethylformamide and the like.

An example of a reaction temperature is 0 to 100° C.

An example of a reaction time is 0.5 to 24 hours.

The resulting compound represented by the general formula (XXXIV) can be isolated and purified by the known means (e.g. chromatography, recrystallization etc.).

Synthesis of (I-m) from (XXXIV)

An amide compound represented by the general formula (I-m) can be synthesized by condensing an amine compound represented by the general formula (XXXIV) with carboxylic acid represented by the general formula (XXXV) in the presence of a condensing agent.

The compound represented by the general formula (XXXV) can be used at 0.5 to 2 mole equivalent based on the compound represented by the general formula (XXXIV).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, ethyl chlorocarbonate, isobutyl chlorocarbonate, thionyl chloride, oxalyl chloride and the like, and the condensing agent can be used at 0.5 to 2 mole equivalent based on the compound represented by the general formula (XXXIV). 1-Hydroxybenzotriazole or the like may be used as a condensation assistant at 0.5 to 2 mole equivalent.

Examples of the base include triethylamine, N-methylmorpholine, 4-dimethylaminopyridine and the like, and these can be used alone or by mixing. The base can be used at 0.05 to 2 mole equivalent based on the compound represented by the general formula (XXXIV).

An example of a reaction temperature is 0 to 100° C.

An example of a reaction time is 0.5 to 72 hours.

The resulting compound represented by the general formula (I-m) can be isolated and purified by the known means (e.g. chromatography, recrystallization etc.).

N Method: Synthesis of (I-n) from Compound (XVIII):

[Chemical formula 27]

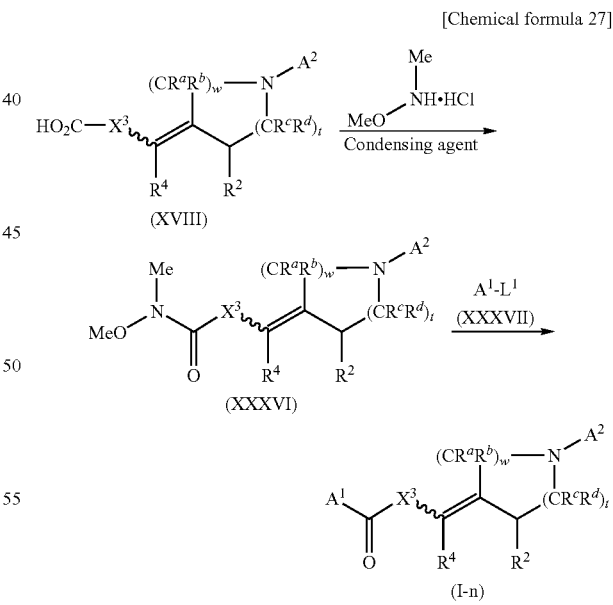

wherein respective symbols are as defined above.

Synthesis of (XXXVI) from (XVIII)

An amide compound represented by the general formula (XXXVI) can be synthesized by condensing carboxylic acid represented by the general formula (XVIII) with N,O-dimethylhydroxylamine hydrochloride in the presence of a condensing agent.

N,O-dimethylhydroxylamine hydrochloride can be used at 0.5 to 3 mole equivalent based on the compound represented by the general formula (XVIII).

Examples of a reaction solvent include methylene chloride, tetrahydrofuran, N,N-dimethylformamide and the like, and these can be used alone, or by mixing.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 1 to 3 mole equivalent based on the compound represented by the general formula (XVIII). 1-Hydroxybenzotriazole or the like may be used as a condensation assistant at 0.5 to 2 mole equivalent.

Examples of a base include triethylamine, N-methylmorpholine, 4-dimethylaminopyridine and the like, and these may be used alone, or by mixing. The base can be used at 0.05 to 3 mole equivalent based on the compound represented by the general formula (XVIII).

An example of a reaction temperature is 0 to 80° C.

An example of a reaction time is 0.5 to 72 hours.

The resulting compound represented by the general formula (XXXVI) can be isolated and purified by the known means (e.g. chromatography, recrystallization etc.).

Synthesis of (I-n) from (XXXVI)

A compound represented by the general formula (I-n) can be synthesized by reacting the amide compound represented by the general formula (XXXVI) with an organometallic compound represented by the general formula (XXXVII).

The compound represented by the general formula (XXXVII) can be used at 1 to 3 mole equivalent based on the amide compound represented by the general formula (XXXVI).

Examples of a reaction solvent include diethylether, tetrahydrofuran and the like.

An example of a reaction temperature is −70 to 50° C.

An example of a reaction time is 0.5 to 24 hours.

The resulting compound represented by the general formula (I-n) can be isolated and purified by the known means (e.g. chromatography, recrystallization etc.).

O Method: Synthesis of (I-o) from (I-n)

A compound represented by the general formula (I-o) can be synthesized by reducing the compound represented by the general formula (I-n) with hydrogen:

[Chemical formula 28]

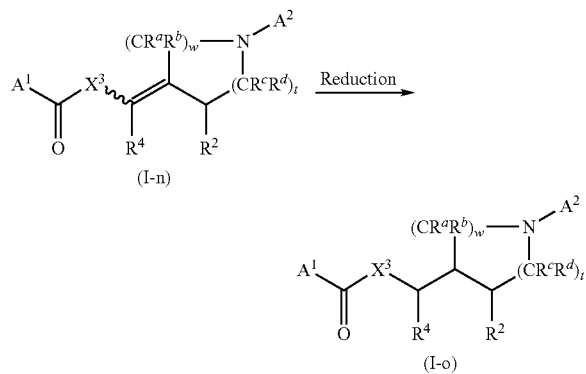

wherein respective symbols are as defined above.

Examples of a reaction solvent include methanol, ethanol, ethyl acetate, tetrahydrofuran, N,N-dimethylformamide and the like.

Examples of a metal catalyst include 5% palladium-carbon, 10% palladium-carbon, platinum oxide, chlorotris(triphenylphosphine)rehodium (I), and the metal catalyst can be used at 0.01 to 0.5 weight percent based on the compound represented by the general formula (I-n).

An example of a hydrogen pressure is 1 to 50 atm.

An example of a reaction temperature is 20° C. to a refluxing temperature of a solvent.

An example of a reaction time is 0.5 to 72 hours.

The resulting compound represented by the general formula (I-o) can be isolated and purified by the known means (e.g. chromatography, recrystallization etc.).

P Method: Synthesis of (I-p) from Compound (I-n) or (I-o)

An oxime compound represented by the general formula (I-p) can be synthesized by reacting ketone represented by the general formula (I-n) or (I-o) with a compound represented by the general formula (XXXVIII):

[Chemical formula 29]

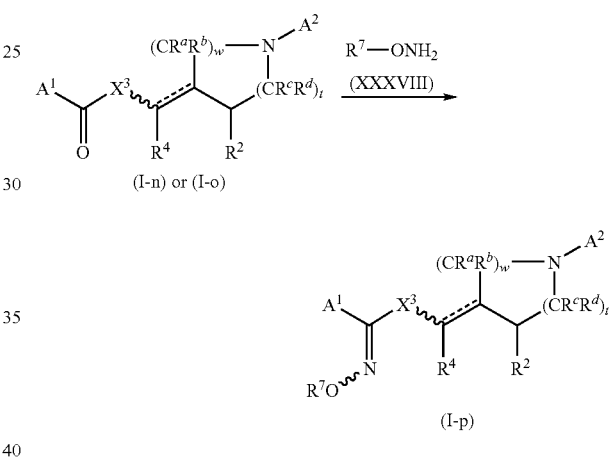

wherein respective symbols are as defined above.

The compound represented by the general formula (XXXVIII) can be used at 0.5 to 3 mole equivalent based on the ketone represented by the general formula (I-n) or (I-o). Hydrochloride or sulfate of the compound represented by the general formula (XXXVIII) may be used.

Examples of a reaction solvent include methanol, ethanol, isopropanol, butanol, water and the like, and these can be used alone, or by mixing.

A base such as triethylamine, and a salt such as sodium acetate, potassium acetate and the like may be used at 0.5 to 5 mole equivalent based on the ketone represented by the general formula (I-n) or (I-o).

An example of a reaction temperature is 0 to 80° C.

An example of a reaction time is 0.5 to 72 hours.

The resulting compound represented by the general formula (I-p) can be isolated and purified by the known means (e.g. chromatography, recrystallization etc.).

Q Method: Synthesis of (I-q) from Compound (I-n) or (I-o)

An alcohol represented by the general formula (I-q) can be synthesized by reducing the compound represented by the general formula (I-n) or (I-o) in the presence of a reducing agent:

[Chemical formula 30]

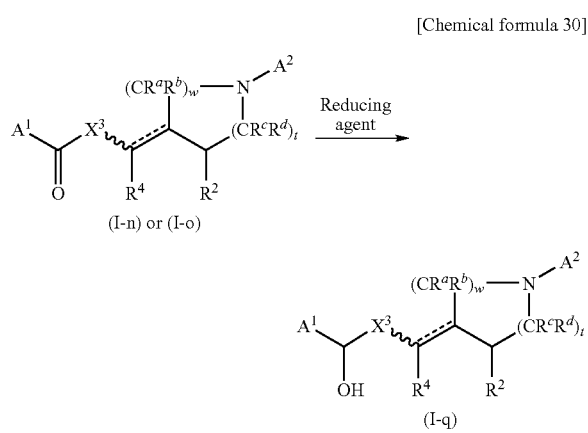

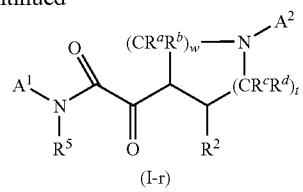

wherein respective symbols are as defined above.

Examples of a reaction solvent include diethyl ether, tetrahydrofuran, toluene, ethanol and the like, and these can be used alone, or by mixing.

Examples of the reducing agent include sodium borohydride, lithium borohydride, lithium aluminum hydride, diisopropyl aluminum hydride and the like and the reducing agent can be used at 0.5 to 6 mole equivalent based on the compound represented by the general formula (I-n) or (I-o).

An example of a reaction temperature is 0° C. to a refluxing temperature of a solvent.

An example of a reaction time is 0.5 to 72 hours.

The resulting compound represented by general formula (I-q) can be isolated and purified by the known means (e.g. chromatography, a recrystallization etc.).

R Method: Synthesis of (I-r) from Compound (II):

[Chemical formula 31]

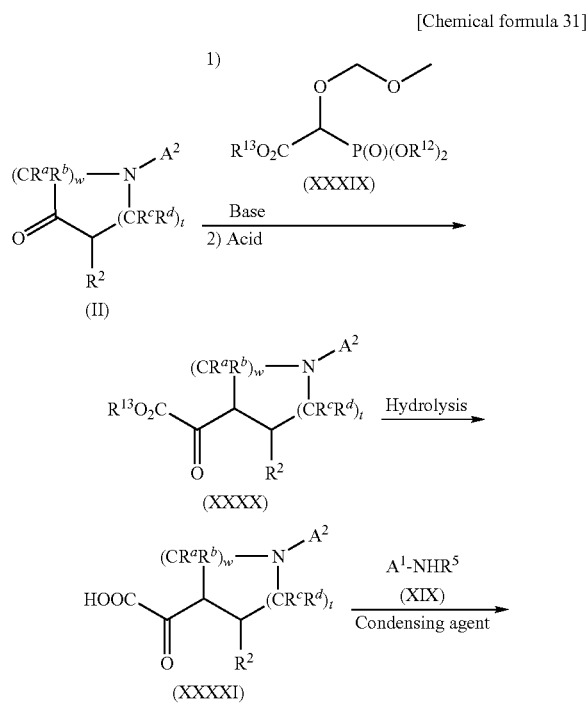

wherein respective symbols are as defined above.

The compound represented by the general formula (XXXIX) can be synthesized by the method described in JP-A No. 62-258342, and a method similar thereto.

Synthesis of (XXXX) from (II)

A compound represented by the general formula (XXXX) can be synthesized by condensing the compound represented by the general formula (II) and the organophosphorus compound represented by the general formula (XXXIX) in the presence of a base, followed by treatment with an acid.

The organophosphorus compound represented by the general formula (XXXIX) can be used at 1 to 5 mole equivalent based on the compound represented by the general formula (II).

Examples of a reaction solvent include tetrahydrofuran, diethyl ether, acetonitrile, N,N-dimethylformamide, dimethyl sulfoxide, liquid ammonia and the like.

Examples of the base include lithium hydroxide, sodium hydroxide, potassium hydroxide, sodium hydride, potassium hydride, sodium methoxide, potassium tert-butoxide, n-butyllithium, lithiumhexamethyldisilazide, sodium hexamethyldisilazide, potassium hexamethyldisilazide, sodium amide and the like. The base can be used at 1.0 to 5 mole equivalent based on the compound represented by the general formula (II).

An example of a reaction temperature is –70 to 100° C.

An example of a reaction time is 0.5 to 72 hours.

Examples of an acid used in treatment with an acid include p-toluenesulfonic acid, benzenesulfonic acid, hydrochloric acid, sulfuric acid and the like, and the acid can be used at 0.1 to 10 mole equivalent based on the compound represented by (II).

Examples of a reaction solvent include methanol, ethanol, toluene, water and the like, and these can be used alone, or by mixing.

An example of a reaction temperature is 20 to 100° C.

An example of a reaction time is 0.5 to 24 hours.

The resulting compound represented by the general formula (XXXX) can be isolated and purified by the known means (e.g. chromatography, recrystallization etc.)

Synthesis of (XXXXI) from (XXXX)

Carboxylic acid represented by the general formula (XXXXI) can be synthesized by hydrolyzing the compound represented by the general formula (XXXX).

Lithium hydroxide, sodium hydroxide, potassium hydroxide or the like can be used at 1.0 to 5 mole equivalent based on the compound represented by the general formula (XXXX).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The resulting compound represented by the general formula (XXXXI) can be isolated and purified by the known means (e.g. chromatography, recrystallization etc.).

Synthesis of (I-r) from (XXXXI)

An amide compound represented by the general formula (I-r) can be synthesized by condensing carboxylic acid represented by the general formula (XXXXI) with an amine compound represented by the general formula (XIX) in the presence of a condensing agent.

The compound represented by the general formula (XIX) can be used at 0.5 to 2 mole equivalent based on the compound represented by the general formula (XXXXI).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXXXI). 1-Hydroxybenzotriazole or the like may be used as a condensation assistant at 0.5 to 2 mole equivalent.

Examples of the base include triethylamine, N-methylmorpholine, 4-dimethylaminopyridine and the like, and these can be used alone, or by mixing. The base can be used at 0.05 to 2 mole equivalent based on the compound represented by the general formula (XXXXI).

An example of a reaction temperature is 0 to 100° C.

An example of a reaction time is 0.5 to 72 hours.

When ethyl chlorocarbonate, isobutyl chlorocarbonate, thionyl chloride, oxalyl chloride or the like is used as the condensing agent, a reaction time can be shortened.

The resulting compound represented by the general formula (I-r) can be isolated and purified by the known means (e.g. chromatography, recrystallization etc.).

S Method: Synthesis of (I-s) from Compound (XXXX):

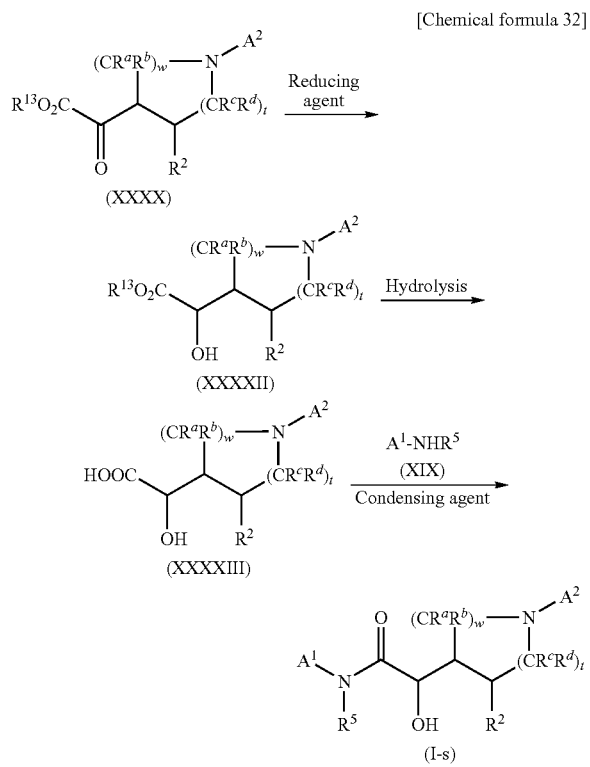

[Chemical formula 32]

wherein respective symbols are as defined above.

Synthesis of (XXXXII) from (XXXX)

An alcohol represented by the general formula (XXXXII) can be synthesized by reducing the compound represented by the general formula (XXXX) in the presence of a reducing agent.

Examples of a reaction solvent include diethyl ether, tetrahydrofuran, toluene, ethanol and the like, and these can be used alone, or by mixing.

Examples of the reducing agent include sodium borohydride and the like, and the reducing agent can be used at 0.5 to 6 mole equivalent based on the compound represented by the general formula (XXXX).

An example of a reaction temperature is 0° C. to a refluxing temperature of a solvent.

An example of a reaction time is 0.5 to 72 hours.

The resulting compound represented by the general formula (XXXXII) can be isolated and purified by the known means (e.g. chromatography, recrystallization etc.).

Synthesis of (XXXXIII) from (XXXXII)

Carboxylic acid represented by the general formula (XXXXIII) can be synthesized by hydrolyzing the compound represented by the general formula (XXXXII).

Lithium hydroxide, sodium hydroxide, potassium hydroxide or the like can be used at 1.0 to 5 mole equivalent based on the compound represented by the general formula (XXXXII).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The resulting compound represented by the general formula (XXXXIII) can be isolated and purified by the known means (e.g. chromatography, recrystallization etc.).

Synthesis of (I-s) from (XXXXIII)

An amide compound represented by the general formula (I-s) can be synthesized by condensing carboxylic acid represented by the general formula (XXXXIII) with an amine compound represented by the general formula (XIX) in the presence of a condensing agent.

The compound represented by the general formula (XIX) can be used at 0.5 to 2 mole equivalent based on the compound represented by the general formula (XXXXIII).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXXXIII). 1-Hydroxybenzotriazole or the like may be used at 0.5 to 2 mole equivalent as a condensation assistant.

Examples of a base include triethylamine, N-methylmorpholine, 4-dimethylaminopyridine and the like, and these can be used alone, or by mixing. The base can be used at 0.05 to 2 mole equivalent based on the compound represented by the general formula (XXXXIII).

An example of a reaction temperature is 0 to 100° C.

An example of a reaction time is 0.5 to 72 hours.

The resulting compound represented by the general formula (I-s) can be isolated and purified by the known means (e.g. chromatography, recrystallization).

T Method: Synthesis of (I-t) from Compound (XXXXII):

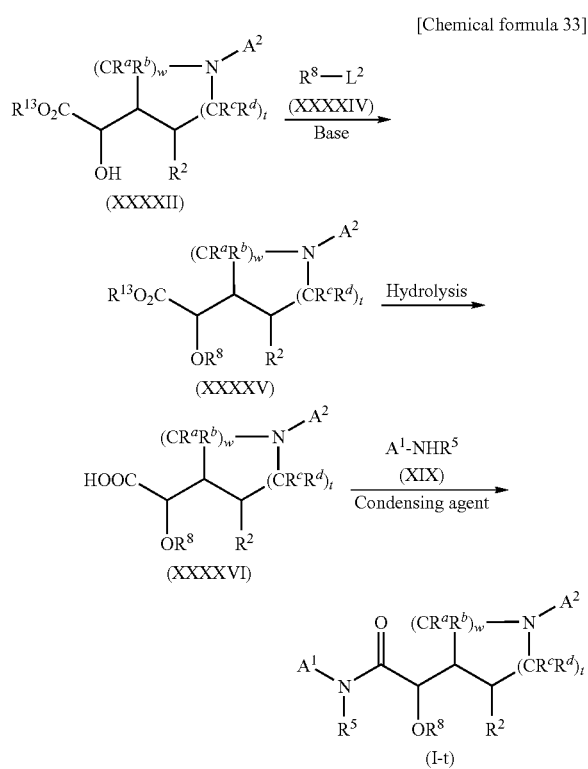

[Chemical formula 33]

wherein respective symbols are as defined above.
Synthesis of (XXXXV) from (XXXXII)

A compound represented by the general formula (XXXXV) can be synthesized by reacting the compound represented by the general formula (XXXXII) and the compound represented by the general formula (XXXXIV) in the presence of a base.

The compound represented by the general formula (XXXXIV) can be used at 1 to 5 mole equivalent based on the compound represented by the general formula (XXXXII).

Examples of a reaction solvent include tetrahydrofuran, diethyl ether, acetonitrile, N,N-dimethylformamide, dimethyl sulfoxide and the like.

Examples of the base include lithium hydroxide, sodium hydroxide, potassium hydroxide, sodium hydride, potassium hydride, sodium methoxide, potassium tert-butoxide, n-butyllithium, lithium hexamethyldisilazide, sodium hexamethyldisilazide, potassium hexamethyldisilazide and the like. The base can be used at 1.0 to 5 mole equivalent based on the compound represented by the general formula (XXXXII).

An example of a reaction temperature is −70 to 100° C.

An example of a reaction time is 0.5 to 72 hours.

The resulting compound represented by the general formula (XXXXV) can be isolated and purified by the known means (e.g. chromatography, recrystallization etc.).
Synthesis of (XXXXVI) from (XXXXV)

Carboxylic acid represented by the general formula (XXXXVI) can be synthesized by hydrolyzing the compound represented by the general formula (XXXXV).

Lithium hydroxide, sodium hydroxide, potassium hydroxide or the like can be used at 1.0 to 5 mole equivalent based on the compound represented by the general formula (XXXXV).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The resulting compound represented by the general formula (XXXXVI) can be isolated and purified by the known means (e.g. chromatography, recrystallization etc.)
Synthesis of (I-t) from (XXXXVI)

An amide compound represented by the general formula (I-t) can be synthesized by condensing the carboxylic acid represented by the general formula (XXXXVI) with an amine compound represented by the general formula (XIX) in the presence of a condensing agent.

The compound represented by the general formula (XIX) can be used at 0.5 to 2 mole equivalent based on the compound represented by the general formula (XXXXVI).

Examples of a reaction solvent include methylene chloride, tetrahydrofuran, N,N-dimethylformamide etc.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXXXVI). 1-Hydroxybenzotriazole may be used as a condensation assistant at 0.5 to 2 mole equivalent.

Examples of a base include triethylamine, N-methylmorpholine, 4-dimethylaminopyridine and the like, and these can be used alone, or by mixing. The base can be used at 0.05 to 2 mole equivalent based on the compound represented by the general formula (XXXXVI).

An example of a reaction temperature is 0 to 100° C.

An example of a reaction time is 0.5 to 72 hours.

The resulting compound represented by the general formula (I-t) can be isolated and purified by the known means (e.g. chromatography, recrystallization etc.).
U Method: Synthesis of (I-u) from Compound (II):

[Chemical formula 34]

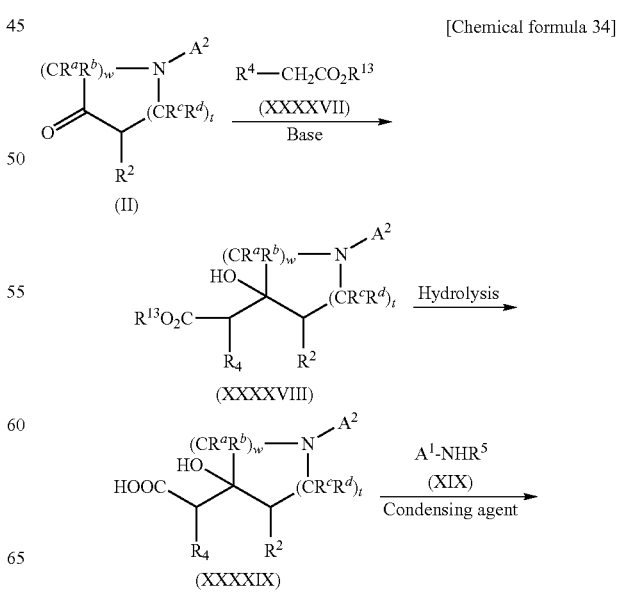

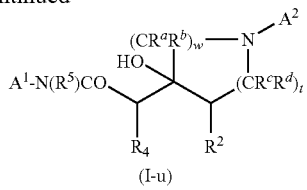

(I-u)

wherein respective symbols are as defined above.

Synthesis of (XXXXVIII) from (II)

A compound represented by the general formula (XXXX-VIII) can be synthesized by condensing the compound represented by the general formula (II) and the compound represented by the general formula (XXXXVII) in the presence of a base.

The compound represented by the general formula (XXXXVII) can be used at 1 to 5 mole equivalent based on the compound represented by the general formula (II).

Examples of a reaction solvent include tetrahydrofuran, diethyl ether, acetonitrile, N,N-dimethylformamide, dimethyl sulfoxide and the like.

Examples of the base include sodium hydride, potassium hydride, sodium methoxide, potassium tert-butoxide, n-butyllithium, lithium diisopropylamide, lithium hexamethyldisilazide, sodium hexamethyldisilazide, potassium hexamethyldisilazide and the like. The base can be used at 1.0 to 5 mole equivalent based on the compound represented by the general formula (II).

An example of a reaction temperature is −100 to 20° C.

An example of a reaction time is 0.5 to 24 hours.

The resulting compound represented by the general formula (XXXXVIII) can be isolated and purified by the known means (e.g. chromatography, recrystallization etc.).

Synthesis of (XXXXIX) from (XXXXVIII)

Carboxylic acid represented by the general formula (XXXXIX) can be synthesized by hydrolyzing the compound represented by the general formula (XXXXVIII).

Lithium hydroxide, sodium hydroxide, potassium hydroxide or the like can be used at 1.0 to 5 mole equivalent based on the compound represented by the general formula (XXXX-VIII).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The compound represented by the resulting general formula (XXXXIX) can be isolated and purified by the known means (e.g. chromatography, recrystallization etc.).

Synthesis of (I-u) from (XXXXIX)

An amide compound represented by the general formula (I-u) can be synthesized by condensing carboxylic acid represented by the general formula (XXXXIX) with an amine compound represented by the general formula (XIX) in the presence of a condensing agent.

The compound represented by the general formula (XIX) can be used at 0.5 to 2 mole equivalent based on the compound represented by the general formula (XXXXIX).

Examples of a reaction solvent include methylene chloride, tetrahydrofuran, N,N-dimethylformamide etc.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (XXXXIX). 1-Hydroxybenzotriazole may be used as a condensation assistant at 0.5 to 2 mole equivalent.

Examples of a base include triethylamine, N-methylmorpholine, 4-dimethylaminopyridine and the like, and these can be used alone, or by mixing. The base can be used at 0.05 to 2 mole equivalent based on the compound represented by the general formula (XXXXIX).

An example of a reaction temperature is 0 to 100° C.

An example of a reaction time is 0.5 to 72 hours.

The resulting compound represented by the general formula (I-u) can be isolated and purified by the known means (e.g. chromatography, recrystallization etc.).

V Method: Synthesis of (I-v) from Compound (XVII-a):

[Chemical formula 35]

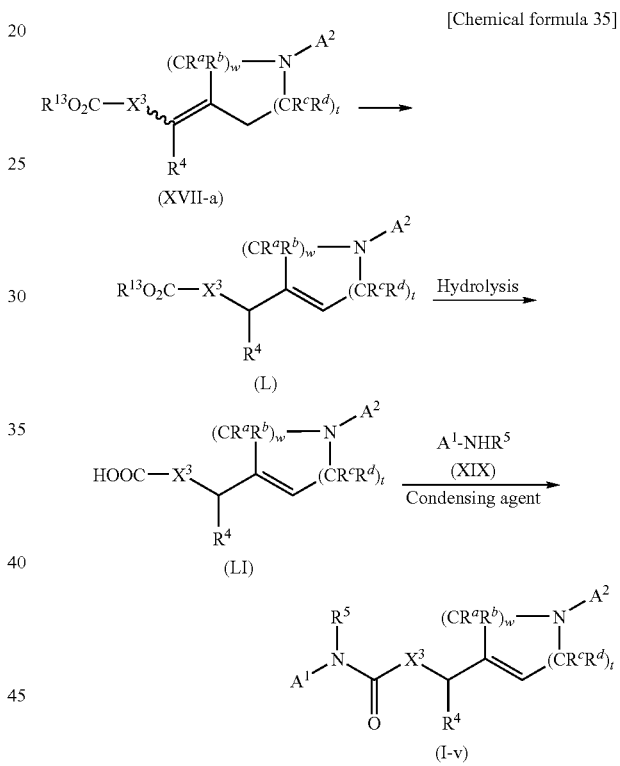

wherein respective symbols are as defined above.

Synthesis of (L) from (XVII-a)

A compound represented by the general formula (L) can be synthesized by treating the compound represented by the general formula (XVII-a) with a base.

A base such as lithium diisopropylamide, lithium hexamethyldisilazide, n-butyllithium, potassium tert-butoxide, 1,8-diazabicyclo[5.4.0]undec-7-ene and the like can be used at 0.1 to 10 mole equivalent based on the compound represented by the general formula (XVII-a).

Examples of a reaction solvent include tetrahydrofuran, diethyl ether, toluene and the like.

An example of a reaction temperature is −70 to 100° C.

An example of a reaction time is 0.5 to 72 hours.

The resulting compound represented by the general formula (L) can be isolated and purified by the known means (e.g. chromatography, recrystallization etc.).

Synthesis of (LI) from (L)

Carboxylic acid represented by the general formula (L1) can be synthesized by hydrolyzing the compound represented by the general formula (L).

Lithium hydroxide, sodium hydroxide, potassium hydroxide or the like can be used at 1.0 to 5 mole equivalent based on the compound represented by the general formula (L).

Examples of a reaction solvent include methanol, ethanol, propanol, isopropanol, butanol, water and the like, and these can be used alone, or by mixing.

An example of a reaction temperature is 0° C. to a refluxing temperature of a solvent.

An example of a reaction time is 0.5 to 24 hours.

The resulting compound represented by the general formula (L1) can be isolated and purified by the known means (e.g. chromatography, recrystallization etc.).

Synthesis of (I-v) from (LI)

An amide compound represented by the general formula (I-v) can be synthesized by condensing the carboxylic acid represented by the general formula (LI) with an amine compound represented by the general formula (XIX) in the presence of a condensing agent.

The compound represented by the general formula (XIX) can be used at 0.5 to 2 mole equivalent based on the compound represented by the general formula (LI).

Examples of a reaction solvent include methylene chloride, tetrahydrofuran, N,N-dimethylformamide and the like.

Examples of the condensing agent include dicyclohexylcarbodiimide, 1-(3-dimethylaminopropyl)-2-ethylcarbodiimide hydrochloride, N,N'-carbonyldiimidazole, ethyl chlorocarbonate, isobutyl chlorocarbonate, thionyl chloride, oxalyl chloride and the like. The condensing agent can be used at 0.5 to 2 mole equivalent based on the compound represented by the general formula (L1). 1-Hydroxybenzotriazole or the like may be used as a condensation assistant at 0.5 to 2 mole equivalent.

Examples of a base include triethylamine, N-methylmorpholine, 4-dimethylaminopyridine and the like, and these can be used alone, or by mixing. The base can be used as 0.05 to 2 mole equivalent based on the compound represented by the general formula (L1).

An example of a reaction temperature is 0 to 100° C.

An example of a reaction time is 0.5 to 72 hours.

The resulting compound represented by the general formula (I-v) can be isolated and purified by the known means (e.g. chromatography, recrystallization etc.).

W Method: Synthesis from (I-w) from Compound (LII)

A compound represented by the general formula (I-w) can be synthesized by condensing the aldehyde represented by the general formula (LII) with an organophosphorus compound represented by the general formula (LIII) or (LIV) in the presence of a base:

[Chemical formula 36]

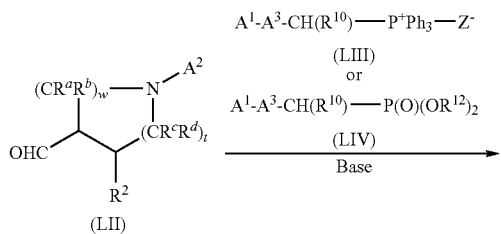

$A^1$-$A^3$-CH($R^{10}$)—$P^+Ph_3$—$Z^-$
(LIII)
or
$A^1$-$A^3$-CH($R^{10}$)—P(O)(O$R^{12}$)$_2$
(LIV)
Base

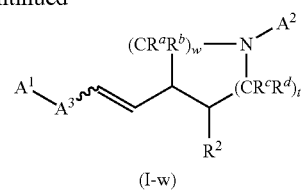

(I-w)

wherein respective symbols are as defined above.

The compound represented by the general formula (XXXII) can be later, and a method similar thereto. The organophosphorus compound represented by the general formula (LIII) and (LIV) can be synthesized by the method described in New Experimental Chemistry Course 14, Maruzen Co. Ltd., (1977), and a method similar thereto.

The organophosphorus compound represented by the general formula (LIII) or (LIV) can be used at 1 to 5 mole equivalent based on the compound represented by the general formula (LII).

Examples of a reaction solvent include tetrahydrofuran, diethyl ether, acetonitrile, N,N-dimethylformamide, dimethyl sulfoxide, liquid ammonia and the like.

Examples of the base include lithium hydroxide, sodium hydroxide, potassium hydroxide, sodium hydride, potassium hydride, sodium methoxide, potassium tert-butoxide, n-butyllithium, lithium hexamethyldisilazide, sodium hexamethyldisilazide, potassium hexamethyldisilazide, sodium amide and the like. The base can be used at 1.0 to 5 mole equivalent based on the compound represented by the general formula (LII).

An example of a reaction temperature is –70 to 100° C.

An example of a reaction time is 0.5 to 72 hours.

The resulting compound represented by the general formula (I-w) can be isolated and purified by the known means (e.g. chromatography, recrystallization etc.).

X Method: Synthesis of (I-x) from Compound (I-w)

A compound represented by the general formula (I-x) can be synthesized by reducing the compound represented by the general formula synthesized by reducing the compound represented by the general formula (I-w) with hydrogen in the presence of a metal catalyst:

[Chemical formula 37]

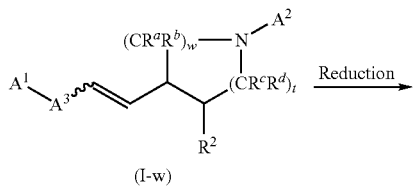 Reduction (I-w)

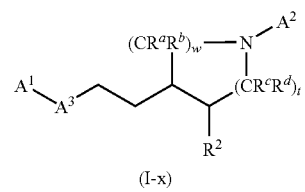

(I-x)

wherein respective symbols are as defined above.

Examples of a reaction solvent include methanol, ethanol, ethyl acetate, tetrahydrofuran, N,N-dimethylformamide and the like.

Examples of a metal catalyst include 5% palladium-carbon, 10% palladium-carbon, platinum oxide, chlorotris(triphenylphosphine)rhodium (I). The metal catalyst can be used at 0.01 to 0.5 weight % based on the compound represented by the general formula (I-a).

An example of a hydrogen atom is 1 to 50 atm.

An example of a reaction temperature is 20° C. to a refluxing temperature of a solvent.

An example of a reaction time is 0.5 to 72 hours.

The resulting compound represented by the general formula (I-x) can be isolated and purified by the known means (e.g. chromatography, recrystallization etc.).

Y Method: Synthesis of (I-y) from Compound (II)

A compound represented by the general formula (I-y) can be synthesized by reductively condensing the compound represented by the general formula (II) and the compound represented by the general formula (LV):

[Chemical formula 38]

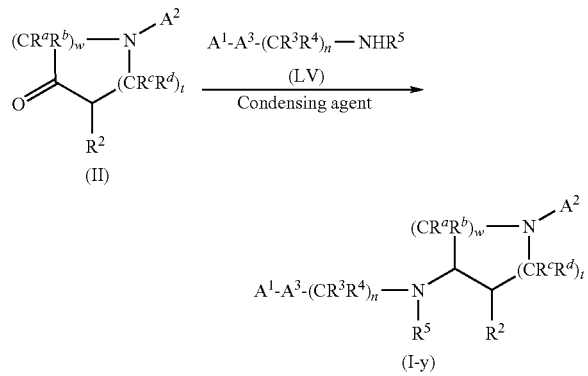

wherein respective symbols are as defined above.

The compound represented by the general formula (LV) can be used at 0.5 to 2 mole equivalent based on the compound represented by the general formula (II).

Examples of a reaction solvent include 1,2-dichloroethane, tetrahydrofuran and the like.

Examples of the reducing agent include sodium triacetoxyborohydride and the like, and the reducing agent can be used at 0.5 to 6 mole equivalent based on the general formula (II).

An example of a reaction temperature is 0 to 80° C.

If necessary, acetic acid or the like as an acid can be used at 0.5 to 2 mole equivalent based on the compound represented by the general formula (II).

An example of a reaction time is 0.5 to 72 hours.

The resulting compound represented by the general formula (I-y) can be isolated and purified by the known means (e.g. chromatography, recrystallization etc.).

Z Method: Synthesis of (I-z) from Compound (LVI):

[Chemical formula 39]

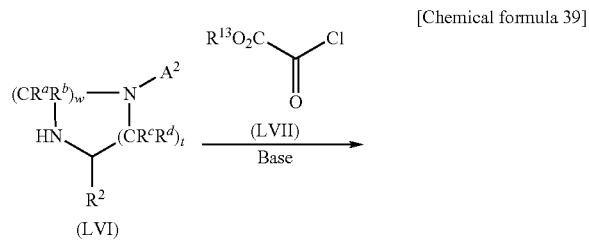

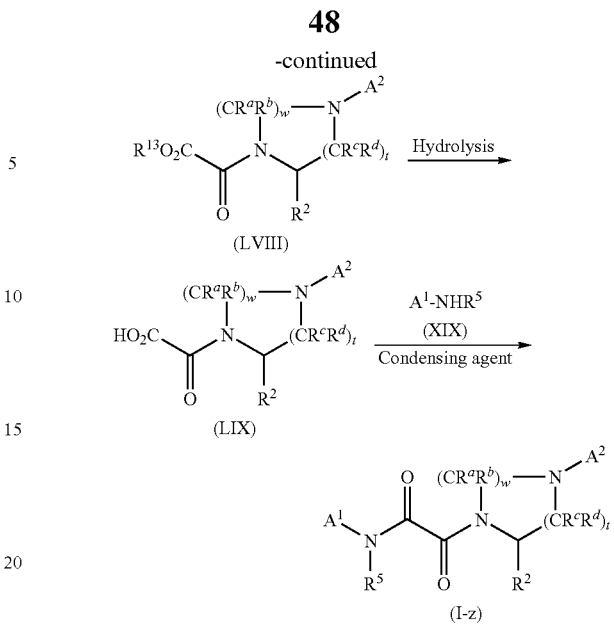

wherein respective symbols are as defined above.

Synthesis of (LVIII) from (LVI)

A compound represented by the general formula (LVIII) can be synthesized by condensing the compound represented by the general formula (LVI) and the compound represented by the general formula (LVII) in the presence of a base.

The compound represented by the general formula (LVII) can be used at 1 to 3 mole equivalent based on the compound represented by the general formula (LVI).

Examples of a reaction solvent include tetrahydrofuran, diethyl ether, acetonitrile, methylene chloride, chloroform, toluene, water and the like, and these can be used alone, or by mixing.

Examples of the base include sodium hydroxide, potassium hydroxide, sodium bicarbonate, sodium carbonate, potassium carbonate, sodium N-methylmorpholine and the like. The base can be used at 1.0 to 5 mole based on the compound represented by the general formula (LVI).

An example of a reaction temperature is −10 to 50° C.

An example of a reaction time is 0.5 to 24 hours.

The resulting compound represented by the general formula (LVIII) can be isolated and purified by the known means (e.g. chromatography, recrystallization etc.).

Synthesis of (LIX) from (LVIII)

Carboxylic acid represented by the general formula (LIX) can be synthesized by hydrolyzing the compound represented by the general formula (LVIII).

Lithium hydroxide, sodium hydroxide, potassium hydroxide or the like can be used at 1.0 to 5 mole equivalent can be used based on the compound represented by the general formula (LVIII).

Examples of a reaction solvent include methanol, ethanol, propanol, isopropanol, butanol, water and the like, and these can be used alone, or by mixing.

An example of a reaction time is 0.5 to 24 hours.

The resulting compound represented by the general formula (LIX) can be isolated and purified by the known means (e.g. chromatography, recrystallization etc.).

Synthesis of (I-z) from (LIX)

An amide compound represented by the general formula (I-z) can be synthesized by condensing the carboxylic acid represented by the general formula (LIX) with an amide compound represented by the general formula (XIX) in the presence of a condensing agent.

The compound represented by the general formula (XIX) can be used at 0.5 to 2 mole equivalent based on the compound represented by the general formula (LIX).

Examples of a reaction solvent include methylene chloride, tetrahydrofuran, N,N-dimethylformamide, N,N-dimethylacetamide, 1,3-dimethyl-2-imidazolidinone, N-methyl-2-pyrrolidone and the like.

Examples of the condensing agent include dicyclohexylcarbodiimide, 1-(3-dimethylaminopropyl)-3-ethylcarbodiimide hydrochloride, N,N'-carbonyldiimidazole, ethyl chlorocarbonate, isobutyl chlorocarbonate, thionyl chloride, oxalyl chloride and the like, and the condensing agent can be used at 0.5 to 2 mole equivalent based on the compound represented by the general formula (LIX). 1-Hydroxybenzotriazole or the like may be used as a condensation assistant at 0.5 to 2 mole equivalent.

Examples of a base include triethylamine, N-methylmorpholine, 4-dimethylaminopyridine and the like, and these can be used alone, or by mixing. The base can be used at 0.05 to 2 mole equivalent based on the compound represented by the general formula (LIX).

An example of a reaction temperature is 0 to 100° C.

An example of a reaction time is 0.5 to 72 hours.

When ethyl chlorocarbonate, isobutyl chlorocarbonate, thionyl chloride, oxalyl chloride or the like is used as the condensing agent, a reaction time can be shortened.

The resulting compound represented by the general formula (I-z) can be isolated and purified by the known means (e.g. chromatography, recrystallization etc.).

In addition, when $A^1$ is the nitrogen-containing aromatic monocyclic group or the nitrogen-containing aromatic fused cyclic group having at least one of protected hydroxy and/or protected amino and, further, optionally substituted with other group, or the nitrogen-containing aromatic monocyclic group or the nitrogen-containing aromatic fused cyclic group containing —NH— in the ring, and in which other ring constituting atoms may be substituted with a substituent other than protected hydroxy and protected amino, the protecting group can be deprotected under the normally used reaction conditions (e.g. the method described in T. W. Green et al., Protective Groups in Organic Synthesis, Second Edition, John Wiley & Sons (1991)).

When the present compound contains an optical isomer, a steric isomer, a positional isomer, and a rotational isomer, these are also included as the present compound, and can be obtained as a single product, respectively, by the known per se synthesizing procedure, and the separating procedure. For example, when an optical isomer is present in the present compound, an optical isomer resolved from the compound is also included in the present compound. The optical isomer can be produced by the known per se method. Specifically, an optical isomer is obtained by optically resolving a final racemate mixture using an optically active synthetic intermediate, or according to a conventional method.

As the optical resolution method, the known per se method, for example, a fractionation recrystallization method, a chiral column method, and a diastereomer method which are described in detail below, are used.

1) Fractionation Recrystallization Method

A salt is formed between a racemate and an optically active compound (e.g. (+)-mandelic acid), (−)-mandelic acid, (+)-tartaric acid, (−)-tartaric acid, (+)-1-phenethylamine, (−)-1-phenethylamine, cinchonine, (−)-cinchonidine, brucine etc.), this is separated by a fractionation recrystallization method and, if desired, a neutralization step is performed, thereby, a free optical isomar is obtained.

2) Chiral Column Method

A method of separating a racemate or a salt thereof by applying it to a column for separating an optical isomer (chiral column). For example, in the case of liquid chromatography, optical isomers are separated by adding a mixture of optical isomers to a chiral column such as ENANTIO-OVM (manufactured by Tosoh Corporation) and CHIRAL series manufactured by Daicel, and developing the column with water, various buffers (e.g. phosphate buffer), or an organic solvent (e.g. ethanol, methanol, isopropanol, acetonitrile, trifluoroacetic acid, diethylamine, etc) alone or as a mixed solution. Alternatively, for example, in the case of gas chromatography, optical isomers are separated using a chiral column such as CP-Chirasil-Dex CB (manufactured by GL Sciences).

3) Diastereomer Method

A method of converting a mixture of racemates into a mixture of diastereomers by a chemical reaction with an optically active reagent, converting this into a single substance via a conventional separation means (e.g. fractionation recrystallization, chromatography method etc.), and cutting off an optically active reagent site by chemical treatment such as a hydrolysis reaction to obtain an optical isomer. For example, when the present compound has hydroxy or primary or secondary amino in a molecule, diastereomers of an ester form and an amide form can be obtained, respectively, by subjecting the compound and an optically active organic acid (e.g. MTPA [α-methoxy-α-(trifluoromethyl)phenylacetic acid], (−)-methoxyacetic acid etc.) to a condensation reaction. On the other hand, when the present compound has a carboxylic acid group, diastereomers of an amide form and an ester form are obtained, respectively, by subjecting the compound and optically active amine or an alcohol reagent to a condensation reaction. Separated diastereomers are converted into optical isomers of the original compound by subjecting to acid hydrolysis or basic hydrolysis reaction.

As a salt of the present compound, a pharmaceutically acceptable salt can be used, and examples of the basic addition salt include alkali metal salts such as sodium salt, potassium salt etc.; alkaline earth metal salts such as calcium salt, magnesium salt etc.; ammonium salts; trimethylamine salt, triethylamine salt; aliphatic amine salts such as dicyclohexylamine salt, ethanolamine salt, diethanol amine salt, triethanolamine salt, procaine salt etc.; aralkylamine salts such as N,N-dibenzylethylenediamine etc.; heterocyclic aromatic amine salts such as pyridine salt, picoline salt, quinoline salt, isoquinoline salt etc.; quaternary ammonium salts such as tetramethylammonium salt, tetraethylammonium salt, benzyltrimethylammonium salt, benzyltriethylammonium salt, benzyltributylammonium salt, methyltrioctylammonium salt, tetrabutylammonium salt etc.; basic amino acid salts such as arginine salt, lysine salt etc.

Examples of the acid addition salts include inorganic acid salts such as hydrochloride, sulfate, nitrate, phosphate, carbonate, bicarbonate, perchlorate etc.; organic acid salts such as oxalate, acetate, propionate, lactate, maleate, fumarate, tartarate, malate, citrate, ascorbate etc.; sulfonates such as methanesulfonate, isethionate, benzenesulfonate, p-toluenesulfonate etc.; acidic amino acids such as aspartate, glutamate etc.

The compound (I) may be a solvate of water, acetonitrile, acetone, ethyl acetate, methanol, ethanol and the like. And, the solvation number of solvates of the present compound can usually vary depending on a synthesis method, a purification method and the crystallization condition, and for example, is in a range of 0.5 to 5 molecules per one molecule of the compound.

Among the present compound (I), the following compounds are particularly preferable.

In the formula (I), $(CR^aR^b)w$ is $(CH_2)_2$ or $(CH_2)_3$, and $(CR^cR^d)t$ is CHMe or CHMe, 1) a compound in which $A^1$ is pyridyl substituted with at least hydroxy, benzoxazolyl substituted with at least hydroxy, benzimidazolyl substituted with at least hydroxy, pyridyl substituted with at least optionally protected amino, imidazolyl in which ring constituting atoms other than —NH— may be substituted, pyrrolyl in which ring constituting atoms other than —NH— may be substituted, pyrazolyl in which ring constituting atoms other than —NH— may be substituted, or benzimidazolyl in which ring constituting atoms other than —NH— may be substituted (hereinafter, $A^1$ being a1),
2) a compound in which $A^1$ is hydroxypyridyl, hydroxybenzoxazolyl, hydroxybenzimidazolyl, benzpyrazolyl, benzimidazolyl, unsubstituted imidazolyl, unsubstituted pyrrolyl, unsubstituted pyrazolyl, or unsubstituted benzimidazolyl (hereinafter, $A^1$ being a2),
3) a compound in which $A^1$ is hydroxypyridyl, hydroxybenzoxazolyl, hydroxybenzimidazolyl, unsubstituted imidazolyl, unsubstituted pyrazolyl, or unsubstituted pyrrolyl (hereinafter, $A^1$ being a3),
4) a compound in which $A^1$ is hydroxybenzoxazolyl (hereinafter, $A^1$ being a4),
5) a compound in which X is —$(CHR^3)m$-, —$CO(CHR^3)n$-, —$CONH(CHR^3)n$-, —$NHCO(CHR^3)n$-, —NHCONH—, —NHCOCO— or —$NH(CHR^3)mCO$— (each $R^3$ may be different), Z is N or $CR^1$, $R^1$ and $R^2$ are each independently hydrogen, hydroxy or methyl, or $R^1$ and $R^2$ may be taken together to form a single bond, when m or n is 1 or more, $R^1$ may be taken together with $R^3$ on $CR^3R^4$ adjacent to a carbon atom to which $R^1$ binds, to form a single bond (when Z is N, $R^1$ is absent, the same hereinafter) (hereinafter, X, $R^1$ and $R^2$ being xr1),
6) a compound in which X is —$CO(CHR^3)n$-, —$CONH(CHR^3)n$-, —$NHCO(CHR^3)n$-, —NHCOCO— or —$NH(CHR^3)mCO$—, Z is N or $CR^1$, $R^1$ is hydrogen or hydroxy, and $R^2$ is hydrogen or methyl (hereinafter, X being xr2),
7) a compound in which X is —$CO(CHR^3)n$-, —$CONH(CHR^a)n$- or —$NHCO(CHR^3)n$-, Z is $CR^1$, and $R^1$ and $R^2$ are taken together to form a single bond, (hereinafter, X being xr3),
8) a compound in which X is —$CO(CHR^3)n$-, —$CONH(CHR^3)n$- or —$NHCO(CHR^3)n$-, Z is $CR^1$, $R^1$ is taken together with $R^3$ on $CR^3R^4$ adjacent to a carbon atom to which $R^1$ binds, to form a single bond, and $R^2$ is hydrogen (hereinafter, X being xr4),
9) a compound in which X is —$CO(CHR^3)_3$—, —$CONH(CHR^3)_2$—, —$NHCO(CHR^3)_2$—, —NHCOCO— or —$NHCHR^3CO$—, $R^3$ is hydrogen or methyl (each $R^3$ may be different), Z is N or $CR^1$, $R^1$ is hydrogen or hydroxy, and $R^2$ is hydrogen or methyl (hereinafter, X being xr5),
10) a compound in which X is —$CO(CHR^3)_3$—, —$CONH(CHR^3)_2$— or —$NHCO(CHR^3)_2$—, $R^3$ is hydrogen or methyl (each $R^3$ may be different), Z is $CR^1$, and $R^1$ and $R^2$ are taken together to form a single bond (hereinafter, X being xr6),
11) a compound in which X is —$CO(CHR^3)_3$—, —$CONH(CHR^3)_2$— or —$NHCO(CHR^3)_2$—, $R^3$ is hydrogen or methyl (each $R^3$ may be different), Z is $CR^1$, $R^1$ is taken together with $R^3$ on $CR^3R^4$ adjacent to a carbon atom to which $R^1$ binds, to form a single bond, and $R^3$ is hydrogen (hereinafter, X being xr7),
12) a compound in which X is —$CO(CHR^3)_3$—, —$CONH(CHR^3)_2$—, —$NHCO(CHR^3)_2$—, —NHCOCO— or —$NHCHR^3CO$—, $R^3$ is hydrogen or methyl (each $R^3$ may be different), Z is N or CH, and $R^2$ is hydrogen (hereinafter, X being xr8),
13) a compound in which X is —$CO(CHR^3)_3$—, —$CONH(CHR^3)_2$—, —$NHCO(CHR^3)_2$—, —NHCOCO— or —$NHCHR^3CO$—, $R^3$ is hydrogen or methyl (each $R^3$ may be different), and Z is $CR^1$ or N (hereinafter, X being xr9),
14) a compound in which $A^2$ is phenyl optionally substituted with one or more groups selected from halogen, cyano, lower alkyl, halogeno lower alkyl, lower alkoxy and halogeno lower alkoxy or pyridyl optionally substituted with one or more groups selected from halogen, cyano, lower alkyl, halogeno lower alkyl, lower alkoxy and halogeno lower alkoxy (hereinafter, $A^2$ being a5),
15) a compound in which $A^2$ is phenyl substituted with one or more groups selected from halogen, C1-C3 alkyl, halogeno C1-C3 alkyl, C1-C3 alkoxy and halogeno C1-C3 alkoxy or pyridyl optionally substituted with one or more groups selected from halogen, C1-C3 alkyl, halogeno C1-C3 alkyl, C1-C3 alkoxy and halogeno C1-C3 alkoxy (hereinafter, $A^2$ being a6),
16) a compound in which $A^2$ is phenyl substituted with one or more groups selected from halogen, C1-C3 alkyl, halogeno C1-C3 alkyl, C1-C3 alkoxy and halogeno C1-C3 alkoxy at a para-position or pyridyl substituted with one or more groups selected from halogen, C1-C3 alkyl, halogeno C1-C3 alkyl, C1-C3 alkoxy and halogeno C1-C3 alkoxy at a para-position (hereinafter, $A^2$ being a7),
17) a compound in which $A^2$ is phenyl substituted with one or more groups selected from halogen, C1-C3 alkyl, halogeno C1-C3 alkyl, C1-C3 alkoxy and halogeno C1-C3 alkoxy at a meta-position and a para-position (hereinafter, $A^2$ being a8),
18) a compound is which a combination of $A^1$, X, $R^1$, $R^2$ and $A^2$ ($A^1$, xr, $A^2$) is the following:

($A^1$, xr, $A^2$)=(a1,xr1,a5), (a1,xr1,a6), (a1,xr1,a7), (a1,xr1,a8), (a1, xr2,a5), (a1,xr2,a6), (a1, xr2,a7), (a11,xr2,a8), (a1,xr3,a5), (a1,xr3,a6), (a1,xr3,a7), (a1,xr3,a8), (a1,xr4,a5), (a1,xr4, a6), (a1,xr4, a7), (a1,xr4, a8), (a1,xr5, a5), (a1,xr5,a6), (a1,xr5,a7), (a1,xr5, a8), (a11,xr6,a5), (a11,xr6, a6), (a1, xr6,a7), (a11,xr6,a8), (a11,xr7, a5), (a 1,xr7,a6), (a1, xr7, a7), (a1,xr7,a8), (a1,xr8,a5), (a1,xr8,a6), (a1,xr8,a7), (a1, xr8, a8), (a1,xr9,a5), (a1,xr9,a6), (a1,xr9,a7), (a1,xr9, a8),
(a2,xr1,a5), (a2,xr1,a6), (a2,xr1,a7), (a2,xr1,a8), (a2,xr2,a5), (a2,xr2,a6), (a2,xr2, a7), (a2,xr2,a8), (a2, xr3,a5), (a2,xr3, a6), (a2,xr3, a7), (a2,xr4,a5), (a2,xr4, a6), (a2, xr4,a7), (a2,xr4,a8), (a2,xr5,a5), (a2,xr5, a6), (a2,xr5,a7), (a2,xr5, a8), (a2,xr6,a5), (a2,xr6,a6), (a2,xr6,a7), (a2,xr6, a8), (a2, xr7, a5), (a2,xr7,a6), (a2,xr7,a7), (a2,xr7, a8), (a2,xr8,a5), (a2,xr8,a6), (a2,xr8,a7), (a2,xr8, a8), (a2,xr9,a5), (a2,xr9, a6), (a2, xr9,a7), (a2,xr9,a8),
(a3,xr1,a5), (a3,xr1,a6), (a3,xr1,a7), (a3,xr1,a8), (a3,xr2,a5), (a3,xr2,a6), (a3,xr2, a7), (a3,xr2,a8), (a3,xr3,a5), (a3,xr3, a6), (a3,xr3,a7), (a3,xr3,a8), (a3,xr4,a5), (a3, xr4,a6), (a3, xr4,a7), (a3,xr4,a8), (a3,xr5,a5), (a3,xr5,a6), (a3,xr5,a7), (a3,xr5,a8), (a3,xr6,a5), (a3,xr6,a6), (a3,xr6,a7), (a3,xr6, a8), (a3,xr7,a5), (a3,xr7,a6), (a3,xr7, a7), (a3,xr7,a8), (a3, xr8,a5), (a3,xr8,a6), (a3,xr8,a7), (a3,xr8,a8), (a3,xr9,a5), (a3, xr9,a6), (a3,xr9,a7), (a3,xr9,a8),
(a4,xr1,a5), (a4,xr1,a6), (a4,xr1,a7), (a4,xr1,a8), (a4,xr2,a5), (a4,xr2,a6), (a4,xr2, a7), (a4,xr2,a8), (a4,xr3,a5), (a4,xr3, a6), (a4,xr3,a7), (a4,xr3,a8), (a4,xr4,a5), (a4, xr4,a6), (a4, xr4,a7), (a4,xr4,a8), (a4,xr5,a5), (a4,xr5,a6), (a4,xr5,a7), (a4,xr5,a8), (a4,xr6,a5), (a4,xr6,a6), (a4,xr6,a7), (a4,xr6, a8), (a4,xr7,a5), (a4,xr7,a6), (a4,xr7, a7), (a4,xr7,a8), (a4, xr8,a5), (a4,xr8,a6), (a4,xr8,a7), (a4,xr8,a8), (a4,xr9,a5), (a4, xr9,a6), (a4,xr9,a7), (a4,xr9,a8)

In the formula (I) or (I'), 16) a compound in which $A^1$ is pyridyl having at least one of optionally protected hydroxy, and optionally protected amino, —X— is —CONH(CHR$^3$)n-, —NHCO(CHR$^3$)n- or —NHCOCO—, and n is 2 or more, 17) a compound in which $A^1$ is benzoxazolyl having at least one of optionally protected hydroxy and optionally protected amino or benzoimidazolyl having at least one of optionally protected hydroxy and optionally protected amino, and X is —CONH(CHR$^3$)n-, —NR$^5$CO(CR$^3$R$^4$)n-, —NR$^5$CONR$^6$— or —NHCOCO—, or a pharmaceutically acceptable salt, or a solvate thereof A compound in which a combination of $A^1$, $A^2$ and X ($A^1$, $A^2$, X) is the following in the following formula (1) to (7), or a pharmaceutically acceptable salt, or a solvate thereof is also a preferable aspect of the present invention.

[Chemical formula 40]

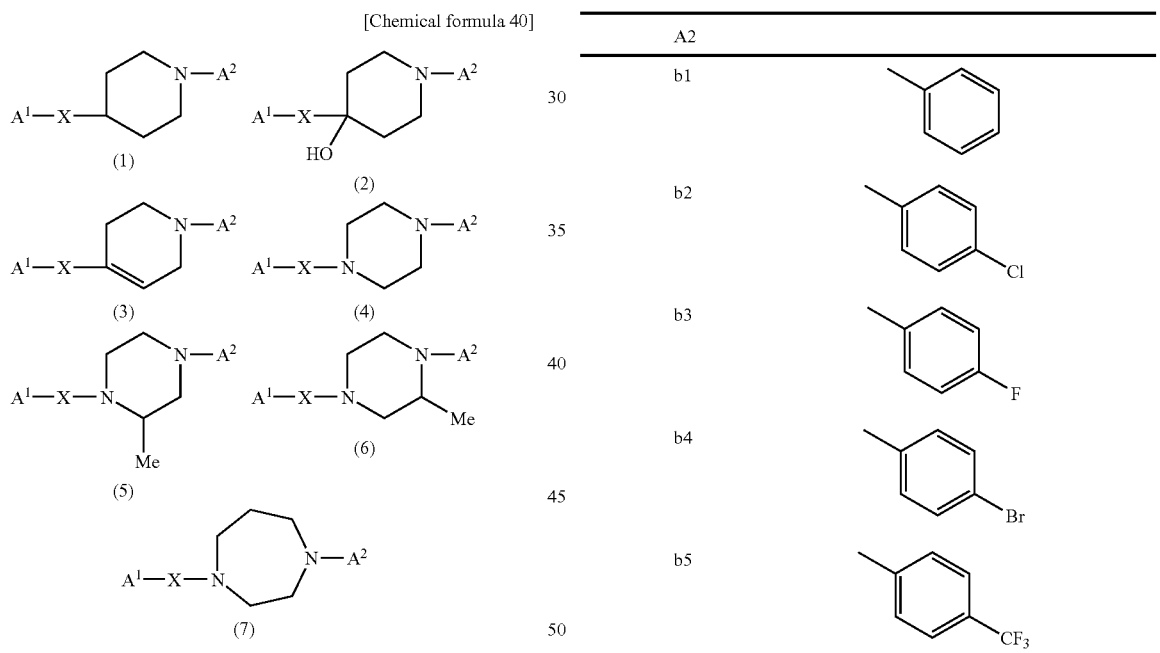

TABLE 1

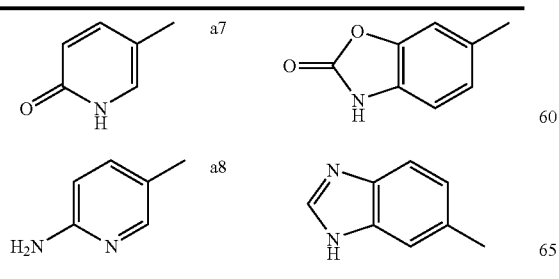

TABLE 1-continued

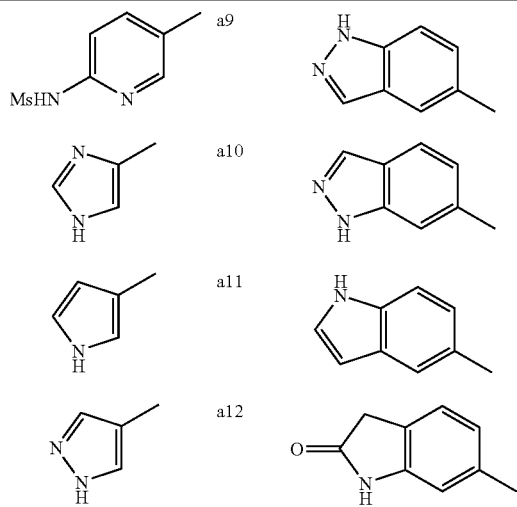

TABLE 2

TABLE 2-continued

| A2 | |
|---|---|
| b9 | 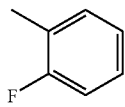 |
| b11 | 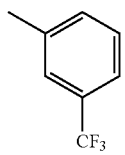 |
| b12 | 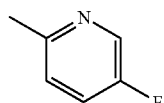 |
| b13 | 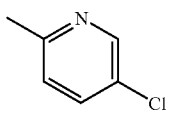 |
| b14 | 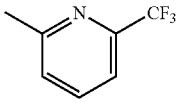 |
| b15 | 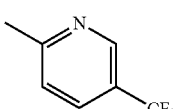 |
| b16 | 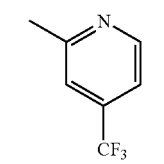 |
| b17 | 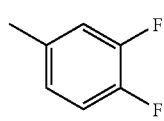 |
| b18 | 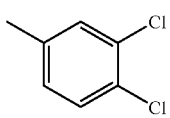 |
| b20 | 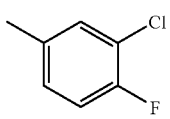 |
| b21 | 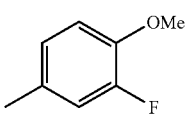 |
| b22 | 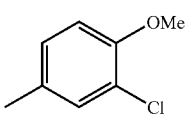 |

TABLE 2-continued

| A2 | |
|---|---|
| b23 | 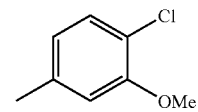 |
| b24 | 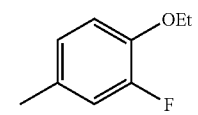 |
| b25 | 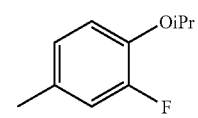 |
| b26 | 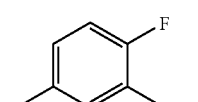 |
| b27 | 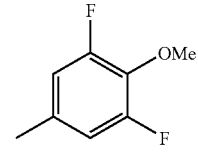 |

TABLE 3

| X | | X | |
|---|---|---|---|
| X1 | COCH$_2$CH$_2$ | X10 | NHCOCH$_2$CH$_2$ |
| X2 | COCH$_2$CH$_2$CH$_2$ | X11 | NHCOCH(OH) |
| X3* | COCH$_2$CH$_2$CH= | X12 | NHCOCO |
| X4 | CONHCH$_2$ | X13* | NHCOCH= |
| X5 | CONHCH$_2$CH$_2$ | X14* | NHCOCF= |
| X6 | CONHCH(Me)CH$_2$ | X15 | NHCONH |
| X7 | CONHCH$_2$CH(Me) | X16 | 2-methyl-oxazol-4-yl-CH$_2$CH$_2$ |
| X8 | NHCO | X17 | 6-methyl-pyridin-3-yl-CH$_2$ |
| X9 | NHCOCH$_2$ | X18 | NHCH$_2$CO |

*Only the case of (1)

In table, Ms represents methanesulfonyl, Me represents methyl, and iPr represents isopropyl.

(A$^1$, A$^2$, X)=(a1, b1, X1), (a1, b1, X2), (a1, b1, X3), (a1, b1, X4), (a1, b1, X5), (a1, b1, X6), (a1, b1, X7), (a1, b1, X8), (a1, b1, X9), (a1, b1, X10), (a1, b1, X11), (a1, b1, X12), (a1, b1, X13), (a1, b1, X14), (a1, b1, X15), (a1, b1, X16), (a1, b1, X17), (a1, b1, X18), (a1, b2, X1), (a1, b2, X2), (a1, b2, X3), (a1, b2, X4), (a1, b2, X5), (a1, b2, X6), (a1, b2, X7), (a1, b2, X8), (a1, b2, X9), (a1, b2, X10), (a1, b2, X11), (a1, b2, X12), (a1, b2, X13), (a1, b2, X14), (a1, b2, X15), (a1, b2, X16), (a1, b2, X17), (a1, b2, X18), (a1, b3, X1), (a1, b3, X2), (a1, b3, X3), (a1, b3, X4), (a1, b3, X5), (a1, b3, X6), (a1, b3, X7), (a1, b3, X8), (a1, b3, X9), (a1, b3, X10), (a1, b3, X11), (a1, b3, X12), (a1, b3, X13), (a1, b3, X14), (a1, b3, X15), (a1, b3, X16), (a1, b3, X17), (a1, b3,

X18), (a1, b4, X1), (a1, b4, X2), (a1, b4, X3), (a1, b4, X4), (a1, b4, X5), (a1, b4, X6), (a1, b4, X7), (a1, b4, X8), (a1, b4, X9), (a1, b4, X10), (a1, b4, X11), (a1, b4, X12), (a1, b4, X13), (a1, b4, X14), (a1, b4, X15), (a1, b4, X16), (a1, b4, X17), (a1, b4, X18), (a1, b5, X1), (a1, b5, X2), (a1, b5, X3), (a1, b5, X4), (a1, b5, X5), (a1, b5, X6), (a1, b5, X7), (a1, b5, X8), (a1, b5, X9), (a1, b5, X10), (a1, b5, X11), (a1, b5, X12), (a1, b5, X13), (a1, b5, X14), (a1, b5, X15), (a1, b5, X16), (a1, b5, X17), (a1, b5, X18), (a1, b6, X1), (a1, b6, X2), (a1, b6, X3), (a1, b6, X4), (a1, b6, X5), (a1, b6, X6), (a1, b6,X7), (a1, b6, X8), (a1, b6, X9), (a1, b6, X10), (a1, b6, X11), (a1, b6, X12), (a1, b6, X13), (a1, b6, X14), (a1, b6, X15), (a1, b6, X16), (a1, b6, X17), (a1, b6, X18), (a1, b7, X1), (a1, b7, X2), (a1, b7, X3), (a1, b7, X4), (a1, b7, X5), (a1, b7, X6), (a1, b7, X7), (a1, b7, X8), (a1, b7, X9), (a1, b7, X10), (a1, b7, X11), (a1, b7, X12), (a1, b7, X13), (a1, b7, X14), (a1, b7, X15), (a1, b7, X16), (a1, b7, X17), (a1, b7, X18), (a1, b8, X1), (a1, b8, X2), (a1, b8, X3), (a1, b8, X4), (a1, b8, X5), (a1, b8, X6), (a1, b8, X7), (a1, b8, X8), (a1, b8, X9), (a1, b8, X10), (a1, b8, X11), (a1, b8, X12), (a1, b8, X13), (a1, b8, X14), (a1, b8, X15), (a1, b8, X16), (a1, b8, X17), (a1, b8, X18), (a1, b9, X1), (a1, b9, X2), (a1, b9, X3), (a1, b9, X4), (a1, b9, X5), (a1, b9, X6), (a1, b9, X7), (a1, b9, X8), (a1, b9, X9), (a1, b9, X10), (a1, b9, X11), (a1, b9, X12), (a1, b9, X13), (a1, b9, X14), (a1, b9, X15), (a1, b9, X16), (a1, b9, X17), (a1, b9, X18), (a1, b10, X1), (a1, b10, X2), (a1, b10, X3), (a1, b10, X4), (a1, b10, X5), (a1, b10, X6), (a1, b10, X7), (a1, b10, X8), (a1, b10, X9), (a1, b10, X10), (a1, b10, X11), (a1, b10, X12), (a1, b10, X13), (a1, b10, X14), (a1, b10, X15), (a1, b10, X16), (a1, b10, X17), (a1, b10, X18), (a1, b11, X1), (a1, b11, X2), (a1, b11, X3), (a1, b11, X4), (a1, b11, X5), (a1, b11, X6), (a1, b11, X7), (a1, b11, X8), (a1, b11, X9), (a1, b11, X10), (a1, b11, X11), (a1, b1, X12), (a1, b11, X13), (a1, b11, X14), (a1, b11, X15), (a1, b11, X16), (a1, b11, X17), (a1, b1, X18), (a1, b12, X1), (a1, b12, X2), (a1, b12, X3), (a1, b12, X4), (a1, b12, X5), (a1, b12, X6), (a1, b12, X7), (a1, b12, X8), (a1, b12, X9), (a1, b12, X10), (a1, b12, X11), (a1, b12, X12), (a1, b12, X13), (a1, b12, X14), (a1, b12, X15), (a1, b12, X16), (a1, b12, X17), (a1, b12, X18), (a1, b13, X1), (a1, b13, X2), (a1, b13, X3), (a1, b13, X4), (a1, b13, X5), (a1, b13, X6), (a1, b13, X7), (a1, b13, X8), (a1, b13, X9), (a1, b13, X10), (a1, b13, X11), (a1, b13, X12), (a1, b13, X13), (a1, b13, X14), (a1, b13, X15), (a1, b13, X16), (a1, b13, X17), (a1, b13, X18), (a1, b14, X1), (a1, b14, X2), (a1, b14, X3), (a1, b14, X4), (a1, b14, X5), (a1, b14, X6), (a1, b14, X7), (a1, b14, X8), (a1, b14, X9), (a1, b14, X10), (a1, b14, X11), (a1, b14, X12), (a1, b14, X13), (a1, b14, X14), (a1, b14, X15), (a1, b14, X16), (a1, b14, X17), (a1, b14, X18), (a1, b15, X1), (a1, b15, X2), (a1, b15, X3), (a1, b15, X4), (a1, b15, X5), (a1, b15, X6), (a1, b15, X7), (a1, b15, X8), (a1, b15, X9), (a1, b15, X10), (a1, b15, X11), (a1, b15, X12), (a1, b15, X13), (a1, b15, X14), (a1, b15, X15), (a1, b15, X16), (a1, b15, X17), (a1, b15, X18), (a1, b16, X1), (a1, b16, X2), (a1, b16, X3), (a1, b16, X4), (a1, b16, X5), (a1, b16, X6), (a1, b16, X7), (a1, b16, X8), (a1, b16, X9), (a1, b16, X10), (a1, b16, X11), (a1, b16, X12), (a1, b16, X13), (a1, b16, X14), (a1, b16, X11), (a1, b16, X16), (a1, b16, X17), (a1, b16, X18), (a1, b17, X1), (a1, b17, X2), (a1, b17, X3), (a1, b17, X4), (a1, b17, X5), (a1, b17, X6), (a1, b17, X7), (a1, b17, X8), (a1, b17, X9), (a1, b17, X10), (a1, b17, X11), (a1, b17, X12), (a1, b17, X13), (a1, b17, X14), (a1, b17, X15), (a1, b17, X16), (a1, b17, X17), (a1, b17, X18), (a1, b18, X1), (a1, b18, X2), (a1, b18, X3), (a1, b18, X4), (a1, b18, X5), (a1, b18, X6), (a1, b18, X7), (a1, b18, X8), (a1, b18, X9), (a1, b18, X10), (a1, b18, X11), (a1, b18, X12), (a1, b18, X13), (a1, b18, X14), (a1, b18, X15), (a1, b18, X16), (a1, b18, X17), (a1, b18, X18), (a1, b19, X1), (a1, b19, X2), (a1, b19, X3), (a1, b19, X4), (a1, b19, X5), (a1, b19, X6), (a1, b19, X7), (a1, b19, X8), (a1, b19, X9), (a1, b19, X10), (a1, b19, X11), (a1, b19, X12), (a1, b19, X13), (a1, b19, X14), (a1, b19, X15), (a1, b19, X16), (a1, b19, X17), (a1, b19, X18), (a1, b20, X1), (a1, b20, X2), (a1, b20, X3), (a1, b20, X4), (a1, b20, X5), (a1, b20, X6), (a1, b20, X7), (a1, b20, X8), (a1, b20, X9), (a1, b20, X10), (a1, b20, X11), (a1, b20, X12), (a1, b20, X13), (a1, b20, X14), (a1, b20, X15), (a1, b20, X16), (a1, b20, X17), (a1, b20, X18), (a1, b21, X1), (a1, b21, X2), (a1, b21, X3), (a1, b21, X4), (a1, b21, X5), (a1, b21, X6), (a1, b21, X7), (a1, b21, X8), (a1, b21, X9), (a1, b21, X10), (a1, b21, X11), (a1, b21, X12), (a1, b21, X13), (a1, b21, X14), (a1, b21, X15), (a1, b21, X16), (a1, b21, X17), (a1, b21, X18), (a1, b22, X1), (a1, b22, X2), (a1, b22, X3), (a1, b22, X4), (a1, b22, X5), (a1, b22, X6), (a1, b22, X7), (a1, b22, X8), (a1, b22, X9), (a1, b22, X10), (a1, b22, X11), (a1, b22, X12), (a1, b22, X13), (a1, b22, X14), (a1, b22, X15), (a1, b22, X16), (a1, b22, X17), (a1, b22, X18), (a1, b23, X1), (a1, b23, X2), (a1, b23, X3), (a1, b23, X4), (a1, b23, X5), (a1, b23, X6), (a1, b23, X7), (a1, b23, X8), (a1, b23, X9), (a1, b23, X10), (a1, b23, X11), (a1, b23, X12), (a1, b23, X13), (a1, b23, X14), (a1, b23, X15), (a1, b23, X16), (a1, b23, X17), (a1, b23, X18), (a1, b24, X1), (a1, b24, X2), (a1, b24, X3), (a1, b24, X4), (a1, b24, X5), (a1, b24, X6), (a1, b24, X7), (a1, b24, X8), (a1, b24, X9), (a1, b24, X10), (a1, b24, X11), (a1, b24, X12), (a1, b24, X13), (a1, b24, X14), (a1, b24, X15), (a1, b24, X16), (a1, b24, X17), (a1, b24, X18), (a1, b25, X1), (a1, b25, X2), (a1, b25, X3), (a1, b25, X4), (a1, b25, X5), (a1, b25, X6), (a1, b25, X7), (a1, b25, X8), (a1, b25, X9), (a1, b25, X10), (a1, b25, X11), (a1, b25, X12), (a1., b25, X13), (a1, b25, X14), (a1, b25, X15), (a1, b25, X16), (a1, b25, X17), (a1, b25, X18), (a1, b26, X1), (a1, b26, X2), (a1, b26, X3), (a1, b26, X4), (a1, b26, X5), (a1, b26, X6), (a1, b26, X7), (a1, b26, X8), (a1, b26, X9), (a1, b26, X10), (a1, b26, X11), (a1, b26, X12), (a1, b26, X13), (a1, b26, X14), (a1, b26, X15), (a1, b26, X16), (a1, b26, X17), (a1, b26, X18), (a1, b27, X1), (a1, b27, X2), (a1, b27, X3), (a1, b27, X4), (a1, b27, X5), (a1, b27, X6), (a1, b27, X7), (a1, b27, X8), (a1, b27, X9), (a1, b27, X10), (a1, b27, X11), (a1, b27, X12), (a1, b27, X13), (a1, b27, X14), (a1, b27, X15), (a1, b27, X16), (a1, b27, X17), (a1, b27, X18), (a2, b1, X1), (a2, b1, X2), (a2, b1, X3), (a2, b1, X4), (a2, b1, X5), (a2, b1, X6), (a2, b1, X7), (a2, b1, X8), (a2, b1, X9), (a2, b1, X10), (a2, b1, X11), (a2, b1, X12), (a2, b1, X13), (a2, b1, X14), (a2, b1, X15), (a2, b1, X16), (a2, b1, X17), (a2, b1, X18), (a2, b2, X1), (a2, b2, X2), (a2, b2, X3), (a2, b2, X4), (a2, b2, X5), (a2, b2, X6), (a2, b2, X7), (a2, b2, X8), (a2, b2, X9), (a2, b2, X10), (a2, b2, X11), (a2, b2, X12), (a2, b2, X13), (a2, b2, X14), (a2, b2, X15), (a2, b2, X16), (a2, b2, X17), (a2, b2, X18), (a2, b3, X1), (a2, b3, X2), (a2, b3, X3), (a2, b3, X4), (a2, b3, X5), (a2, b3, X6), (a2, b3, X7), (a2, b3, X8), (a2, b3, X9), (a2, b3, X10), (a2, b3, X11), (a2, b3, X12), (a2, b3, X13), (a2, b3, X14), (a2, b3, X15), (a2, b3, X16), (a2, b3, X17), (a2, b3, X18), (a2, b4, X1), (a2, b4, X2), (a2, b4, X3), (a2, b4, X4), (a2, b4, X5), (a2, b4, X6), (a2, b4, X7), (a2, b4, X8), (a2, b4, X9), (a2, b4, X10), (a2, b4, X11), (a2, b4, X12), (a2, b4, X13), (a2, b4, X14), (a2, b4, X15), (a2, b4, X16), (a2, b4, X17), (a2, b4, X18), (a2, b5, X1), (a2, b5, X2), (a2, b5, X3), (a2, b5, X4), (a2, b5, X5), (a2, b5, X6), (a2, b5, X7), (a2, b5, X8), (a2, b5, X9), (a2, b5, X10), (a2, b5, X11), (a2, b5, X12), (a2, b5, X13), (a2, b5, X14), (a2, b5, X15), (a2, b5, X16), (a2, b5, X17), (a2, b5, X18), (a2, b6, X1), (a2, b6, X2), (a2, b6, X3), (a2, b6, X4), (a2, b6, X5), (a2, b6, X6), (a2, b6, X7), (a2, b6, X8), (a2, b6, X9), (a2, b6, X10), (a2, b6, X11), (a2, b6, X12), (a2, b6, X13), (a2, b6, X14), (a2, b6, X15), (a2, b6, X16), (a2, b6, X17), (a2, b6, X18), (a2, b7, X1), (a2, b7, X2), (a2, b7, X3), (a2, b7, X4), (a2, b7, X5), (a2, b7, X6), (a2, b7, X7), (a2, b7, X8), (a2, b7, X9), (a2, b7, X10), (a2, b7, X11), (a2, b7, X12), (a2, b7, X13), (a2, b7, X14), (a2, b7, X15), (a2, b7, X16), (a2, b7, X17), (a2, b7, X18), (a2, b8, X1), (a2, b8, X2), (a2, b8, X3), (a2, b8, X4), (a2, b8, X5), (a2, b8, X6), (a2, b8, X7), (a2, b8, X8), (a2, b8, X9), (a2, b8, X10), (a2, b8, X11), (a2, b8, X12), (a2, b8, X13), (a2, b8, X14), (a2, b8, X15), (a2, b8, X16), (a2, b8, X17), (a2, b8, X18), (a2, b9, X1), (a2, b9, X2), (a2, b9, X3), (a2, b9, X4), (a2, b9, X5), (a2, b9, X6), (a2, b9, X7), (a2, b9, X8), (a2, b9, X9), (a2, b9, X10), (a2, b9, X11), (a2, b9, X12), (a2, b9, X13), (a2, b9, X14), (a2, b9, X15), (a2, b9, X16), (a2, b9, X17), (a2, b9, X18), (a2, b10, X1), (a2, b10, X2), (a2, b10, X3), (a2, b10, X4), (a2, b10, X5), (a2, b10, X6), (a2, b10, X7), (a2, b10, X8), (a2, b10, X9), (a2, b10, X10), (a2, b10, X11), (a2, b10, X12), (a2, b10, X13), (a2, b10, X14), (a2, b10, X15), (a2, b10, X16), (a2, b10, X17), (a2, b10, X18), (a2, b11, X1), (a2, b11, X2), (a2, b11, X3), (a2, b11, X4), (a2, b11, X5), (a2, b11, X6), (a2, b11, X7), (a2, b11, X8), (a2, b11, X9), (a2, b11, X10), (a2, b11, X11), (a2, b11, X12), (a2, b11, X13), (a2, b11, X14), (a2, b11, X15), (a2, b11, X16), (a2, b11, X17), (a2, b11, X18), (a2, b12, X1), (a2, b12, X2), (a2, b12, X3), (a2, b12, X4), (a2, b12, Xs), (a2, b12, X6), (a2, b12, X7), (a2, b12, X8), (a2, b12, X9), (a2, b12, X10), (a2, b12, X11), (a2, b12, X12), (a2, b12, X13), (a2, b12, X14), (a2, b12, X15), (a2, b12, X16), (a2, b12, X17), (a2, b12, X18), (a2, b13, X1), (a2, b13, X2), (a2, b13, X3), (a2, b13, X4), (a2, b13, X5), (a2, b13, X6), (a2, b13, X7), (a2, b13, X8), (a2, b13, X9), (a2, b13, X10), (a2, b13, X11), (a2, b13, X12), (a2, b13, X13), (a2, b13, X14), (a2, b13, X15), (a2, b13, X16), (a2, b13, X17), (a2, b13, X18), (a2, b14, X1), (a2, b14, X2), (a2, b14, X3), (a2, b14, X4), (a2, b14, X5), (a2, b14, X6), (a2, b14, X7), (a2, b14, X8), (a2, b14, X9), (a2, b14, X10), (a2, b14, X11), (a2, b14, X12), (a2, b14, X13), (a2, b14, X14), (a2, b14, X15), (a2, b14, X16), (a2, b14, X17), (a2, b14, X18), (a2, b15, X1), (a2, b15, X2), (a2, b15, X3), (a2, b15, X4), (a2, b15, X5), (a2, b15, X6), (a2, b15, X7), (a2, b15, X8), (a2, b15, X9), (a2, b15, X10), (a2, b15, X11), (a2, b15, X12), (a2, b15, X13), (a2, b15, X14), (a2, b15, X15), (a2, b15, X16), (a2, b15, X17), (a2, b15, X18), (a2, b16, X1), (a2, b16, X2), (a2, b16, X3), (a2, b16, X4), (a2, b16, X5), (a2, b16, X6), (a2, b16, X7), (a2, b16, X8), (a2, b16, X9), (a2, b16, X10), (a2, b16, X11), (a2, b16, X12), (a2, b16, X13), (a2, b16, X14), (a2, b16, X15), (a2, b16, X16), (a2, b16, X17), (a2, b16, X18), (a2, b17, X1), (a2, b17, X2), (a2, b17, X3), (a2, b17, X4), (a2, b17, X5), (a2, b17, X6), (a2, b17, X7), (a2, b17, X8), (a2, b17, X9), (a2, b17, X10), (a2, b17, X11), (a2, b17, X12), (a2, b17, X13), (a2, b17, X14), (a2, b17, X15), (a2, b17, X16), (a2, b17, X17), (a2, b17, X18), (a2, b18, X1), (a2, b18, X2), (a2, b18, X3), (a2, b18, X4), (a2, b18, X5), (a2, b18, X6), (a2, b18, X7), (a2, b18, X8), (a2, b18, X9), (a2, b18, X10), (a2, b18, X11), (a2, b18, X12), (a2, b18, X13), (a2, b18, X14), (a2, b18, X15), (a2, b18, X16), (a2, b18, X17), (a2, b18, X18), (a2, b19, X1), (a2, b19, X2), (a2, b19, X3), (a2, b19, X4), (a2, b19, X5), (a2, b19, X6), (a2, b19, X7), (a2, b19, X8), (a2, b19, X9), (a2, b19, X10), (a2, b19, X11), (a2, b19, X12), (a2, b19, X13), (a2, b19, X14), (a2, b19, X15), (a2, b19, X16), (a2, b19, X17), (a2, b19, X18), (a2, b20, X1), (a2, b20, X2), (a2, b20, X3), (a2, b20, X4), (a2, b20, X5), (a2, b20, X6), (a2, b20, X7), (a2, b20, X8), (a2, b20, X9), (a2, b20, X10), (a2, b20, X11), (a2, b20, X12), (a2, b20, X13), (a2, b20, X14), (a2, b20, X15), (a2, b20, X16), (a2, b20, X17), (a2, b20, X18), (a2, b21, X1), (a2, b21, X2), (a2, b21, X3), (a2, b21, X4), (a2, b21, X5), (a2, b21, X6), (a2, b21, X7), (a2, b21, X8), (a2, b21, X9), (a2, b21, X10), (a2, b21, X11), (a2, b21, X12), (a2, b21, X13), (a2, b21, X14), (a2, b21, X15), (a2, b21, X16), (a2, b21, X17), (a2, b21, X18), (a2, b22, X1), (a2, b22, X2), (a2, b22, X3), (a2, b22, X4), (a2, b22, X5), (a2, b22, X6), (a2, b22, X7), (a2, b22, X8), (a2, b22, X9), (a2, b22, X10), (a2, b22, X11), (a2, b22, X12), (a2, b22, X13), (a2, b22, X14), (a2, b22, X15), (a2, b22, X16), (a2, b22, X17), (a2, b22, X18), (a2, b23, X1), (a2, b23, X2), (a2, b23, X3), (a2, b23, X4), (a2, b23, X5), (a2, b23, X6), (a2, b23, X7), (a2, b23, X8), (a2, b23, X9), (a2, b23, X10), (a2, b23, X11), (a2, b23, X12), (a2, b23, X13), (a2, b23, X14), (a2, b23, X15), (a2, b23, X16), (a2, b23, X17), (a2, b23, X18), (a2, b24, X1), (a2, b24, X2), (a2, b24, X3), (a2, b24, X4), (a2, b24, X5), (a2, b24, X6), (a2, b24, X7), (a2, b24, X8), (a2, b24, X9), (a2, b24, X10), (a2, b24, X11), (a2, b24, X12), (a2, b24, X13), (a2, b24, X14), (a2, b24, X15), (a2, b24, X16), (a2, b24, X17), (a2, b24, X18), (a2, b25, X1), (a2, b25, X2), (a2, b25, X3), (a2, b25, X4), (a2, b25, X5), (a2, b25, X6), (a2, b25, X7), (a2, b25, X8), (a2, b25, X9), (a2, b25, X10), (a2, b25, X11), (a2, b25, X12), (a2, b25, X13), (a2, b25, X14), (a2, b25, X15), (a2, b25, X16), (a2, b25, X17), (a2, b25, X18), (a2, b26, X1), (a2, b26, X2), (a2, b26, X3), (a2, b26, X4), (a2, b26, X5), (a2, b26, X6), (a2, b26, X7), (a2, b26, X8), (a2, b26, X9), (a2, b26, X10), (a2, b26, X11), (a2, b26, X12), (a2, b26, X13), (a2, b26, X14), (a2, b26, X15), (a2, b26, X16), (a2, b26, X17), (a2, b26, X18), (a2, b27, X1), (a2, b27, X2), (a2, b27, X3), (a2, b27, X4), (a2, b27, X5), (a2, b27, X6), (a2, b27, X7), (a2, b27, X8), (a2, b27, X9), (a2, b27, X10), (a2, b27, X11), (a2, b27, X12), (a2, b27, X13), (a2, b27, X14), (a2, b27, X15), (a2, b27, X16), (a2, b27, X17), (a2, b27, X18), (a3, b1, X1), (a3, b1, X2), (a3, b1, X3), (a3, b1, X4), (a3, b1, X5), (a3, b1, X6), (a3, b1, X7), (a3, b1, X8), (a3, b1, X9), (a3, b1, X10), (a3, b1, X11), (a3, b1, X12), (a3, b1, X13), (a3, b1, X14), (a3, b1, X15), (a3, b1, X16), (a3, b1, X17), (a3, b1, X18), (a3, b2, X1), (a3, b2, X2), (a3, b2, X3), (a3, b2, X4), (a3, b2, X5), (a3, b2, X6), (a3, b2, X7), (a3, b2, X8), (a3, b2, X9), (a3, b2, X10), (a3, b2, X11), (a3, b2, X12), (a3, b2, X13), (a3, b2, X14), (a3, b2, X15), (a3, b2, X16), (a3, b2, X17), (a3, b2, X18), (a3, b3, X1), (a3, b3, X2), (a3, b3, X3), (a3, b3, X4), (a3, b3, X5), (a3, b3, X6), (a3, b3, X7), (a3, b3, X8), (a3, b3, X9), (a3, b3, X10), (a3, b3, X11), (a3, b3, X12), (a3, b3, X13), (a3, b3, X14), (a3, b3, X15), (a3, b3, X16), (a3, b3, X17), (a3, b3, X18), (a3, b4, X1), (a3, b4, X2), (a3, b4, X3), (a3, b4, X4), (a3, b4, X5), (a3, b4, X6), (a3, b4, X7), (a3, b4, X8), (a3, b4, X9), (a3, b4, X10), (a3, b4, X11), (a3, b4, X12), (a3, b4, X13), (a3, b4, X14), (a3, b4, X15), (a3, b4, X16), (a3, b4, X17), (a3, b4, X18), (a3, b5, X1), (a3, b5, X2), (a3, b5, X3), (a3, b5, X4), (a3, b5, X5), (a3, b5, X6), (a3, b5, X7), (a3, b5, X8), (a3, b5, X9), (a3, b5, X10), (a3, b5, X11), (a3, b5, X12), (a3, b5, X13), (a3, b5, X14), (a3, b5, X15), (a3, b5, X16), (a3, b5, X17), (a3, b5, X18), (a3, b6, X1), (a3, b6, X2), (a3, b6, X3), (a3, b6, X4), (a3, b6, X5), (a3, b6, X6), (a3, b6, X7), (a3, b6, X8), (a3, b6, X9), (a3, b6, X10), (a3, b6, X11), (a3, b6, X12), (a3, b6, X13), (a3, b6, X14), (a3, b6, X15), (a3, b6, X16), (a3, b6, X17), (a3, b6, X18), (a3, b7, X1), (a3, b7, X2), (a3, b7, X3), (a3, b7, X4), (a3, b7, X5), (a3, b7, X6), (a3, b7, X7), (a3, b7, X8), (a3, b7, X9), (a3, b7, X10), (a3, b7, X11), (a3, b7, X12), (a3, b7, X13), (a3, b7, X14), (a3, b7, X15), (a3, b7, X16), (a3, b7, X17), (a3, b7, X18), (a3, b8, X1), (a3, b8, X2), (a3, b8, X3), (a3, b8, X4), (a3, b8, X5), (a3, b8, X6), (a3, b8, X7), (a3, b8, X8), (a3, b8, X9), (a3, b8, X10), (a3, b8, X11), (a3, b8,

X12), (a3, b8, X13), (a3, b8, X14), (a3, b8, X15), (a3, b8, X16), (a3, b8, X17), (a3, b8, X18), (a3, b9, X1), (a3, b9, X2), (a3, b9, X3), (a3, b9, X4), (a3, b9, X5), (a3, b9, X6), (a3, b9, X7), (a3, b9, X8), (a3, b9, X9), (a3, b9, X10), (a3, b9, X11), (a3, b9, X12), (a3, b9, X13), (a3, b9, X14), (a3, b9, X15), (a3, b9, X16), (a3, b9, X17), (a3, b9, X18), (a3, b10, X1), (a3, b10, X2), (a3, b10, X3), (a3, b10, X4), (a3, b10, X5), (a3, b10, X6), (a3, b10, X7), (a3, b10, X8), (a3, b10, X9), (a3, b10, X10), (a3, b10, X11), (a3, b10, X12), (a3, b10, X13), (a3, b10, X14), (a3, b10, X15), (a3, b10, X16), (a3, b10, X17), (a3, b10, X18), (a3, b11, X1), (a3, b11, X2), (a3, b11, X3), (a3, b11, X4), (a3, b11, X5), (a3, b11, X6), (a3, b11, X7), (a3, b11, X8), (a3, b11, X9), (a3, b11, X10), (a3, b11, X11), (a3, b11, X12), (a3, b11, X13), (a3, b11, X14), (a3, b11, X15), (a3, b11, X16), (a3, b11, X17), (a3, b11, X18), (a3, b12, X1), (a3, b12, X2), (a3, b12, X3), (a3, b12, X4), (a3, b12, X5), (a3, b12, X6), (a3, b12, X7), (a3, b12, X8), (a3, b12, X9), (a3, b12, X10), (a3, b12, X11), (a3, b12, X12), (a3, b12, X13), (a3, b12, X14), (a3, b12, X15), (a3, b12, X16), (a3, b12, X17), (a3, b12, X18), (a3, b13, X1), (a3, b13, X2), (a3, b13, X3), (a3, b13, X4), (a3, b13, X5), (a3, b13, X6), (a3, b13, X7), (a3, b13, X8), (a3, b13, X9), (a3, b13, X10), (a3, b13, X11), (a3, b13, X12), (a3, b13, X13), (a3, b13, X14), (a3, b13, X15), (a3, b13, X16), (a3, b13, X17), (a3, b13, X18), (a3, b14, X1), (a3, b14, X2), (a3, b14, X3), (a3, b14, X4), (a3, b14, X5), (a3, b14, X6), (a3, b14, X7), (a3, b14, X8), (a3, b14, X9), (a3, b14, X10), (a3, b14, X11), (a3, b14, X12), (a3, b14, X13), (a3, b14, X14), (a3, b14, X15), (a3, b14, X16), (a3, b14, X17), (a3, b14, X18), (a3, b15, X1), (a3, b15, X2), (a3, b15, X3), (a3, b15, X4), (a3, b15, X5), (a3, b15, X6), (a3, b15, X7), (a3, b15, X8), (a3, b15, X9), (a3, b15, X10), (a3, b11, X11), (a3, b15, X12), (a3, b15, X13), (a3, b11, X14), (a3, b15, X15), (a3, b15, X16), (a3, b15, X17), (a3, b15, X18), (a3, b16, X1), (a3, b16, X2), (a3, b16, X3), (a3, b16, X4), (a3, b16, X5), (a3, b16, X6), (a3, b16, X7), (a3, b16, X8), (a3, b16, X9), (a3, b16, X10), (a3, b16, X11), (a3, b16, X12), (a3, b16, X13), (a3, b16, X14), (a3, b16, X15), (a3, b16, X16), (a3, b16, X17), (a3, b16, X18), (a3, b17, X1), (a3, b17, X2), (a3, b17, X3), (a3, b17, X4), (a3, b17, X5), (a3, b17, X6), (a3, b17, X7), (a3, b17, X8), (a3, b17, X9), (a3, b17, X10), (a3, b17, X11), (a3, b17, X12), (a3, b17, X13), (a3, b17, X14), (a3, b17, X15), (a3, b17, X16), (a3, b17, X17), (a3, b17, X18), (a3, b18, X1), (a3, b18, X2), (a3, b18, X3), (a3, b18, X4), (a3, b18, X5), (a3, b18, X6), (a3, b18, X7), (a3, b18, X8), (a3, b18, X9), (a3, b18, X10), (a3, b18, X11), (a3, b18, X12), (a3, b18, X13), (a3, b18, X14), (a3, b18, X15), (a3, b18, X16), (a3, b18, X17), (a3, b18, X18), (a3, b19, X1), (a3, b19, X2), (a3, b19, X3), (a3, b19, X4), (a3, b19, X5), (a3, b19, X6), (a3, b19, X7), (a3, b19, X8), (a3, b19, X9), (a3, b19, X10), (a3, b19, X11), (a3, b19, X12), (a3, b19, X13), (a3, b19, X14), (a3, b19, X15), (a3, b19, X16), (a3, b19, X17), (a3, b19, X18), (a3, b20, X1), (a3, b20, X2), (a3, b20, X3), (a3, b20, X4), (a3, b20, X5), (a3, b20, X6), (a3, b20, X7), (a3, b20, X8), (a3, b20, X9), (a3, b20, X10), (a3, b20, X11), (a3, b20, X12), (a3, b20, X13), (a3, b20, X14), (a3, b20, X15), (a3, b20, X16), (a3, b20, X17), (a3, b20, X18), (a3, b21, X1), (a3, b21, X2), (a3, b21, X3), (a3, b21, X4), (a3, b21, X5), (a3, b21, X6), (a3, b21, X7), (a3, b21, X8), (a3, b21, X9), (a3, b21, X10), (a3, b21, X11), (a3, b21, X12), (a3, b21, X13), (a3, b21, X14), (a3, b21, X15), (a3, b21, X16), (a3, b21, X17), (a3, b21, X18), (a3, b22, X1), (a3, b22, X2), (a3, b22, X3), (a3, b22, X4), (a3, b22, X5), (a3, b22, X6), (a3, b22, X7), (a3, b22, X8), (a3, b22, X9), (a3, b22, X10), (a3, b22, X11), (a3, b22, X12), (a3, b22, X13), (a3, b22, X14), (a3, b22, X15), (a3, b22, X16), (a3, b22, X17), (a3, b22, X18), (a3, b23, X1), (a3, b23, X2), (a3, b23, X3), (a3, b23, X4), (a3, b23, X5), (a3, b23, X6), (a3, b23, X7), (a3, b23, X8), (a3, b23, X9), (a3, b23, X10), (a3, b23, X11), (a3, b23, X12), (a3, b23, X13), (a3, b23, X14), (a3, b23, X15), (a3, b23, X16), (a3, b23, X17), (a3, b23, X18), (a3, b24, X1), (a3, b24, X2), (a3, b24, X3), (a3, b24, X4), (a3, b24, X5), (a3, b24, X6), (a3, b24, X7), (a3, b24, X8), (a3, b24, X9), (a3, b24, X10), (a3, b24, X11), (a3, b24, X12), (a3, b24, X13), (a3, b24, X14), (a3, b24, X15), (a3, b24, X16), (a3, b24, X17), (a3, b24, X18), (a3, b25, X1), (a3, b25, X2), (a3, b25, X3), (a3, b25, X4), (a3, b25, X5), (a3, b25, X6), (a3, b25, X7), (a3, b25, X8), (a3, b25, X9), (a3, b25, X10), (a3, b25, X11), (a3, b25, X12), (a3, b25, X13), (a3, b25, X14), (a3, b25, X15), (a3, b25, X16), (a3, b25, X17), (a3, b25, X18), (a3, b26, X1), (a3, b26, X2), (a3, b26, X3), (a3, b26, X4), (a3, b26, X5), (a3, b26, X6), (a3, b26, X7), (a3, b26, X8), (a3, b26, X9), (a3, b26, X10), (a3, b26, X11), (a3, b26, X12), (a3, b26, X13), (a3, b26, X14), (a3, b26, X15), (a3, b26, X16), (a3, b26, X17), (a3, b26, X18), (a3, b27, X1), (a3, b27, X2), (a3, b27, X3), (a3, b27, X4), (a3, b27, X5), (a3, b27, X6), (a3, b27, X7), (a3, b27, X8), (a3, b27, X9), (a3, b27, X10), (a3, b27, X11), (a3, b27, X12), (a3, b27, X13), (a3, b27, X14), (a3, b27, X15), (a3, b27, X16), (a3, b27, X17), (a3, b27, X18), (a4, b1, X1), (a4, b1, X2), (a4, b1, X3), (a4, b1, X4), (a4, b1, X5), (a4, b1, X6), (a4, b1, X7), (a4, b1, X8), (a4, b1, X9), (a4, b1, X10), (a4, b1, X11), (a4, b1, X12), (a4, b1, X13), (a4, b1, X14), (a4, b1, X15), (a4, b1, X16), (a4, b1, X17), (a4, b1, X18), (a4, b2, X1), (a4, b2, X2), (a4, b2, X3), (a4, b2, X4), (a4, b2, X5), (a4, b2, X6), (a4, b2, X7), (a4, b2, X8), (a4, b2, X9), (a4, b2, X10), (a4, b2, X11), (a4, b2, X12), (a4, b2, X13), (a4, b2, X14), (a4, b2, X15), (a4, b2, X16), (a4, b2, X17), (a4, b2, X18), (a4, b3, X1), (a4, b3, X2), (a4, b3, X3), (a4, b3, X4), (a4, b3, X5), (a4, b3, X6), (a4, b3, X7), (a4, b3, X8), (a4, b3, X9), (a4, b3, X10), (a4, b3, X11), (a4, b3, X12), (a4, b3, X13), (a4, b3, X14), (a4, b3, X15), (a4, b3, X16), (a4, b3, X17), (a4, b3, X18), (a4, b4, X1), (a4, b4, X2), (a4, b4, X3), (a4, b4, X4), (a4, b4, X5), (a4, b4, X6), (a4, b4, X7), (a4, b4, X8), (a4, b4, X9), (a4, b4, X10), (a4, b4, X11), (a4, b4, X12), (a4, b4, X13), (a4, b4, X14), (a4, b4, X15), (a4, b4, X16), (a4, b4, X17), (a4, b4, X18), (a4, b5, X1), (a4, b5, X2), (a4, b5, X3), (a4, b5, X4), (a4, b5, X5), (a4, b5, X6), (a4, b5, X7), (a4, b5, X8), (a4, b5, X9), (a4, b5, X10), (a4, b5, X11), (a4, b5, X12), (a4, b5, X13), (a4, b5, X14), (a4, b5, X15), (a4, b5, X16), (a4, b5, X17), (a4, b5, X18), (a4, b6, X1), (a4, b6, X2), (a4, b6, X3), (a4, b6, X4), (a4, b6, X5), (a4, b6, X6), (a4, b6, X7), (a4, b6, X8), (a4, b6, X9), (a4, b6, X10), (a4, b6, X11), (a4, b6, X12), (a4, b6, X13), (a4, b6, X14), (a4, b6, X15), (a4, b6, X16), (a4, b6, X17), (a4, b6, X18), (a4, b7, X1), (a4, b7, X2), (a4, b7, X3), (a4, b7, X4), (a4, b7, X5), (a4, b7, X6), (a4, b7, X7), (a4, b7, X8), (a4, b7, X9), (a4, b7, X10), (a4, b7, X11), (a4, b7, X12), (a4, b7, X13), (a4, b7, X14), (a4, b7, X15), (a4, b7, X16), (a4, b7, X17), (a4, b7, X18), (a4, b8, X1), (a4, b8, X2), (a4, b8, X3), (a4, b8, X4), (a4, b8, X5), (a4, b8, X6), (a4, b8, X7), (a4, b8, X8), (a4, b8, X9), (a4, b8, X10), (a4, b8, X11), (a4, b8, X12), (a4, b8, X13), (a4, b8, X14), (a4, b8, X15), (a4, b8, X16), (a4, b8, X17), (a4, b8, X18), (a4, b9, X1), (a4, b9, X2), (a4, b9, X3), (a4, b9, X4), (a4, b9, X5), (a4, b9, X6), (a4, b9, X7), (a4, b9, X8), (a4, b9, X9), (a4, b9, X10), (a4, b9, X11), (a4, b9, X12), (a4, b9, X13), (a4, b9, X14), (a4, b9, X15), (a4, b9, X16), (a4, b9, X17), (a4, b9, X18), (a4, b10, X1), (a4, b10, X2), (a4, b10, X3), (a4, b10, X4), (a4, b10, X5), (a4, b10, X6), (a4, b10, X7), (a4, b10, X8), (a4, b10, X9), (a4, b10, X10), (a4, b10, X11), (a4, b10, X12), (a4, b10, X13), (a4, b10, X14), (a4, b10, X15), (a4, b10,

X16), (a4, b10, X17), (a4, b10, X18), (a4, b11, X1), (a4, b11, X2), (a4, b11, X3), (a4, b11, X4), (a4, b11, X5), (a4, b11, X6), (a4, b11, X7), (a4, b11, X8), (a4, b11, X9), (a4, b11, X10), (a4, b11, X11), (a4, b11, X12), (a4, b11, X13), (a4, b11, X14), (a4, b11, X15), (a4, b11, X16), (a4, b11, X17), (a4, b11, X18), (a4, b12, X1), (a4, b12, X2), (a4, b12, X3), (a4, b12, X4), (a4, b12, X5), (a4, b12, X6), (a4, b12, X7), (a4, b12, X8), (a4, b12, X9), (a4, b12, X10), (a4, b12, X11), (a4, b12, X12), (a4, b12, X13), (a4, b12, X14), (a4, b12, X15), (a4, b12, X16), (a4, b12, X17), (a4, b12, X18), (a4, b13, X1), (a4, b13, X2), (a4, b13, X3), (a4, b13, X4), (a4, b13, X5), (a4, b13, X6), (a4, b13, X7), (a4, b13, X8), (a4, b13, X9), (a4, b13, X10), (a4, b13, X11), (a4, b13, X12), (a4, b13, X13), (a4, b13, X14), (a4, b13, X15), (a4, b13, X16), (a4, b13, X17), (a4, b13, X18), (a4, b14, X1), (a4, b14, X2), (a4, b14, X3), (a4, b14, X4), (a4, b14, X5), (a4, b14, X6), (a4, b14, X7), (a4, b14, X8), (a4, b14, X9), (a4, b14, X10), (a4, b14, X11), (a4, b14, X12), (a4, b14, X13), (a4, b14, X14), (a4, b14, X15), (a4, b14, X16), (a4, b14, X17), (a4, b14, X18), (a4, b15, X1), (a4, b15, X2), (a4, b15, X3), (a4, b15, X4), (a4, b15, X5), (a4, b15, X6), (a4, b15, X7), (a4, b15, X8), (a4, b15, X9), (a4, b15, X10), (a4, b15, X11), (a4, b15, X12), (a4, b15, X13), (a4, b15, X14), (a4, b15, X15), (a4, b15, X16), (a4, b15, X17), (a4, b15, X18), (a4, b16, X1), (a4, b16, X2), (a4, b16, X3), (a4, b16, X4), (a4, b16, X5), (a4, b16, X6), (a4, b16, X7), (a4, b16, X8), (a4, b16, X9), (a4, b16, X10), (a4, b16, X11), (a4, b16, X12), (a4, b16, X13), (a4, b16, X14), (a4, b16, X15), (a4, b16, X6), (a4, b16, X7), (a4, b16, X8), (a4, b17, X1), (a4, b17, X2), (a4, b17, X3), (a4, b17, X4), (a4, b17, X5), (a4, b17, X6), (a4, b17, X7), (a4, b17, X8), (a4, b17, X9), (a4, b17, X10), (a4, b17, X11), (a4, b17, X12), (a4, b17, X13), (a4, b17, X14), (a4, b17, X15), (a4, b17, X16), (a4, b17, X17), (a4, b17, X18), (a4, b18, X1), (a4, b18, X2), (a4, b18, X3), (a4, b18, X4), (a4, b18, X5), (a4, b18, X6), (a4, b18, X7), (a4, b18, X8), (a4, b18, X9), (a4, b18, X10), (a4, b18, X11), (a4, b18, X12), (a4, b18, X13), (a4, b18, X14), (a4, b18, X15), (a4, b18, X16), (a4, b18, X17), (a4, b18, X18), (a4, b19, X1), (a4, b19, X2), (a4, b19, X3), (a4, b19, X4), (a4, b19, X5), (a4, b19, X6), (a4, b19, X7), (a4, b19, X8), (a4, b19, X9), (a4, b19, X10), (a4, b19, X11), (a4, b19, X12), (a4, b19, X13), (a4, b19, X14), (a4, b19, X15), (a4, b19, X16), (a4, b19, X17), (a4, b19, X18), (a4, b20, X1), (a4, b20, X2), (a4, b20, X3), (a4, b20, X4), (a4, b20, X5), (a4, b20, X6), (a4, b20, X7), (a4, b20, X8), (a4, b20, X9), (a4, b20, X10), (a4, b20, X11), (a4, b20, X12), (a4, b20, X13), (a4, b20, X14), (a4, b20, X15), (a4, b20, X16), (a4, b20, X17), (a4, b20, X18), (a4, b21, X1), (a4, b21, X2), (a4, b21, X3), (a4, b21, X4), (a4, b21, X5), (a4, b21, X6), (a4, b21, X7), (a4, b21, X8), (a4, b21, X9), (a4, b21, X10), (a4, b21, X11), (a4, b21, X12), (a4, b21, X13), (a4, b21, X14), (a4, b21, X15), (a4, b21, X16), (a4, b21, X17), (a4, b21, X18), (a4, b22, X1), (a4, b22, X2), (a4, b22, X3), (a4, b22, X4), (a4, b22, X5), (a4, b22, X6), (a4, b22, X7), (a4, b22, X8), (a4, b22, X9), (a4, b22, X10), (a4, b22, X11), (a4, b22, X12), (a4, b22, X13), (a4, b22, X14), (a4, b22, X15), (a4, b22, X16), (a4, b22, X17), (a4, b22, X18), (a4, b23, X1), (a4, b23, X2), (a4, b23, X3), (a4, b23, X4), (a4, b23, X5), (a4, b23, X6), (a4, b23, X7), (a4, b23, X8), (a4, b23, X9), (a4, b23, X10), (a4, b23, X11), (a4, b23, X12), (a4, b23, X13), (a4, b23, X14), (a4, b23, X15), (a4, b23, X16), (a4, b23, X17), (a4, b23, X18), (a4, b24, X1), (a4, b24, X2), (a4, b24, X3), (a4, b24, X4), (a4, b24, X5), (a4, b24, X6), (a4, b24, X7), (a4, b24, X8), (a4, b24, X9), (a4, b24, X10), (a4, b24, X11), (a4, b24, X12), (a4, b24, X13), (a4, b24, X14), (a4, b24, X15), (a4, b24, X16), (a4, b24, X17), (a4, b24, X18), (a4, b25, X1), (a4, b25, X2), (a4, b25, X3), (a4, b25, X4), (a4, b25, X5), (a4, b25, X6), (a4, b25, X7), (a4, b25, X8), (a4, b25, X9), (a4, b25, X10), (a4, b25, X11), (a4, b25, X12), (a4, b25, X13), (a4, b25, X14), (a4, b25, X15), (a4, b25, X16), (a4, b25, X17), (a4, b25, X18), (a4, b26, X1), (a4, b26, X2), (a4, b26, X3), (a4, b26, X4), (a4, b26, X5), (a4, b26, X6), (a4, b26, X7), (a4, b26, X8), (a4, b26, X9), (a4, b26, X10), (a4, b26, X11), (a4, b26, X12), (a4, b26, X13), (a4, b26, X14), (a4, b26, X15), (a4, b26, X16), (a4, b26, X17), (a4, b26, X18), (a4, b27, X1), (a4, b27, X2), (a4, b27, X3), (a4, b27, X4), (a4, b27, X5), (a4, b27, X6), (a4, b27, X7), (a4, b27, X8), (a4, b27, X9), (a4, b27, X10), (a4, b27, X11), (a4, b27, X12), (a4, b27, X13), (a4, b27, X14), (a4, b27, X15), (a4, b27, X16), (a4, b27, X17), (a4, b27, X18), (a5, b1, X1), (a5, b1, X2), (a5, b1, X3), (a5, b1, X4), (a5, b1, X5), (a5, b1, X6), (a5, b1, X7), (a5, b1, X8), (a5, b1, X9), (a5, b1, X10), (a5, b1, X11), (a5, b1, X12), (a5, b1, X13), (a5, b1, X14), (a5, b1, X15), (a5, b1, X16), (a5, b1, X17), (a5, b1, X18), (a5, b2, X1), (a5, b2, X2), (a5, b2, X3), (a5, b2, X4), (a5, b2, X5), (a5, b2, X6), (a5, b2, X7), (a5, b2, X8), (a5, b2, X9), (a5, b2, X10), (a5, b2, X11), (a5, b2, X12), (a5, b2, X13), (a5, b2, X14), (a5, b2, X15), (a5, b2, X16), (a5, b2, X17), (a5, b2, X18), (a5, b3, X1), (a5, b3, X2), (a5, b3, X3), (a5, b3, X4), (a5, b3, X5), (a5, b3, X6), (a5, b3, X7), (a5, b3, X8), (a5, b3, X9), (a5, b3, X10), (a5, b3, X11), (a5, b3, X12), (a5, b3, X13), (a5, b3, X14), (a5, b3, X15), (a5, b3, X16), (a5, b3, X17), (a5, b3, X18), (a5, b4, X1), (a5, b4, X2), (a5, b4, X3), (a5, b4, X4), (a5, b4, X5), (a5, b4, X6), (a5, b4, X7), (a5, b4, X8), (a5, b4, X9), (a5, b4, X10), (a5, b4, X11), (a5, b4, X12), (a5, b4, X13), (a5, b4, X14), (a5, b4, X15), (a5, b4, X16), (a5, b4, X17), (a5, b4, X18), (a5, b5, X1), (a5, b5, X2), (a5, b5, X3), (a5, b5, X4), (a5, b5, X5), (a5, b5, X6), (a5, b5, X7), (a5, b5, X8), (a5, b5, X9), (a5, b5, X10), (a5, b5, X11), (a5, b5, X12), (a5, b5, X13), (a5, b5, X14), (a5, b5, X15), (a5, b5, X16), (a5, b5, X17), (a5, b5, X18), (a5, b6, X1), (a5, b6, X2), (a5, b6, X3), (a5, b6, X4), (a5, b6, X5), (a5, b6, X6), (a5, b6, X7), (a5, b6, X8), (a5, b6, X9), (a5, b6, X10), (a5, b6, X11), (a5, b6, X12), (a5, b6, X13), (a5, b6, X14), (a5, b6, X15), (a5, b6, X16), (a5, b6, X17), (a5, b6, X18), (a5, b7, X1), (a5, b7, X2), (a5, b7, X3), (a5, b7, X4), (a5, b7, X5), (a5, b7, X6), (a5, b7, X7), (a5, b7, X8), (a5, b7, X9), (a5, b7, X10), (a5, b7, X11), (a5, b7, X12), (a5, b7, X13), (a5, b7, X14), (a5, b7, X15), (a5, b7, X16), (a5, b7, X17), (a5, b7, X18), (a5, b8, X1), (a5, b8, X2), (a5, b8, X3), (a5, b8, X4), (a5, b8, X5), (a5, b8, X6), (a5, b8, X7), (a5, b8, X8), (a5, b8, X9), (a5, b8, X10), (a5, b8, X11), (a5, b8, X12), (a5, b8, X13), (a5, b8, X14), (a5, b8, X15), (a5, b8, X16), (a5, b8, X17), (a5, b8, X18), (a5, b9, X1), (a5, b9, X2), (a5, b9, X3), (a5, b9, X4), (a5, b9, X5), (a5, b9, X6), (a5, b9, X7), (a5, b9, X8), (a5, b9, X9), (a5, b9, X10), (a5, b9, X11), (a5, b9, X12), (a5, b9, X13), (a5, b9, X14), (a5, b9, X15), (a5, b9, X16), (a5, b9, X17), (a5, b9, X18), (a5, b10, X1), (a5, b10, X2), (a5, b10, X3), (a5, b10, X4), (a5, b10, X5), (a5, b10, X6), (a5, b10, X7), (a5, b10, X8), (a5, b10, X9), (a5, b10, X10), (a5, b10, X11), (a5, b10, X12), (a5, b10, X13), (a5, b10, X14), (a5, b10, X15), (a5, b10, X16), (a5, b10, X17), (a5, b10, X18), (a5, b11, X1), (a5, b11, X2), (a5, b11, X3), (a5, b11, X4), (a5, b11, X5), (a5, b11, X6), (a5, b11, X7), (a5, b11, X8), (a5, b11, X9), (a5, b11, X10), (a5, b11, X11), (a5, b11, X12), (a5, b11, X13), (a5, b11, X14), (a5, b11, X15), (a5, b11, X16), (a5, b11, X17), (a5, b11, X18), (a5, b12, X1), (a5, b12, X2), (a5, b12, X3), (a5, b12, X4), (a5, b12, X5), (a5, b12, X6), (a5, b12, X7), (a5, b12, X8), (a5, b12, X9), (a5, b12, X10), (a5, b12, X11), (a5, b12, X12), (a5, b12, X13), (a5, b12, X14), (a5, b12, X15), (a5, b12, X16), (a5, b12, X17), (a5, b12, X18), (a5, b13, X1), (a5, b13, X2), (a5, b13, X3), (a5, b13, X4), (a5, b13, X5), (a5, b13, X6), (a5, b13, X7), (a5, b13, X8), (a5, b13, X9), (a5, b13, X10), (a5, b13, X11), (a5, b13, X12), (a5, b13, X13), (a5, b13, X14), (a5, b13, X15), (a5, b13, X16), (a5, b13, X17), (a5, b13, X18), (a5, b14, X1), (a5, b14, X2), (a5, b14, X3), (a5, b14, X4), (a5, b14, X5), (a5, b14, X6), (a5, b14, X7), (a5, b14, X8), (a5, b14, X9), (a5, b14, X10), (a5, b14, X11), (a5, b14, X12), (a5, b14, X13), (a5, b14, X14), (a5, b14, X15), (a5, b14, X16), (a5, b14, X17), (a5, b14, X18), (a5, b15, X1), (a5, b15, X2), (a5, b15, X3), (a5, b15, X4), (a5, b15, X5), (a5, b15, X6), (a5, b15, X7), (a5, b15, X8), (a5, b15, X9), (a5, b15, X10), (a5, b15, X11), (a5, b15, X12), (a5, b15, X13), (a5, b15, X14), (a5, b15, X15), (a5, b15, X16), (a5, b15, X17), (a5, b15, X18), (a5, b16, X1), (a5, b16, X2), (a5, b16, X3), (a5, b16, X4), (a5, b16, X5), (a5, b16, X6), (a5, b16, X7), (a5, b16, X8), (a5, b16, X9), (a5, b16, X10), (a5, b16, X11), (a5, b16, X12), (a5, b16, X13), (a5, b16, X14), (a5, b16, X15), (a5, b16, X16), (a5, b16, X17), (a5, b16, X18), (a5, b17, X1), (a5, b17, X2), (a5, b17, X3), (a5, b17, X4), (a5, b17, X5), (a5, b17, X6), (a5, b17, X7), (a5, b17, X8), (a5, b17, X9), (a5, b17, X10), (a5, b17, X11), (a5, b17, X12), (a5, b17, X13), (a5, b17, X14), (a5, b17, X15), (a5, b17, X16), (a5, b17, X17), (a5, b17, X18), (a5, b18, X1), (a5, b18, X2), (a5, b18, X3), (a5, b18, X4), (a5, b18, X5), (a5, b18, X6), (a5, b18, X7), (a5, b18, X8), (a5, b18, X9), (a5, b18, X10), (a5, b18, X11), (a5, b18, X12), (a5, b18, X13), (a5, b18, X14), (a5, b18, X15), (a5, b18, X16), (a5, b18, X17), (a5, b18, X18), (a5, b19, X1), (a5, b19, X2), (a5, b19, X3), (a5, b19, X4), (a5, b19, X5), (a5, b19, X6), (a5, b19, X7), (a5, b19, X8), (a5, b19, X9), (a5, b19, X10), (a5, b19, X11), (a5, b19, X12), (a5, b19, X13), (a5, b19, X14), (a5, b19, X15), (a5, b19, X16), (a5, b19, X17), (a5, b19, X18), (a5, b20, X1), (a5, b20, X2), (a5, b20, X3), (a5, b20, X4), (a5, b20, X5), (a5, b20, X6), (a5, b20, X7), (a5, b20, X8), (a5, b20, X9), (a5, b20, X10), (a5, b20, X11), (a5, b20, X12), (a5, b20, X13), (a5, b20, X14), (a5, b20, X15), (a5, b20, X16), (a5, b20, X17), (a5, b20, X18), (a5, b21, X1), (a5, b21, X2), (a5, b21, X3), (a5, b21, X4), (a5, b21, X5), (a5, b21, X6), (a5, b21, X7), (a5, b21, X8), (a5, b21, X9), (a5, b21, X10), (a5, b21, X11), (a5, b21, X12), (a5, b21, X13), (a5, b21, X14), (a5, b21, X15), (a5, b21, X16), (a5, b21, X17), (a5, b21, X18), (a5, b22, X1), (a5, b22, X2), (a5, b22, X3), (a5, b22, X4), (a5, b22, X5), (a5, b22, X6), (a5, b22, X7), (a5, b22, X8), (a5, b22, X9), (a5, b22, X10), (a5, b22, X11), (a5, b22, X12), (a5, b22, X13), (a5, b22, X14), (a5, b22, X15), (a5, b22, X16), (a5, b22, X17), (a5, b22, X18), (a5, b23, X1), (a5, b23, X2), (a5, b23, X3), (a5, b23, X4), (a5, b23, X5), (a5, b23, X6), (a5, b23, X7), (a5, b23, X8), (a5, b23, X9), (a5, b23, X10), (a5, b23, X11), (a5, b23, X12), (a5, b23, X13), (a5, b23, X14), (a5, b23, X15), (a5, b23, X16), (a5, b23, X17), (a5, b23, X18), (a5, b24, X1), (a5, b24, X2), (a5, b24, X3), (a5, b24, X4), (a5, b24, X5), (a5, b24, X6), (a5, b24, X7), (a5, b24, X8), (a5, b24, X9), (a5, b24, X10), (a5, b24, X11), (a5, b24, X12), (a5, b24, X13), (a5, b24, X14), (a5, b24, X15), (a5, b24, X16), (a5, b24, X17), (a5, b24, X18), (a5, b25, X1), (a5, b25, X2), (a5, b25, X3), (a5, b25, X4), (a5, b25, X5), (a5, b25, X6), (a5, b25, X7), (a5, b25, X8), (a5, b25, X9), (a5, b25, X10), (a5, b25, X11), (a5, b25, X12), (a5, b25, X13), (a5, b25, X14), (a5, b25, X15), (a5, b25, X16), (a5, b25, X17), (a5, b25, X18), (a5, b26, X1), (a5, b26, X2), (a5, b26, X3), (a5, b26, X4), (a5, b26, X5), (a5, b26, X6), (a5, b26, X7), (a5, b26, X8), (a5, b26, X9), (a5, b26, X10), (a5, b26, X11), (a5, b26, X12), (a5, b26, X13), (a5, b26, X14), (a5, b26, X15), (a5, b26, X16), (a5, b26, X17), (a5, b26, X18), (a5, b27, X1), (a5, b27, X2), (a5, b27, X3), (a5, b27, X4), (a5, b27, X5), (a5, b27, X6), (a5, b27, X7), (a5, b27, X8), (a5, b27, X9), (a5, b27, X10), (a5, b27, X11), (a5, b27, X12), (a5, b27, X13), (a5, b27, X14), (a5, b27, X15), (a5, b27, X16), (a5, b27, X17), (a5, b27, X18), (a6, b1, X1), (a6, b1, X2), (a6, b1, X3), (a6, b1, X4), (a6, b1, X5), (a6, b1, X6), (a6, b1, X7), (a6, b1, X8), (a6, b1, X9), (a6, b1, X10), (a6, b1, X11), (a6, b1, X12), (a6, b1, X13), (a6, b1, X14), (a6, b1, X15), (a6, b1, X16), (a6, b1, X17), (a6, b1, X18), (a6, b2, X1), (a6, b2, X2), (a6, b2, X3), (a6, b2, X4), (a6, b2, X5), (a6, b2, X6), (a6, b2, X7), (a6, b2, X8), (a6, b2, X9), (a6, b2, X10), (a6, b2, X11), (a6, b2, X12), (a6, b2, X13), (a6, b2, X14), (a6, b2, X15), (a6, b2, X16), (a6, b2, X17), (a6, b2, X18), (a6, b3, X1), (a6, b3, X2), (a6, b3, X3), (a6, b3, X4), (a6, b3, X5), (a6, b3, X6), (a6, b3, X7), (a6, b3, X8), (a6, b3, X9), (a6, b3, X10), (a6, b3, X11), (a6, b3, X12), (a6, b3, X13), (a6, b3, X14), (a6, b3, X15), (a6, b3, X16), (a6, b3, X17), (a6, b3, X18), (a6, b4, X1), (a6, b4, X2), (a6, b4, X3), (a6, b4, X4), (a6, b4, X5), (a6, b4, X6), (a6, b4, X7), (a6, b4, X8), (a6, b4, X9), (a6, b4, X10), (a6, b4, X11), (a6, b4, X12), (a6, b4, X13), (a6, b4, X14), (a6, b4, X15), (a6, b4, X16), (a6, b4, X17), (a6, b4, X18), (a6, b5, X1), (a6, b5, X2), (a6, b5, X3), (a6, b5, X4), (a6, b5, X5), (a6, b5, X6), (a6, b5, X7), (a6, b5, X8), (a6, b5, X9), (a6, b5, X10), (a6, b5, X11), (a6, b5, X12), (a6, b5, X13), (a6, b5, X14), (a6, b5, X15), (a6, b5, X16), (a6, b5, X17), (a6, b5, X18), (a6, b6, X1), (a6, b6, X2), (a6, b6, X3), (a6, b6, X4), (a6, b6, X5), (a6, b6, X6), (a6, b6, X7), (a6, b6, X8), (a6, b6, X9), (a6, b6, X10), (a6, b6, X11), (a6, b6, X12), (a6, b6, X13), (a6, b6, X14), (a6, b6, X15), (a6, b6, X16), (a6, b6, X17), (a6, b6, X18), (a6, b7, X1), (a6, b7, X2), (a6, b7, X3), (a6, b7, X4), (a6, b7, X5), (a6, b7, X6), (a6, b7, X7), (a6, b7, X8), (a6, b7, X9), (a6, b7, X10), (a6, b7, X11), (a6, b7, X12), (a6, b7, X13), (a6, b7, X14), (a6, b7, X15), (a6, b7, X16), (a6, b7, X17), (a6, b7, X18), (a6, b8, X1), (a6, b8, X2), (a6, b8, X3), (a6, b8, X4), (a6, b8, X5), (a6, b8, X6), (a6, b8, X7), (a6, b8, X8), (a6, b8, X9), (a6, b8, X10), (a6, b8, X11), (a6, b8, X12), (a6, b8, X13), (a6, b8, X14), (a6, b8, X15), (a6, b8, X16), (a6, b8, X17), (a6, b8, X18), (a6, b9, X1), (a6, b9, X2), (a6, b9, X3), (a6, b9, X4), (a6, b9, X5), (a6, b9, X6), (a6, b9, X7), (a6, b9, X8), (a6, b9, X9), (a6, b9, X10), (a6, b9, X11), (a6, b9, X12), (a6, b9, X13), (a6, b9, X14), (a6, b9, X15), (a6, b9, X16), (a6, b9, X17), (a6, b9, X18), (a6, b10, X1), (a6, b10, X2), (a6, b10, X3), (a6, b10, X4), (a6, b10, X5), (a6, b10, X6), (a6, b10, X7), (a6, b10, X8), (a6, b10, X9), (a6, b10, X10), (a6, b10, X11), (a6, b10, X12), (a6, b10, X13), (a6, b10, X14), (a6, b10, X15), (a6, b10, X16), (a6, b10, X17), (a6, b10, X18), (a6, b11, X1), (a6, b11, X2), (a6, b11, X3), (a6, b11, X4), (a6, b11, X5), (a6, b11, X6), (a6, b11, X7), (a6, b11, X8), (a6, b11, X9), (a6, b11, X10), (a6, b11, X11), (a6, b11, X12), (a6, b11, X13), (a6, b11, X14), (a6, b11, X15), (a6, b11, X16), (a6, b11, X17), (a6, b11, X18), (a6, b12, X1), (a6, b12, X2), (a6, b12, X3), (a6, b12, X4), (a6, b12, X5), (a6, b12, X6), (a6, b12, X7), (a6, b12, X8), (a6, b12, X9), (a6, b12, X10), (a6, b12, X11), (a6, b12, X12), (a6, b12, X13), (a6, b12, X14), (a6, b12, X15), (a6, b12, X16), (a6, b12, X17), (a6, b12, X18), (a6, b13, X1), (a6, b13, X2), (a6, b13, X3), (a6, b13, X4), (a6, b13, X5), (a6, b13, X6), (a6, b13, X7), (a6, b13, X8), (a6, b13, X9), (a6, b13, X10), (a6, b13, X11), (a6, b13, X12), (a6, b13, X13), (a6, b13, X14), (a6, b13, X15), (a6, b13, X16), (a6, b13, X17), (a6, b13, X18), (a6, b14, X1), (a6, b14, X2), (a6, b14, X3), (a6, b14, X4), (a6, b14, X5), (a6, b14, X6), (a6, b14, X7), (a6, b14, X8), (a6, b14, X9), (a6, b14, X10), (a6, b14, X11), (a6, b14, X12), (a6, b14, X13), (a6, b14, X14), (a6, b14, X15), (a6, b14, X16), (a6, b14, X17), (a6, b14, X18), (a6, b15, X1), (a6, b15, X2), (a6, b15, X3), (a6, b15, X4), (a6, b15, X5), (a6, b15, X6), (a6, b15, X7), (a6, b15, X8), (a6, b15, X9), (a6, b15, X10), (a6, b15, X11), (a6, b15, X12), (a6, b15, X13), (a6, b15, X14), (a6, b15, X15), (a6, b15, X16), (a6, b15, X17), (a6, b15, X18), (a6, b16, X1), (a6, b16, X2), (a6, b16, X3), (a6, b16, X4), (a6, b16, X5), (a6, b16, X6), (a6, b16, X7), (a6, b16, X8), (a6, b16, X9), (a6, b16, X10), (a6, b16, X11), (a6, b16, X12), (a6, b16, X13), (a6, b16, X14), (a6, b16, X15), (a6, b16, X16), (a6, b16, X17), (a6, b16, X18), (a6, b17, X1), (a6, b17, X2), (a6, b17, X3), (a6, b17, X4), (a6, b17, X5), (a6, b17, X6), (a6, b17, X7), (a6, b17, X8), (a6, b17, X9), (a6, b17, X10), (a6, b17, X11), (a6, b17, X12), (a6, b17, X13), (a6, b17, X14), (a6, b17, X15), (a6, b17, X16), (a6, b17, X17), (a6, b17, X18), (a6, b18, X1), (a6, b18, X2), (a6, b18, X3), (a6, b18, X4), (a6, b18, X5), (a6, b18, X6), (a6, b18, X7), (a6, b18, X8), (a6, b18, X9), (a6, b18, X10), (a6, b18, X11), (a6, b18, X12), (a6, b18, X13), (a6, b18, X14), (a6, b18, X15), (a6, b18, X16), (a6, b18, X17), (a6, b18, X18), (a6, b19, X1), (a6, b19, X2), (a6, b19, X3), (a6, b19, X4), (a6, b19, X5), (a6, b19, X6), (a6, b19, X7), (a6, b19, X8), (a6, b19, X9), (a6, b19, X10), (a6, b19, X11), (a6, b19, X12), (a6, b19, X13), (a6, b19, X14), (a6, b19, X15), (a6, b19, X16), (a6, b19, X17), (a6, b19, X18), (a6, b20, X1), (a6, b20, X2), (a6, b20, X3), (a6, b20, X4), (a6, b20, X5), (a6, b20, X6), (a6, b20, X7), (a6, b20, X8), (a6, b20, X9), (a6, b20, X10), (a6, b20, X11), (a6, b20, X12), (a6, b20, X13), (a6, b20, X14), (a6, b20, X15), (a6, b20, X16), (a6, b20, X17), (a6, b20, X18), (a6, b21, X1), (a6, b21, X2), (a6, b21, X3), (a6, b21, X4), (a6, b21, X5), (a6, b21, X6), (a6, b21, X7), (a6, b21, X8), (a6, b21, X9), (a6, b21, X10), (a6, b21, X11), (a6, b21, X12), (a6, b21, X13), (a6, b21, X14), (a6, b21, X15), (a6, b21, X16), (a6, b21, X17), (a6, b21, X18), (a6, b22, X1), (a6, b22, X2), (a6, b22, X3), (a6, b22, X4), (a6, b22, X5), (a6, b22, X6), (a6, b22, X7), (a6, b22, X8), (a6, b22, X9), (a6, b22, X10), (a6, b22, X11), (a6, b22, X12), (a6, b22, X13), (a6, b22, X14), (a6, b22, X15), (a6, b22, X16), (a6, b22, X17), (a6, b22, X18), (a6, b23, X1), (a6, b23, X2), (a6, b23, X3), (a6, b23, X4), (a6, b23, X5), (a6, b23, X6), (a6, b23, X7), (a6, b23, X8), (a6, b23, X9), (a6, b23, X10), (a6, b23, X11), (a6, b23, X12), (a6, b23, X13), (a6, b23, X14), (a6, b23, X15), (a6, b23, X16), (a6, b23, X17), (a6, b23, X18), (a6, b24, X1), (a6, b24, X2), (a6, b24, X3), (a6, b24, X4), (a6, b24, X5), (a6, b24, X6), (a6, b24, X7), (a6, b24, X8), (a6, b24, X9), (a6, b24, X10), (a6, b24, X11), (a6, b24, X12), (a6, b24, X13), (a6, b24, X14), (a6, b24, X15), (a6, b24, X16), (a6, b24, X17), (a6, b24, X18), (a6, b25, X1), (a6, b25, X2), (a6, b25, X3), (a6, b25, X4), (a6, b25, X5), (a6, b25, X6), (a6, b25, X7), (a6, b25, X8), (a6, b25, X9), (a6, b25, X10), (a6, b25, X11), (a6, b25, X12), (a6, b25, X13), (a6, b25, X14), (a6, b25, X15), (a6, b25, X16), (a6, b25, X17), (a6, b25, X18), (a6, b26, X), (a6, b26, X2), (a6, b26, X3), (a6, b26, X4), (a6, b26, X5), (a6, b26, X6), (a6, b26, X7), (a6, b26, X8), (a6, b26, X9), (a6, b26, X10), (a6, b26, X11), (a6, b26, X12), (a6, b26, X13), (a6, b26, X14), (a6, b26, X15), (a6, b26, X16), (a6, b26, X17), (a6, b26, X18), (a6, b27, X1), (a6, b27, X2), (a6, b27, X3), (a6, b27, X4), (a6, b27, X5), (a6, b27, X6), (a6, b27, X7), (a6, b27, X8), (a6, b27, X9), (a6, b27, X10), (a6, b27, X11), (a6, b27, X12), (a6, b27, X13), (a6, b27, X14), (a6, b27, X15), (a6, b27, X16), (a6, b27, X17), (a6, b27, X18), (a7, b1, X1), (a7, b1, X2), (a7, b1, X3), (a7, b1, X4), (a7, b1, X5), (a7, b1, X6), (a7, b1, X7), (a7, b1, X8), (a7, b1, X9), (a7, b1, X10), (a7, b1, X11), (a7, b1, X12), (a7, b1, X13), (a7, b1, X14), (a7, b1, X15), (a7, b1, X16), (a7, b1, X17), (a7, b1, X18), (a7, b2, X1), (a7, b2, X2), (a7, b2, X3), (a7, b2, X4), (a7, b2, X5), (a7, b2, X6), (a7, b2, X7), (a7, b2, X8), (a7, b2, X9), (a7, b2, X10), (a7, b2, X11), (a7, b2, X12), (a7, b2, X13), (a7, b2, X14), (a7, b2, X15), (a7, b2, X16), (a7, b2, X17), (a7, b2, X18), (a7, b3, X1), (a7, b3, X2), (a7, b3, X3), (a7, b3, X4), (a7, b3, X5), (a7, b3, X6), (a7, b3, X7), (a7, b3, X8), (a7, b3, X9), (a7, b3, X10), (a7, b3, X11), (a7, b3, X12), (a7, b3, X13), (a7, b3, X14), (a7, b3, X15), (a7, b3, X16), (a7, b3, X17), (a7, b3, X18), (a7, b4, X1), (a7, b4, X2), (a7, b4, X3), (a7, b4, X4), (a7, b4, X5), (a7, b4, X6), (a7, b4, X7), (a7, b4, X8), (a7, b4, X9), (a7, b4, X10), (a7, b4, X11), (a7, b4, X12), (a7, b4, X13), (a7, b4, X14), (a7, b4, X15), (a7, b4, X16), (a7, b4, X17), (a7, b4, X18), (a7, b5, X1), (a7, b5, X2), (a7, b5, X3), (a7, b5, X4), (a7, b5, X5), (a7, b5, X6), (a7, b5, X7), (a7, b5, X8), (a7, b5, X9), (a7, b5, X10), (a7, b5, X11), (a7, b5, X12), (a7, b5, X13), (a7, b5, X14), (a7, b5, X15), (a7, b5, X16), (a7, b5, X17), (a7, b5, X18), (a7, b6, X1), (a7, b6, X2), (a7, b6, X3), (a7, b6, X4), (a7, b6, X5), (a7, b6, X6), (a7, b6, X7), (a7, b6, X8), (a7, b6, X9), (a7, b6, X10), (a7, b6, X11), (a7, b6, X12), (a7, b6, X13), (a7, b6, X14), (a7, b6, X15), (a7, b6, X16), (a7, b6, X17), (a7, b6, X18), (a7, b7, X1), (a7, b7, X2), (a7, b7, X3), (a7, b7, X4), (a7, b7, X5), (a7, b7, X6), (a7, b7, X7), (a7, b7, X8), (a7, b7, X9), (a7, b7, X10), (a7, b7, X11), (a7, b7, X12), (a7, b7, X13), (a7, b7, X14), (a7, b7, X15), (a7, b7, X16), (a7, b7, X17), (a7, b7, X18), (a7, b8, X1), (a7, b8, X2), (a7, b8, X3), (a7, b8, X4), (a7, b8, X5), (a7, b8, X6), (a7, b8, X7), (a7, b8, X8), (a7, b8, X9), (a7, b8, X10), (a7, b8, X11), (a7, b8, X12), (a7, b8, X13), (a7, b8, X14), (a7, b8, X15), (a7, b8, X16), (a7, b8, X17), (a7, b8, X18), (a7, b9, X1), (a7, b9, X2), (a7, b9, X3), (a7, b9, X4), (a7, b9, X5), (a7, b9, X6), (a7, b9, X7), (a7, b9, X8), (a7, b9, X9), (a7, b9, X10), (a7, b9, X11), (a7, b9, X12), (a7, b9, X13), (a7, b9, X14), (a7, b9, X15), (a7, b9, X16), (a7, b9, X17), (a7, b9, X18), (a7, b10, X1), (a7, b10, X2), (a7, b10, X3), (a7, b10, X4), (a7, b10, X5), (a7, b10, X6), (a7, b10, X7), (a7, b10, X8), (a7, b10, X9), (a7, b10, X10), (a7, b10, X11), (a7, b10, X12), (a7, b10, X13), (a7, b10, X14), (a7, b10, X15), (a7, b10, X16), (a7, b10, X17), (a7, b10, X18), (a7, b11, X1), (a7, b11, X2), (a7, b11, X3), (a7, b11, X4), (a7, b11, X5), (a7, b11, X6), (a7, b11, X7), (a7, b11, X8), (a7, b11, X9), (a7, b11, X10), (a7, b11, X11), (a7, b11, X12), (a7, b11, X13), (a7, b11, X14), (a7, b11, X15), (a7, b11, X16), (a7, b11, X17), (a7, b11, X18), (a7, b12, X1), (a7, b12, X2), (a7, b12, X3), (a7, b12, X4), (a7, b12, X5), (a7, b12, X6), (a7, b12, X7), (a7, b12, X8), (a7, b12, X9), (a7, b12, X10), (a7, b12, X11), (a7, b12, X12), (a7, b12, X13), (a7, b12, X14), (a7, b12, X15), (a7, b12, X16), (a7, b12, X17), (a7, b12, X18), (a7, b13, X1), (a7, b13, X2), (a7, b13, X3), (a7, b13, X4), (a7, b13, X5), (a7, b13, X6), (a7, b13, X7), (a7, b13, X8), (a7, b13, X9), (a7, b13, X10), (a7, b13, X11), (a7, b13, X12), (a7, b13, X13), (a7, b13, X14), (a7, b13, X15), (a7, b13, X16), (a7, b13, X17), (a7, b13, X18), (a7, b14, X1), (a7, b14, X2), (a7, b14, X3), (a7, b14, X4), (a7, b14, X5), (a7, b14, X6), (a7, b14, X7), (a7, b14, X8), (a7, b14, X9), (a7, b14, X10), (a7, b14, X11), (a7, b14, X12), (a7, b14, X13), (a7, b14, X14), (a7, b14, X15), (a7, b14, X16), (a7, b14, X17), (a7, b14, X18), (a7, b15, X1), (a7, b15, X2), (a7, b15, X3), (a7, b15, X4), (a7, b15, X5), (a7, b15, X6), (a7, b15, X7), (a7, b15, X8), (a7, b15, X9), (a7, b15, X10), (a7, b15, X11), (a7, b15, X12), (a7, b15, X13), (a7, b15, X14), (a7, b15, X15), (a7, b15, X16), (a7, b15, X17), (a7, b15, X18), (a7, b16, X1), (a7, b16, X2), (a7, b16, X3), (a7, b16, X4), (a7, b16, X5), (a7, b16, X6), (a7, b16, X7), (a7, b16, X8), (a7, b16, X9), (a7, b16, X10), (a7, b16, X11), (a7, b16, X12), (a7, b16, X13), (a7, b16, X14), (a7, b16, X15), (a7, b16, X16), (a7, b16, X17), (a7, b16, X18), (a7, b17, X1), (a7, b17, X2), (a7, b17, X3), (a7, b17, X4), (a7, b17, X5), (a7, b17, X6), (a7, b17, X7), (a7, b17, X8), (a7, b17, X9), (a7, b17, X10), (a7, b17, X11), (a7, b17, X12), (a7, b17, X13), (a7, b17, X14), (a7, b17, X15), (a7, b17, X16), (a7, b17, X17), (a7, b17, X18), (a7, b18, X1), (a7, b18, X2), (a7, b18, X3), (a7, b18, X4), (a7, b18, X5), (a7, b18, X6), (a7, b18, X7), (a7, b18, X8), (a7, b18, X9), (a7, b18, X10), (a7, b18, X11), (a7, b18, X12), (a7, b18, X13), (a7, b18, X14), (a7, b18, X15), (a7, b18, X16), (a7, b18, X17), (a7, b18, X18), (a7, b19, X1), (a7, b19, X2), (a7, b19, X3), (a7, b19, X4), (a7, b19, X5), (a7, b19, X6), (a7, b19, X7), (a7, b19, X8), (a7, b19, X9), (a7, b19, X10), (a7, b19, X11), (a7, b19, X12), (a7, b19, X13), (a7, b19, X14), (a7, b19, X15), (a7, b19, X16), (a7, b19, X17), (a7, b19, X18), (a7, b20, X1), (a7, b20, X2), (a7, b20, X3), (a7, b20, X4), (a7, b20, X5), (a7, b20, X6), (a7, b20, X7), (a7, b20, X8), (a7, b20, X9), (a7, b20, X10), (a7, b20, X11), (a7, b20, X12), (a7, b20, X13), (a7, b20, X14), (a7, b20, X15), (a7, b20, X16), (a7, b20, X17), (a7, b20, X18), (a7, b21, X1), (a7, b21, X2), (a7, b21, X3), (a7, b21, X4), (a7, b21, X5), (a7, b21, X6), (a7, b21, X7), (a7, b21, X8), (a7, b21, X9), (a7, b21, X10), (a7, b21, X11), (a7, b21, X12), (a7, b21, X13), (a7, b21, X14), (a7, b21, X15), (a7, b21, X16), (a7, b21, X17), (a7, b21, X18), (a7, b22, X1), (a7, b22, X2), (a7, b22, X3), (a7, b22, X4), (a7, b22, X5), (a7, b22, X6), (a7, b22, X7), (a7, b22, X8), (a7, b22, X9), (a7, b22, X10), (a7, b22, X11), (a7, b22, X12), (a7, b22, X13), (a7, b22, X14), (a7, b22, X15), (a7, b22, X16), (a7, b22, X17), (a7, b22, X18), (a7, b23, X1), (a7, b23, X2), (a7, b23, X3), (a7, b23, X4), (a7, b23, X5), (a7, b23, X6), (a7, b23, X7), (a7, b23, X8), (a7, b23, X9), (a7, b23, X10), (a7, b23, X11), (a7, b23, X12), (a7, b23, X13), (a7, b23, X14), (a7, b23, X15), (a7, b23, X16), (a7, b23, X17), (a7, b23, X18), (a7, b24, X1), (a7, b24, X2), (a7, b24, X3), (a7, b24, X4), (a7, b24, X5), (a7, b24, X6), (a7, b24, X7), (a7, b24, X8), (a7, b24, X9), (a7, b24, X10), (a7, b24, X11), (a7, b24, X12), (a7, b24, X13), (a7, b24, X14), (a7, b24, X15), (a7, b24, X16), (a7, b24, X17), (a7, b24, X18), (a7, b25, X1), (a7, b25, X2), (a7, b25, X3), (a7, b25, X4), (a7, b25, X5), (a7, b25, X6), (a7, b25, X7), (a7, b25, X8), (a7, b25, X9), (a7, b25, X10), (a7, b25, X11), (a7, b25, X12), (a7, b25, X13), (a7, b25, X14), (a7, b25, X15), (a7, b25, X16), (a7, b25, X17), (a7, b25, X18), (a7, b26, X1), (a7, b26, X2), (a7, b26, X3), (a7, b26, X4), (a7, b26, X5), (a7, b26, X6), (a7, b26, X7), (a7, b26, X8), (a7, b26, X9), (a7, b26, X10), (a7, b26, X11), (a7, b26, X12), (a7, b26, X13), (a7, b26, X14), (a7, b26, X15), (a7, b26, X16), (a7, b26, X17), (a7, b26, X18), (a7, b27, X1), (a7, b27, X2), (a7, b27, X3), (a7, b27, X4), (a7, b27, X5), (a7, b27, X6), (a7, b27, X7), (a7, b27, X8), (a7, b27, X9), (a7, b27, X10), (a7, b27, X11), (a7, b27, X12), (a7, b27, X13), (a7, b27, X14), (a7, b27, X15), (a7, b27, X16), (a7, b27, X17), (a7, b27, X18), (a8, b1, X1), (a8, b1, X2), (a8, b1, X3), (a8, b1, X4), (a8, b1, X5), (a8, b1, X6), (a8, b1, X7), (a8, b1, X8), (a8, b1, X9), (a8, b1, X10), (a8, b1, X11), (a8, b1, X12), (a8, b1, X13), (a8, b1, X14), (a8, b1, X15), (a8, b1, X16), (a8, b1, X17), (a8, b1, X18), (a8, b2, X1), (a8, b2, X2), (a8, b2, X3), (a8, b2, X4), (a8, b2, X5), (a8, b2, X6), (a8, b2, X7), (a8, b2, X8), (a8, b2, X9), (a8, b2, X10), (a8, b2, X11), (a8, b2, X12), (a8, b2, X13), (a8, b2, X14), (a8, b2, X15), (a8, b2, X16), (a8, b2, X17), (a8, b2, X18), (a8, b3, X1), (a8, b3, X2), (a8, b3, X3), (a8, b3, X4), (a8, b3, X5), (a8, b3, X6), (a8, b3, X7), (a8, b3, X8), (a8, b3, X9), (a8, b3, X10), (a8, b3, X11), (a8, b3, X12), (a8, b3, X13), (a8, b3, X14), (a8, b3, X15), (a8, b3, X16), (a8, b3, X17), (a8, b3, X18), (a8, b4, X1), (a8, b4, X2), (a8, b4, X3), (a8, b4, X4), (a8, b4, X5), (a8, b4, X6), (a8, b4, X7), (a8, b4, X8), (a8, b4, X9), (a8, b4, X10), (a8, b4, X11), (a8, b4, X12), (a8, b4, X13), (a8, b4, X14), (a8, b4, X15), (a8, b4, X16), (a8, b4, X17), (a8, b4, X18), (a8, b5, X1), (a8, b5, X2), (a8, b5, X3), (a8, b5, X4), (a8, b5, X5), (a8, b5, X6), (a8, b5, X7), (a8, b5, X8), (a8, b5, X9), (a8, b5, X10), (a8, b5, X11), (a8, b5, X12), (a8, b5, X13), (a8, b5, X14), (a8, b5, X15), (a8, b5, X16), (a8, b5, X17), (a8, b5, X18), (a8, b6, X1), (a8, b6, X2), (a8, b6, X3), (a8, b6, X4), (a8, b6, X5), (a8, b6, X6), (a8, b6, X7), (a8, b6, X8), (a8, b6, X9), (a8, b6, X10), (a8, b6, X11), (a8, b6, X12), (a8, b6, X13), (a8, b6, X14), (a8, b6, X15), (a8, b6, X16), (a8, b6, X17), (a8, b6, X18), (a8, b7, X1), (a8, b7, X2), (a8, b7, X3), (a8, b7, X4), (a8, b7, X5), (a8, b7, X6), (a8, b7, X7), (a8, b7, X8), (a8, b7, X9), (a8, b7, X10), (a8, b7, X11), (a8, b7, X12), (a8, b7, X13), (a8, b7, X14), (a8, b7, X15), (a8, b7, X16), (a8, b7, X17), (a8, b7, X18), (a8, b8, X1), (a8, b8, X2), (a8, b8, X3), (a8, b8, X4), (a8, b8, X5), (a8, b8, X6), (a8, b8, X7), (a8, b8, X8), (a8, b8, X9), (a8, b8, X10), (a8, b8, X11), (a8, b8, X12), (a8, b8, X13), (a8, b8, X14), (a8, b8, X15), (a8, b8, X16), (a8, b8, X17), (a8, b8, X18), (a8, b9, X1), (a8, b9, X2), (a8, b9, X3), (a8, b9, X4), (a8, b9, X5), (a8, b9, X6), (a8, b9, X7), (a8, b9, X8), (a8, b9, X9), (a8, b9, X10), (a8, b9, X11), (a8, b9, X12), (a8, b9, X13), (a8, b9, X14), (a8, b9, X15), (a8, b9, X16), (a8, b9, X17), (a8, b9, X18), (a8, b10, X1), (a8, b10, X2), (a8, b10, X3), (a8, b10, X4), (a8, b10, X5), (a8, b10, X6), (a8, b10, X7), (a8, b10, X8), (a8, b10, X9), (a8, b10, X10), (a8, b10, X11), (a8, b10, X12), (a8, b10, X13), (a8, b10, X14), (a8, b10, X15), (a8, b10, X16), (a8, b10, X17), (a8, b10, X18), (a8, b11, X1), (a8, b11, X2), (a8, b11, X3), (a8, b11, X4), (a8, b11, X5), (a8, b11, X6), (a8, b11, X7), (a8, b11, X8), (a8, b11, X9), (a8, b11, X10), (a8, b11, X11), (a8, b11, X12), (a8, b11, X13), (a8, b11, X14), (a8, b11, X15), (a8, b11, X16), (a8, b11, X17), (a8, b11, X18), (a8, b12, X1), (a8, b12, X2), (a8, b12, X3), (a8, b12, X4), (a8, b12, X5), (a8, b12, X6), (a8, b12, X7), (a8, b12, X8), (a8, b12, X9), (a8, b12, X10), (a8, b12, X11), (a8, b12, X12), (a8, b12, X13), (a8, b12, X14), (a8, b12, X15), (a8, b12, X16), (a8, b12, X17), (a8, b12, X18), (a8, b13, X1), (a8, b13, X2), (a8, b13, X3), (a8, b13, X4), (a8, b13, X5), (a8, b13, X6), (a8, b13, X7), (a8, b13, X8), (a8, b13, X9), (a8, b13, X10), (a8, b13, X11), (a8, b13, X12), (a8, b13, X13), (a8, b13, X14), (a8, b13, X15), (a8, b13, X16), (a5, b13, X17), (a8, b13, X18), (a8, b14, X1), (a8, b14, X2), (a8, b14, X3), (a8, b14, X4), (a8, b14, X5), (a8, b14, X6), (a8, b14, X7), (a8, b14, X8), (a8, b14, X9), (a8, b14, X10), (a8, b14, X11), (a8, b14, X12), (a8, b14, X13), (a8, b14, X14), (a8, b14, X15), (a8, b14, X16), (a8, b14, X17), (a8, b14, X18), (a8, b15, X1), (a8, b15, X2), (a8, b15, X3), (a8, b15, X4), (a8, b15, X5), (a8, b15, X6), (a8, b15, X7), (a8, b15, X8), (a8, b15, X9), (a8, b15, X10), (a8, b15, X11), (a8, b15, X12), (a8, b15, X13), (a8, b15, X14), (a8, b15, X15), (a8, b15, X16), (a8, b15, X17), (a8, b15, X18), (a8, b16, X1), (a8, b16, X2), (a8, b16, X3), (a8, b16, X4), (a8, b16, X5), (a8, b16, X6), (a8, b16, X7), (a8, b16, X8), (a8, b16, X9), (a8, b16, X10), (a8, b16, X11), (a8, b16, X12), (a8, b16, X13), (a8, b16, X14), (a8, b16, X15), (a8, b16, X16), (a8, b16, X17), (a8, b16, X18), (a8, b17, X1), (a8, b17, X2), (a8, b17, X3), (a8, b17, X4), (a8, b17, X5), (a8, b17, X6), (a8, b17, X7), (a8, b17, X8), (a8, b17, X9), (a8, b17, X10), (a8, b17, X11), (a8, b17, X12), (a8, b17, X13), (a8, b17, X14), (a8, b17, X15), (a8, b17, X16), (a8, b17, X17), (a8, b17, X18), (a8, b18, X1), (a8, b18, X2), (a8, b18, X3), (a8, b18, X4), (a8, b18, X5), (a8, b18, X6), (a8, b18, X7), (a8, b18, X8), (a8, b18, X9), (a8, b18, X10), (a8, b18, X11), (a8, b18, X12), (a8, b18, X13), (a8, b18, X14), (a8, b18, X15), (a8, b18, X16), (a8, b18, X17), (a8, b18, X18), (a8, b19, X1), (a8, b19, X2), (a8, b19, X3), (a8, b19, X4), (a8, b19, X5), (a8, b19, X6), (a8, b19, X7), (a8, b19, X8), (a8, b19, X9), (a8, b19, X10), (a8, b19, X11), (a8, b19,

X12), (a8, b19, X13), (a8, b19, X14), (a8, b19, X15), (a8, b19, X16), (a8, b19, X17), (a8, b19, X18), (a8, b20, X1), (a8, b20, X2), (a8, b20, X3), (a8, b20, X4), (a8, b20, X5), (a8, b20, X6), (a8, b20, X7), (a8, b20, X8), (a8, b20, X9), (a8, b20, X10), (a8, b20, X11), (a8, b20, X12), (a8, b20, X13), (a8, b20, X14), (a8, b20, X15), (a8, b20, X16), (a8, b20, X17), (a8, b20, X18), (a8, b21, X1), (a8, b21, X2), (a8, b21, X3), (a8, b21, X4), (a8, b21, X5), (a8, b21, X6), (a8, b21, X7), (a8, b21, X8), (a8, b21, X9), (a8, b21, X10), (a8, b21, X11), (a8, b21, X12), (a8, b21, X13), (a8, b21, X14), (a8, b21, X15), (a8, b21, X16), (a8, b21, X17), (a8, b21, X18), (a8, b22, X1), (a8, b22, X2), (a8, b22, X3), (a8, b22, X4), (a8, b22, X5), (a8, b22, X6), (a8, b22, X7), (a8, b22, X8), (a8, b22, X9), (a8, b22, X10), (a8, b22, X11), (a8, b22, X12), (a8, b22, X13), (a8, b22, X14), (a8, b22, X15), (a8, b22, X16), (a8, b22, X17), (a8, b22, X18), (a8, b23, X1), (a8, b23, X2), (a8, b23, X3), (a8, b23, X4), (a8, b23, X5), (a8, b23, X6), (a8, b23, X7), (a8, b23, X8), (a8, b23, X9), (a8, b23, X10), (a8, b23, X11), (a8, b23, X12), (a8, b23, X13), (a8, b23, X14), (a8, b23, X15), (a8, b23, X16), (a8, b23, X17), (a8, b23, X18), (a8, b24, X1), (a8, b24, X2), (a8, b24, X3), (a8, b24, X4), (a8, b24, X5), (a8, b24, X6), (a8, b24, X7), (a8, b24, X8), (a8, b24, X9), (a8, b24, X10), (a8, b24, X11), (a8, b24, X12), (a8, b24, X13), (a8, b24, X14), (a8, b24, X15), (a8, b24, X16), (a8, b24, X17), (a8, b24, X18), (a8, b25, X1), (a8, b25, X2), (a8, b25, X3), (a8, b25, X4), (a8, b25, X5), (a8, b25, X6), (a8, b25, X7), (a8, b25, X8), (a8, b25, X9), (a8, b25, X10), (a8, b25, X11), (a8, b25, X12), (a8, b25, X13), (a8, b25, X14), (a8, b25, X15), (a8, b25, X16), (a8, b25, X17), (a8, b25, X18), (a8, b26, X1), (a8, b26, X2), (a8, b26, X3), (a8, b26, X4), (a8, b26, X5), (a8, b26, X6), (a8, b26, X7), (a8, b26, X8), (a8, b26, X9), (a8, b26, X10), (a8, b26, X11), (a8, b26, X12), (a8, b26, X13), (a8, b26, X14), (a8, b26, X15), (a8, b26, X16), (a8, b26, X17), (a8, b26, X18), (a8, b27, X1), (a8, b27, X2), (a8, b27, X3), (a8, b27, X4), (a8, b27, X5), (a8, b27, X6), (a8, b27, X7), (a8, b27, X8), (a8, b27, X9), (a8, b27, X10), (a8, b27, X11), (a8, b27, X12), (a8, b27, X13), (a8, b27, X14), (a8, b27, X15), (a8, b27, X16), (a8, b27, X17), (a8, b27, X18), (a9, b1, X1), (a9, b1, X2), (a9, b1, X3), (a9, b1, X4), (a9, b1, X5), (a9, b1, X6), (a9, b1, X7), (a9, b1, X8), (a9, b1, X9), (a9, b1, X10), (a9, b1, X11), (a9, b1, X12), (a9, b1, X13), (a9, b1, X14), (a9, b1, X15), (a9, b1, X16), (a9, b1, X17), (a9, b1, X18), (a9, b2, X1), (a9, b2, X2), (a9, b2, X3), (a9, b2, X4), (a9, b2, X5), (a9, b2, X6), (a9, b2, X7), (a9, b2, X8), (a9, b2, X9), (a9, b2, X10), (a9, b2, X11), (a9, b2, X12), (a9, b2, X13), (a9, b2, X14), (a9, b2, X15), (a9, b2, X16), (a9, b2, X17), (a9, b2, X18), (a9, b3, X1), (a9, b3, X2), (a9, b3, X3), (a9, b3, X4), (a9, b3, X5), (a9, b3, X6), (a9, b3, X7), (a9, b3, X8), (a9, b3, X9), (a9, b3, X10), (a9, b3, X11), (a9, b3, X12), (a9, b3, X13), (a9, b3, X14), (a9, b3, X15), (a9, b3, X16), (a9, b3, X17), (a9, b3, X18), (a9, b4, X1), (a9, b4, X2), (a9, b4, X3), (a9, b4, X4), (a9, b4, X5), (a9, b4, X6), (a9, b4, X7), (a9, b4, X8), (a9, b4, X9), (a9, b4, X10), (a9, b4, X11), (a9, b4, X12), (a9, b4, X13), (a9, b4, X14), (a9, b4, X15), (a9, b4, X16), (a9, b4, X17), (a9, b4, X18), (a9, b5, X1), (a9, b5, X2), (a9, b5, X3), (a9, b5, X4), (a9, b5, X5), (a9, b5, X6), (a9, b5, X7), (a9, b5, X8), (a9, b5, X9), (a9, b5, X10), (a9, b5, X11), (a9, b5, X12), (a9, b5, X13), (a9, b5, X14), (a9, b5, X15), (a9, b5, X16), (a9, b5, X17), (a9, b5, X18), (a9, b6, X1), (a9, b6, X2), (a9, b6, X3), (a9, b6, X4), (a9, b6, X5), (a9, b6, X6), (a9, b6, X7), (a9, b6, X8), (a9, b6, X9), (a9, b6, X10), (a9, b6, X11), (a9, b6, X12), (a9, b6, X13), (a9, b6, X14), (a9, b6, X15), (a9, b6, X16), (a9, b6, X17), (a9, b6, X18), (a9, b7, X1), (a9, b7, X2), (a9, b7, X3), (a9, b7, X4), (a9, b7, X5), (a9, b7, X6), (a9, b7, X7), (a9, b7, X8), (a9, b7, X9), (a9, b7, X10), (a9, b7, X11), (a9, b7, X12), (a9, b7, X13), (a9, b7, X14), (a9, b7, X15), (a9, b7, X16), (a9, b7, X17), (a9, b8, X1), (a9, b8, X2), (a9, b8, X3), (a9, b8, X4), (a9, b8, X5), (a9, b8, X6), (a9, b8, X7), (a9, b8, X8), (a9, b8, X9), (a9, b8, X10), (a9, b8, X11), (a9, b8, X12), (a9, b8, X13), (a9, b8, X14), (a9, b8, X15), (a9, b8, X16), (a9, b8, X17), (a9, b8, X18), (a9, b9, X1), (a9, b9, X2), (a9, b9, X3), (a9, b9, X4), (a9, b9, X5), (a9, b9, X6), (a9, b9, X7), (a9, b9, X8), (a9, b9, X9), (a9, b9, X10), (a9, b9, X11), (a9, b9, X12), (a9, b9, X13), (a9, b9, X14), (a9, b9, X15), (a9, b9, X16), (a9, b9, X17), (a9, b9, X18), (a9, b10, X1), (a9, b10, X2), (a9, b10, X3), (a9, b10, X4), (a9, b10, X5), (a9, b10, X6), (a9, b10, X7), (a9, b10, X8), (a9, b10, X9), (a9, b10, X10), (a9, b10, X11), (a9, b10, X12), (a9, b10, X13), (a9, b10, X14), (a9, b10, X15), (a9, b10, X16), (a9, b10, X17), (a9, b10, X18), (a9, b11, X1), (a9, b11, X2), (a9, b11, X3), (a9, b11, X4), (a9, b11, X5), (a9, b11, X6), (a9, b11, X7), (a9, b11, X8), (a9, b11, X9), (a9, b11, X10), (a9, b11, X11), (a9, b11, X12), (a9, b11, X13), (a9, b11, X14), (a9, b11, X15), (a9, b11, X16), (a9, b11, X17), (a9, b11, X18), (a9, b12, X1), (a9, b12, X2), (a9, b12, X3), (a9, b12, X4), (a9, b12, X5), (a9, b12, X6), (a9, b12, X7), (a9, b12, X8), (a9, b12, X9), (a9, b12, X10), (a9, b12, X11), (a9, b12, X12), (a9, b12, X13), (a9, b12, X14), (a9, b12, X15), (a9, b12, X16), (a9, b12, X17), (a9, b12, X18), (a9, b13, X1), (a9, b13, X2), (a9, b13, X3), (a9, b13, X4), (a9, b13, X5), (a9, b13, X6), (a9, b13, X7), (a9, b13, X8), (a9, b13, X9), (a9, b13, X10), (a9, b13, X11), (a9, b13, X12), (a9, b13, X13), (a9, b13, X14), (a9, b13, X15), (a9, b13, X16), (a9, b13, X17), (a9, b13, X18), (a9, b14, X1), (a9, b14, X2), (a9, b14, X3), (a9, b14, X4), (a9, b14, X5), (a9, b14, X6), (a9, b14, X7), (a9, b14, X8), (a9, b14, X9), (a9, b14, X10), (a9, b14, X11), (a9, b14, X12), (a9, b14, X13), (a9, b14, X14), (a9, b14, X15), (a9, b14, X16), (a9, b14, X17), (a9, b14, X18), (a9, b15, X1), (a9, b15, X2), (a9, b15, X3), (a9, b15, X4), (a9, b15, X5), (a9, b15, X6), (a9, b15, X7), (a9, b15, X8), (a9, b15, X9), (a9, b15, X10), (a9, b15, X11), (a9, b15, X12), (a9, b15, X13), (a9, b15, X14), (a9, b15, X15), (a9, b15, X16), (a9, b15, X17), (a9, b15, X18), (a9, b16, X1), (a9, b16, X2), (a9, b16, X3), (a9, b16, X4), (a9, b16, X5), (a9, b16, X6), (a9, b16, X7), (a9, b16, X8), (a9, b16, X9), (a9, b16, X10), (a9, b16, X11), (a9, b16, X12), (a9, b16, X13), (a9, b16, X14), (a9, b16, X15), (a9, b16, X16), (a9, b16, X17), (a9, b16, X18), (a9, b17, X1), (a9, b17, X2), (a9, b17, X3), (a9, b17, X4), (a9, b17, X5), (a9, b17, X6), (a9, b17, X7), (a9, b17, X8), (a9, b17, X9), (a9, b17, X10), (a9, b17, X11), (a9, b17, X12), (a9, b17, X13), (a9, b17, X14), (a9, b17, X15), (a9, b17, X16), (a9, b17, X17), (a9, b17, X18), (a9, b18, X1), (a9, b18, X2), (a9, b18, X3), (a9, b18, X4), (a9, b18, X5), (a9, b18, X6), (a9, b18, X7), (a9, b18, X8), (a9, b18, X9), (a9, b18, X10), (a9, b18, X11), (a9, b18, X12), (a9, b18, X13), (a9, b18, X14), (a9, b18, X15), (a9, b18, X16), (a9, b18, X17), (a9, b18, X18), (a9, b19, X1), (a9, b19, X2), (a9, b19, X3), (a9, b19, X4), (a9, b19, X5), (a9, b19, X6), (a9, b19, X7), (a9, b19, X8), (a9, b19, X9), (a9, b19, X10), (a9, b19, X11), (a9, b19, X12), (a9, b19, X13), (a9, b19, X14), (a9, b19, X15), (a9, b19, X16), (a9, b19, X17), (a9, b19, X18), (a9, b20, X1), (a9, b20, X2), (a9, b20, X3), (a9, b20, X4), (a9, b20, X5), (a9, b20, X6), (a9, b20, X7), (a9, b20, X8), (a9, b20, X9), (a9, b20, X10), (a9, b20, X11), (a9, b20, X12), (a9, b20, X13), (a9, b20, X14), (a9, b20, X15), (a9, b20, X16), (a9, b20, X17), (a9, b20, X18), (a9, b21, X1), (a9, b21, X2), (a9, b21, X3), (a9, b21, X4), (a9, b21, X5), (a9, b21, X6), (a9, b21, X7), (a9, b21, X8), (a9, b21, X9), (a9, b21, X10), (a9, b21, X11), (a9, b21, X12), (a9, b21, X13), (a9, b21, X14), (a9, b21, X15), (a9, b21, X16), (a9, b21, X17), (a9, b21, X18), (a9, b22, X1), (a9, b22, X2), (a9, b22, X3), (a9, b22, X4), (a9, b22, X5), (a9, b22, X6), (a9, b22, X7), (a9, b22, X8), (a9, b22, X9), (a9, b22, X10), (a9, b22, X11), (a9, b22, X12), (a9, b22, X13), (a9, b22, X14), (a9, b22, X15), (a9, b22, X16), (a9, b22, X17), (a9, b22, X18), (a9, b23, X1), (a9, b23, X2), (a9, b23, X3), (a9, b23, X4), (a9, b23, X5), (a9, b23, X6), (a9, b23, X7), (a9, b23, X8), (a9, b23, X9), (a9, b23, X10), (a9, b23, X11), (a9, b23, X12), (a9, b23, X13), (a9, b23, X14), (a9, b23, X15), (a9, b23, X16), (a9, b23, X17), (a9, b23, X18), (a9, b24, X1), (a9, b24, X2), (a9, b24, X3), (a9, b24, X4), (a9, b24, X5), (a9, b24, X6), (a9, b24, X7), (a9, b24, X8), (a9, b24, X9), (a9, b24, X10), (a9, b24, X11), (a9, b24, X12), (a9, b24, X13), (a9, b24, X14), (a9, b24, X15), (a9, b24, X16), (a9, b24, X17), (a9, b24, X18), (a9, b25, X1), (a9, b25, X2), (a9, b25, X3), (a9, b25, X4), (a9, b25, X5), (a9, b25, X6), (a9, b25, X7), (a9, b25, X8), (a9, b25, X9), (a9, b25, X10), (a9, b25, X11), (a9, b25, X12), (a9, b25, X13), (a9, b25, X14), (a9, b25, X15), (a9, b25, X16), (a9, b25, X17), (a9, b25, X18), (a9, b26, X1), (a9, b26, X2), (a9, b26, X3), (a9, b26, X4), (a9, b26, X5), (a9, b26, X6), (a9, b26, X7), (a9, b26, X8), (a9, b26, X9), (a9, b26, X10), (a9, b26, X11), (a9, b26, X12), (a9, b26, X13), (a9, b26, X14), (a9, b26, X15), (a9, b26, X16), (a9, b26, X17), (a9, b26, X18), (a9, b27, X1), (a9, b27, X2), (a9, b27, X3), (a9, b27, X4), (a9, b27, X5), (a9, b27, X6), (a9, b27, X7), (a9, b27, X8), (a9, b27, X9), (a9, b27, X10), (a9, b27, X11), (a9, b27, X12), (a9, b27, X13), (a9, b27, X14), (a9, b27, X15), (a9, b27, X16), (a9, b27, X17), (a9, b27, X18), (a10, b1, X1), (a10, b1, X2), (a10, b1, X3), (a10, b1, X4), (a10, b1, X5), (a10, b1, X6), (a10, b1, X7), (a10, b1, X8), (a10, b1, X9), (a10, b1, X10), (a10, b1, X11), (a10, b1, X12), (a10, b1, X13), (a10, b1, X14), (a10, b1, X15), (a10, b1, X16), (a10, b1, X17), (a10, b1, X18), (a10, b2, X1), (a10, b2, X2), (a10, b2, X3), (a10, b2, X4), (a10, b2, X5), (a10, b2, X6), (a10, b2, X7), (a10, b2, X8), (a10, b2, X9), (a10, b2, X10), (a10, b2, X11), (a10, b2, X12), (a10, b2, X13), (a10, b2, X14), (a10, b2, X15), (a10, b2, X16), (a10, b2, X17), (a10, b2, X18), (a10, b3, X1), (a10, b3, X2), (a10, b3, X3), (a10, b3, X4), (a10, b3, X5), (a10, b3, X6), (a10, b3, X7), (a10, b3, X8), (a10, b3, X9), (a10, b3, X10), (a10, b3, X11), (a10, b3, X12), (a10, b3, X13), (a10, b3, X14), (a10, b3, X15), (a10, b3, X16), (a10, b3, X17), (a10, b3, X18), (a10, b4, X1), (a10, b4, X2), (a10, b4, X3), (a10, b4, X4), (a10, b4, X5), (a10, b4, X6), (a10, b4, X7), (a10, b4, X8), (a10, b4, X9), (a10, b4, X10), (a10, b4, X11), (a10, b4, X12), (a10, b4, X13), (a10, b4, X14), (a10, b4, X15), (a10, b4, X16), (a10, b4, X17), (a10, b4, X18), (a10, b5, X1), (a10, b5, X2), (a10, b5, X3), (a10, b5, X4), (a10, b5, X5), (a10, b5, X6), (a10, b5, X7), (a10, b5, X8), (a10, b5, X9), (a10, b5, X10), (a10, b5, X11), (a10, b5, X12), (a10, b5, X13), (a10, b5, X14), (a10, b5, X15), (a10, b5, X16), (a10, b5, X17), (a10, b5, X18), (a10, b6, X1), (a10, b6, X2), (a10, b6, X3), (a10, b6, X4), (a10, b6, X5), (a10, b6, X6), (a10, b6, X7), (a10, b6, X8), (a10, b6, X9), (a10, b6, X10), (a10, b6, X11), (a10, b6, X12), (a10, b6, X13), (a10, b6, X14), (a10, b6, X15), (a10, b6, X16), (a10, b6, X17), (a10, b6, X18), (a10, b7, X1), (a10, b7, X2), (a10, b7, X3), (a10, b7, X4), (a10, b7, X5), (a10, b7, X6), (a10, b7, X7), (a10, b7, X8), (a10, b7, X9), (a10, b7, X10), (a10, b7, X11), (a10, b7, X12), (a10, b7, X13), (a10, b7, X14), (a10, b7, X15), (a10, b7, X16), (a10, b7, X17), (a10, b7, X18), (a10, b8, X1), (a10, b8, X2), (a10, b8, X3), (a10, b8, X4), (a10, b8, X5), (a10, b8, X6), (a10, b8, X7), (a10, b8, X8), (a10, b8, X9), (a10, b8, X10), (a10, b8, X11), (a10, b8, X12), (a10, b8, X13), (a10, b8, X14), (a10, b8, X15), (a10, b8, X16), (a10, b8, X17), (a10, b8, X18), (a10, b9, X1), (a10, b9, X2), (a10, b9, X3), (a10, b9, X4), (a10, b9, X5), (a10, b9, X6), (a10, b9, X7), (a10, b9, X8), (a10, b9, X9), (a10, b9, X10), (a10, b9, X11), (a10, b9, X12), (a10, b9, X13), (a10, b9, X14), (a10, b9, X15), (a10, b9, X16), (a10, b9, X17), (a10, b9, X18), (a10, b10, X1), (a10, b10, X2), (a10, b10, X3), (a10, b10, X4), (a10, b10, X5), (a10, b10, X6), (a10, b10, X7), (a10, b10, X8), (a10, b10, X9), (a10, b10, X10), (a10, b10, X11), (a10, b10, X12), (a10, b10, X13), (a10, b10, X14), (a10, b10, X15), (a10, b10, X16), (a10, b10, X17), (a10, b10, X18), (a10, b11, X1), (a10, b11, X2), (a10, b11, X3), (a10, b11, X4), (a10, b11, X5), (a10, b11, X6), (a10, b11, X7), (a10, b11, X8), (a10, b11, X9), (a10, b11, X10), (a10, b11, X11), (a10, b11, X12), (a10, b11, X13), (a10, b11, X14), (a10, b11, X15), (a10, b11, X16), (a10, b11, X17), (a10, b11, X18), (a10, b12, X1), (a10, b12, X2), (a10, b12, X3), (a10, b12, X4), (a10, b12, X5), (a10, b12, X6), (a10, b12, X7), (a10, b12, X8), (a10, b12, X9), (a10, b12, X10), (a10, b12, X11), (a10, b12, X12), (a10, b12, X13), (a10, b12, X14), (a10, b12, X15), (a10, b12, X16), (a10, b12, X17), (a10, b12, X18), (a10, b13, X1), (a10, b13, X2), (a10, b13, X3), (a10, b13, X4), (a10, b13, X5), (a10, b13, X6), (a10, b13, X7), (a10, b13, X8), (a10, b13, X9), (a10, b13, X10), (a10, b13, X11), (a10, b13, X12), (a10, b13, X13), (a10, b13, X14), (a10, b13, X15), (a10, b13, X16), (a10, b13, X17), (a10, b13, X18), (a10, b14, X1), (a10, b14, X2), (a10, b14, X3), (a10, b14, X4), (a10, b14, X5), (a10, b14, X6), (a10, b14, X7), (a10, b14, X8), (a10, b14, X9), (a10, b14, X10), (a10, b14, X11), (a10, b14, X12), (a10, b14, X13), (a10, b14, X14), (a10, b14, X15), (a10, b14, X16), (a10, b14, X17), (a10, b14, X18), (a10, b15, X1), (a10, b15, X2), (a10, b15, X3), (a10, b15, X4), (a10, b15, X5), (a10, b15, X6), (a10, b15, X7), (a10, b15, X8), (a10, b15, X9), (a10, b15, X10), (a10, b15, X11), (a10, b15, X12), (a10, b15, X13), (a10, b15, X14), (a10, b15, X15), (a10, b15, X16), (a10, b15, X17), (a10, b15, X18), (a10, b16, X1), (a10, b16, X2), (a10, b16, X3), (a10, b16, X4), (a10, b16, X5), (a10, b16, X6), (a10, b16, X7), (a10, b16, X8), (a10, b16, X9), (a10, b16, X10), (a10, b16, X11), (a10, b16, X12), (a10, b16, X13), (a10, b16, X14), (a10, b16, X15), (a10, b16, X16), (a10, b16, X17), (a10, b16, X18), (a10, b17, X1), (a10, b17, X2), (a10, b17, X3), (a10, b17, X4), (a10, b17, X5), (a10, b17, X6), (a10, b17, X7), (a10, b17, X8), (a10, b17, X9), (a10, b17, X10), (a10, b17, X11), (a10, b17, X12), (a10, b17, X13), (a10, b17, X14), (a10, b17, X15), (a10, b17, X16), (a10, b17, X17), (a10, b17, X18), (a10, b18, X1), (a10, b18, X2), (a10, b18, X3), (a10, b18, X4), (a10, b18, X5), (a10, b18, X6), (a10, b18, X7), (a10, b18, X8), (a10, b18, X9), (a10, b18, X10), (a10, b18, X11), (a10, b18, X12), (a10, b18, X13), (a10, b18, X14), (a10, b18, X15), (a10, b18, X16), (a10, b18, X17), (a10, b18, X18), (a10, b19, X1), (a10, b19, X2), (a10, b19, X3), (a10, b19, X4), (a10, b19, X5), (a10, b19, X6), (a10, b19, X7), (a10, b19, X8), (a10, b19, X9), (a10, b19, X10), (a10, b19, X11), (a10, b19, X12), (a10, b19, X13), (a10, b19, X14), (a10, b19, X15), (a10, b19, X16), (a10, b19, X17), (a10, b19, X18), (a10, b20, X1), (a10, b20, X2), (a10, b20, X3), (a10, b20, X4), (a10, b20, X5), (a10, b20, X6), (a10, b20, X7), (a10, b20, X8), (a10, b20, X9), (a10, b20, X10), (a10, b20, X11), (a10, b20, X12), (a10, b20, X13), (a10, b20, X14), (a10, b20, X15), (a10, b20, X16), (a10, b20, X17), (a10, b20, X18), (a10, b21, X1), (a10, b21, X2), (a10, b21, X3), (a10, b21, X4), (a10, b21, X5), (a10, b21, X6), (a10, b21, X7), (a10, b21, X8), (a10, b21, X9), (a10, b21, X10), (a10, b21, X11), (a10, b21, X12), (a10, b21, X13), (a10, b21, X14), (a10, b21, X15), (a10, b21, X16), (a10, b21, X17), (a10, b21, X18), (a10, b22,

X1), (a10, b22, X2), (a10, b22, X3), (a10, b22, X4), (a10, b22, X5), (a10, b22, X6), (a10, b22, X7), (a10, b22, X8), (a10, b22, X9), (a10, b22, X10), (a10, b22, X11), (a10, b22, X12), (a10, b22, X13), (a10, b22, X14), (a10, b22, X15), (a10, b22, X16), (a10, b22, X17), (a10, b22, X18), (a10, b23, X1), (a10, b23, X2), (a10, b23, X3), (a10, b23, X4), (a10, b23, X5), (a10, b23, X6), (a10, b23, X7), (a10, b23, X8), (a10, b23, X9), (a10, b23, X10), (a10, b23, X11), (a10, b23, X12), (a10, b23, X13), (a10, b23, X14), (a10, b23, X15), (a10, b23, X16), (a10, b23, X17), (a10, b23, X18), (a10, b24, X1), (a10, b24, X2), (a10, b24, X3), (a10, b24, X4), (a10, b24, X5), (a10, b24, X6), (a10, b24, X7), (a10, b24, X8), (a10, b24, X9), (a10, b24, X10), (a10, b24, X11), (a10, b24, X12), (a10, b24, X13), (a10, b24, X14), (a10, b24, X15), (a10, b24, X16), (a10, b24, X17), (a10, b24, X18), (a10, b25, X1), (a10, b25, X2), (a10, b25, X3), (a10, b25, X4), (a10, b25, X5), (a10, b25, X6), (a10, b25, X7), (a10, b25, X8), (a10, b25, X9), (a10, b25, X10), (a10, b25, X11), (a10, b25, X12), (a10, b25, X13), (a10, b25, X14), (a10, b25, X15), (a10, b25, X16), (a10, b25, X17), (a10, b25, X18), (a10, b26, X1), (a10, b26, X2), (a10, b26, X3), (a10, b26, X4), (a10, b26, X5), (a10, b26, X6), (a10, b26, X7), (a10, b26, X8), (a10, b26, X9), (a10, b26, X10), (a10, b26, X11), (a10, b26, X12), (a10, b26, X13), (a10, b26, X14), (a10, b26, X15), (a10, b26, X16), (a10, b26, X17), (a10, b26, X18), (a10, b27, X1), (a10, b27, X2), (a10, b27, X3), (a10, b27, X4), (a10, b27, X5), (a10, b27, X6), (a10, b27, X7), (a10, b27, X8), (a10, b27, X9), (a10, b27, X10), (a10, b27, X11), (a10, b27, X12), (a10, b27, X13), (a10, b27, X14), (a10, b27, X15), (a10, b27, X16), (a10, b27, X17), (a10, b27, X18), (a11, b1, X1), (a11, b1, X2), (a11, b1, X3), (a11, b1, X4), (a11, b1, X5), (a11, b1, X6), (a11, b1, X7), (a11, b1, X8), (a11, b1, X9), (a11, b1, X10), (a11, b1, X11), (a11, b1, X12), (a11, b1, X13), (a11, b1, X14), (a11, b1, X15), (a11, b1, X16), (a11, b1, X17), (a11, b1, X18), (a11, b2, X1), (a11, b2, X2), (a11, b2, X3), (a11, b2, X4), (a11, b2, X5), (a11, b2, X6), (a11, b2, X7), (a11, b2, X8), (a11, b2, X9), (a11, b2, X10), (a11, b2, X11), (a11, b2, X12), (a11, b2, X13), (a11, b2, X14), (a11, b2, X15), (a11, b2, X16), (a11, b2, X17), (a11, b2, X18), (a11, b3, X1), (a11, b3, X2), (a11, b3, X3), (a11, b3, X4), (a11, b3, X5), (a11, b3, X6), (a11, b3, X7), (a11, b3, X8), (a11, b3, X9), (a11, b3, X10), (a11, b3, X11), (a11, b3, X12), (a11, b3, X13), (a11, b3, X14), (a11, b3, X15), (a11, b3, X16), (a11, b3, X17), (a11, b3, X18), (a11, b4, X1), (a11, b4, X2), (a11, b4, X3), (a11, b4, X4), (a11, b4, X5), (a11, b4, X6), (a11, b4, X7), (a11, b4, X8), (a11, b4, X9), (a11, b4, X10), (a11, b4, X11), (a11, b4, X12), (a11, b4, X13), (a11, b4, X14), (a11, b4, X15), (a11, b4, X16), (a11, b4, X17), (a11, b4, X18), (a11, b5, X1), (a11, b5, X2), (a11, b5, X3), (a11, b5, X4), (a11, b5, X5), (a11, b5, X6), (a11, b5, X7), (a11, b5, X8), (a11, b5, X9), (a11, b5, X10), (a11, b5, X11), (a11, b5, X12), (a11, b5, X13), (a11, b5, X14), (a11, b5, X15), (a11, b5, X16), (a11, b5, X17), (a11, b5, X18), (a11, b6, X1), (a11, b6, X2), (a11, b6, X3), (a11, b6, X4), (a11, b6, X5), (a11, b6, X6), (a11, b6, X7), (a11, b6, X8), (a11, b6, X9), (a11, b6, X10), (a11, b6, X11), (a11, b6, X12), (a11, b6, X13), (a11, b6, X14), (a11, b6, X15), (a11, b6, X16), (a11, b6, X17), (a11, b6, X18), (a11, b7, X1), (a11, b7, X2), (a11, b7, X3), (a11, b7, X4), (a11, b7, X5), (a11, b7, X6), (a11, b7, X7), (a11, b7, X8), (a11, b7, X9), (a11, b7, X10), (a11, b7, X11), (a11, b7, X12), (a11, b7, X13), (a11, b7, X14), (a11, b7, X15), (a11, b7, X16), (a11, b7, X17), (a11, b7, X18), (a11, b8, X1), (a11, b8, X2), (a11, b8, X3), (a11, b8, X4), (a11, b8, X5), (a11, b8, X6), (a11, b8, X7), (a11, b8, X8), (a11, b8, X9), (a11, b8, X10), (a11, b8, X11), (a11, b8, X12), (a11, b8, X13), (a11, b8, X14), (a11, b8, X15), (a11, b8, X16), (a11, b8, X17), (a11, b8, X18), (a11, b9, X1), (a11, b9, X2), (a11, b9, X3), (a11, b9, X4), (a11, b9, X5), (a11, b9, X6), (a11, b9, X7), (a11, b9, X8), (a11, b9, X9), (a11, b9, X10), (a11, b9, X11), (a11, b9, X12), (a11, b9, X13), (a11, b9, X14), (a11, b9, X15), (a11, b9, X16), (a11, b9, X17), (a11, b9, X18), (a11, b10, X1), (a11, b10, X2), (a11, b10, X3), (a11, b10, X4), (a11, b10, X5), (a11, b10, X6), (a11, b10, X7), (a11, b10, X8), (a11, b10, X9), (a11, b10, X10), (a11, b10, X11), (a11, b10, X12), (a11, b10, X13), (a11, b10, X14), (a11, b10, X15), (a11, b10, X16), (a11, b10, X17), (a11, b10, X18), (a11, b11, X1), (a11, b11, X2), (a11, b11, X3), (a11, b11, X4), (a11, b11, X5), (a11, b11, X6), (a11, b11, X7), (a11, b11, X8), (a11, b11, X9), (a11, b11, X10), (a11, b11, X11), (a11, b11, X12), (a11, b11, X13), (a11, b11, X14), (a11, b11, X15), (a11, b11, X16), (a11, b11, X17), (a11, b11, X18), (a11, b12, X1), (a11, b12, X2), (a11, b12, X3), (a11, b12, X4), (a11, b12, X5), (a11, b12, X6), (a11, b12, X7), (a11, b12, X8), (a11, b12, X9), (a11, b12, X10), (a11, b12, X11), (a11, b12, X12), (a11, b12, X13), (a11, b12, X14), (a11, b12, X15), (a11, b12, X16), (a11, b12, X17), (a11, b12, X18), (a11, b13, X1), (a11, b13, X2), (a11, b13, X3), (a11, b13, X4), (a11, b13, X5), (a11, b13, X6), (a11, b13, X7), (a11, b13, X8), (a11, b13, X9), (a11, b13, X10), (a11, b13, X11), (a11, b13, X12), (a11, b13, X13), (a11, b13, X14), (a11, b13, X15), (a11, b13, X16), (a11, b13, X17), (a11, b13, X18), (a11, b14, X1), (a11, b14, X2), (a11, b14, X3), (a11, b14, X4), (a11, b14, X5), (a11, b14, X6), (a11, b14, X7), (a11, b14, X8), (a11, b14, X9), (a11, b14, X10), (a11, b14, X11), (a11, b14, X12), (a11, b14, X13), (a11, b14, X14), (a11, b14, X15), (a11, b14, X16), (a11, b14, X17), (a11, b14, X18), (a11, b15, X1), (a11, b15, X2), (a11, b15, X3), (a11, b15, X4), (a11, b15, X5), (a11, b15, X6), (a11, b15, X7), (a11, b15, X8), (a11, b15, X9), (a11, b15, X10), (a11, b15, X11), (a11, b15, X12), (a11, b15, X13), (a11, b15, X14), (a11, b15, X15), (a11, b15, X16), (a11, b15, X17), (a11, b15, X18), (a11, b16, X1), (a11, b16, X2), (a11, b16, X3), (a11, b16, X4), (a11, b16, X5), (a11, b16, X6), (a11, b16, X7), (a11, b16, X8), (a11, b16, X9), (a11, b16, X10), (a11, b16, X11), (a11, b16, X12), (a11, b16, X13), (a11, b16, X14), (a11, b16, X15), (a11, b16, X16), (a11, b16, X17), (a11, b16, X18), (a11, b17, X1), (a11, b17, X2), (a11, b17, X3), (a11, b17, X4), (a11, b17, X5), (a11, b17, X6), (a11, b17, X7), (a11, b17, X8), (a11, b17, X9), (a11, b17, X10), (a11, b17, X11), (a11, b17, X12), (a11, b17, X13), (a11, b17, X14), (a11, b17, X15), (a11, b17, X16), (a11, b17, X17), (a11, b17, X18), (a11, b18, X1), (a11, b18, X2), (a11, b18, X3), (a11, b18, X4), (a11, b18, X5), (a11, b18, X6), (a11, b18, X7), (a11, b18, X8), (a11, b18, X9), (a11, b18, X10), (a11, b18, X11), (a11, b18, X12), (a11, b18, X13), (a11, b18, X14), (a11, b18, X15), (a11, b18, X16), (a11, b18, X17), (a11, b18, X18), (a11, b19, X1), (a11, b19, X2), (a11, b19, X3), (a11, b19, X4), (a11, b19, X5), (a11, b19, X6), (a11, b19, X7), (a11, b19, X8), (a11, b19, X9), (a11, b19, X10), (a11, b19, X11), (a11, b19, X12), (a11, b19, X13), (a11, b19, X14), (a11, b19, X15), (a11, b19, X16), (a11, b19, X17), (a11, b19, X18), (a11, b20, X1), (a11, b20, X2), (a11, b20, X3), (a11, b20, X4), (a11, b20, X5), (a11, b20, X6), (a11, b20, X7), (a11, b20, X8), (a11, b20, X9), (a11, b20, X10), (a11, b20, X11), (a11, b20, X12), (a11, b20, X13), (a11, b20, X14), (a11, b20, X15), (a11, b20, X16), (a11, b20, X17), (a11, b20, X18), (a11, b21, X1), (a11, b21, X2), (a11, b21, X3), (a11, b21, X4), (a11, b21, X5), (a11, b21, X6), (a11, b21, X7), (a11, b21, X8), (a11, b21, X9), (a11, b21, X10), (a11, b21, X11), (a11, b21, X12), (a11, b21, X13), (a11, b21, X14), (a11, b21, X15), (a11, b21, X16), (a11, b21, X17), (a11, b21, X18), (a11, b22, X1), (a11, b22, X2), (a11, b22, X3), (a11, b22, X4), (a11, b22, X5), (a11, b22, X6), (a11, b22, X7), (a11, b22, X8), (a11, b22, X9), (a11, b22, X10), (a11, b22, X11), (a11, b22, X12), (a11, b22, X13), (a11, b22, X14), (a11, b22, X15), (a11, b22, X16), (a11, b22, X17), (a11, b22, X18), (a11, b23, X1), (a11, b23, X2), (a11, b23, X3), (a11, b23, X4), (a11, b23, X5), (a11, b23, X6), (a11, b23, X7), (a11, b23, X8), (a11, b23, X9), (a11, b23, X10), (a11, b23, X11), (a11, b23, X12), (a11, b23, X13), (a11, b23, X14), (a11, b23, X15), (a11, b23, X16), (a11, b23, X17), (a11, b23, X18), (a11, b24, X1), (a11, b24, X2), (a11, b24, X3), (a11, b24, X4), (a11, b24, X5), (a11, b24, X6), (a11, b24, X7), (a11, b24, X8), (a11, b24, X9), (a11, b24, X10), (a11, b24, X11), (a11, b24, X12), (a11, b24, X13), (a11, b24, X14), (a11, b24, X15), (a11, b24, X16), (a11, b24, X17), (a11, b24, X18), (a11, b25, X1), (a11, b25, X2), (a11, b25, X3), (a11, b25, X4), (a11, b25, X5), (a11, b25, X6), (a11, b25, X7), (a11, b25, X8), (a11, b25, X9), (a11, b25, X10), (a11, b25, X11), (a11, b25, X12), (a11, b25, X13), (a11, b25, X14), (a11, b25, X15), (a11, b25, X16), (a11, b25, X17), (a11, b25, X18), (a11, b26, X1), (a11, b26, X2), (a11, b26, X3), (a11, b26, X4), (a11, b26, X5), (a11, b26, X6), (a11, b26, X7), (a11, b26, X8), (a11, b26, X9), (a11, b26, X10), (a11, b26, X11), (a11, b26, X12), (a11, b26, X13), (a11, b26, X14), (a11, b26, X15), (a11, b26, X16), (a11, b26, X17), (a11, b26, X18), (a11, b27, X1), (a11, b27, X2), (a11, b27, X3), (a11, b27, X4), (a11, b27, X5), (a11, b27, X6), (a11, b27, X7), (a11, b27, X8), (a11, b27, X9), (a11, b27, X10), (a11, b27, X11), (a11, b27, X12), (a11, b27, X13), (a11, b27, X14), (a11, b27, X15), (a11, b27, X16), (a11, b27, X17), (a11, b27, X18), (a12, b1, X1), (a12, b1, X2), (a12, b1, X3), (a12, b1, X4), (a12, b1, X5), (a12, b1, X6), (a12, b1, X7), (a12, b1, X8), (a12, b1, X9), (a12, b1, X10), (a12, b1, X11), (a12, b1, X12), (a12, b1, X13), (a12, b1, X14), (a12, b1, X15), (a12, b1, X16), (a12, b1, X17), (a12, b1, X18), (a12, b2, X1), (a12, b2, X2), (a12, b2, X3), (a12, b2, X4), (a12, b2, X5), (a12, b2, X6), (a12, b2, X7), (a12, b2, X8), (a12, b2, X9), (a12, b2, X10), (a12, b2, X11), (a12, b2, X12), (a12, b2, X13), (a12, b2, X14), (a12, b2, X15), (a12, b2, X16), (a12, b2, X17), (a12, b2, X18), (a12, b3, X1), (a12, b3, X2), (a12, b3, X3), (a12, b3, X4), (a12, b3, X5), (a12, b3, X6), (a12, b3, X7), (a12, b3, X8), (a12, b3, X9), (a12, b3, X10), (a12, b3, X11), (a12, b3, X12), (a12, b3, X13), (a12, b3, X14), (a12, b3, X15), (a12, b3, X16), (a12, b3, X17), (a12, b3, X18), (a12, b4, X1), (a12, b4, X2), (a12, b4, X3), (a12, b4, X4), (a12, b4, X5), (a12, b4, X6), (a12, b4, X7), (a12, b4, X8), (a12, b4, X9), (a12, b4, X10), (a12, b4, X11), (a12, b4, X12), (a12, b4, X13), (a12, b4, X14), (a12, b4, X15), (a12, b4, X16), (a12, b4, X17), (a12, b4, X18), (a12, b5, X1), (a12, b5, X2), (a12, b5, X3), (a12, b5, X4), (a12, b5, X5), (a12, b5, X6), (a12, b5, X7), (a12, b5, X8), (a12, b5, X9), (a12, b5, X10), (a12, b5, X11), (a12, b5, X12), (a12, b5, X13), (a12, b5, X14), (a12, b5, X15), (a12, b5, X16), (a12, b5, X17), (a12, b5, X18), (a12, b6, X1), (a12, b6, X2), (a12, b6, X3), (a12, b6, X4), (a12, b6, X5), (a12, b6, X6), (a12, b6, X7), (a12, b6, X8), (a12, b6, X9), (a12, b6, X10), (a12, b6, X11), (a12, b6, X12), (a12, b6, X13), (a12, b6, X14), (a12, b6, X15), (a12, b6, X16), (a12, b6, X17), (a12, b6, X18), (a12, b7, X1), (a12, b7, X2), (a12, b7, X3), (a12, b7, X4), (a12, b7, X5), (a12, b7, X6), (a12, b7, X7), (a12, b7, X8), (a12, b7, X9), (a12, b7, X10), (a12, b7, X11), (a12, b7, X12), (a12, b7, X13), (a12, b7, X14), (a12, b7, X15), (a12, b7, X16), (a12, b7, X17), (a12, b7, X18), (a12, b8, X1), (a12, b8, X2), (a12, b8, X3), (a12, b8, X4), (a12, b8, X5), (a12, b8, X6), (a12, b8, X7), (a12, b8, X8), (a12, b8, X9), (a12, b8, X10), (a12, b8, X11), (a12, b8, X12), (a12, b8, X13), (a12, b8, X14), (a12, b8, X15), (a12, b8, X16), (a12, b8, X17), (a12, b8, X18), (a12, b9, X1), (a12, b9, X2), (a12, b9, X3), (a12, b9, X4), (a12, b9, X5), (a12, b9, X6), (a12, b9, X7), (a12, b9, X8), (a12, b9, X9), (a12, b9, X10), (a12, b9, X11), (a12, b9, X12), (a12, b9, X13), (a12, b9, X14), (a12, b9, X15), (a12, b9, X16), (a12, b9, X17), (a12, b9, X18), (a12, b10, X1), (a12, b10, X2), (a12, b10, X3), (a12, b10, X4), (a12, b10, X5), (a12, b10, X6), (a12, b10, X7), (a12, b10, X8), (a12, b10, X9), (a12, b10, X10), (a12, b10, X11), (a12, b10, X12), (a12, b10, X13), (a12, b10, X14), (a12, b10, X15), (a12, b10, X16), (a12, b10, X17), (a12, b10, X18), (a12, b11, X1), (a12, b11, X2), (a12, b11, X3), (a12, b11, X4), (a12, b11, X5), (a12, b11, X6), (a12, b11, X7), (a12, b11, X8), (a12, b11, X9), (a12, b11, X10), (a12, b11, X11), (a12, b11, X12), (a12, b11, X13), (a12, b11, X14), (a12, b11, X15), (a12, b11, X16), (a12, b11, X17), (a12, b11, X18), (a12, b12, X1), (a12, b12, X2), (a12, b12, X3), (a12, b12, X4), (a12, b12, X5), (a12, b12, X6), (a12, b12, X7), (a12, b12, X8), (a12, b12, X9), (a12, b12, X10), (a12, b12, X11), (a12, b12, X12), (a12, b12, X13), (a12, b12, X14), (a12, b12, X15), (a12, b12, X16), (a12, b12, X17), (a12, b12, X18), (a12, b13, X1), (a12, b13, X2), (a12, b13, X3), (a12, b13, X4), (a12, b13, X5), (a12, b13, X6), (a12, b13, X7), (a12, b13, X8), (a12, b13, X9), (a12, b13, X10), (a12, b13, X11), (a12, b13, X12), (a12, b13, X13), (a12, b13, X14), (a12, b13, X15), (a12, b13, X16), (a12, b13, X17), (a12, b13, X18), (a12, b14, X1), (a12, b14, X2), (a12, b14, X3), (a12, b14, X4), (a12, b14, X5), (a12, b14, X6), (a12, b14, X7), (a12, b14, X8), (a12, b14, X9), (a12, b14, X10), (a12, b14, X11), (a12, b14, X12), (a12, b14, X13), (a12, b14, X14), (a12, b14, X15), (a12, b14, X16), (a12, b14, X17), (a12, b14, X18), (a12, b15, X1), (a12, b15, X2), (a12, b15, X3), (a12, b15, X4), (a12, b15, X5), (a12, b15, X6), (a12, b15, X7), (a12, b15, X8), (a12, b15, X9), (a12, b15, X10), (a12, b15, X11), (a12, b15, X12), (a12, b15, X13), (a12, b15, X14), (a12, b15, X15), (a12, b15, X16), (a12, b15, X17), (a12, b15, X18), (a12, b16, X1), (a12, b16, X2), (a12, b16, X3), (a12, b16, X4), (a12, b16, X5), (a12, b16, X6), (a12, b16, X7), (a12, b16, X8), (a12, b16, X9), (a12, b16, X10), (a12, b16, X11), (a12, b16, X12), (a12, b16, X13), (a12, b16, X14), (a12, b16, X15), (a12, b16, X16), (a12, b16, X17), (a12, b16, X18), (a12, b17, X1), (a12, b17, X2), (a12, b17, X3), (a12, b17, X4), (a12, b17, X5), (a12, b17, X6), (a12, b17, X7), (a12, b17, X8), (a12, b17, X9), (a12, b17, X10), (a12, b17, X11), (a12, b17, X12), (a12, b17, X13), (a12, b17, X14), (a12, b17, X15), (a12, b17, X16), (a12, b17, X17), (a12, b17, X18), (a12, b18, X1), (a12, b18, X2), (a12, b18, X3), (a12, b18, X4), (a12, b18, X5), (a12, b18, X6), (a12, b18, X7), (a12, b18, X8), (a12, b18, X9), (a12, b18, X10), (a12, b18, X11), (a12, b18, X12), (a12, b18, X13), (a12, b18, X14), (a12, b18, X15), (a12, b18, X16), (a12, b18, X17), (a12, b18, X18), (a12, b19, X1), (a12, b19, X2), (a12, b19, X3), (a12, b19, X4), (a12, b19, X5), (a12, b19, X6), (a12, b19, X7), (a12, b19, X8), (a12, b19, X9), (a12, b19, X10), (a12, b19, X11), (a12, b19, X12), (a12, b19, X13), (a12, b19, X14), (a12, b19, X15), (a12, b19, X16), (a12, b19, X17), (a12, b19, X18), (a12, b20, X1), (a12, b20, X2), (a12, b20, X3), (a12, b20, X4), (a12, b20, X5), (a12, b20, X6), (a12, b20, X7), (a12, b20, X8), (a12, b20, X9), (a12, b20, X10), (a12, b20, X11), (a12, b20, X12), (a12, b20, X13), (a12, b20, X14), (a12, b20, X15), (a12, b20, X16), (a12, b20, X17), (a12, b20, X18), (a12, b21, X1), (a12, b21, X2), (a12, b21, X3), (a12, b21, X4), (a12, b21, X5), (a12, b21, X6), (a12, b21, X7), (a12, b21, X8), (a12, b21, X9), (a12, b21, X10), (a12, b21, X11), (a12, b21, X12), (a12, b21, X13), (a12, b21, X14), (a12, b21, X15), (a12, b21, X16), (a12, b21, X17), (a12, b21, X18), (a12, b22, X1), (a12, b22, X2), (a12, b22, X3), (a12, b22, X4), (a12, b22, X5), (a12, b22, X6), (a12, b22, X7), (a12, b22, X8), (a12, b22, X9), (a12, b22, X10), (a12, b22, X11), (a12, b22, X12), (a12, b22, X13), (a12, b22, X14), (a12, b22, X15), (a12, b22, X16), (a12, b22, X17), (a12, b22, X18), (a12, b23, X1), (a12, b23, X2), (a12, b23, X3), (a12, b23, X4), (a12, b23, X5), (a12, b23, X6), (a12, b23, X7), (a12, b23, X8), (a12, b23, X9), (a12, b23, X10), (a12, b23, X11), (a12, b23, X12), (a12, b23, X13), (a12, b23, X14), (a12, b23, X15), (a12, b23, X16), (a12, b23, X17), (a12, b23, X18), (a12, b24, X1), (a12, b24, X2), (a12, b24, X3), (a12, b24, X4), (a12, b24, X5), (a12, b24, X6), (a12, b24, X7), (a12, b24, X8), (a12, b24, X9), (a12, b24, X10), (a12, b24, X11), (a12, b24, X12), (a12, b24, X13), (a12, b24, X14), (a12, b24, X15), (a12, b24, X16), (a12, b24, X17), (a12, b24, X18), (a12, b25, X1), (a12, b25, X2), (a12, b25, X3), (a12, b25, X4), (a12, b25, X5), (a12, b25, X6), (a12, b25, X7), (a12, b25, X8), (a12, b25, X9), (a12, b25, X10), (a12, b25, X11), (a12, b25, X12), (a12, b25, X13), (a12, b25, X14), (a12, b25, X15), (a12, b25, X16), (a12, b25, X17), (a12, b25, X18), (a12, b26, X1), (a12, b26, X2), (a12, b26, X3), (a12, b26, X4), (a12, b26, X5), (a12, b26, X6), (a12, b26, X7), (a12, b26, X8), (a12, b26, X9), (a12, b26, X10), (a12, b26, X11), (a12, b26, X12), (a12, b26, X13), (a12, b26, X14), (a12, b26, X15), (a12, b26, X16), (a12, b26, X17), (a12, b26, X18), (a12, b27, X1), (a12, b27, X2), (a12, b27, X3), (a12, b27, X4), (a12, b27, X5), (a12, b27, X6), (a12, b27, X7), (a12, b27, X8), (a12, b27, X9), (a12, b27, X10), (a12, b27, X11), (a12, b27, X12), (a12, b27, X13), (a12, b27, X14), (a12, b27, X15), (a12, b27, X16), (a12, b27, X17), (a12, b27, X18).

Since the compound (I) has high affinity for the NMDA receptor, particularly, NR1/NR2B receptor, and has high subtype selectivity, and high selectivity for other receptor, it can be a medicament with the reduced side effect (e.g. influence on motion function). In addition, the compound (I) also has an advantage that stability is high, oral absorbability is high, good bioavailability is exhibited, clearance is low, brain transferability is high, a half life is long, a non-protein binding rate is high, drug efficacy sustainability is high, and/or the liver enzyme inhibiting activity is low.

The compound (I) can be orally or parenterally administered to an animal including a human, as a medicament, particularly, as a preventive/remedy for various central diseases resulting from the NMDA receptor, particularly the $NR^1$/NR2B receptor (e.g. cerebral stroke, cerebral infarction, brain trauma, chronic neurodegenerative diseases), or as an analgesic for cancer pain. Examples of a dosage form include granules, tablets, capsules, injectables and the like. Upon formulation into preparations, if desired, various additives, for example, excipients, disintegrating agents, binders, lubricants, stabilizers, coloring agents, and coating agents can be used. A dose is different depending on an age, a weight and condition of a subject, and an administration method, and is not particularly limited, but usually, is about 1 mg to about 5000 mg in the case of oral administration, and about 0.1 mg to about 1000 mg in the case of parenteral administration, per adult one day.

The present invention will be explained in more detail below by way of Examples, but the present invention is not limited by these Examples. A melting point described in the text is an uncorrected value. In addition, $^1$H-NMR was measured in a solvent of deuterium chloroform (CDCl$_3$) or deuterium dimethyl sulfoxide (DMSO-d$_6$) using tetramethylsilane as an internal standard. A δ value is expressed in ppm, and a binding constant (J) is expressed in Hz. In data, s means singlet, d means doublet, t means triplet, q means quartet, m means multiplet, br means broad, and brs means broad singlet.

Each abbreviation has the following meaning.

THF: Tetrahydrofuran

DMF: N,N-dimethylformamide

HOBt: 1-Hydroxybenzotriazole

DMAP: 4-Dimethylaminopyridine

EDC: 1-(3-Dimethylaminopropyl)-3-ethylcarbodiimide hydrochloride

IBX: 1-Hydroxy-1,2-benziodooxol-3(1H)-one 1-oxide

Me: Methyl

Et: Ethyl

Bu$^t$: tert-Butyl

Ts: p-Toluenesulfonyl

BINAP: 2,2'-Bis(diphenylphosphino)-1,1'-binaphthyl

Pd$_2$(dba)$_3$: Bis(dibenzylideneacetone)palladium(0)

DMPO: 1,3-Dimethyl-3,4,5,6-tetrahydro-2(1H)-pyrimidinone

MOM: Methoxymethyl

REFERENCE EXAMPLE 1

Synthesis of Compound 3

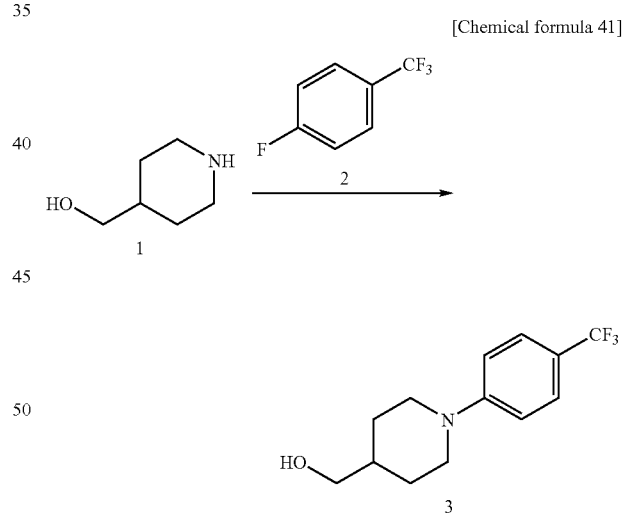

[Chemical formula 41]

Under the nitrogen atmosphere, Compound 1 (576 mg, 5.0 mmol) and Compound 2 (985 mg, 6.0 mmol) were dissolved in DMF (5 ml), potassium carbonate (829 mg, 6.0 mmol) was added, and the mixture was stirred at 120° C. for 24 hours. The solvent was distilled off, and water was added to the residue, followed by extraction with chloroform. After dried with anhydrous magnesium sulfate, the solvent was distilled off under reduced pressure, and the resulting residue was purified by silica gel column chromatography (chloroform/acetonitrile) to obtain Compound 3 (671 mg, yield 52%).

$^1$H-NMR (CDCl$_3$/TMS) δppm: 1.40-1.50 (br, 3H), 1.74 (m, 2H), 1.88 (d, J=12.3 Hz, 2H), 2.85 (t, J=12.3 Hz, 2H), 3.56 (d, J=4.2 Hz, 2H), 3.83 (d, J=12.3 Hz, 2H), 7.00 (br, 2H), 7.48 (d, J=9.0 Hz, 2H).

REFERENCE EXAMPLE 2

Synthesis of Compound 5

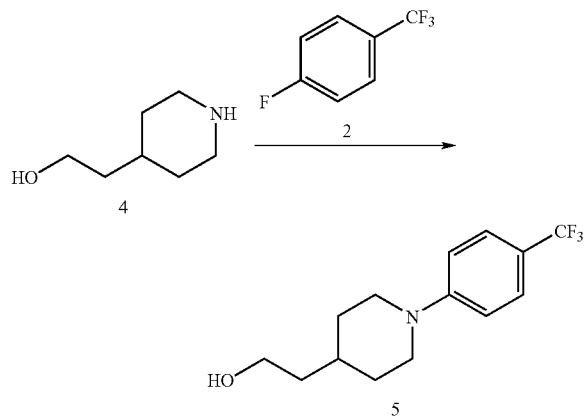

[Chemical formula 42]

According to the same manner as that of Reference Example 1 except that Compound 4 was used in place of Compound 1, a reaction was performed to obtain Compound 5 (yield 47%).

$^1$H-NMR (CDCl$_3$/TMS) δppm: 1.26-1.39 (m, 2H), 1.56 (q, J=6.6 Hz, 2H), 1.64-1.69 (m, 1H), 1.83 (d, J=12.6 Hz, 2H), 2.87 (t, J=12.6 Hz, 2H), 3.71-3.81 (m, 4H), 6.93 (d, J=8.7 Hz, 2H), 7.46 (d, J=8.7 Hz, 2H).

REFERENCE EXAMPLE 3

Synthesis of Compound 7

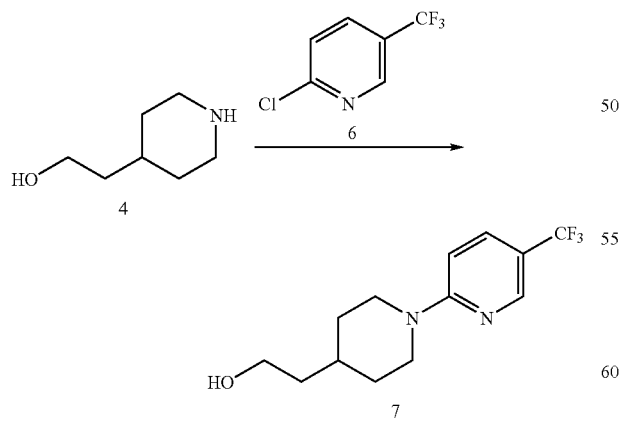

[Chemical formula 43]

Compound 4 (646 mg, 5.0 mmol) and Compound 6 (908 mg, 5.0 mmol) were dissolved in DMF (15 ml), sodium bicarbonate (504 mg, 6.0 mmol) was added, and the mixture was stirred at 80° C. for 2 hours. After cooling, water was added, followed by extraction with ethyl acetate. The organic layer was washed with an aqueous saturated sodium chloride solution, and dried with anhydrous magnesium sulfate, and the solvent was distilled off under reduced pressure. The resulting residue was purified by silica gel column chromatography (hexane/ethyl acetate) to obtain Compound 7 (1.08 g, yield 78%).

$^1$H-NMR (CDCl$_3$/TMS) δppm: 1.16-1.32 (m, 3H), 1.50-1.60 (m, 2H), 1.68-1.86 (m, 3H), 2.84-2.97 (m, 2H), 3.69-3.78 (m, 2H), 4.34-4.44 (m, 2H), 6.63 (d, J=9.0 Hz, 1H), 7.59 (dd, J=9.0, 1.5 Hz, 1H), 8.37 (d, J=1.5 Hz, 1H).

REFERENCE EXAMPLE 4

Synthesis of Compound 10

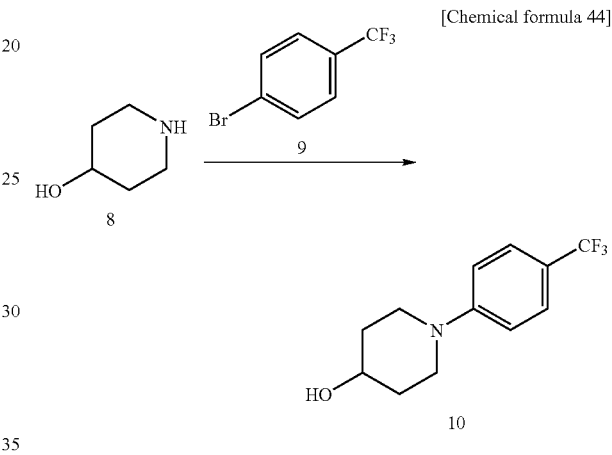

[Chemical formula 44]

Under the nitrogen atmosphere, toluene was added to BINAP (187 mg, 0.3 mmol), Pd$_2$(dba)$_3$ (92 mg, 0.1 mmol), sodium tert-butoxide (1.19 g, 12.0 mmol), Compound 8 (1.14 g, 11.2 mmol), and Compound 9 (1.36 ml, 10.0 mmol) to react them at 120° C. for 1 hour under microwave irradiation. The reaction solution was filtered using Celite, and the solid was washed with ethyl acetate. The filtrate and the washing solution were combined, and concentrated under reduced pressure, and the resulting residue was purified by silica gel column chromatography (hexane-ethyl acetate) to obtain Compound 10 (1.45 g, yield 59%).

mp 97-98° C.

$^1$H-NMR (CDCl$_3$/TMS) δppm: 1.49-1.56 (m, 2H), 1.62-1.74 (m, 2H), 2.03 (brs, 2H), 3.03-3.10 (m, 2H), 3.63-3.71 (m, 2H), 3.93 (brs, 1H), 6.97 (br, 2H), 7.48 (d, J=8.7 Hz, 2H).

REFERENCE EXAMPLE 5

Synthesis of Compound 12

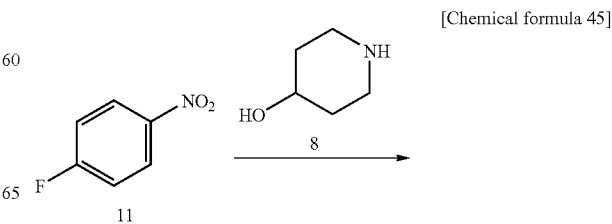

[Chemical formula 45]

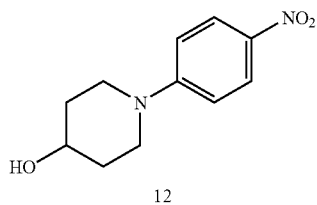

Compound 11 (2.12 g, 15.0 mmol) and Compound 8 (1.82 g, 18.0 mmol) were dissolved in DMF (15 ml), potassium carbonate (2.52 g, 18.0 mmol) was added, and the mixture was stirred at 85° C. for 1 hour. The solvent was distilled off under reduced pressure, water was added to the residue, followed by extraction with chloroform. After dried with anhydrous magnesium sulfate, the solvent was distilled off under reduced pressure, and the resulting residue was purified by silica gel column chromatography (chloroform-acetonitrile) to obtain Compound 12 (3.10 g, yield 93%).

mp 115.6-117° C.

$^1$H-NMR (CDCl$_3$/TMS) δppm: 1.62-1.74 (m, 2H), 1.99-2.02 (m, 2H), 2.87-2.95 (m, 2H), 3.47-3.54 (m, 2H), 3.82-3.88 (m, 1H), 6.85 (d, J=8.7 Hz, 2H), 7.19 (d, J=8.7 Hz, 2H).

REFERENCE EXAMPLE 6

Synthesis of Compound 13

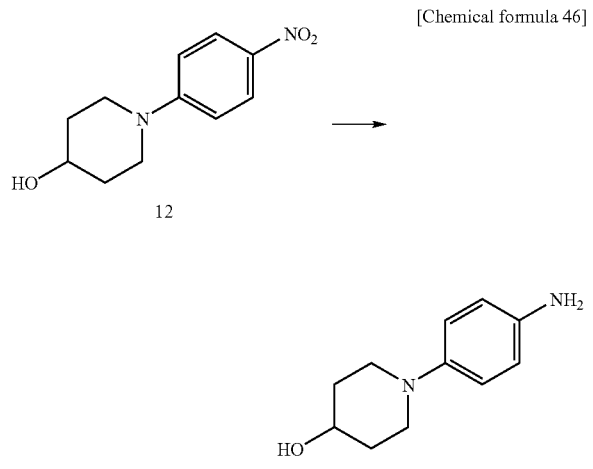

[Chemical formula 46]

Compound 12 (1.50 g, 6.75 mmol) was dissolved in methanol (25 ml), 10% palladium-carbon (150 mg) was added, and the interior of the system was replaced with a hydrogen gas. After stirred at room temperature for 2 hours, the reaction solution was filtered using Celite, and washed with methanol. The filtrate, and the washing solution were combined, and the solvent was distilled off under reduced pressure to obtain Compound 13 (1.28 g, yield 99%).

$^1$H-NMR (CDCl$_3$/TMS) δppm: 1.70-1.80 (m, 2H), 2.07 (br, 2H), 2.84 (br, 2H), 3.37 (br, 3H), 3.85 (br, 1H), 6.65 (d, J=8.4 Hz, 2H), 6.91 (br, 2H).

REFERENCE EXAMPLE 7

Synthesis of Compound 14

[Chemical formula 47]

Compound 13 (1.28 g, 6.66 mmol) was dissolved in 6 mol/L hydrochloric acid (26 ml), and the solution was cooled to −35 to −40° C. with a dry ice-acetone bath. An aqueous solution (5 ml) of sodium nitrite (482 mg, 6.99 mmol) was added dropwise, and this was stirred at −35° C. to −40° C. for 30 minutes. Urea (199 mg, 1.67 mmol), cuprous chloride (725 mg, 7.32 mmol), cupric chloride (985 mg, 7.32 mmol) were added, and the mixture was stirred at 60° C. for 45 minutes. This was cooled with a water bath, aqueous ammonia was added to alkaline, chloroform was added, and insolubles were filtered off using Celite. The filtrate was extracted with chloroform, and the organic layer was washed with water, dried with anhydrous magnesium sulfate, and the solvent was distilled off under reduced pressure. The resulting residue was purified by silica gel column chromatography (chloroform-methanol) to obtain Compound 14 (1.32 g, yield 94%).

$^1$H-NMR (CDCl$_3$/TMS) δppm: 1.62-1.74 (m, 2H), 1.99-2.02 (m, 2H), 2.87-2.95 (m, 2H), 3.47-3.54 (m, 2H), 3.82-3.88 (m, 1H), 6.85 (d, J=8.7 Hz, 2H), 7.19 (d, J=8.7 Hz, 2H).

REFERENCE EXAMPLE 8

Synthesis of Compound 15

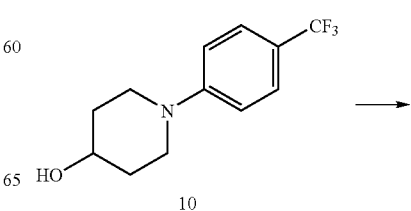

[Chemical formula 48]

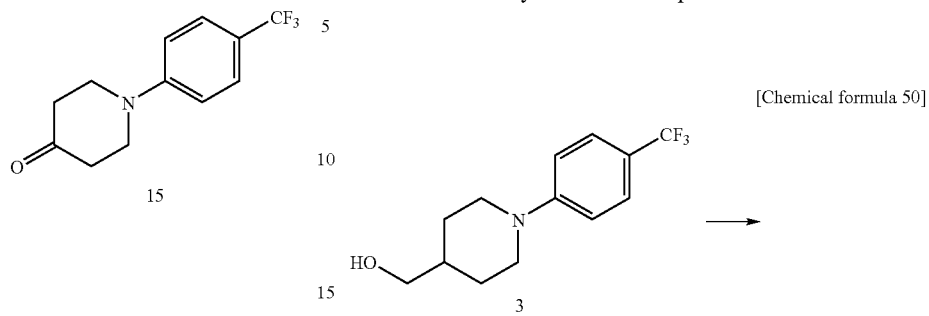

Compound 10 (1.50 g, 6.12 mmol) was dissolved in ethyl acetate (45 ml), IBX (5.14 g, 18.4 mmol) was added, and the mixture was stirred at 80° C. for 8 hours. This was cooled with an ice bath, and the precipitated solid was filtered off, and washed with ethyl acetate. The filtrate, and the washing solution were combined, and concentrated under reduced pressure, and the resulting residue was purified by silica gel column chromatography (chloroform) to obtain Compound 15 (1.34 g, yield 90%).

$^1$H-NMR (CDCl$_3$/TMS) δppm: 2.57 (t, J=6.3 Hz, 4H), 3.71 (t, J=6.3 Hz, 4H), 6.97 (d, J=8.7 Hz, 2H), 7.52 (d, J=8.7 Hz, 2H).

REFERENCE EXAMLE 9

Synthesis of Compound 16

[Chemical formula 49]

According to the same manner as that of Reference Example 8 except that Compound 14 was used in place of Compound 10, a reaction was performed to obtain Compound 16 (yield 92%).

$^1$H-NMR (CDCl$_3$/TMS) δppm: 2.57 (t, J=6.0 Hz, 4H), 3.58 (t, J=6.0 Hz, 4H), 6.91 (d, J=9.0 Hz, 2H), 7.24 (d, J=9.0 Hz, 2H).

REFERENCE EXAMPLE 10

Synthesis of Compound 17

[Chemical formula 50]

According to the same manner as that of Reference Example 8 except that Compound 3 was used in place of Compound 10, a reaction was performed to obtain Compound 17 (yield 79%).

$^1$H-NMR (CDCl$_3$/TMS) δppm: 1.72-1.85 (m, 2H), 2.01-2.09 (m, 2H), 2.43-2.52 (m, 1H), 2.95-3.04 (m, 2H), 3.69-3.76 (m, 2H), 6.94 (d, J=8.7 Hz, 2H), 7.48 (d, J=8.7 Hz, 2H), 9.71 (s, 1H).

REFERENCE EXAMPLE 11

Synthesis of Compound 19

[Chemical formula 51]

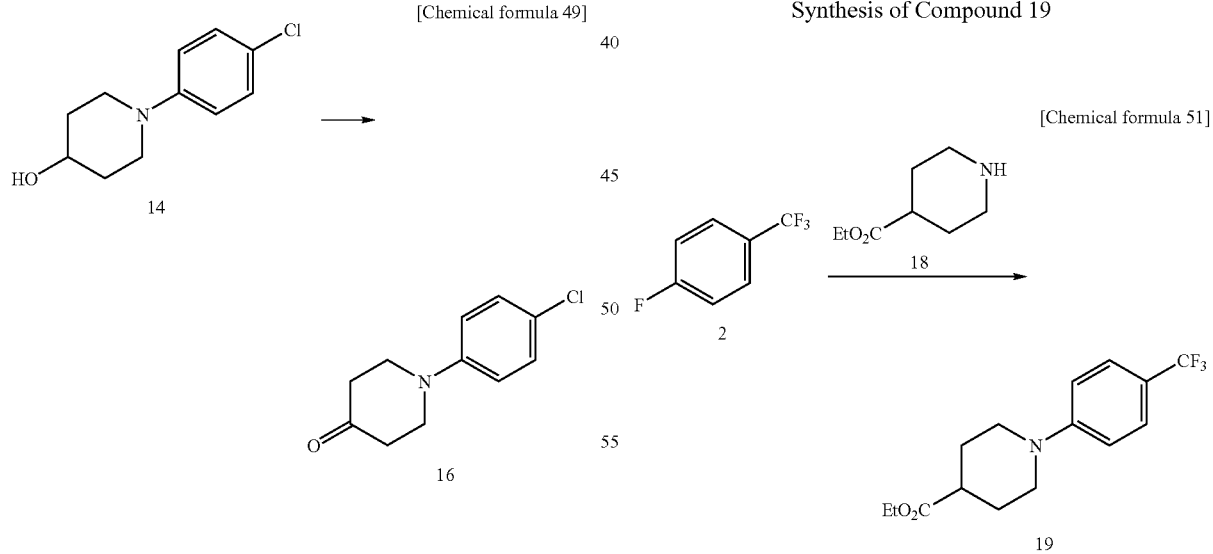

Compound 2 (3.28 g, 20.0 mmol) and Compound 18 (3.77 g, 24.0 mmol) were dissolved in DMF (10 ml), potassium carbonate (3.32 g, 24.0 mmol) was added, and the mixture was stirred at 120° C. for 24 hours. The solvent was distilled off under reduced pressure, and water was added to the residue, followed by extraction with toluene. The organic layer was washed with water, and dried with anhydrous magnesium sulfate, and the solvent was distilled off under reduced pressure. The resulting residue was purified by silica gel column chromatography (toluene-ethyl acetate) to obtain Compound 19 (2.35 g, yield 39%).

$^1$H-NMR (CDCl$_3$/TMS) δppm: 1.27 (t, J=7.1 Hz, 3H), 1.76-1.92 (m, 2H), 1.97-2.08 (m, 2H), 2.42-2.54 (m, 1H), 2.84-2.96 (m, 2H), 3.70-3.79 (m, 2H), 4.16 (q, J=7.1 Hz, 2H), 6.92 (d, J=9.0 Hz, 2H), 7.46 (d, J=9.0 Hz, 2H).

REFERENCE EXAMPLE 12

Synthesis of Compound 21

[Chemical formula 52]

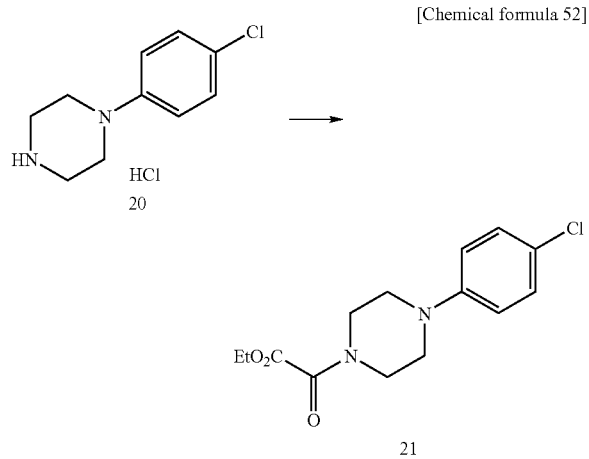

1-(4-Chlorophenyl)piperazine hydrochloride 20 (1.00 g, 4.3 mmol) was dissolved in toluene (5 ml), and the solution was cooled with an ice bath. A solution of ethyl chloroglyoxylate (0.64 g, 4.7 mmol) in toluene (2 ml) was added dropwise, and the mixture was stirred at 0° C. for 0.5 hour. The reaction solution was extracted with ethyl acetate, The organic layer was washed with an aqueous saturated sodium chloride solution, and dried with amhydrous magnesium sulfate. The solvent was distilled off under reduced pressure to obtain Compound 21 (1.27 g, yield 100%).

$^1$H-NMR (CDCl$_3$/TMS) δppm: 1.38 (t, J=7.1 Hz, 3H), 3.15-3.20 (m, 4H), 3.60 (t, J=5.2 Hz, 2H), 3.78 (t, J=5.2 Hz, 2H), 4.36 (q, J=7.1 Hz, 2H), 6.84 (d, J=9.1 Hz, 2H), 7.22 (d, J=9.1 Hz, 2H).

REFERENCE EXAMPLE 13

Synthesis of Compound 24

[Chemical formula 53]

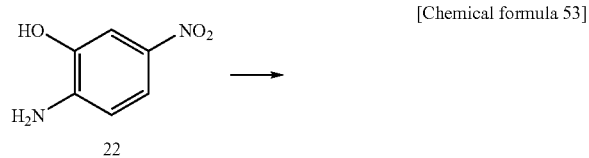

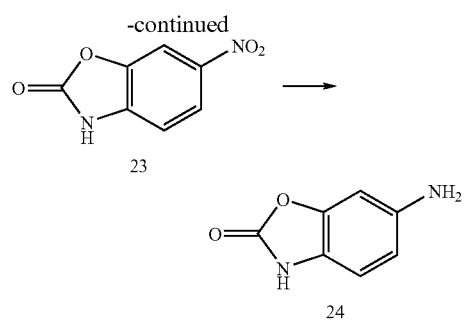

a) Synthesis of Compound 23

2-Amino-5-nitrophenol 22 (22.20 g, 144 mmol) was dissolved in THF (100 ml), and the interior of the system was replaced with a nitrogen gas, and cooled with an ice bath. A suspension (100 ml) of 1,1'-carbonyldiimidazole (28.03 g, 173 mmol) in THF was added in portions at 0 to 5° C., and the mixture was stirred at room temperature for 15 hours. The solvent was distilled off under reduced pressure, water (144 ml) was added to the residue, this was cooled with an ice bath, 2 mol/L hydrochloric acid (144 ml, 288 mmol) was added, and the mixture was stirred at room temperature for 3 hours. The precipitated solid was collected by filtration, washed with water, and dried to obtain Compound 23 (25.81 g, yield 99%).

$^1$H-NMR (DMSO-d$_6$/TMS) δppm: 7.28 (d, J=8.6 Hz, 1H), 8.13 (dd, J=2.0, 8.6 Hz, 1H), 8.19 (d, J=2.0 Hz, 1H), 12.43 (brs, 1H).

b) Synthesis of Compound 24

Compound 23 (40.00 g, 222 mmol) was suspended in THF-water (9:1) mixed solution (400 ml), 10%-palladium-carbon (8.00 g, 53% water-containing product) was added, and the mixture was stirred at room temperature for 9 hours under the hydrogen atmosphere. The reaction solution was filtered using Celite, and the residue was washed with THF-water (9:1) mixed solution (500 ml). The filtrate and the washing solution were combined, and concentrated to 96 g under reduced pressure, water (100 ml) was added, and the solid was collected by filtration. The solid was washed with water, and dried to obtain Compound 24 (32.20 g, yield 97%).

$^1$H-NMR (DMSO-d$_6$/TMS) δppm: 5.01 (s, 1H), 6.35 (dd, J=2.0, 8.2 Hz, 1H), 6.50 (d, J=2.0 Hz, 1H), 6.74 (d, J=8.2 Hz, 1H), 11.03 (brs, 1H).

EXAMPLE 1

Synthesis of Compound (I-2)

[Chemical formula 54]

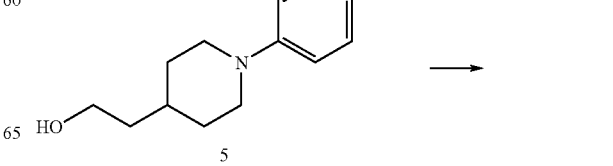

-continued

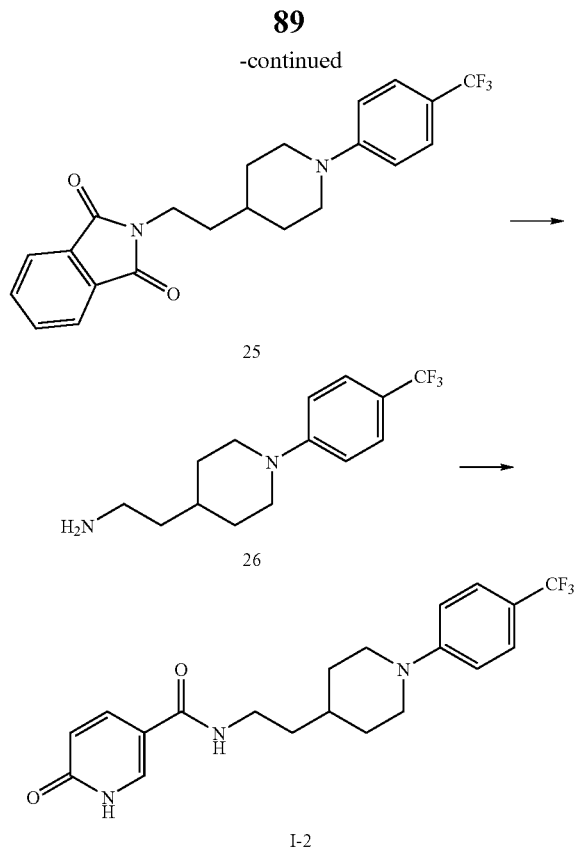

c) Synthesis of Compound (I-2)

To Compound 26 (276 mg, 1.01 mmol) were added DMF (5 ml), 6-hydroxynicotinic acid (155 mg, 1.11 mmol), HOBt (164 mg, 1.11 mmol, triethylamine (0.17 ml, 1.21 mmol), DMAP (6 mg, 0.05 mmol), and EDC (232 mg, 1.21 mmol), and the mixture was stirred at room temperature for 2 hours. The solvent was concentrated under reduced pressure, the resulting residue were added water, and 2 mol/L hydrochloric acid, followed by extraction with chloroform-methanol (9:1 mixed solution). The organic layer was washed with water, an aqueous saturated sodium bicarbonate solution, and water, and dried with anhydrous magnesium sulfate, and the solvent was distilled off under reduced pressure. The resulting residue was recrystallized from methanol-ethyl acetate to obtain Compound (I-2) (256 mg, yield 65%).

mp 232-233° C.

$^1$H-NMR (DMSO-$d_6$/TMS) δppm: 1.14-1.25 (m, 2H), 1.46 (t, J=6.9 Hz, 2H), 1.53 (brs, 1H), 1.77 (d, J=11.7 Hz, 2H), 2.77 (t, J=11.7 Hz, 2H), 3.26 (q, J=5.7 Hz, 2H), 3.85 (d, J=12.9 Hz, 2H), 6.34 (d, J=9.6 Hz, 1H), 7.03 (d, J=8.7 Hz, 2H), 7.46 (d, J=8.7 Hz, 2H), 7.85 (dd, J=9.6, 2.7 Hz, 1H), 7.97 (d, J=2.4 Hz, 1H), 8.19 (t, J=5.0 Hz, 1H), 11.93 (s, 1H).

EXAMPLE 2

Synthesis of Compound (I-7)

a) Synthesis of Compound 25

Under the nitrogen atmosphere, Compound 5 (339 mg, 1.46 mmol) obtained in Reference Example 2 was dissolved in THF (10 ml), phthalimide (279 mg, 1.90 mmol), triphenylphosphine (498 mg, 1.90 mmol), and diisopropyl azodicarboxylate (0.37 ml, 1.90 mmol) were added, and the mixture was stirred at room temperature for 1 hour.

The solvent was concentrated under reduced pressure, and the resulting residue was purified by silica gel column chromatography (toluene-ethyl acetate) to obtain Compound 25 (541 mg, yield 92%).

mp 203-205° C.

$^1$H-NMR (CDCl$_3$/TMS) δppm: 1.38-1.55 (m, 3H), 1.68 (q, J=6.6 Hz, 2H), 1.92 (d, J=9.9 Hz, 2H), 2.81 (t, J=11.4 Hz, 2H), 3.74-3.80 (m, 4H), 6.96 (br, 2H), 7.46 (d, J=9.0 Hz, 2H), 7.71-7.74 (m, 2H), 7.84-7.87 (m, 2H).

b) Synthesis of Compound 21

Compound 26 (537 ng, 1.33 mmol) was dissolved in ethanol (10 ml), hydrazine monohydrate (0.16 ml, 3.33 mmol) was added, and this was refluxed for 2 hours. After allowing to cool, the precipitated solid was filtered off. The filtrate and the solid were heated with chloroform-methanol (9:1 mixed solution), filtered, resulting filtrates were combined, and the solvent was distilled off under reduced pressure. To the residue was added a 1 mol/L aqueous sodium hydroxide solution added, and this was extracted with chloroform. The organic layer was washed with water, dried with anhydrous magnesium dulfate, the solvent was distilled off, and the resulting residue was purified by alumina column chromatography (chloroform-methanol) to obtain Compound 26 (280 mg, yield 77%).

$^1$H-NMR (CDCl$_3$/TMS) δppm: 1.27-1.40 (m, 2H), 1.46-1.60 (m, 3H), 1.79 (d, J=12.9 Hz, 2H), 2.13 (br, 5H), 2.74-2.85 (m, 4H), 3.78 (d, J=12.6 Hz, 2H), 6.91 (d, J=8.7 Hz, 2H), 7.45 (d, J=8.7 Hz, 2H).

[Chemical formula 55]

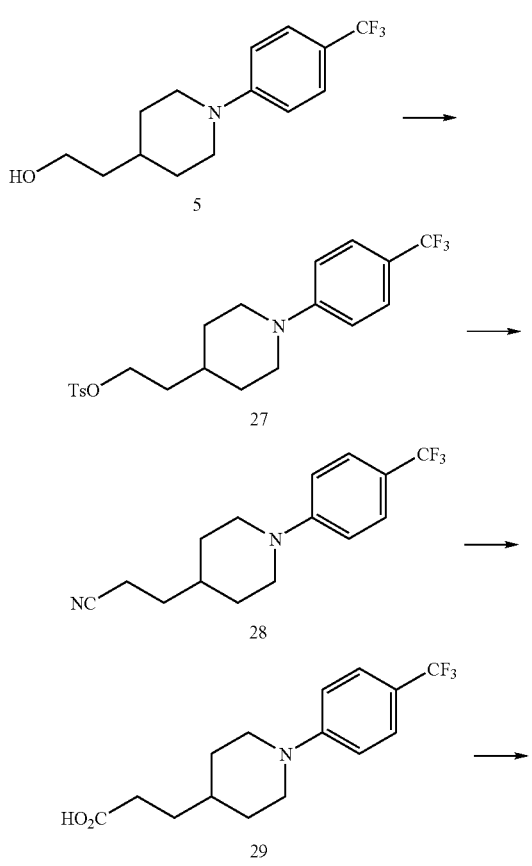

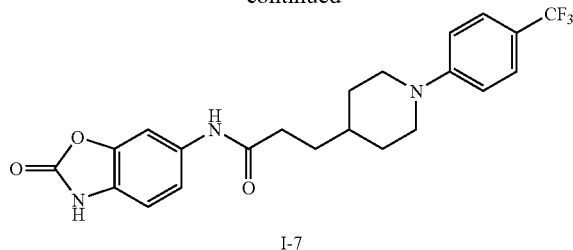

I-7 a) Synthesis of Compound 27

Under the nitrogen atmosphere, Compound 5 (1.37 g, 5.0 mmol) was dissolved in methylene chloride (15 ml), triethylamine (0.84 ml, 6.0 mmol) was added, and this was cooled with an ice bath. p-Toluenesulfonyl chloride (1.14 g, 6.0 mmol) was added, and the mixture was stirred at 0° C. for 45 minutes, and at room temperature for 3.5 hours. Aqueous ammonia was added, this was stirred for 15 minutes, and water was added, followed by extraction with chloroform. The organic layer was dried with anhydrous magnesium sulfate, the solvent was distilled off under reduced pressure, and the resulting residue was purified with silica gel column chromatography (chloroform) to obtain Compound 27 (1.74 g, yield 81%).

$^1$H-NMR (CDCl$_3$/TMS) δppm: 1.22-1.34 (br, 2H), 1.56-1.73 (m, 5H), 2.46 (s, 3H), 2.75 (t, J=11.7 Hz, 2H), 3.74 (d, J=12.6 Hz, 2H), 4.10 (t, J=6.0 Hz, 2H), 6.91 (d, J=8.4 Hz, 2H), 7.36 (d, J=8.4 Hz, 2H), 7.45 (d, J=8.4 Hz, 2H), 7.80 (d, J=8.4 Hz, 2H).

b) Synthesis of Compound 28

Under the nitrogen atmosphere, Compound 22 (1.74 g, 4.07 mmol) was dissolved in DMF (17 ml), sodium cyanide (299 mg, 6.11 mmol) was added, and the mixture was stirred at 60° C. for 5 hours. The solvent was distilled off under reduced pressure, and water was added to the resulting residue, followed by extraction with toluene. The organic layer was washed with water, dried with anhydrous magnesium sulfate, the solvent was distilled off under reduced pressure, and the resulting residue was purified by silica gel column chromatography (toluene-ethyl acetate) to obtain Compound 28 (1.07 g, yield 93%).

$^1$H-NMR (CDCl$_3$/TMS) δppm: 1.31-1.42 (m, 2H), 1.64-1.69 (m, 3H), 1.83 (d, J=13.2 Hz, 2H), 2.42 (t, J=6.9 Hz, 2H), 2.78-2.87 (m, 2H), 3.81 (d, J=13.2 Hz, 2H), 6.93 (d, J=8.4 Hz, 2H), 7.47 (d, J=8.4 Hz, 2H).

c) Synthesis of Compound 29

Compound 28 (1.06 g, 3.75 mmol) was dissolved in methanol (10 ml), and 85% potassium hydroxide (2.31 g, 35.0 mmol), and water (10 ml) were added, followed by refluxing for 20 hours. After allowing to cool to room temperature, the solvent was distilled off under reduced pressure, and the resulting residue was neutralized with 5 mol/L hydrochloric acid. The precipitated solid was collected by filtration, washed with water, and dried to obtain Compound 29 (1.07 g, yield 95%).

mp 204-206° C. (decompose)

$^1$H-NMR (DMSO-d$_6$/TMS) δppm: 1.10-1.22 (m, 2H), 1.45-1.49 (m, 3H), 1.73 (d, J=13.5 Hz, 2H), 2.25 (t, J=7.5 Hz, 2H), 2.75 (t, J=10.5 Hz, 2H), 3.85 (d, J=13.5 Hz, 2H), 7.03 (d, J=8.7 Hz, 2H), 7.46 (d, J=8.7 Hz, 2H).

d) Synthesis of Compound (I-7)

To Compound 29 (362 mg, 1.2 mmol) were added DMF (5 ml), 6-amino-3H-benzoxazole-2-one (150 mg, 1.0 mmol), HOBt (162 mg, 1.2 mmol), triethylamine (0.17 ml, 1.2 mmol), DMAP (6.0 mg, 0.05 mmol), and EDC (230 mg, 1.2 mmol), and the mixture was stirred at room temperature for 15 hours. The solvent was distilled off under reduced pressure, to the residue were added chloroform-methanol (9:1 mixed solution), and an aqueous saturated sodium bicarbonate solution, and the precipitated solid was collected by filtration, washed with water, and dried to obtain 261 mg of a solid. Separately, the filtrate was extracted with chloroform-methanol (9:1 mixed solution), washed with water, and dried with anhydrous magnesium sulfate, the solvent was distilled off under reduced pressure, and the resulting residue was purified by silica gel column chromatography (chloroform-methanol) to obtain 66 mg of a solid. The resulting solids were combined, purified by silica gel column chromatography (chloroform-methanol) and, further, recrystallized from methanol to obtain Compound (I-7) (244 mg yield 56%).

mp 254-256° C. (decompose)

$^1$H-NMR (DMSO-d$_6$/TMS) δppm: 1.16-1.25 (m, 2H), 1.46-1.52 (m, 1H), 1.55 (t, J=7.2 Hz, 2H), 1.76 (d, J=12.0 Hz, 2H), 2.34 (t, J=6.6 Hz, 2H), 2.78 (t, J=12.6 Hz, 2H), 3.87 (d, J=13.5 Hz, 2H), 7.01 (d, J=8.4 Hz, 1H), 7.04 (d, J=9.0 Hz, 2H), 7.21 (dd, J=8.4, 1.8 Hz, 1H), 7.46 (d, J=9.0 Hz, 2H), 7.69 (d, J=1.5 Hz, 1H), 9.95 (s, 1H), 11.51 (s, 1H).

EXAMPLE 3

Synthesis of Compound (I-8)

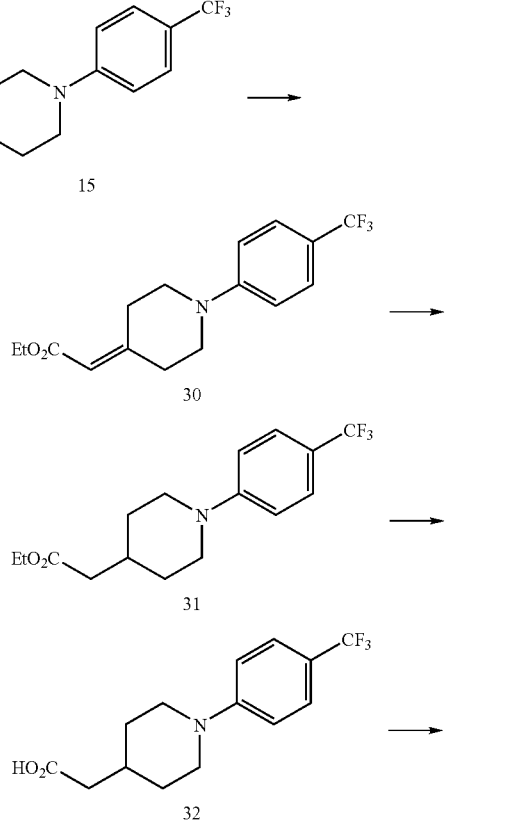

[Chemical formula 56]

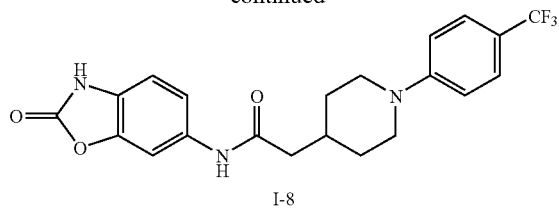

I-8 a) Synthesis of Compound 30

Under the nitrogen atmosphere, Compound 15 (1.34 g, 5.51 mmol) obtained in Reference Example 8 was dissolved in THF (20 ml), and ethyl diethylphosphonoacetate (1.36 g, 6.06 mmol), and lithium hydroxide (435 mg, 18.2 mmol) were added, followed by refluxing for 2 hours. After cooled with an ice bath, 7 ml of 2 mol/l hydrochloric acid was added, followed by extraction with diethyl ether. The organic layer was washed with an aqueous saturated sodium chloride solution, dried with anhydrous sodium sulfate, the solvent was distilled off under reduced pressure, and the resulting residue was purified by silica gel column chromatography (chloroform). Recrystallization with diethyl ether/hexane afforded Compound 30 (1.22 g, yield 71%).

mp 71-74° C.

$^1$H-NMR (CDCl$_3$/TMS) δppm: 1.29 (t, J=7.2 Hz, 3H), 2.46 (t, J=5.7 Hz, 2H), 3.11 (t, J=5.7 Hz, 2H), 3.45 (q, J=6.0 Hz, 4H), 4.17 (q, J=7.2 Hz, 2H), 5.75 (s, 1H), 6.94 (d, J=8.7 Hz, 2H), 7.48 (d, J=8.7 Hz, 2H).

b) Synthesis of Compound 31

Compound 30 (500 mg, 1.60 mmol) was dissolved in ethanol (15 ml), 10% palladium-carbon (50 mg) was added, the interior of the system was replaced with a hydrogen gas, and the mixture was stirred at room temperature for 1.5 hours. The reaction solution was filtered, insolubles were removed, and the filtrate was distilled off under reduced pressure. To the resulting residue was added diethyl ether, this was filtered using Celite, and washed with diethyl ether. The filtrate, and the washing solution were combined, and the solvent was distilled off under reduced pressure to obtain Compound 31 (488 mg, yield 97%).

$^1$H-NMR (CDCl$_3$/TMS) δppm: 1.27 (t, J=7.2 Hz, 3H), 1.38-1.46 (m, 2H), 1.84 (d, J=12.9 Hz, 2H), 1.95-2.04 (m, 1H), 2.28 (d, J=12.9 Hz, 2H), 2.84 (dt, J=2.1, 12.6 Hz, 2H), 4.15 (q, J=7.2 Hz, 2H), 6.93 (d, J=8.7 Hz, 2H), 7.46 (d, J=8.7 Hz, 2H).

c) Synthesis of Compound 32

Compound 31 (485 mg, 1.54 mmol) was dissolved in methanol (10 ml), 2 mol/L sodium hydroxide (2 ml, 4.0 mmol) was added, and the mixture was stirred at 65° C. for 45 minutes. The solvent was distilled off under reduced pressure, and 2 mol/L hydrochloric acid was added to the residue to acidic, and the precipitated crystal was collected by filtration. The crystal was washed with water, and dried to obtain Compound 32 (399 mg, yield 96%).

mp 103-104° C.

$^1$H-NMR (CDCl$_3$/TMS) δppm: 1.36-1.49 (m, 2H), 1.88 (d, J=12.3 Hz, 2H), 1.97-2.05 (m, 1H), 2.35 (d, J=6.9 Hz, 2H), 2.84 (dt, J=2.4, 12.6 Hz, 2H), 3.79 (d, J=12.6 Hz, 2H), 6.93 (d, J=9.0 Hz, 2H), 7.46 (d, J=9.0 Hz, 2H).

d) Synthesis of Compound (I-7)

To Compound 32 (388 mg, 1.35 mmol) were added methylene chloride (10 ml), 6-amino-3H-benzoxazole-2-one (203 mg, 1.35 mmol), HOBt (219 mg, 1.62 mmol), triethylamine (0.23 ml, 1.62 mmol), DMAP (8.0 mg, 0.07 mmol), and EDC (311 mg, 1.62 mmol), and the mixture was stirred at room temperature for 19 hours. An aqueous saturated sodium bicarbonate solution was added, and the precipitated solid was collected by filtration, washed with water, and dried to obtain 105 mg of a solid. Separately, the filtrate was extracted with chloroform, and dried with anhydrous magnesium sulfate, the solvent was distilled off under reduced pressure, and the resulting residue was purified by silica gel column chromatography (acetonitrile-chloroform) and, further, recrystallized from acetone-isopropanol to obtain 121 mg of a solid. The resulting solids were combined, purified by silica gel column chromatography (chloroform-methanol) and, further, recrystallized with ethyl acetate-methanol-isopropanol to obtain Compound (I-7) (153 mg, yield 27%).

mp 245-246° C. (decompose)

$^1$H-NMR (DMSO-d$_6$/TMS) δppm: 1.23-1.34 (m, 2H), 1.75 (d, J=12.0 Hz, 2H), 1.96-2.06 (m, 1H), 2.25 (d, J=7.2 Hz, 2H), 2.83 (t, J=12.3 Hz, 2H), 3.86 (d, J=12.0 Hz, 2H), 7.02 (t, J=9.9 Hz, 3H), 7.22 (dd, J=8.7, 1.8 Hz, 1H), 7.47 (d, J=8.7 Hz, 2H), 7.70 (d, J=1.8 Hz, 1H), 9.95 (s, 1H), 11.51 (s, 1H).

EXAMPLE 4

Synthesis of Compound (I-16)

[Chemical formula 57]

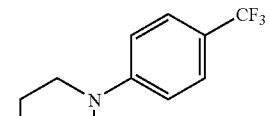

a) Synthesis of Compound 33

Compound 30 (376 mg, 1.2 mmol) was dissolved in methanol (10 ml), lithium hydroxide (252 mg, 6.0 mmol), and water (1 ml) were added, and the mixture was stirred at room temperature for 85 minutes, and at 65° C. for 45 minutes. The solvent was distilled off under reduced pressure, water, and 2 mol/L hydrochloric acid were added to the residue to acidic, and the precipitated crystal was collected by filtration. After washing with water, the solid obtained by drying was purified by silica gel column chromatography (chloroform-methanol) to obtain Compound 33 (286 mg, yield 84%).

$^1$H-NMR (CDCl$_3$/TMS) δppm: 2.36 (br, 1H), 3.14 (s, 2H), 3.49 (t, J=5.7 Hz, 2H), 3.86 (br, 1H), 5.73 and 5.79 (s, 1H), 6.90 (d, J=8.7 Hz, 2H), 7.48 (d, J=8.7 Hz, 2H).

b) Synthesis of Compound (I-16)

To Compound 33 (280 mg, 0.98 mmol) were added methylene chloride (10 ml), 6-amino-3H-benzoxazole-2-one (147 mg, 0.98 mmol), HOBt (159 mg, 1.18 mmol), triethylamine (0.16 ml, 1.18 mmol), DMAP (6.0 mg, 0.05 mmol), and EDC (226 mg, 1.18 mmol), and the mixture was stirred at room temperature for 4 days. The precipitated solid was collected by filtration, washed with methylene chloride, and dried to obtain 338 mg of a solid. Separately, the filtrate was concentrated under reduced pressure, to the residue were added an aqueous saturated sodium bicarbonate solution, and diethyl ether, and the solid was collected by filtration. This was washed with water, and diethyl ether, and dried to obtain 35 mg of a solid. Resulting solids were combined, purified by silica gel column chromatography (chloroform/methanol), and recrystallized from ethyl acetate/methanol to obtain Compound (I-16) (225 mg, yield 55%).

mp 203-205° C. (decompose)

$^1$H-NMR (DMSO-d$_6$/TMS) δppm: 2.26 (br, 2H), 3.09 (s, 2H), 3.47 (t, J=5.7 Hz, 2H), 3.78 (br, 2H), 5.69 (s, 1H), 7.02 (d, J=8.1 Hz, 1H), 7.03 (d, J=8.7 Hz, 2H), 7.23 (dd, J=8.4, 1.8 Hz, 1H), 7.49 (d, J=8.7 Hz, 2H), 7.69 (d, J=1.5 Hz, 1H), 10.06 (s, 1H), 11.53 (s, 1H).

crystal was collected by filtration. After washing with water, drying afforded Compound 34 (2.06 g, yield 97%).

mp 206-208° C. (decompose)

b) Synthesis of Compound (I-18)

To Compound 34 (273 mg, 1.0 mmol) were added DMF (5 ml), 6-amino-3H-benzoxazole-2-one (150 mg, 1.0 mmol), HOBt (162 mg, 1.2 mmol), triethylamine (0.17 ml, 1.2 mmol), DMAP (12.0 mg, 0.1 mmol), and EDC (230 mg, 1.2 mmol), and the mixture was stirred at room temperature for 41 hours. The solvent was distilled off under reduced pressure, to the residue were added an aqueous saturated sodium bicarbonate solution, and water, and the solid was collected by filtration. The resulting solid was purified by silica gel column chromatography (chloroform-acetone), and recrystallized with acetone-methanol to obtain Compound (I-18) (341 mg, yield 84%).

mp 302-304° C. (decompose)

$^1$H-NMR (DMSO-d$_6$/TMS) δppm: 1.63-1.77 (m, 2H), 1.87 (d, J=10.2 Hz, 2H), 2.53-2.61 (m, 1H), 2.87 (t, J=9.9 Hz, 2H), 3.95 (d, J=13.2 Hz, 2H), 7.01 (d, J=8.4 Hz, 1H), 7.08 (d, J=8.7 Hz, 2H), 7.25 (dd, J=8.7, 2.1 Hz, 1H), 7.49 (d, J=8.7 Hz, 2H), 7.70 (d, J=2.1 Hz, 1H), 9.99 (s, 1H), 11.50 (s, 1H).

EXAMPLE 5

Synthesis of Compound (I-18)

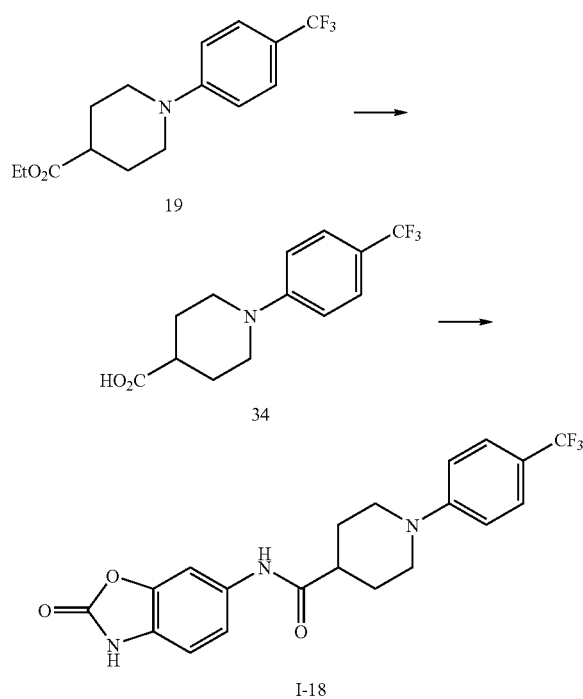

[Chemical formula 58]

a) Synthesis of Compound 34

Compound 19 (2.35 gt, 7.80 mmol) obtained in Reference Example 11 was dissolved in methanol (24 ml), and a 2 mol/L aqueous sodium hydroxide solution (7.8 ml, 15.6 mmol) was added, followed by refluxing for 30 minutes. The solvent was distilled off under reduced pressure, 2 mol/L hydrochloric acid was added to the residue to acidic, and the precipitated

EXAMPLE 6

Synthesis of Compound (I-23)

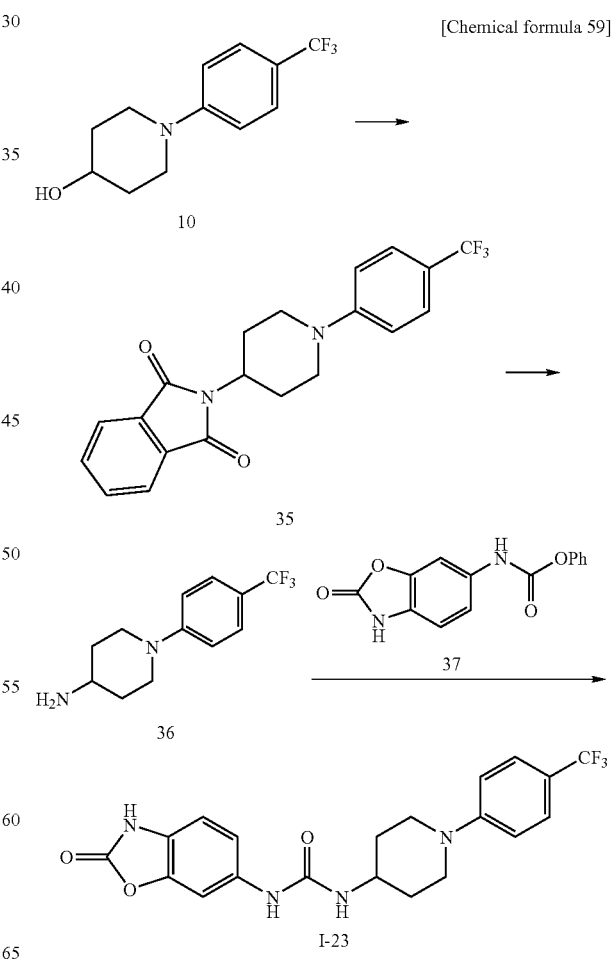

[Chemical formula 59]

a) Synthesis of Compound 35

Compound 10 (981 mg, 4.0 mmol) obtained in Reference Example 4 was dissolved in THF (40 ml), phthalimide (765 mg, 5.2 mmol), triphenylphosphine (1.36 g, 5.2 mmol), and diisopropyl azodicarboxylate (1.08 ml, 5.2 mmol) were added, and the mixture was stirred at room temperature for 16 hours. The solvent was concentrated under reduced pressure, and an aqueous saturated sodium bicarbonate solution, and water were added to the resultant residue, followed by extraction with chloroform. The organic layer was dried with anhydrous magnesium sulfate, the solvent was distilled off under reduced pressure, and the resulting residue was washed with methanol to obtain Compound 35 (1.08 g, yield 72%).

$^1$H-NMR (CDCl$_3$/TMS) δppm: 1.77-1.86 (m, 2H), 2.55-2.72 (m, 2H), 2.86-2.99 (m, 2H), 3.89-3.99 (m, 2H), 4.27-4.40 (m, 1H), 6.96 (d, J=8.7 Hz, 2H), 7.49 (d, J=8.7 Hz, 2H), 7.72 (dd, J=3.0, 5.6 Hz, 2H), 7.84 (dd, J=3.0, 5.6 Hz, 2H).

b) Synthesis of Compound 36

Compound 30 (262 mg, 0.7 mmol) was dissolved in ethanol (7 ml), and hydrazine monohydrate (0.087 ml, 1.75 mmol) was added, followed by refluxing for 2 hours. After allowing to cool, the precipitated solid was filtered off, and the filtrate was distilled off under reduced pressure. The resulting residue was purified by silica gel column chromatography (amino column, chloroform-methanol) to obtain Compound 36 (125 mg, yield 73%).

$^1$H-NMR (CDCl$_3$/TMS) δppm: 1.30 (brs, 2H), 1.38-1.53 (m, 2H), 1.87-1.98 (m, 2H), 2.82-2.94 (m, 3H), 3.71-3.81 (m, 2H), 6.92 (d, J=8.7 Hz, 2H), 7.45 (d, J=8.7 Hz, 2H).

c) Synthesis of Compound (I-23)

Compound 37 (60 mg, 0.22 mmol) was dissolved in acetonitrile (2 ml), and triethylamine (0.034 ml, 0.24 mmol) was added. A solution of Compound 36 (49 mg, 0.20 mmol) in acetonitrile (1 ml) was added, followed by refluxing for 6 hours. The precipitated crystal was filtered off, washed with water, and ethyl acetate, and dried to obtain (I-23) (50 mg, yield 59%).

mp 294-296° C.

$^1$H-NMR (DMSO-d$_6$/TMS) δppm: 1.31-1.55 (m, 2H), 1.80-2.00 (m, 2H), 2.88-3.10 (m, 2H), 3.60-3.85 (m, 3H), 6.17 (s, 1H), 6.95 (s, 2H), 7.06 (d, J=5.4 Hz, 2H), 7.48 (d, J=6.0 Hz, 2H), 7.54 (s, 1H), 8.35 (s, 1H), 11.35 (brs, 1H).

EXAMPLE 7

Synthesis of Compound (I-26)

[Chemical formula 60]

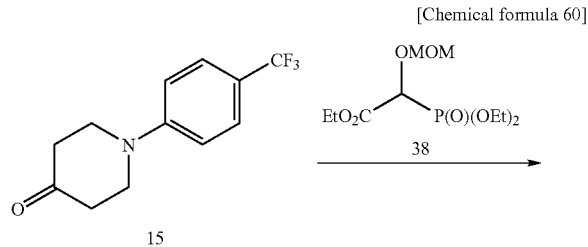

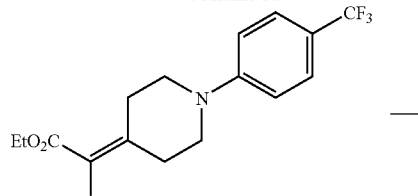
39

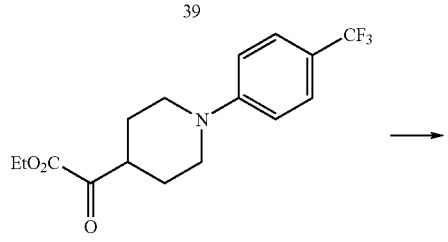
40

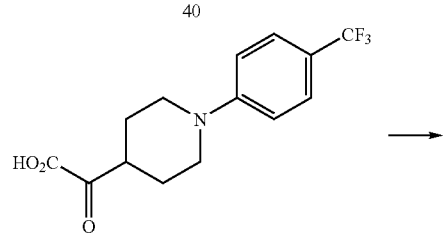
41

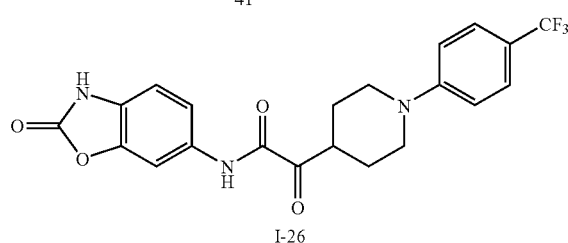
I-26 a) Synthesis of Compound 39

Under the nitrogen atmosphere, a solution of Compound 15 (1.18 g, 4.85 mmol), Compound 38 (1.45 g, 5.09 mmol), DMPO (1.80 g, 14.1 mmol) in THF (10 ml) was cooled with an ice bath, and a suspension of sodium hydride (60% oily, 204 mg, 5.09 mmol) in THF (10 ml) was added dropwise. After stirred at room temperature for 3 hours, ice water was added, followed by extraction with diethyl ether. The organic layer was washed with an aqueous saturated sodium chloride solution, dried with anhydrous magnesium sulfate, the solvent was distilled off under reduced pressure, and the resulting residue was purified by silica gel column chromatography (chloroform) to obtain Compound 39 (1.43 g, yield 79%).

$^1$H-NMR (CDCl$_3$/TMS) δppm: 1.35 (t, J=6.9 Hz, 3H), 2.73 (t, J=6.0 Hz, 2H), 2.79 (t, J=6.0 Hz, 2H), 3.40-3.45 (m, 4H), 3.51 (s, 3H), 4.27 (q, J=6.9 Hz, 2H), 4.85 (s, 2H), 6.93 (d, J=8.7 Hz, 2H), 7.49 (d, J=8.7 Hz, 2H).

b) Synthesis of Compound 40

Compound 39 (1.43 g, 3.83 mmol) was dissolved in ethanol (30 ml), p-toluenesulfonic acid monohydrate (73 mg, 0.38 mmol) was added, followed by refluxing for 15 hours. After allowing to stand to cool to room temperature, the solvent was distilled off under reduced pressure, to the residue were added water, and an aqueous saturated sodium bicarbonate solution, followed by extraction with chloroform. The organic layer was dried with anhydrous magnesium sulfate, the solvent was distilled off under reduced pressure, and the resulting residue was purified by silica gel column chromatography (chloroform-acetonitrile) to obtain Compound 40 (1.19 g, yield 95%).

$^1$H-NMR (CDCl$_3$/TMS) δppm: 1.35 (t, J=6.9 Hz, 3H), 2.73 (t, J=6.0 Hz, 2H), 2.79 (t, J=6.0 Hz, 2H), 3.40-3.45 (m, 4H), 3.51 (a, 3H), 4.27 (q, J=6.9 Hz, 2H), 4.85 (s, 2H), 6.93 (d, J=8.7 Hz, 2H), 7.49 (d, J=8.7 Hz, 2H).

c) Synthesis of Compound 41

Compound 40 (329 mg, 1.0 mmol) was dissolved in ethanol (10 ml), 85% potassium hydroxide (99 mg, 1.5 mmol), and water (1 ml) were added, and the mixture was stirred at room temperature for 75 minutes. The solvent was distilled off under reduced pressure, an ice, and 2 mol/L hydrochloric acid (0.8 ml, 1.6 mmol) were added to the residue to acidic, and the precipitated solid was collected by filtration. After the solid was washed with water, it was dried to obtain crude Compound 41 (261 mg, crude yield 87%).

d) Synthesis of Compound (I-26)

To Compound 41 (261 mg, 0.87 mmol) were added DMF (5 ml), 6-amino-3H-benzoxazole-2-one (156 mg, 1.04 mmol), HOBt (140 mg, 1.04 mmol), triethylamine (0.15 ml, 1.04 mmol), DMAP (11.0 mg, 0.09 mmol), and EDC (199 mg, 1.04 mmol), and the mixture was stirred at room temperature for 64 hours. The solvent was distilled off under reduced pressure, to the residue were added an aqueous saturated sodium bicarbonate solution, and water, and a solid was collected by filtration. The resulting solid was purified by silica gel column chromatography (chloroform-methanol) and, further, recrystallized from acetone-ethyl acetate to obtain Compound (I-26)(179 mg, yield 48%).

mp 230-232° C.

$^1$H-NMR (DMSO-d$_6$/TMS) δppm: 1.48-1.62 (m, 2H), 1.95 (d, J=11.7 Hz, 2H), 2.99 (t, J=11.7 Hz, 2H), 3.53-3.60 (m, 1H), 3.92 (d, J=12.9 Hz, 2H), 7.08 (d, J=8.7 Hz, 3H), 7.49 (d, J=8.7 Hz, 2H), 7.57 (dd, J=8.7, 1.8 Hz, 1H), 7.82 (d, J=1.8 Hz, 1H), 10.63 (s, 1H), 11.64 (s, 1H).

EXAMPLE 8

Synthesis of Compound (I-34)

[Chemical formula 61]

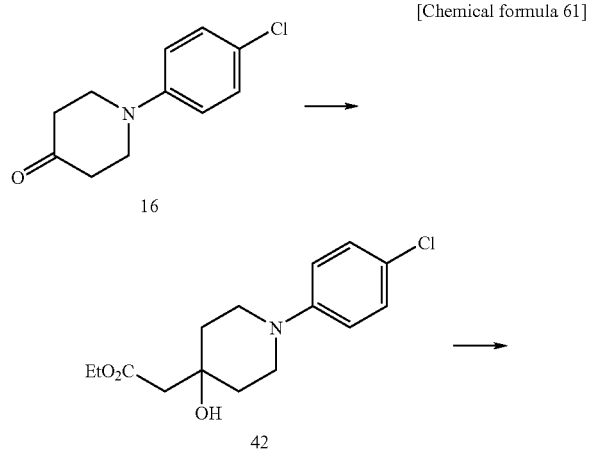

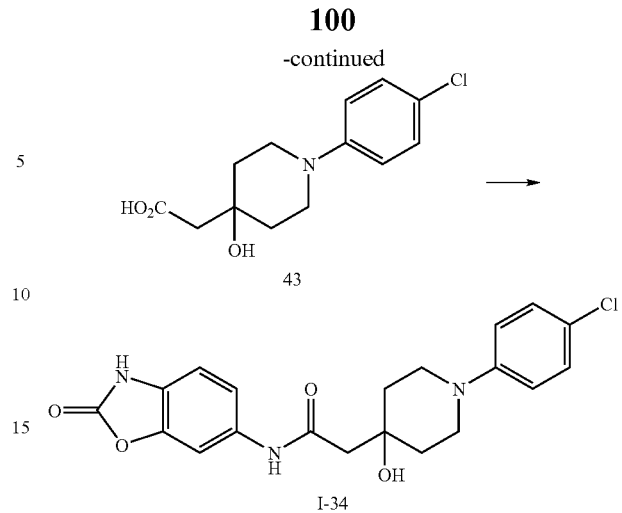

a) Synthesis of Compound 42

Under the nitrogen atmosphere, a solution of diisopropylamine (0.50 ml, 3.57 mmol) in THF (5 ml) was cooled to −78° C. with a dry-ice acetone bath, to this was added dropwise a 2.67M n-butyllithium-hexane solution (1.20 ml, 3.09 mmol), and the mixture was stirred at −78° C. for 15 minutes. A solution of ethyl acetate (0.30 ml, 3.09 mmol) in THF (2 ml) was added dropwise, the mixture was stirred at −78° C. for 30 minutes, a solution of Compound 16 (500 mg, 2.38 mmol) obtained in Reference Example 9 in THF (5 ml was added, and the mixture was stirred at −78° C. for 50 minutes. A solution of ammonium chloride (330 mg, 6.18 mmol) in water (2 ml) was added, a temperature was raised to room temperature, and water was added, followed by extraction with diethyl ether. The organic layer was washed with an aqueous saturated sodium chloride solution, dried with anhydrous magnesium sulfate, the solvent was distilled off under reduced pressure, and the resulting residue was purified by silica gel column chromatography (chloroform-acetonitrile) to obtain Compound 42 (703 mg, yield 99%).

$^1$H-NMR (CDCl$_3$/TMS) δppm: 1.30 (t, J=7.2 Hz, 3H), 1.73-1.84 (m, 4H), 2.51 (s, 2H), 3.20 (t, J=9.9 Hz, 2H), 3.36 (q, J=7.2 Hz, 2H), 3.61 (s, 1H), 6.88 (d, J=8.7 Hz, 2H), 7.20 (d, J=8.7 Hz, 2H).

b) Synthesis of Compound 43

Compound 42 (703 mg, 2.36 mmol) was dissolved in methanol (10 ml), a 2 mol/L aqueous sodium hydroxide solution (2.4 ml, 4.8 mmol) was added, followed by refluxing for 20 minutes. Acetic acid (0.55 ml, 9.6 mmol) was added, the solvent was distilled off under reduced pressure, water was added to the residue, and the precipitated crystal was collected by filtration. After washing with water, drying afforded Compound 43 (526 mg, yield 83%).

mp 130-133° C.

$^1$H-NMR (CDCl$_3$/TMS) δppm: 1.86-1.98 (m, 4H), 2.61 (s, 2H), 3.27-3.40 (m, 4H), 7.09 (d, J=8.7 Hz, 2H), 7.26 (d, J=8.7 Hz, 2H).

c) Synthesis of Compound (I-34)

To Compound 43 (70 mg. 1.0 mmol) were added DMF (5 ml), 6-amino-3H-benzoxazole-2-one (150 mg, 1.0 mmol), HOBt (162 mg, 1.2 mmol), DMAP (12.0 mg, 0.1 mmol), and EDC (230 mg, 1.2 mmol), and the mixture was stirred at room temperature for 63 hours. The solvent was distilled off under reduced pressure, to the residue were added an aqueous saturated sodium bicarbonate solution, and water, and a solid was collected by filtration. The resulting solid was purified by silica gel column chromatography (chloroform-methanol)

and, further, recrystallized from THF-ethyl acetate to obtain Compound (I-34) (314 mg, yield 78%).

mp 255-257° C. (decompose)

$^1$H-NMR (DMSO-d$_6$/TMS) δppm: 1.63-1.80 (m, 4H), 2.46 (s, 2H), 3.04-3.13 (m, 2H), 3.34-3.40 (m, 2H), 4.75 (s, 1H), 6.94 (d, J=8.7 Hz, 2H), 7.01 (d, J=8.7 Hz, 1H), 7.19 (d, J=8.7 Hz, 2H), 7.13 (dd, J=8.7, 1.8 Hz, 1H), 7.70 (d, J=1.8 Hz, 1H), 9.94 (s, 1H), 11.53 (brs, 1H).

EXAMPLE 9

Synthesis of Compound (I-19)

[Chemical formula 62]

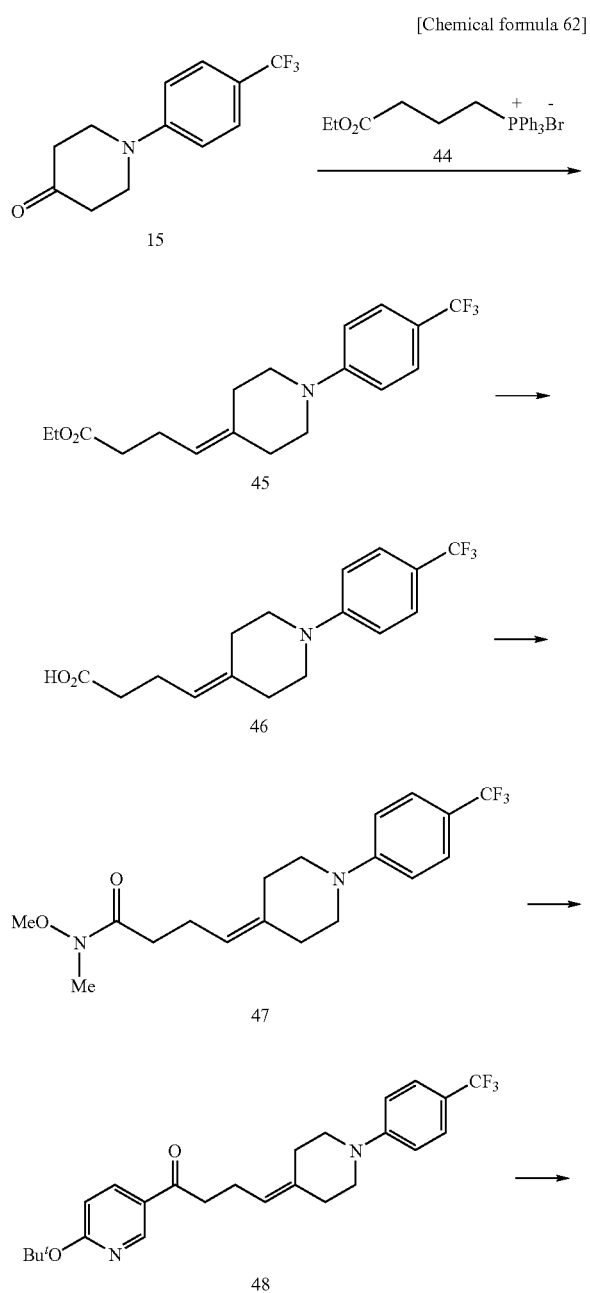

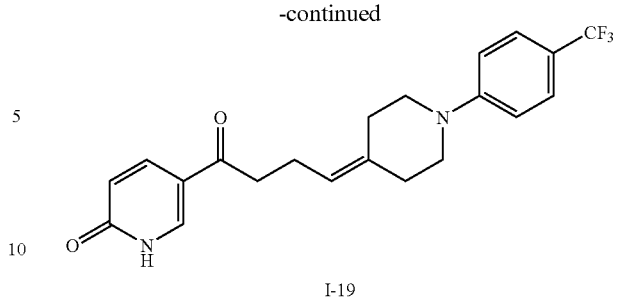
I-19 a) Synthesis of Compound 45

Under the nitrogen atmosphere, Compound 44 (7.52 g, 16.4 mmol) was dissolved in THF (30 ml), potassium hexamethyldisilazide (6.90 g, 32.9 mmol) was added, and the mixture was stirred at room temperature for 30 minutes. A solution of Compound 15 (1.00 g, 4.11 mmol) in THF (10 ml) was added, and the mixture was stirred at room temperature for 3 hours. Water, and 2 mol/L hydrochloric acid were added, followed by extraction with ethyl acetate. The organic layer was washed with an aqueous saturated sodium chloride solution, and dried with anhydrous magnesium sulfate, the solvent was distilled off under reduced pressure, and the resulting residue was purified by silica gel column chromatography (hexane-ethyl acetate) to obtain Compound 45 (0.48 g, yield 34%).

$^1$H-NMR (CDCl$_3$/TMS) δppm: 1.26 (t, J=7.1 Hz, 3H), 2.26-2.32 (m, 2H), 2.34-2.42 (m, 6H), 3.29-3.36 (m, 4H), 4.13 (q, J=7.1 Hz, 2H), 5.20-5.26 (m, 1H), 6.91 (d, J=8.7 Hz, 2H), 7.46 (d, J=8.7 Hz, 2H).

b) Synthesis of Compound 46

Compound 45 (470 mg, 1.38 mmol) was dissolved in methanol (10 ml), a 1 mol/L aqueous sodium hydroxide solution (2.1 ml, 2.1 mmol) was added, and the mixture was stirred at room temperature for 4 hours. 2 mol/L hydrochloric acid was added to acidic, followed by extraction with ethyl acetate. The organic layer was dried with anhydrous magnesium sulfate, and the solvent was distilled off under reduced pressure to obtain Compound 46 (420 mg, yield 99%).

$^1$H-NMR (DMSO-d$_6$/TMS) δppm: 2.12-2.32 (m, 8H), 3.23-3.40 (m, 4H), 5.18-5.27 (m, 1H), 7.05 (d, J=6.3 Hz, 2H), 7.48 (d, J=6.3 Hz, 2H), 12.03 (s, 1H).

c) Synthesis of Compound 47

Compound 46 (420 mg, 1.34 mmol), and N-methylmorpholine (0.15 ml, 1.34 mmol) were dissolved in THF (8 ml), and the solution was cooled with an ice bath. Isobutyl chlorocarbonate (0.17 ml, 1.34 mmol), triethylamine (0.21 ml, 1.47 mmol), and a solution of N,O-dimethoxyamine hydrochloride (131 mg, 1.34 mmol) in DMF (3 ml) were sequentially added, and the mixture was stirred at 0° C. for 30 minutes, and at room temperature for 5 hours. The solvent was distilled off under reduced pressure, the residue was added water, followed by extraction with ethyl acetate. The organic layer was washed with an aqueous saturated sodium chloride solution, and dried with anhydrous magnesium sulfate, the solvent was distilled off, and the resulting residue was purified by silica gel column chromatography (hexane-ethyl acetate) to obtain Compound 47 (427 mg, yield 89%).

$^1$H-NMR (CDCl$_3$/TMS) δppm: 2.26-2.53 (m, 8H), 3.18 (s, 3H), 3.30-3.36 (m, 4H), 3.68 (s, 3H), 5.25-5.30 (m, 1H), 6.91 (d, J=8.7 Hz, 2H), 7.46 (d, J=8.7 Hz, 2H)

d) Synthesis of Compound 48

Under the nitrogen atmosphere, 5-bromo-2-tert-butoxypyridine (400 mg, 1.74 mmol) was dissolved in THF (8 ml), and the solution was cooled to −78° C. with a dry ice-acetone bath. A 2.6 M n-butyllithium-hexane solution (0.72 ml, 1.86 mmol) was added dropwise, the mixture was stirred at −78° C. for 30 minutes, a solution of Compound 42 (415 mg, 1.16 mmol) in THF (4 ml) was added, and the mixture was stirred at −78° C. for 1 hour, and at −40° C. for 5 hours. An aqueous saturated ammonium chloride solution and water were added, a temperature was raised to room temperature, followed by extraction with ethyl acetate. The organic layer was washed with an aqueous saturated sodium chloride solution, and dried with anhydrous magnesium sulfate, the solvent was distilled off under reduced pressure, and the resulting residue was purified by silica gel column chromatography (chloroform-acetonitrile) to obtain Compound 48 (275 mg, yield 53%).

$^1$H-NMR (CDCl$_3$/TMS) δppm: 1.61 (s, 9H), 2.25-2.32 (m, 2H), 2.35-2.42 (m, 2H), 2.43-2.52 (m, 2H), 2.90-2.99 (m, 2H), 3.29-3.34 (m, 4H), 5.26-5.32 (m, 1H), 6.66 (d, J=8.7 Hz, 1H), 6.90 (d, J=8.7 Hz, 2H), 7.46 (d, J=8.7 Hz, 2H), 8.07 (dd, J=2.6, 8.7 Hz, 1H), 8.74 (d, J=2.6 Hz, 1H).

e) Synthesis of Compound (I-19)

Compound 48 (120 mg, 0.27 mmol) was dissolved in chloroform (3 ml), and the solution was cooled with an ice bath. Trifluoroacetic acid (2 ml) was added, the mixture was stirred at 0° C. for 1.5 hours, an aqueous saturated sodium bicarbonate solution was added, followed by extraction with chloroform. The organic layer was dried with anhydrous magnesium sulfate, the solvent was distilled off under reduced pressure, the resulting residue was purified by silica gel column chromatography (chloroform-methanol). The resulting solid was recrystallized from methanol-water to obtain Compound (I-19)(77 mg, yield 73%).

mp 137-139° C.

$^1$H-NMR (DMSO-d$_6$/TMS) δppm: 2.19-2.22 (m, 2H), 2.22-2.39 (m, 4H), 2.78-2.92 (m, 2H), 3.20-3.47 (m, 4H), 5.18-5.30 (m, 1H), 6.36 (d, J=9.6 Hz, 1H), 7.04 (d, J=8.8 Hz, 2H), 7.47 (d, J=8.8 Hz, 2H), 7.87 (dd, J=2.4, 9.6 Hz, 1H), 8.22 (d, J=2.4 Hz, 1H), 12.12 (brs, 1H).

EXAMPLE 10

Synthesis of Compound (I-20)

[Chemical formula 63]

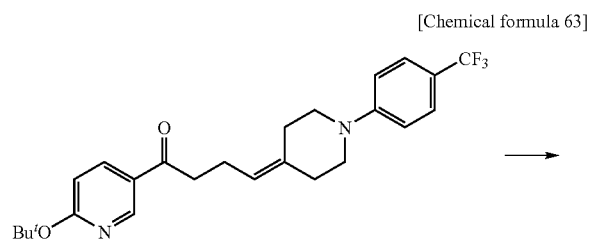

49

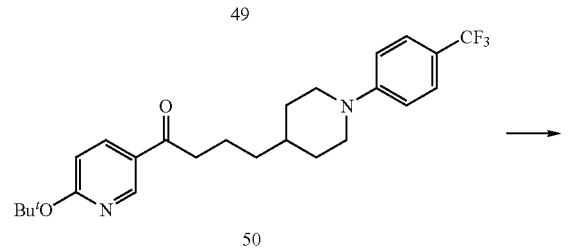

50

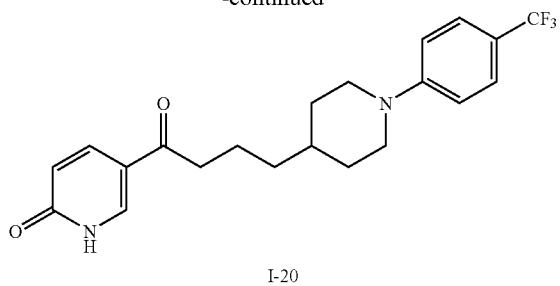

I-20 a) Synthesis of Compound 50

Compound 49 (144 mg, 0.32 mmol) was dissolved in ethyl acetate (5 ml), 10% palladium-carbon (15 mg) was added, the interior of the system was replaced with a hydrogen gas, and the mixture was stirred at room temperature for 16 hours. The reaction solution was filtered using Celite, the filtrate was distilled off under reduced pressure, and the resulting residue was purified by silica gel column chromatography (hexane-ethyl acetate) to obtain Compound 50 (88 mg, yielded 61%).

$^1$H-NMR (CDCl$_3$/TMS) δppm: 1.23-1.53 (m, 5H), 1.62 (s, 9H), 1.73-1.85 (m, 4H), 2.72-2.84 (m, 2H), 2.48-2.94 (m, 2H), 3.76-3.81 (m, 2H), 6.67 (d, J=8.7 Hz, 1H), 6.91 (d, J=8.7 Hz, 2H), 7.45 (d, J=8.7 Hz, 2H), 8.08 (dd, J=2.4, 8.7 Hz, 1H), 8.75 (d, J=2.4 Hz, 1H).

b) Synthesis of Compound (I-20)

Compound 50 (85 mg, 0.19 mmol) was dissolved in chloroform (2 ml), and the solution was cooled with an ice bath. Trifluoroacetic acid (1 ml) was added, the mixture was stirred at 0° C. for 1.5 hours, an aqueous saturated sodium bicarbonate solution was added, followed by extraction with ethyl acetate. The organic layer was washed with an aqueous saturated sodium chloride solution, dried with anhydrous magnesium sulfate, the solvent was distilled off under reduced pressure, and the resulting residue was purified by silica gel column chromatography (chloroform-methanol). The resulting solid was recrystallized from methanol-water to obtain Compound (I-20)(61 mg, yield 82%).

mp 171-173° C.

$^1$H-NMR (DMSO-d$_6$/TMS) δppm: 1.08-1.31 (m, 4H), 1.38-1.51 (m, 1H), 1.52-1.65 (m, 2H), 1.65-1.80 (m, 2H), 2.68-2.87 (m, 4H), 3.72-3.90 (m, 2H), 6.37 (d, J=7.2 Hz, 1H), 7.02 (d, J=6.6 Hz, 2H), 7.46 (d, J=6.6 Hz, 2H), 7.87 (dd, J=1.8, 7.2 Hz, 1H), 8.25 (d, J=1.8 Hz, 1H), 12.11 (brs, 1H).

EXAMPLE 11

Synthesis of Compound (I-24)

[Chemical formula 64]

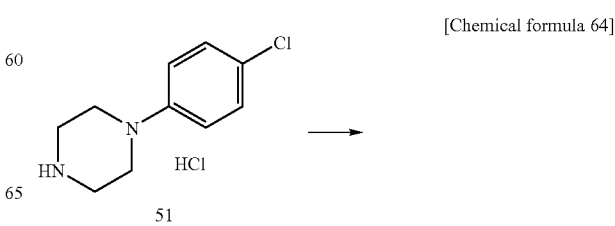

51

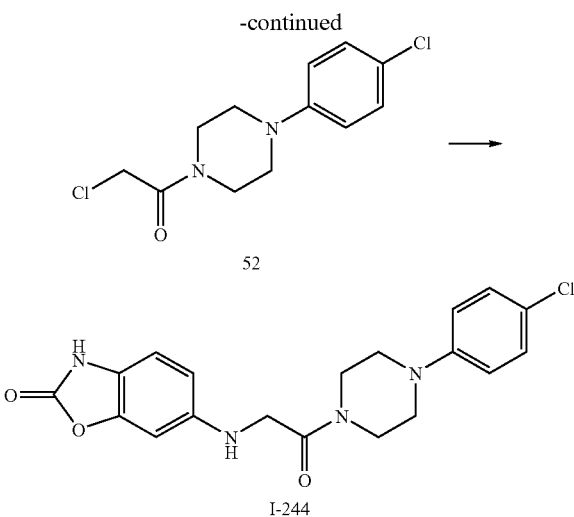

a) Synthesis of Compound 52

In methylene chloride (20 ml) was dissolved 1-(4-chlorophenyl)piperazine hydrochloride 51 (2.33 g, 10.0 mmol), a 2 mol/L aqueous sodium hydroxide solution (13.0 ml, 26.0 mmol) was added, and this was cooled with an ice bath. A solution of chloroacetyl chloride (1.47 g, 13.0 mmol) in methylene chloride (5 ml) was added, the mixture was stirred at 0° C. for 1 hour, 2 mol/L hydrochloric acid (7.0 ml, 14.0 mmol) was added, followed by extraction with ethyl acetate. The organic layer was washed sequentially with an aqueous saturated sodium bicarbonate solution, and an aqueous saturated sodium chloride solution, dried with anhydrous sodium sulfate, and the solvent was distilled off under reduced pressure. The resulting residue was recrystallized from ethyl acetate-hexane to obtain Compound 52 (2.26 g, yielded 83%).

$^1$H-NMR (CDCl$_3$/TMS) δppm: 3.15 (t, J=5.2 Hz, 2H), 3.20 (t, J=5.2 Hz, 2H), 3.68 (t, J=5.2 Hz, 2H), 3.78 (t, J=5.2 Hz, 2H), 4.11 (s, 2H), 6.85 (d, J=9.1 Hz, 2H), 7.23 (d, J=9.1 Hz, 2H).

b) Synthesis of Compound (I-244)

Compound 52 (546 mg, 2.0 mmol) and 6-amino-3H-benzoxazole-2-one (300 mg, 2.0 mmol) was dissolved in DMF (10 ml), and the solution was stirred at 80° C. for 1 hour, and at 100° C. for 4 hours. The solvent was distilled off under reduced pressure, and an aqueous saturated sodium bicarbonate solution was added to the residue, followed by extraction with an ethyl acetate-THF (1:1) mixed solution. The organic layer was dried with anhydrous sodium sulfate, the solvent was distilled off under reduced pressure, and the resulting residue was purified by silica gel column chromatography (chloroform-methanol). An amorphous substance was crystallized using methanol, and this was collected by filtration, washed with diethyl ether, and dried to obtain compound (I-244)(135 mg, yielded 17%).

mp 211-213° C.

$^1$H-NMR (DMSO-d$_6$/TMS) δppm: 3.11-3.23 (m, 4H), 3.58-3.68 (m, 4H), 3.93 (d, J=5.1 Hz, 2H), 5.56 (t, J=5.1 Hz, 1H), 6.48 (dd, J=2.0, 8.6 Hz, 1H), 6.70 (d, J=2.0 Hz, 1H), 6.81 (d, J=8.7 Hz, 1H), 6.98 (d, J=9.1 Hz, 2H), 7.26 (d, J=9.1 Hz, 2H), 11.12 (brs, 1H).

According to the same manner, other Compound (I) is synthesized below. Following are a structural formula and a physical constant.

TABLE 4

| Compound No. | Structural formula | Melting point |
| --- | --- | --- |
| I-1 | | 232-234 |
| I-2 | | 232-233(d) |

TABLE 4-continued

| Compound No. | Structural formula | Melting point |
|---|---|---|
| I-3 | | 283-284(d) |
| I-4 | | 274-275(d) |
| I-5 | | 236-238(d) |
| I-6 | | 232-234 |

TABLE 5

| I-7 | | 254-256 |

TABLE 5-continued
| | | |
|---|---|---|
| I-8 | 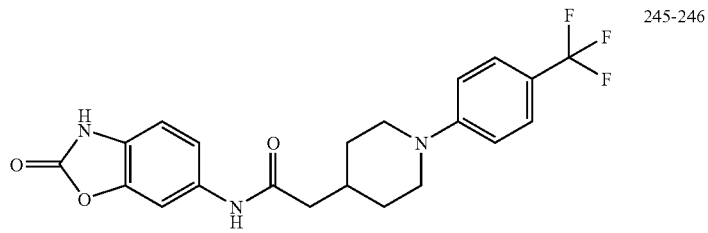 | 245-246 |
| I-9 | 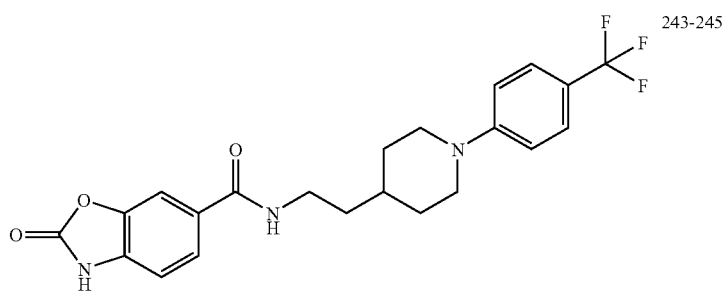 | 243-245 |
| I-10 | 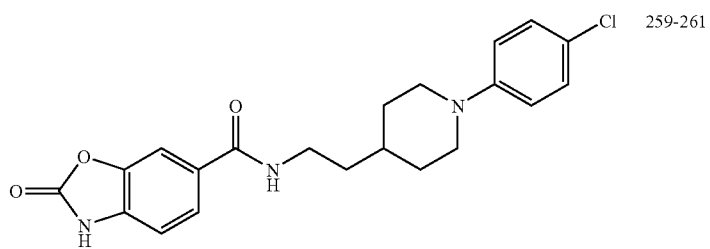 | 259-261 |
| I-11 | 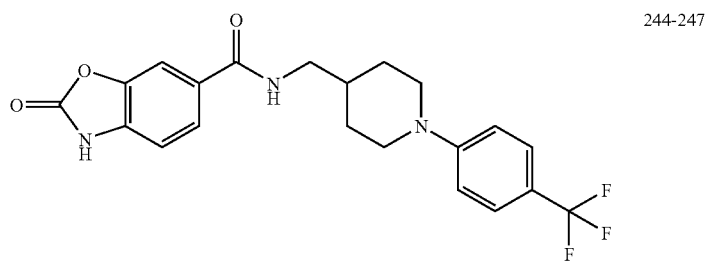 | 244-247 |
| I-12 | 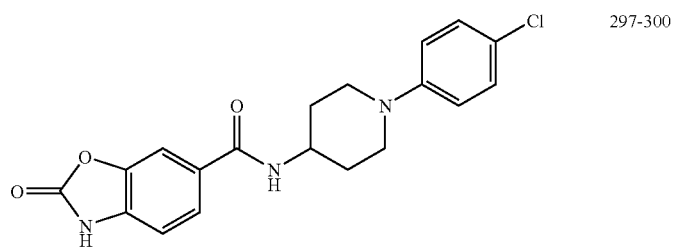 | 297-300 |

TABLE 6
| | | |
|---|---|---|
| I-13 | 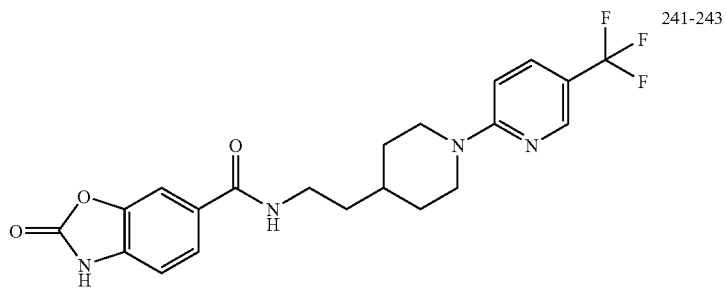 | 241-243 |
| I-14 | 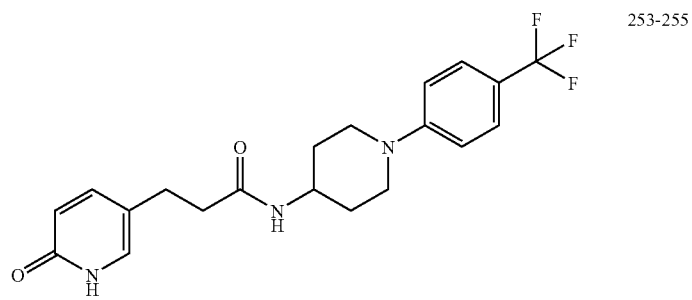 | 253-255 |
| I-15 | 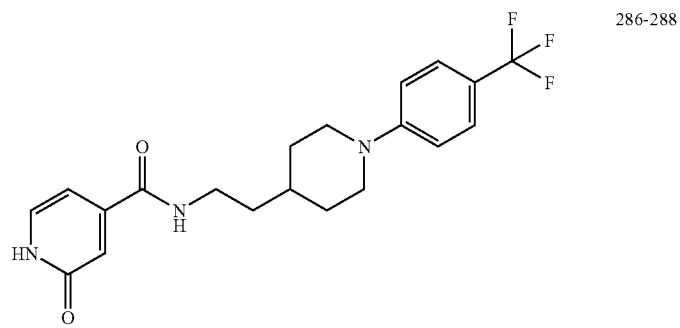 | 286-288 |
| I-16 | 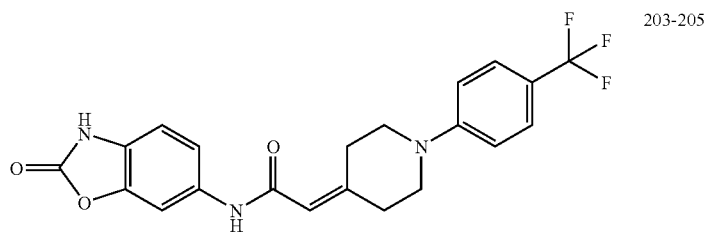 | 203-205 |
| I-17 | 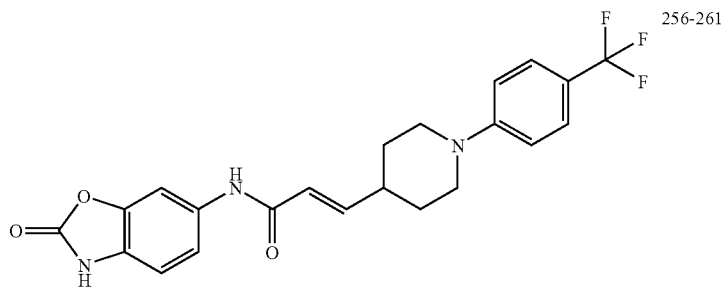 | 256-261 |

TABLE 7
I-18 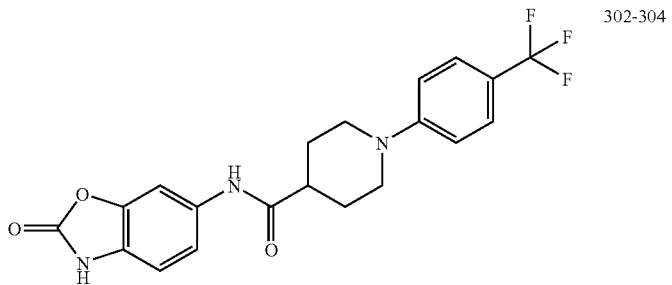 302-304
I-19 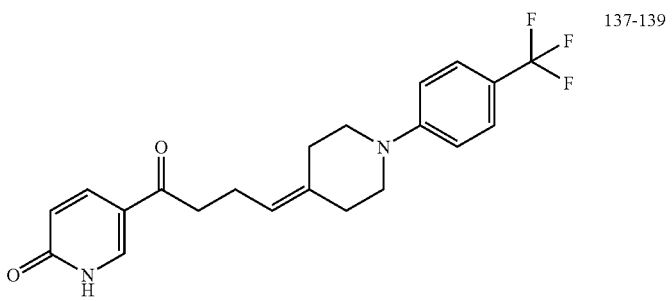 137-139
I-20 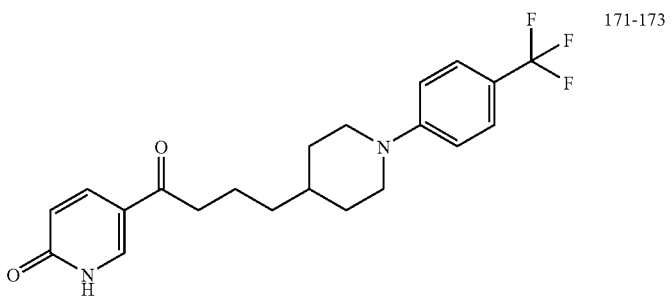 171-173
I-21 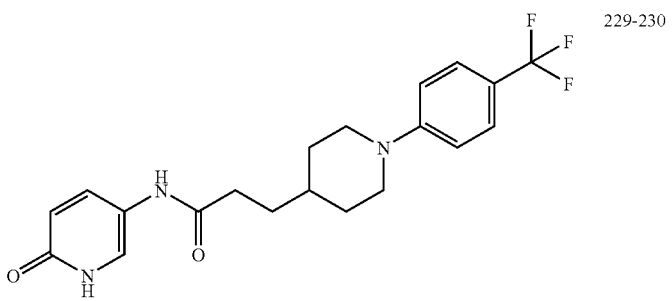 229-230
I-22 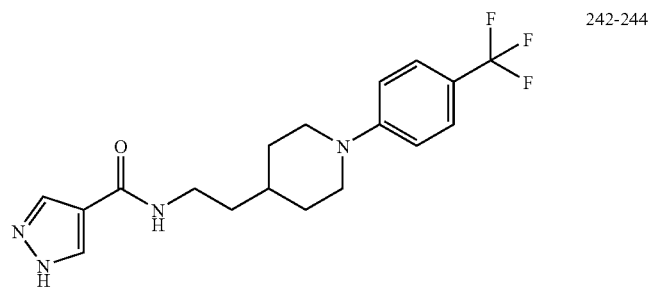 242-244

TABLE 7-continued
| I-23 | 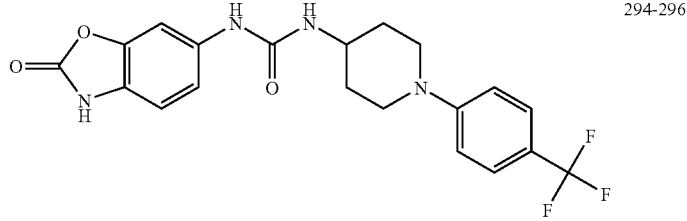 | 294-296 |
TABLE 8
| I-24 | 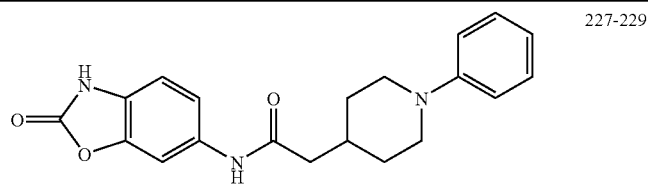 | 227-229 |
| I-25 | 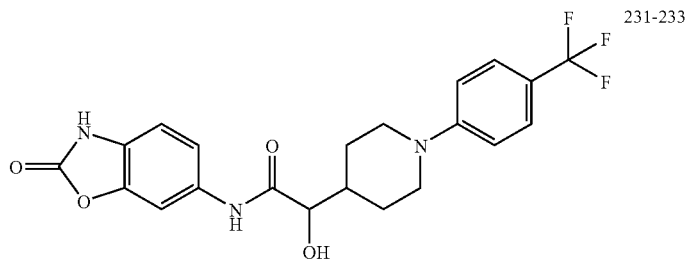 | 231-233 |
| I-26 | 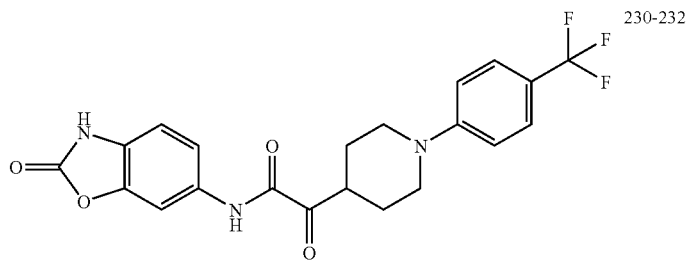 | 230-232 |
| I-27 | 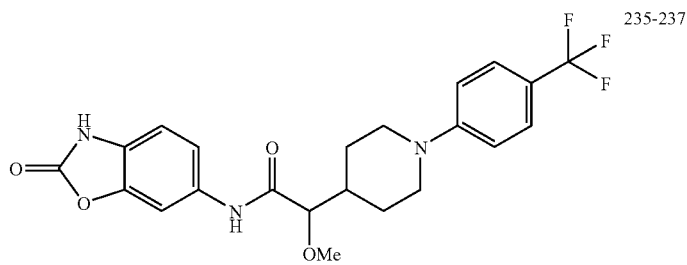 | 235-237 |
| I-28 | 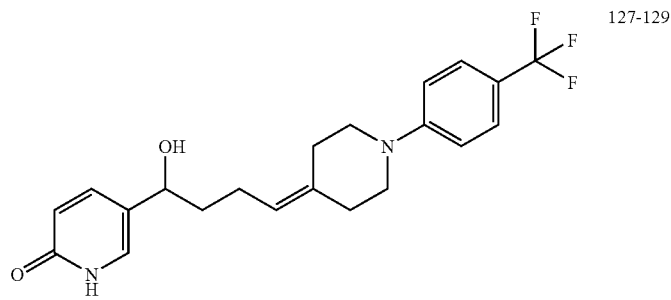 | 127-129 |

TABLE 8-continued
I-29 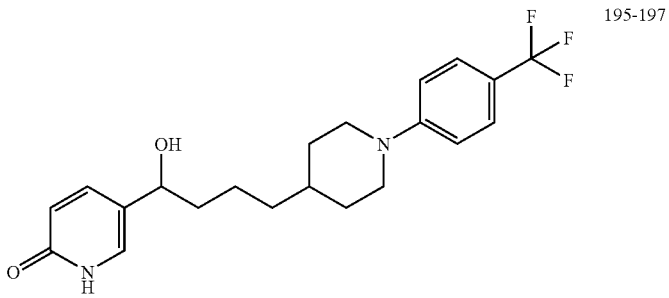 195-197
TABLE 9
I-30 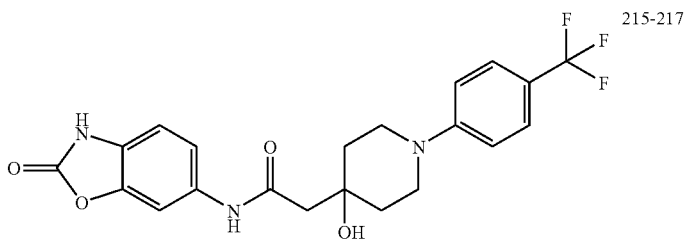 215-217
I-31 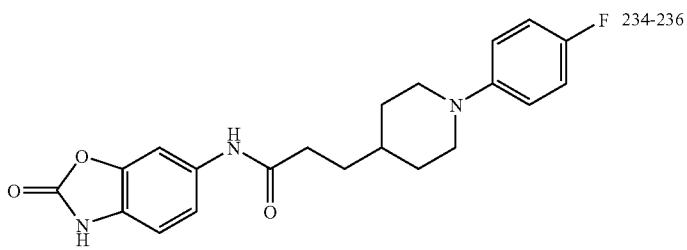 234-236
I-32 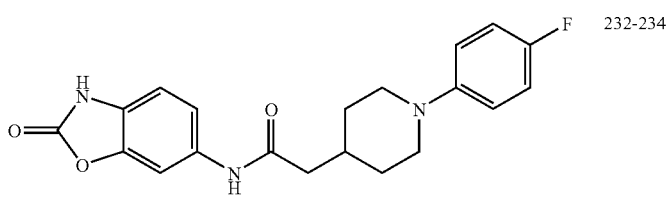 232-234
I-33 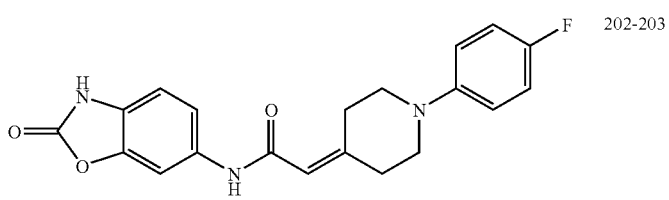 202-203
I-34 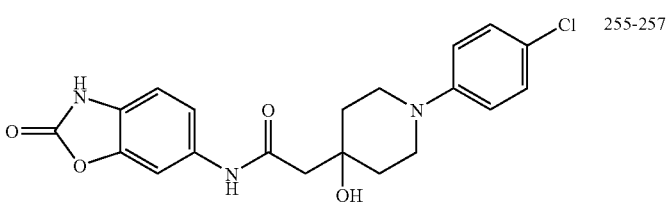 255-257

TABLE 9-continued
| I-35 | 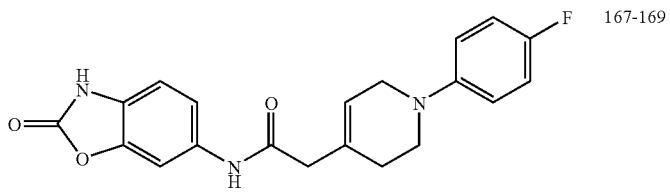 | 167-169 |
TABLE 10
| I-36 | 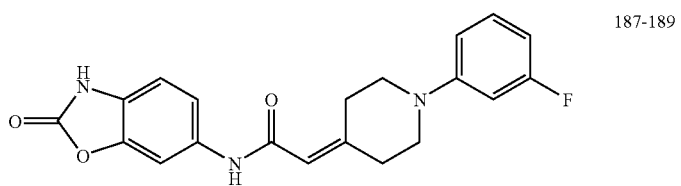 | 187-189 |
| I-37 | 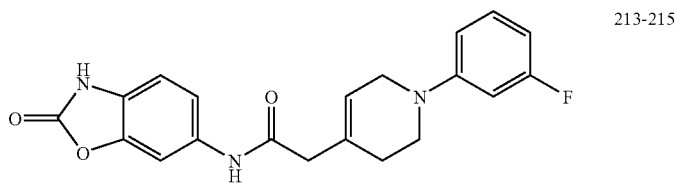 | 213-215 |
| I-38 | 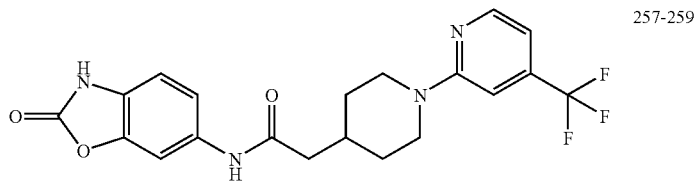 | 257-259 |
| I-39 | 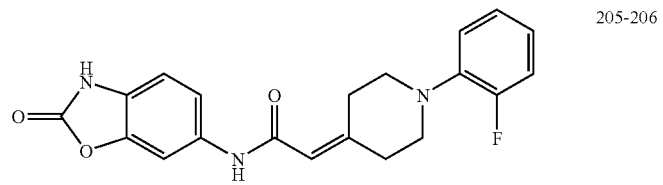 | 205-206 |
| I-40 | 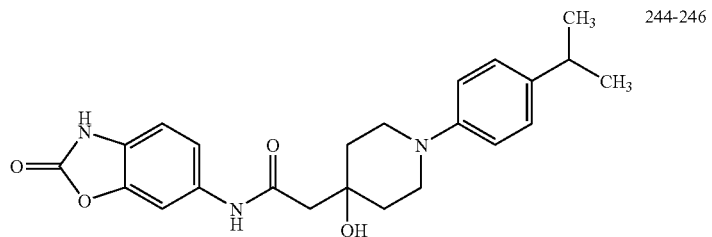 | 244-246 |
| I-41 | 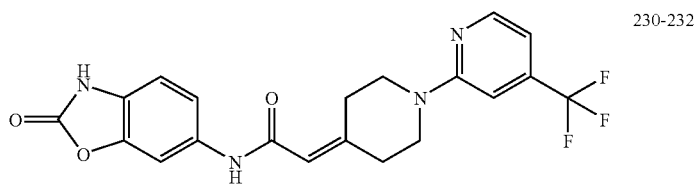 | 230-232 |

TABLE 10-continued
| | | |
|---|---|---|
| I-42 | 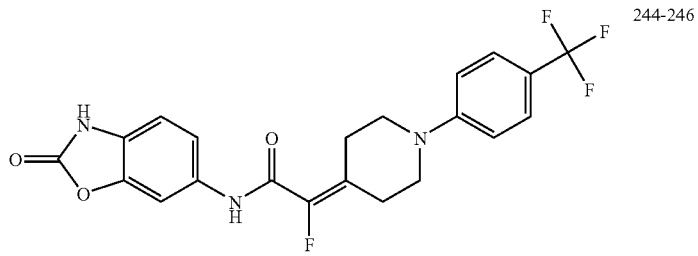 | 244-246 |
TABLE 11
| | | |
|---|---|---|
| I-43 | 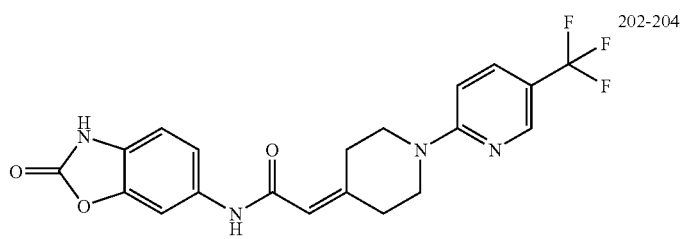 | 202-204 |
| I-44 | 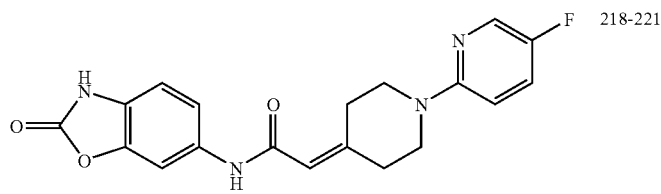 | 218-221 |
| I-45 | 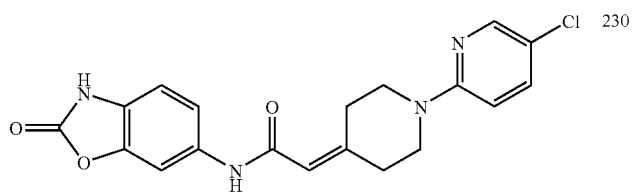 | 230 |
| I-46 | 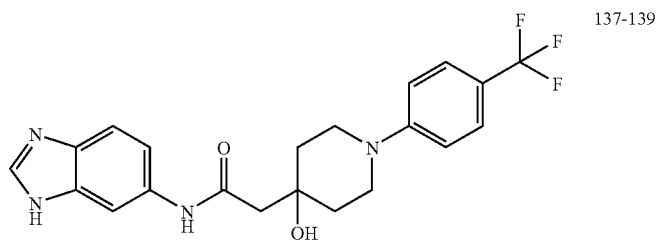 | 137-139 |
| I-47 | 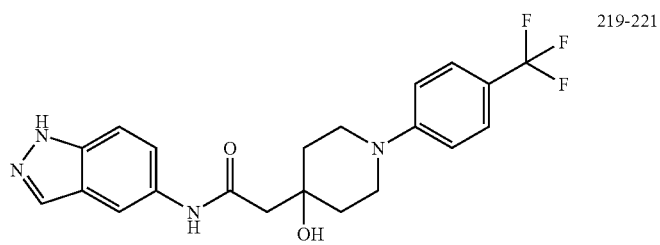 | 219-221 |

TABLE 11-continued
| I-48 | 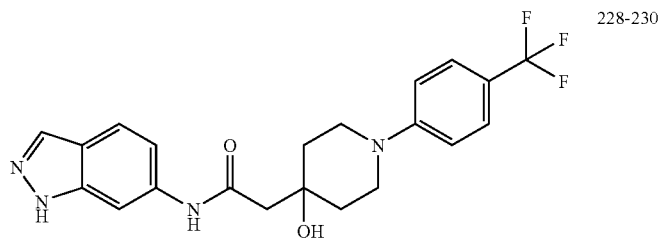 | 228-230 |
TABLE 12
| I-49 | 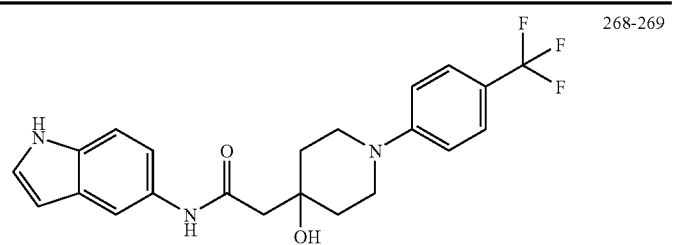 | 268-269 |
| I-50 | 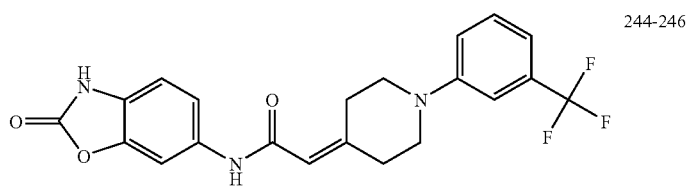 | 244-246 |
| I-51 | 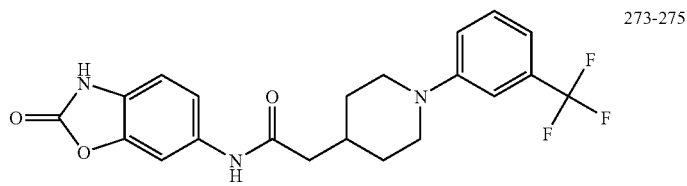 | 273-275 |
| I-52 | 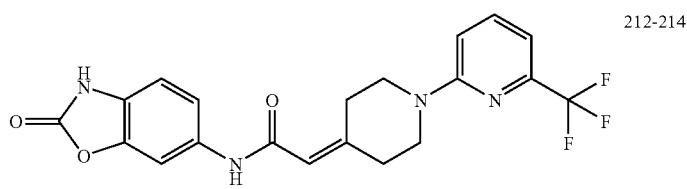 | 212-214 |
| I-53 | 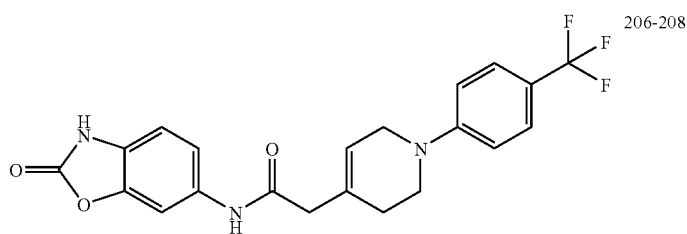 | 206-208 |
| I-54 | 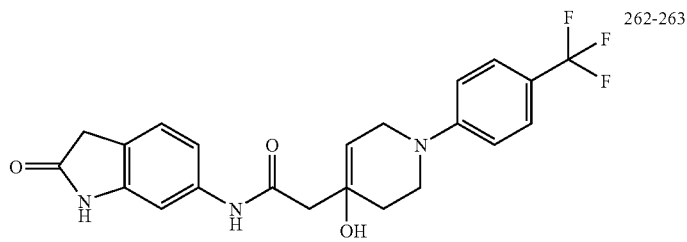 | 262-263 |

TABLE 13
I-55 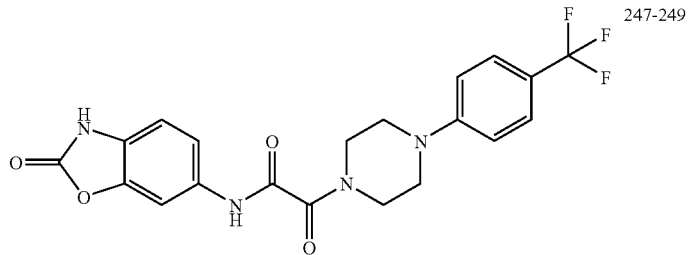 247-249
I-56 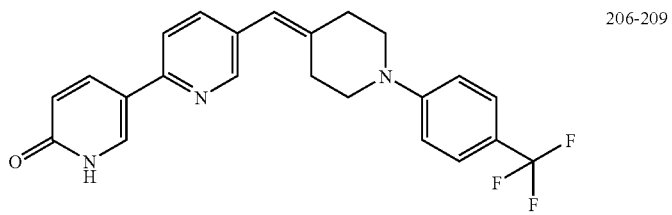 206-209
I-57 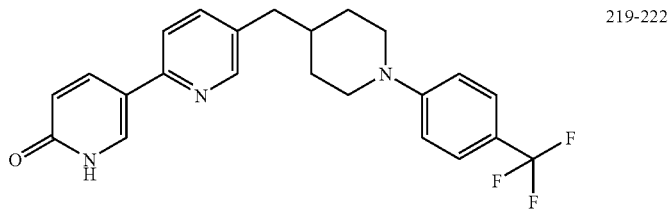 219-222
I-58 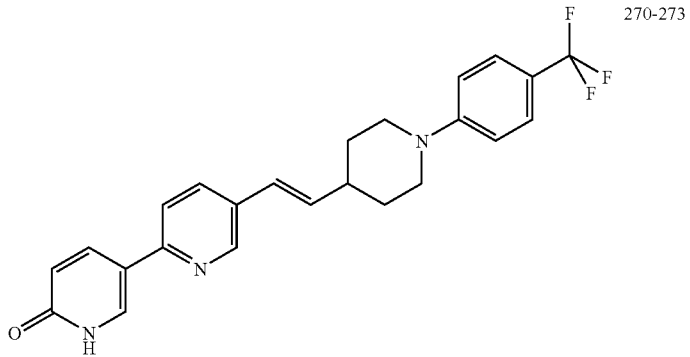 270-273
I-59 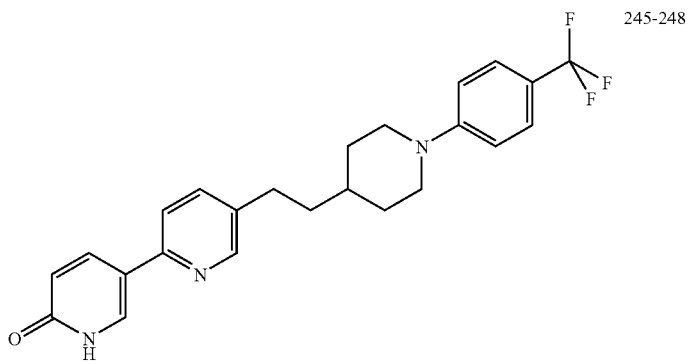 245-248

TABLE 13-continued
| I-60 | 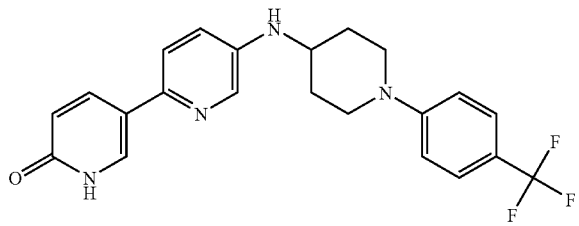 | 266 |
TABLE 14
| Compound No. | Structural formula | Melting point |
|---|---|---|
| I-61 | 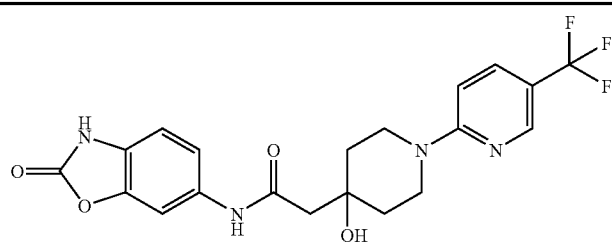 | 218-219 |
| I-62 | 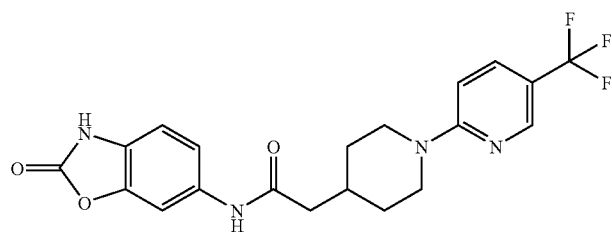 | 229-230 |
| I-63 | 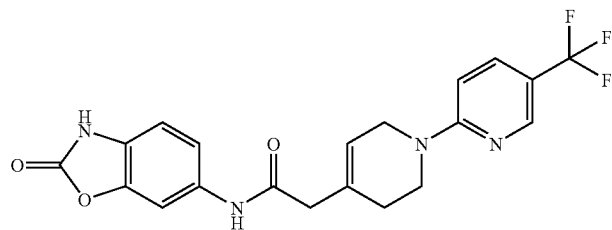 | 236-237 |
| I-64 | 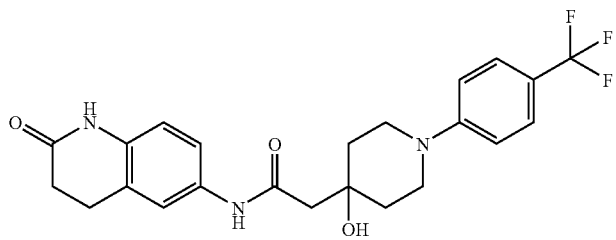 | 222-223 |
| I-65 | 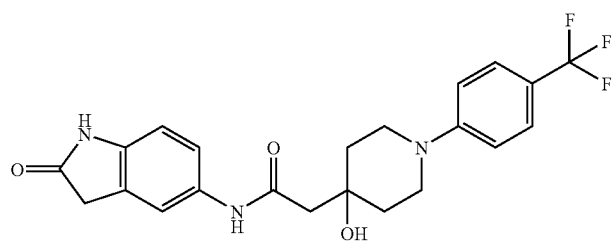 | 260-261 |

TABLE 14-continued

| Compound No. | Structural formula | Melting point |
| --- | --- | --- |
| I-66 | | 219-220 |
| I-67 | | 199-200 |

TABLE 15

| | | |
| --- | --- | --- |
| I-68 | | 243-245 |
| I-69 | | 214-215 |
| I-70 | | 247-248 |
| I-71 | | 243-245 |

TABLE 15-continued
I-72 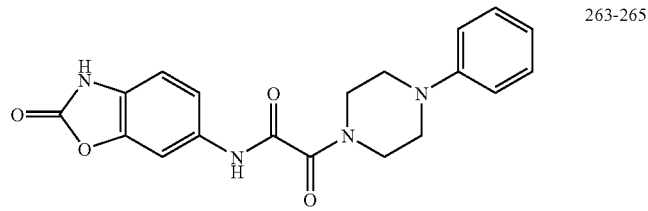 263-265
I-73 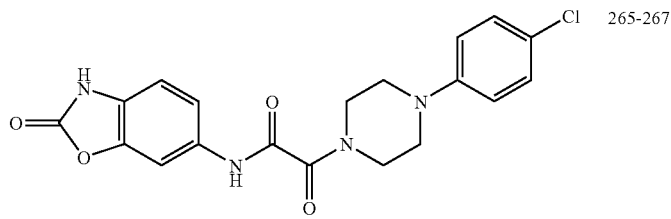 265-267
I-74 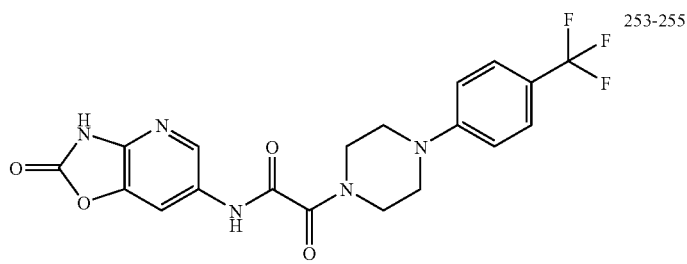 253-255
TABLE 16
I-75 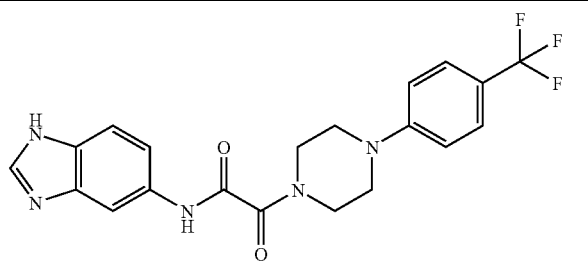 199
I-76 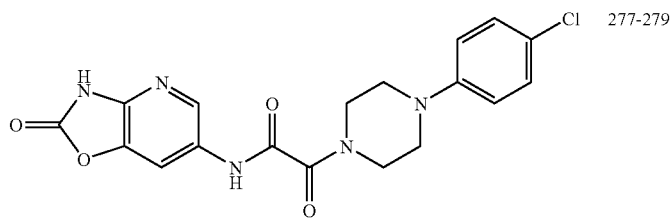 277-279
I-77 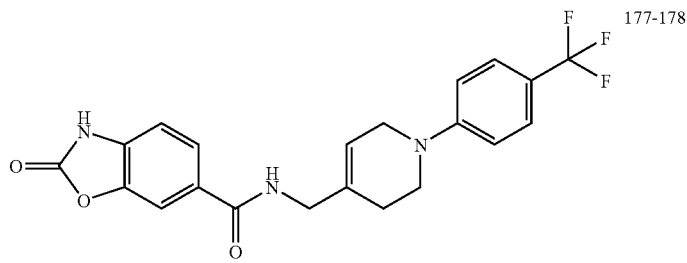 177-178

TABLE 16-continued
I-78 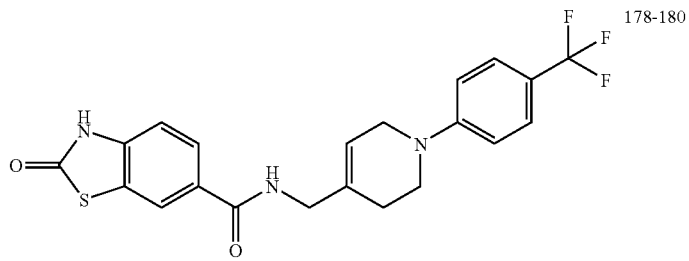 178-180
I-79 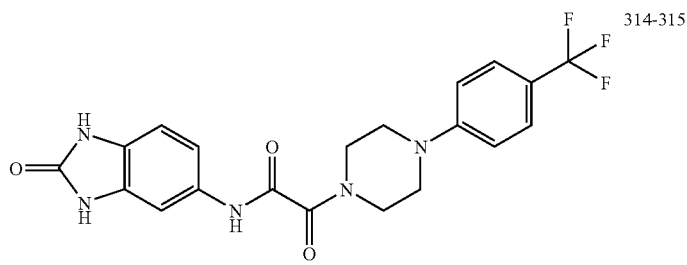 314-315
I-80 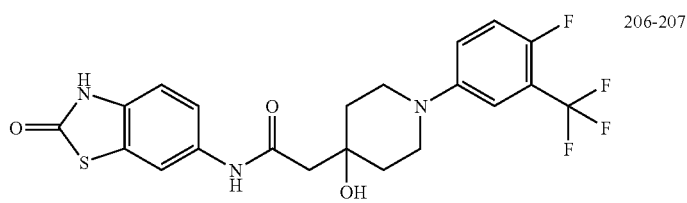 206-207
I-81 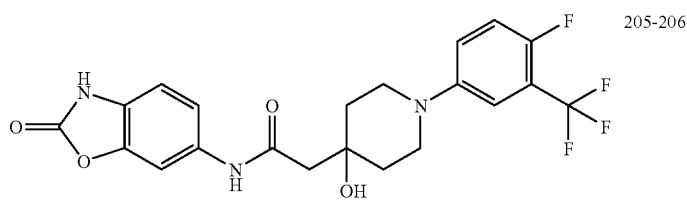 205-206
TABLE 17
I-82 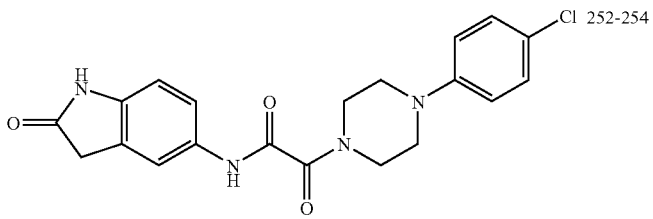 Cl 252-254
I-83 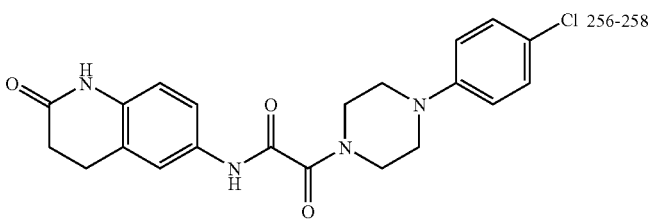 Cl 256-258

TABLE 17-continued
I-84 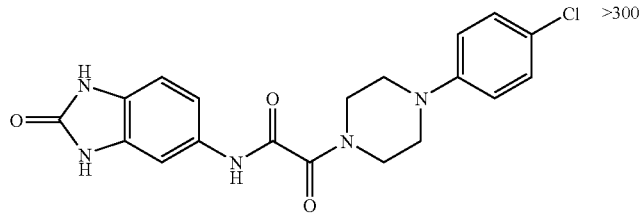 Cl >300
I-85 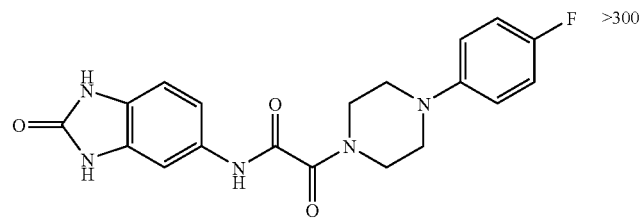 F >300
I-86 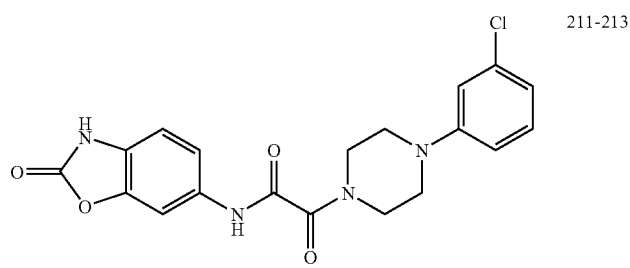 Cl 211-213
I-87 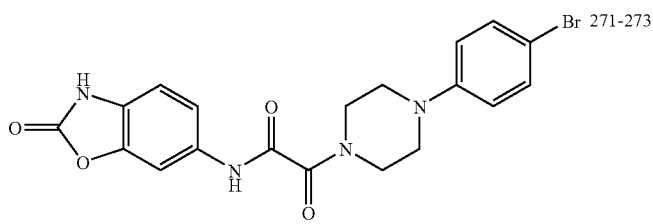 Br 271-273
I-88 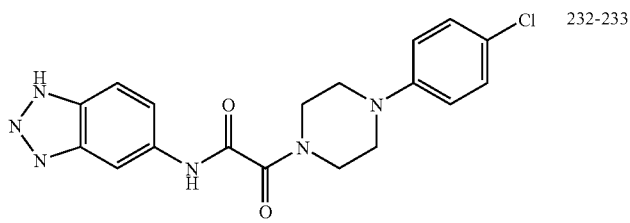 Cl 232-233
TABLE 18
I-89 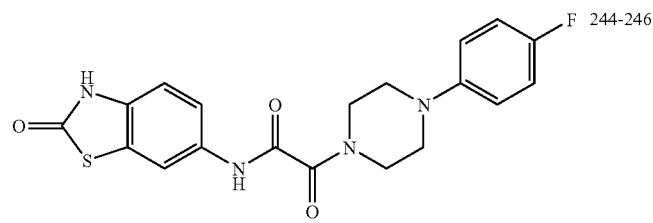 F 244-246

TABLE 18-continued
| I-90 | 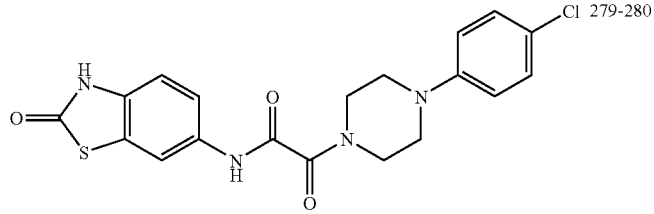 | 279-280 |
| I-91 | 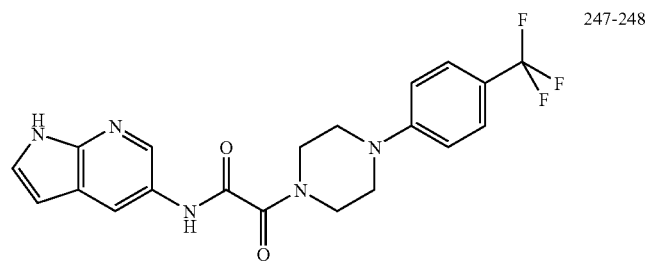 | 247-248 |
| I-92 | 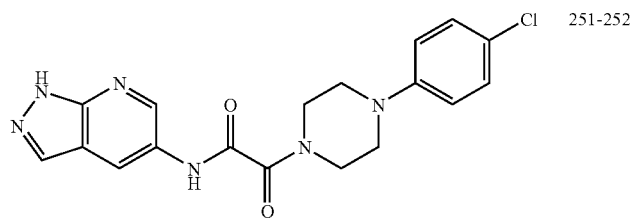 | 251-252 |
| I-93 | 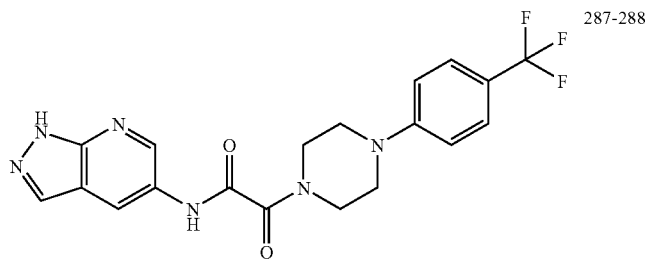 | 287-288 |
| I-94 | 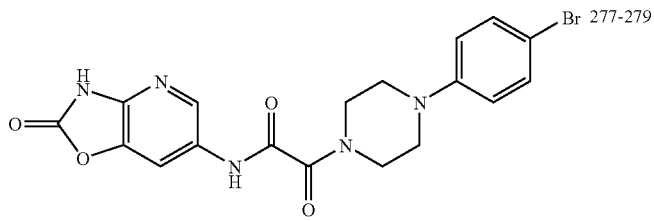 | 277-279 |
TABLE 19
| I-95 | 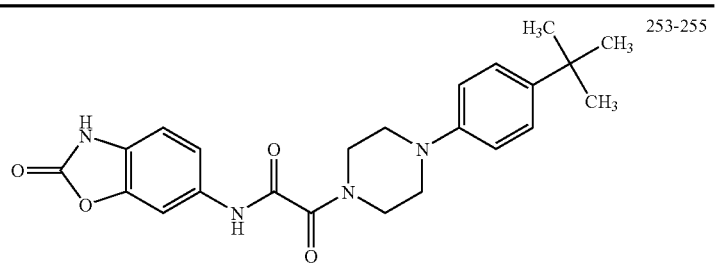 | 253-255 |

TABLE 19-continued
I-96 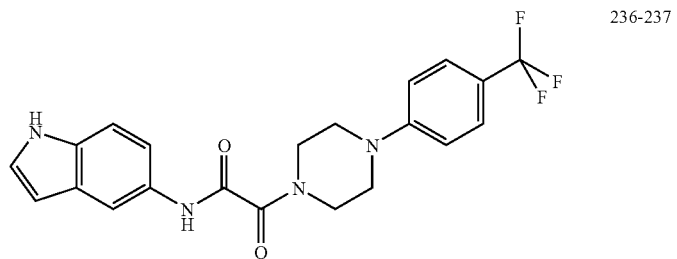 236-237
I-97 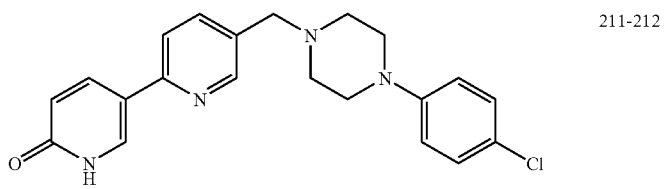 211-212
I-98 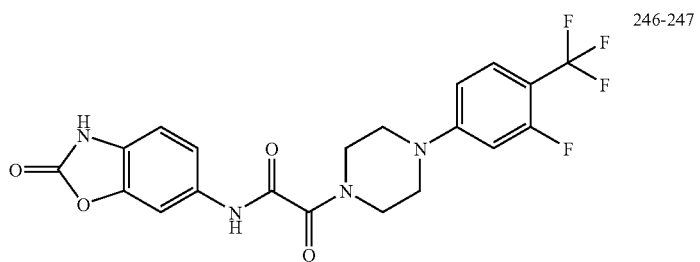 246-247
I-99 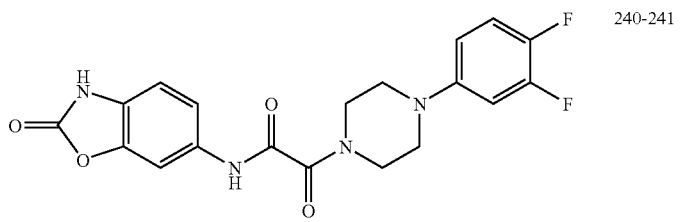 240-241
I-100 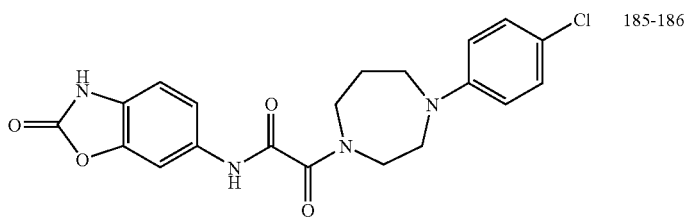 185-186
I-101 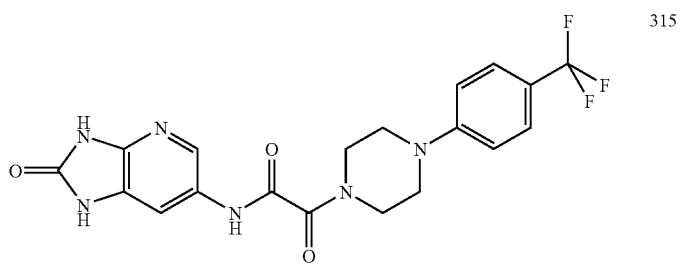 315

TABLE 20
| | | |
|---|---|---|
| I-102 | 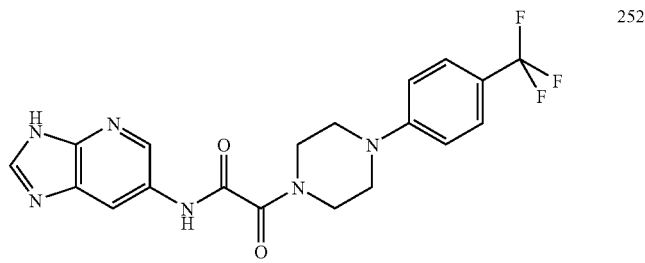 | 252 |
| I-103 | 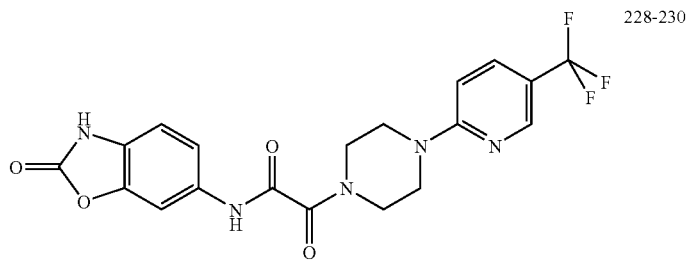 | 228-230 |
| I-104 | 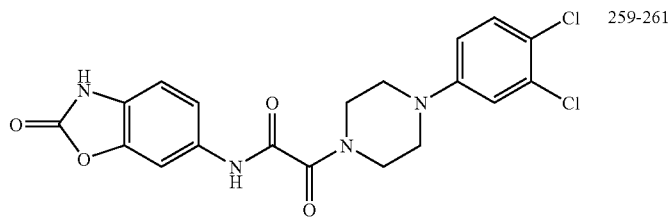 | 259-261 |
| I-105 | 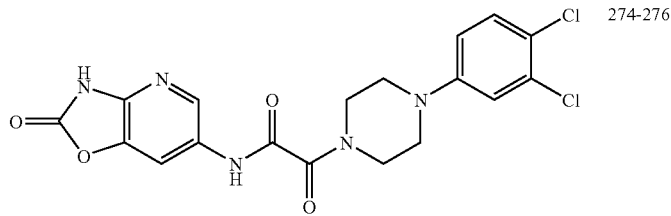 | 274-276 |
| I-106 | 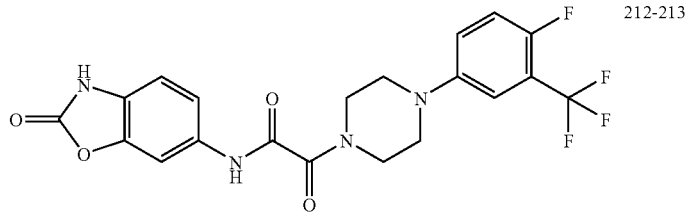 | 212-213 |
| I-107 | 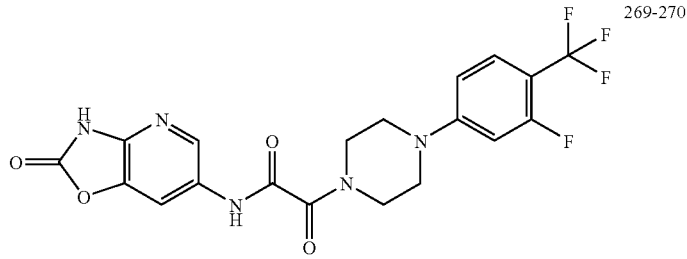 | 269-270 |

TABLE 20-continued
I-108 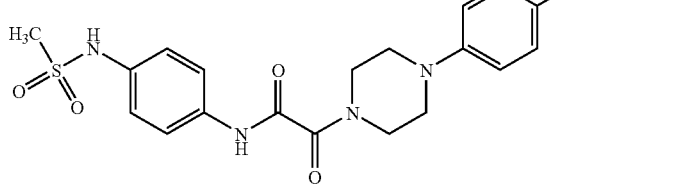 235-236
TABLE 21
I-109 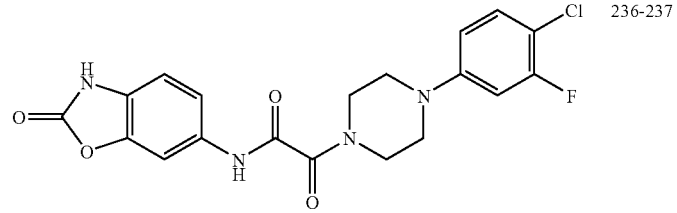 236-237
I-110 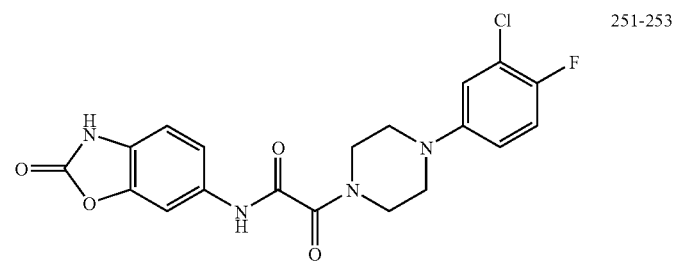 251-253
I-111 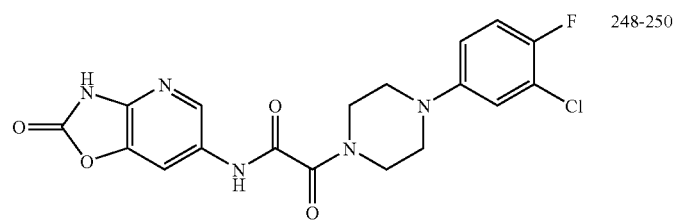 248-250
I-112 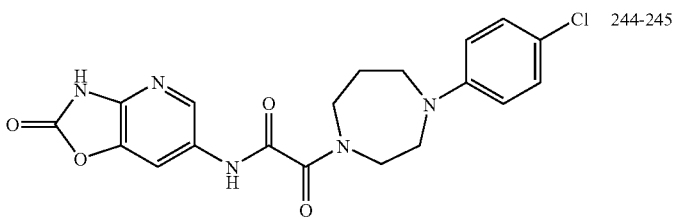 244-245
I-113 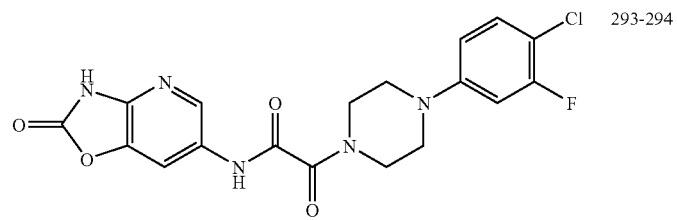 293-294

TABLE 21-continued
| I-114 | 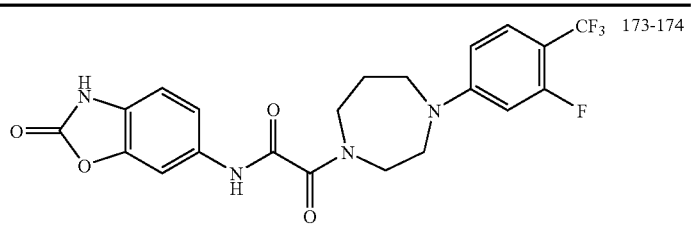 | 173-174 |
| --- | --- | --- |
| I-115 | 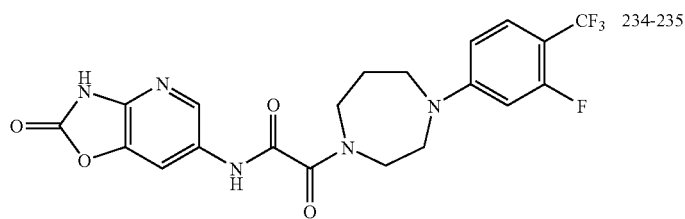 | 234-235 |
TABLE 22
| I-116 | 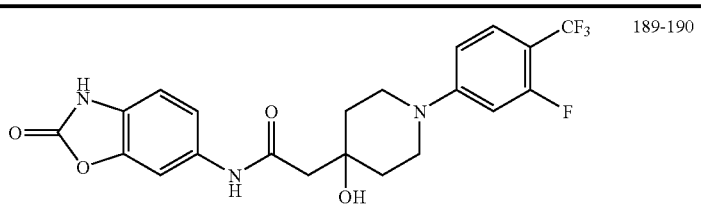 | 189-190 |
| --- | --- | --- |
| I-117 | 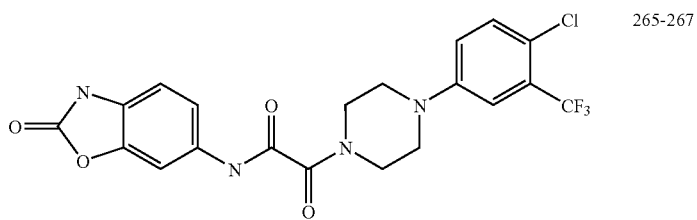 | 265-267 |
| I-118 | 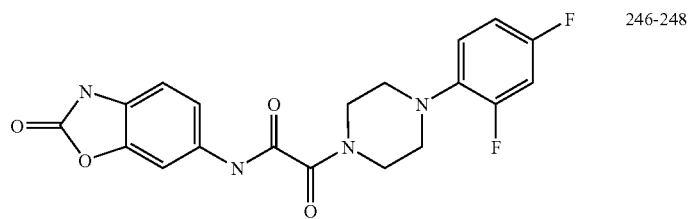 | 246-248 |
| I-119 | 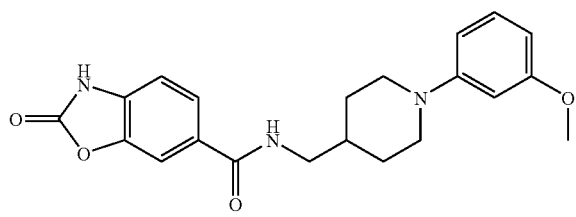 | |
| I-120 | 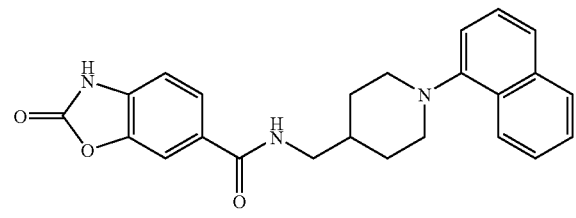 | |

TABLE 22-continued
I-121
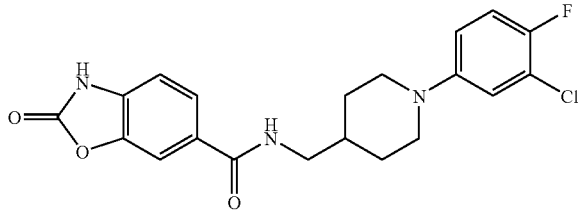
I-122
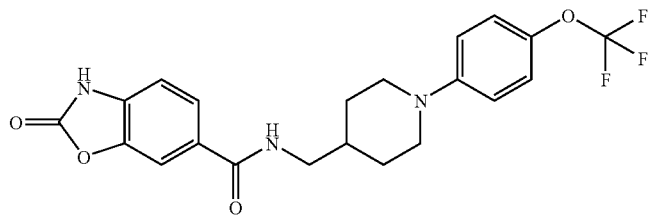
I-123
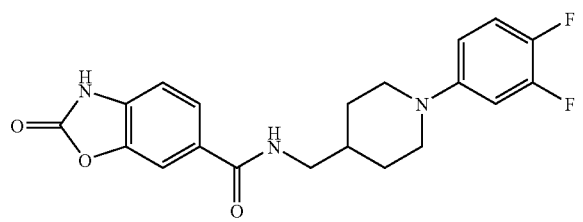
TABLE 23
I-124
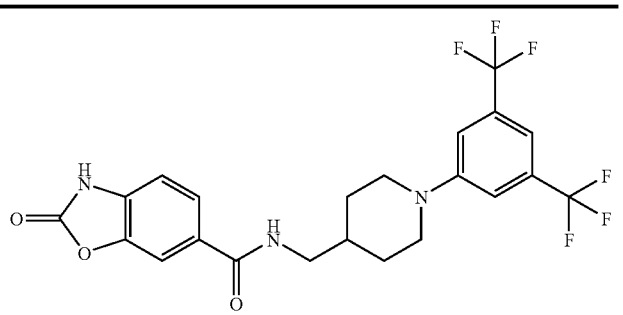
I-125
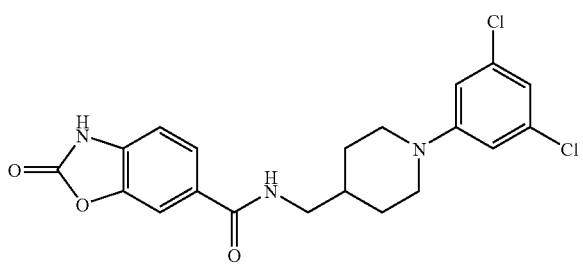
I-126
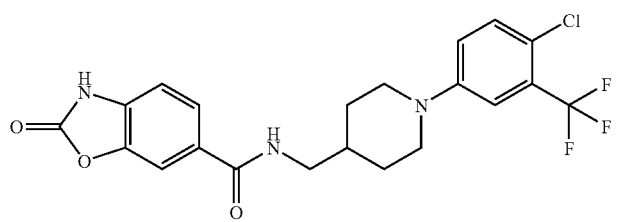

TABLE 23-continued
I-127
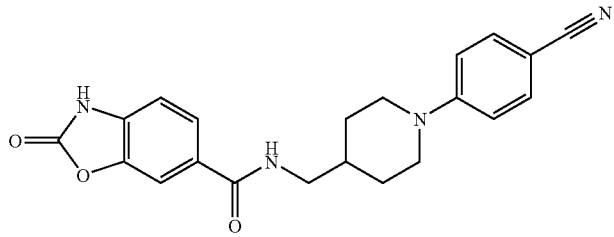
I-128
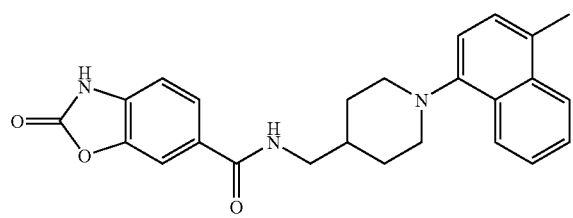
I-129
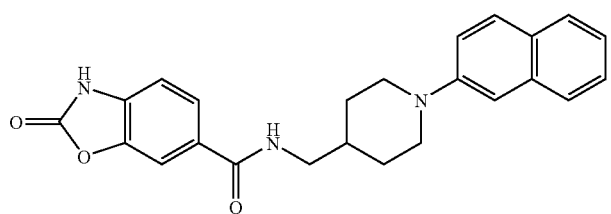
I-130
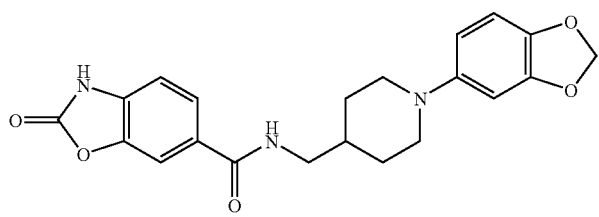
I-131
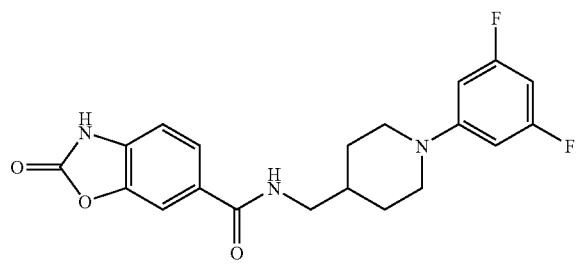
TABLE 24
I-132
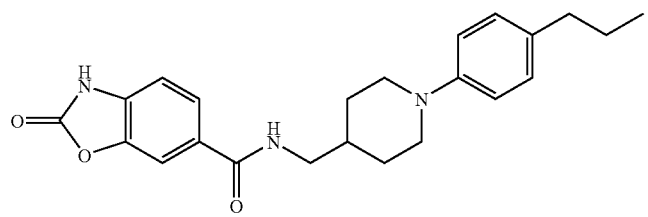

TABLE 24-continued
I-133
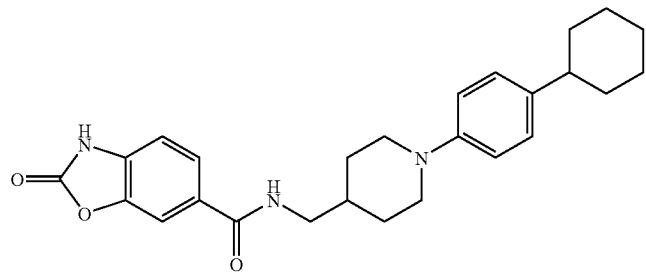
I-134
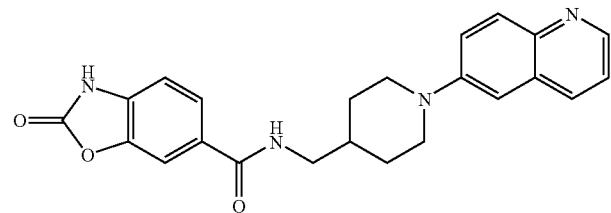
I-135
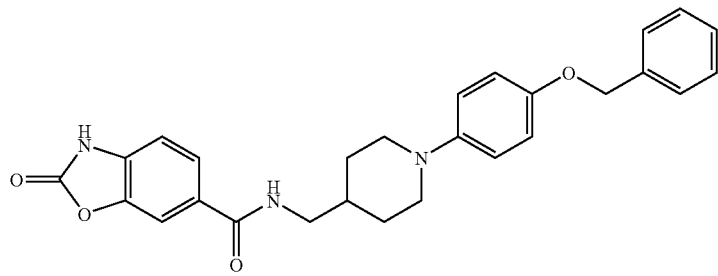
I-136
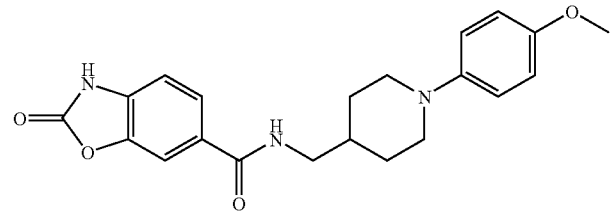
I-137
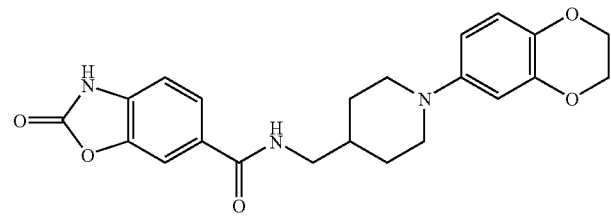
I-138
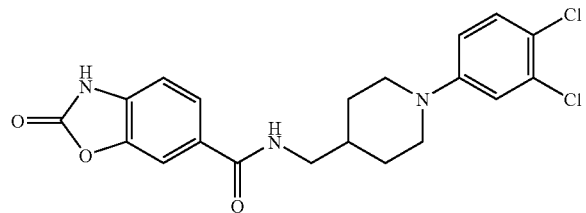

TABLE 24-continued
I-139
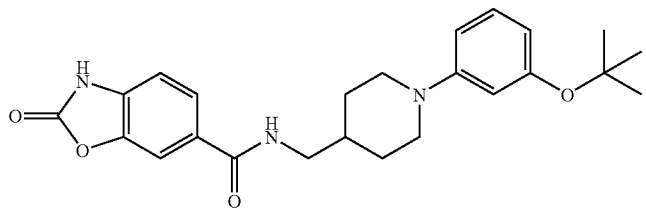
TABLE 25
I-140
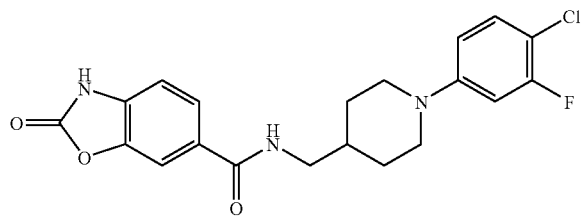
I-141
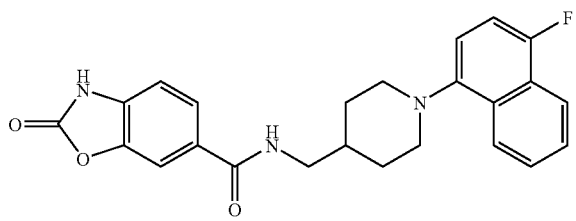
I-142
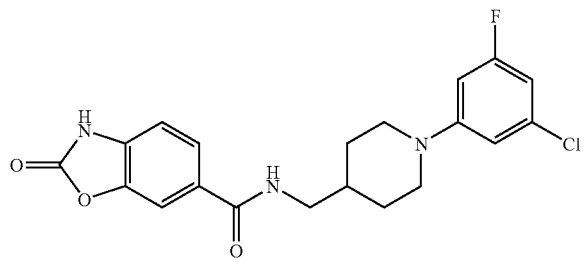
I-143
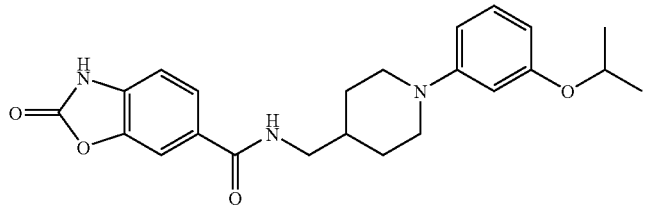
I-144
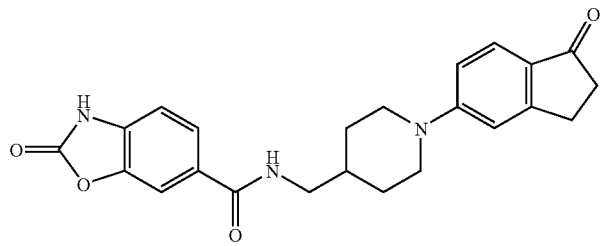

TABLE 25-continued
I-145
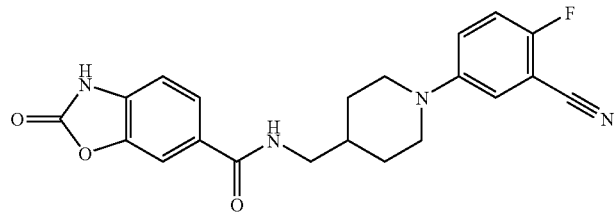
I-146
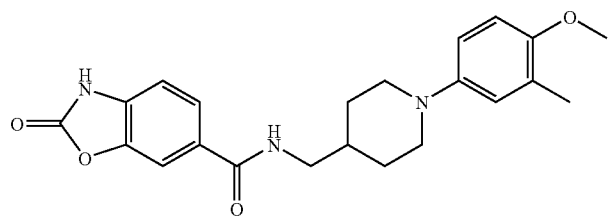
I-147
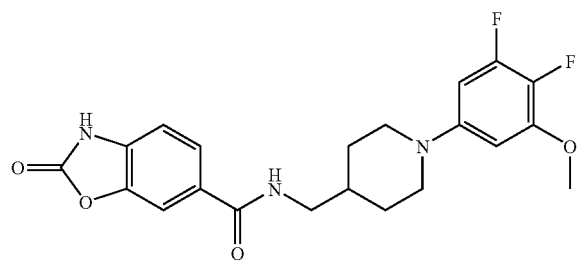
TABLE 26
I-148
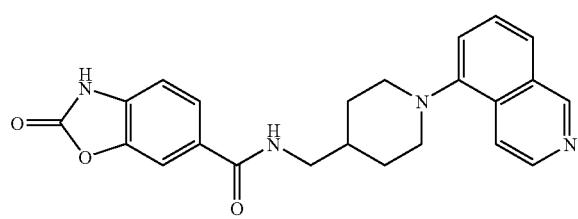
I-149
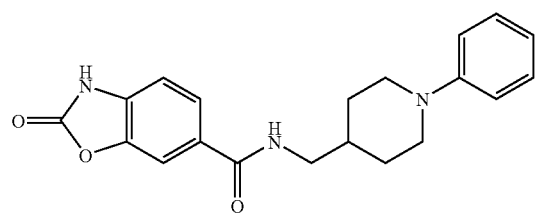
I-150
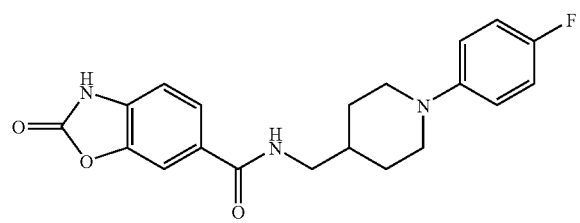

TABLE 26-continued
I-151
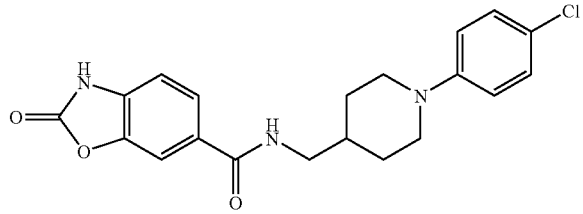
I-152
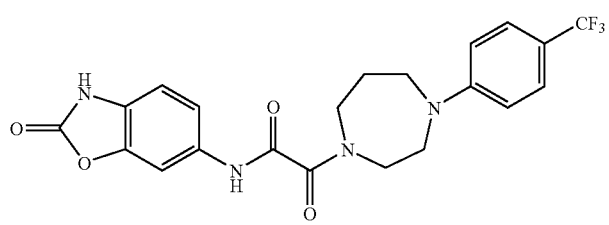
I-153
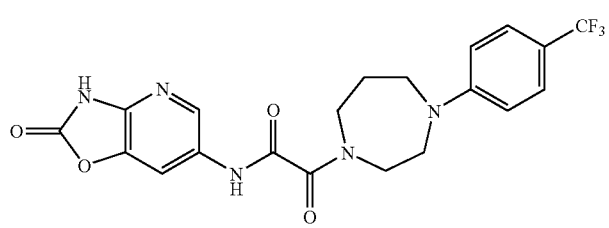
I-154     199-200
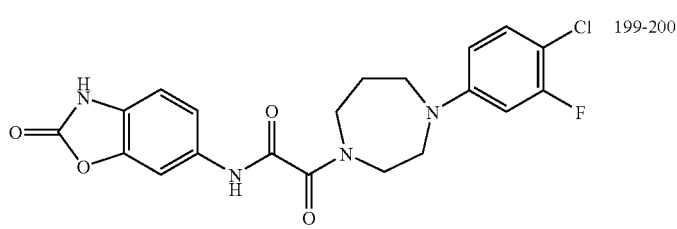
I-155     262-263
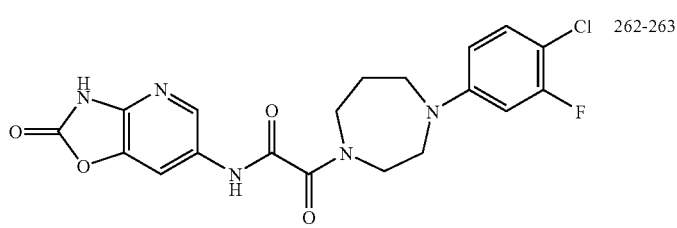
TABLE 27
I-156
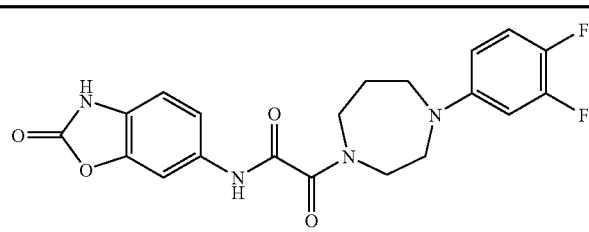

TABLE 27-continued
I-157 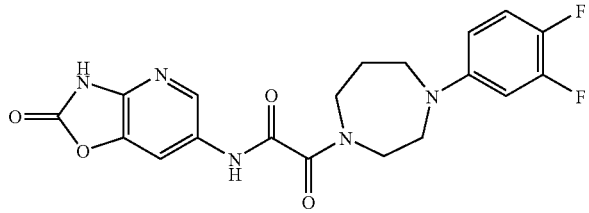
I-158 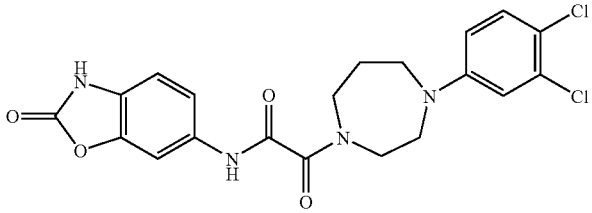
I-159 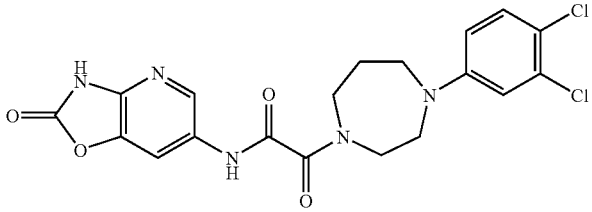
I-160 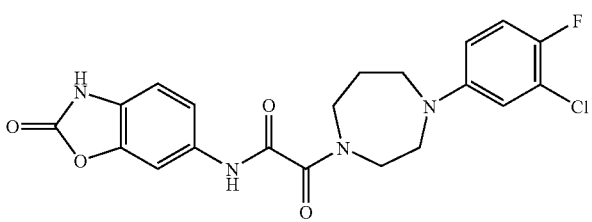
I-161 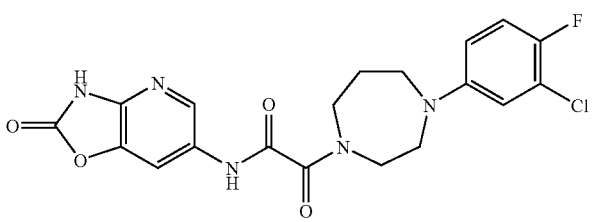
I-162 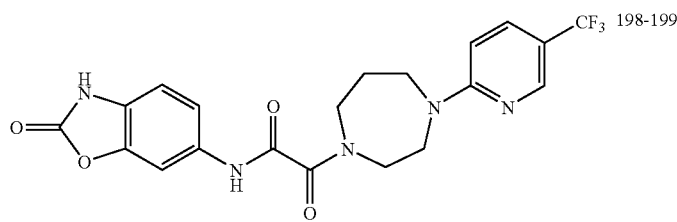   198-199
I-163 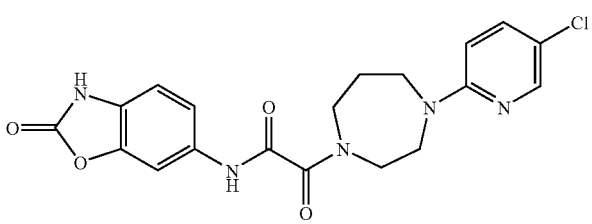

TABLE 28
I-164 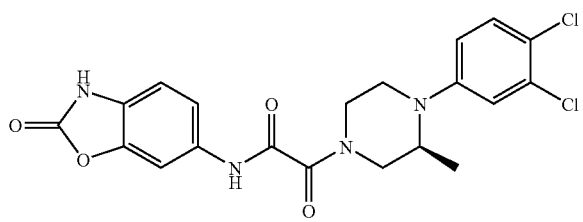
I-165 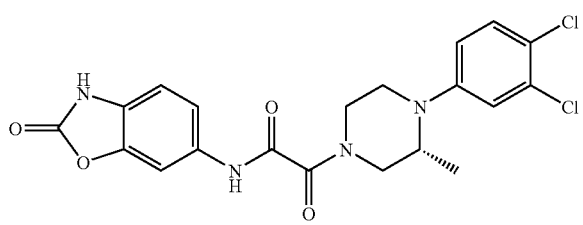
I-166 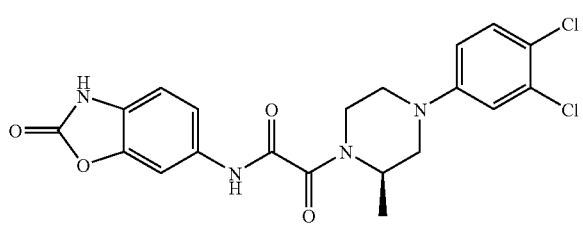
I-167 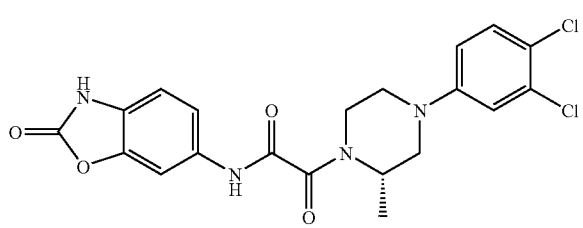
I-168 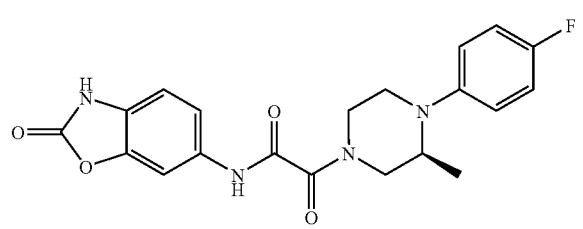
I-169 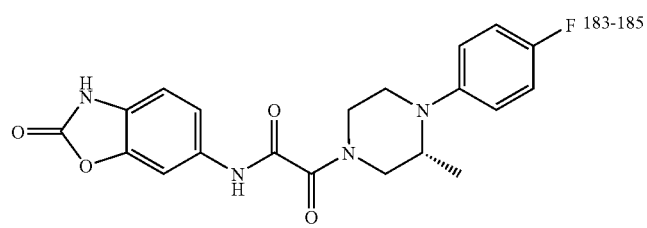
183-185
I-170 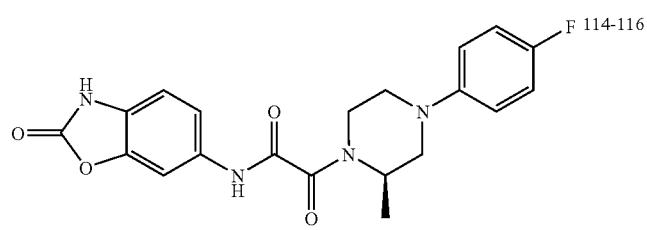
114-116

TABLE 29
I-171 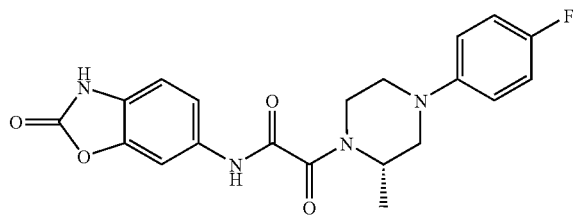
I-172 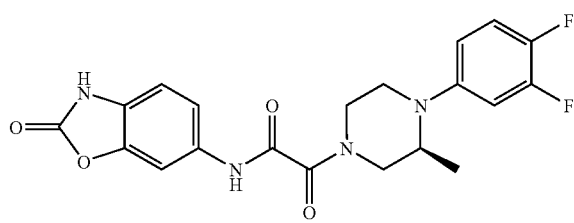
I-173 108-109
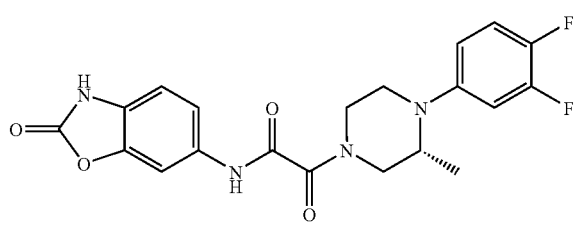
I-174 208-210
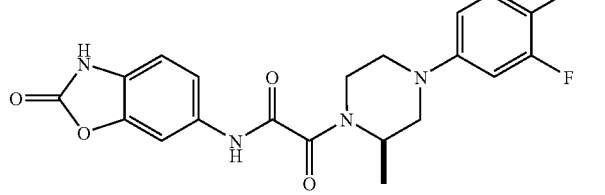
I-175 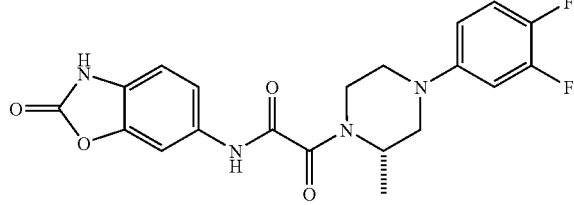
I-176 120-123
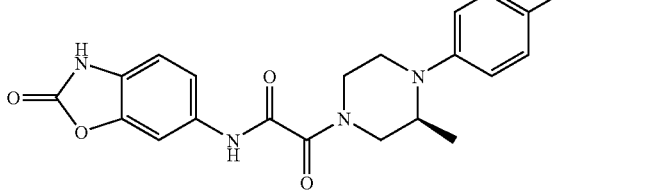
I-177 117-119
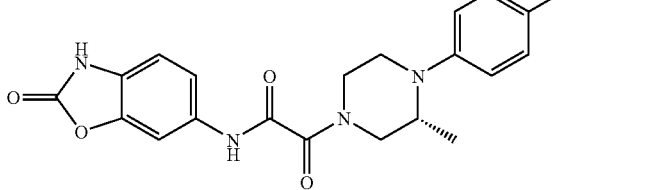

TABLE 29-continued
| I-178 | 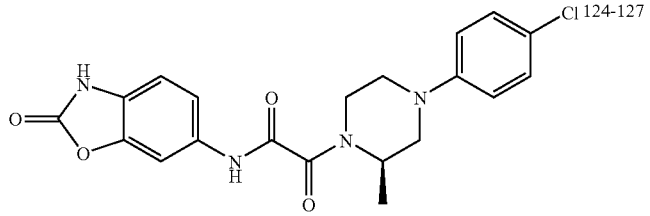 | Cl 124-127 |
TABLE 30
| I-179 | 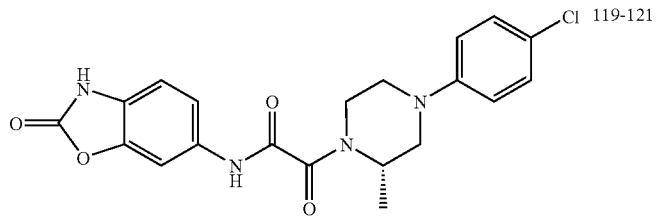 | Cl 119-121 |
| I-180 | 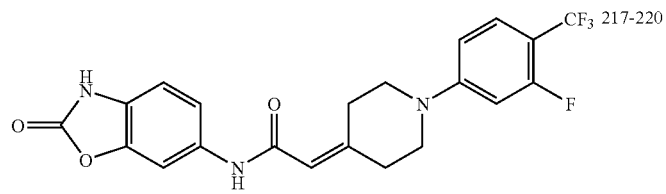 | CF$_3$ 217-220 |
| I-181 | 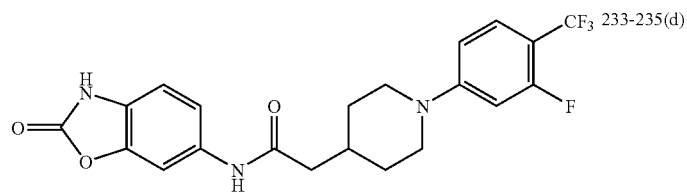 | CF$_3$ 233-235(d) |
| I-182 | 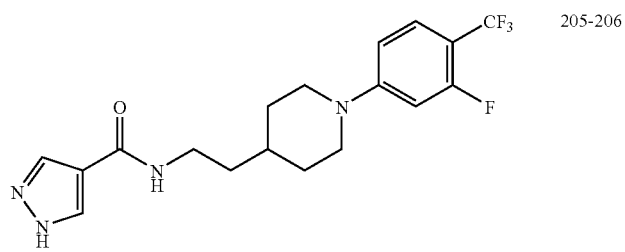 | CF$_3$ 205-206 |
| I-183 | 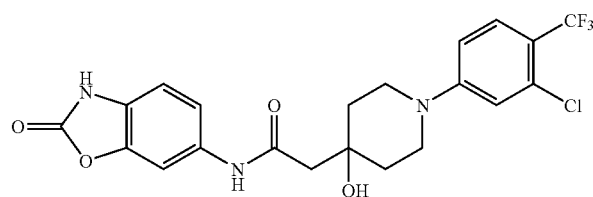 | CF$_3$ |
| I-184 | 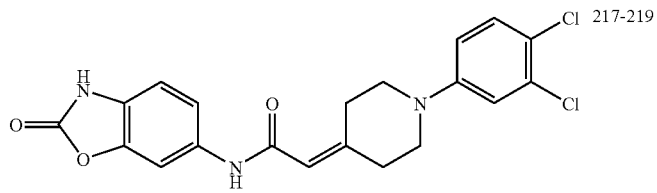 | Cl 217-219 |

TABLE 30-continued
I-185
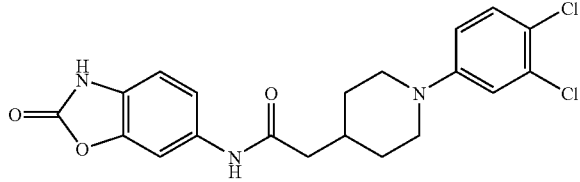
I-186
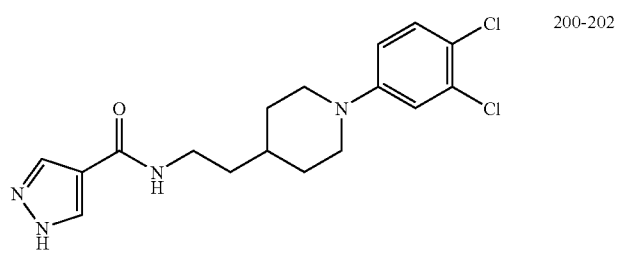
200-202
TABLE 31
I-187
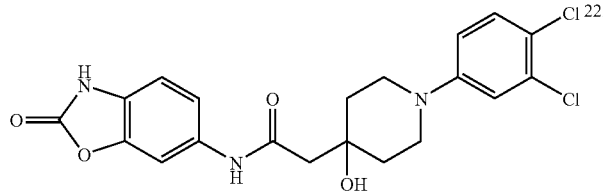
Cl 222-224
I-188
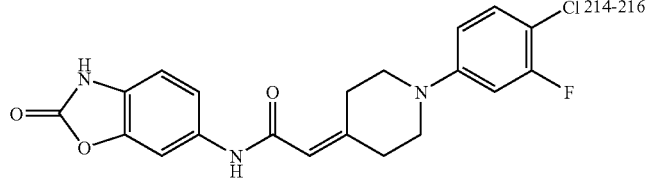
Cl 214-216
I-189
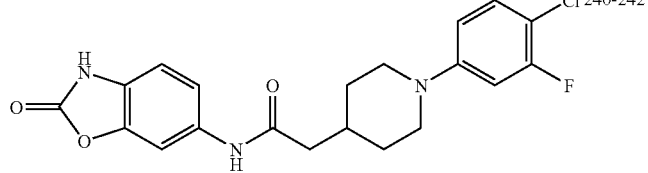
Cl 240-242
I-190
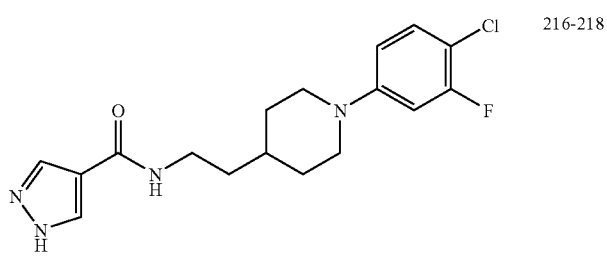
216-218
I-191
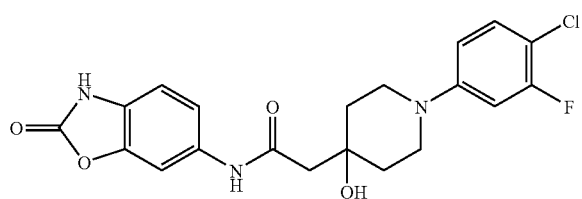

TABLE 31-continued
I-192 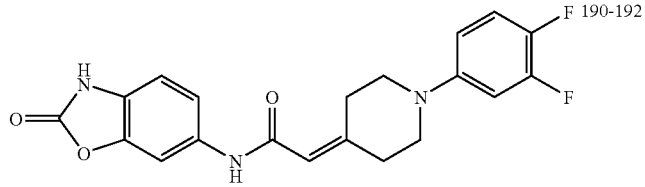 F 190-192
I-193 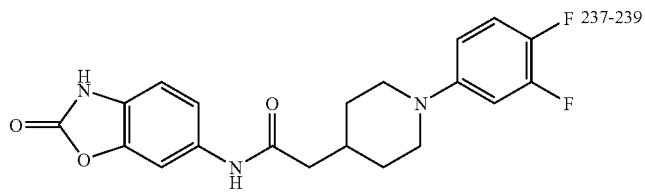 F 237-239
I-194 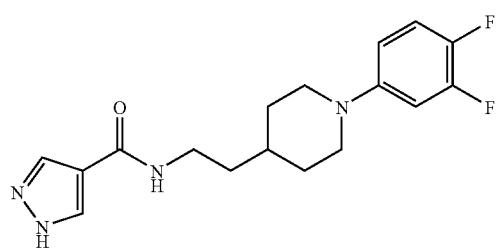
TABLE 32
I-195 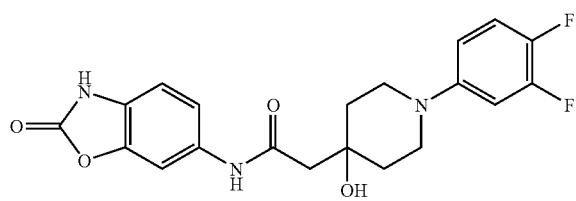
I-196 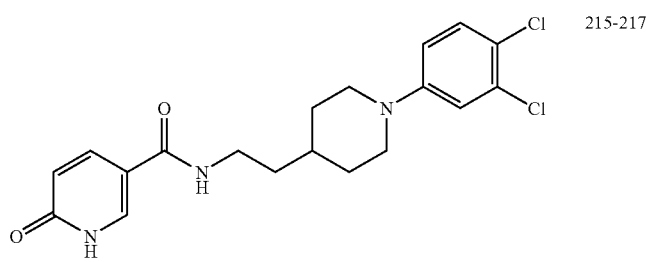 Cl 215-217
I-197 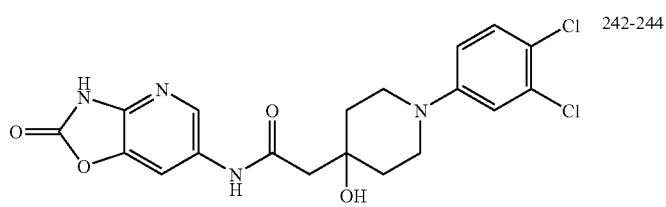 Cl 242-244

TABLE 32-continued
I-198 285-287
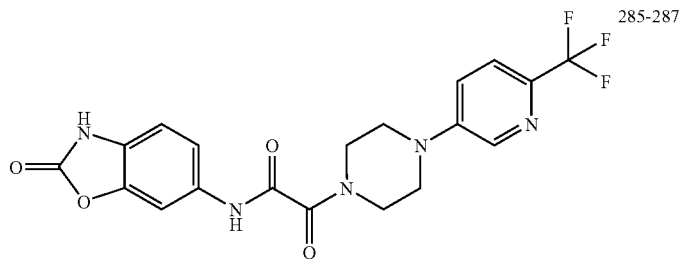
I-199 208-209
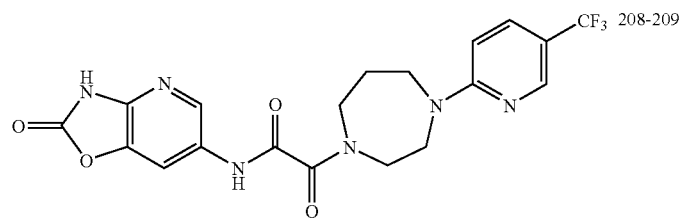
I-200 241-242
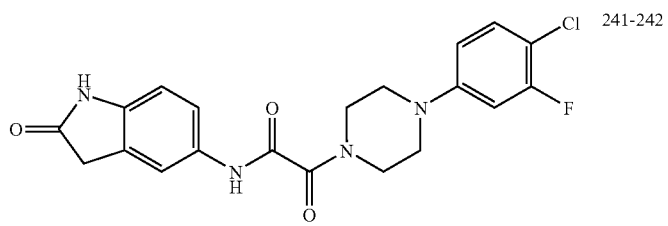
I-201 250-251
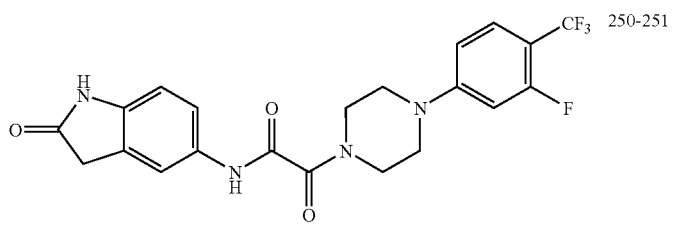
I-202 227-228
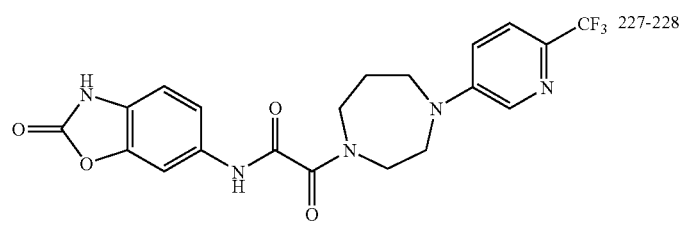

TABLE 33
| Compound No. | Structural formula | Melting point |
|---|---|---|
| I-203 | 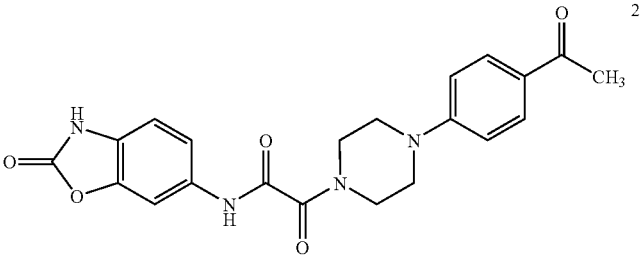 | 264-266(d) |
| I-204 | 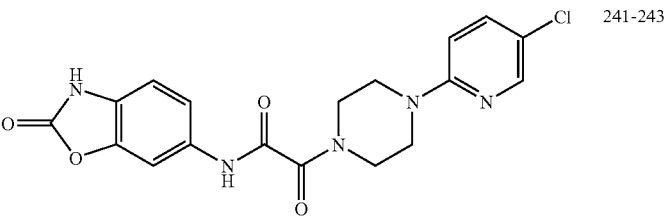 | 241-243 |
| I-205 | 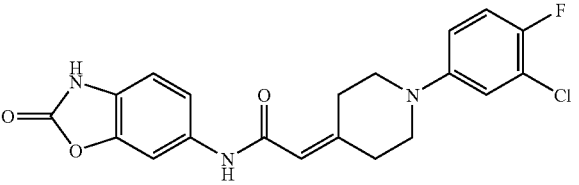 | 209-211 |
| I-206 | 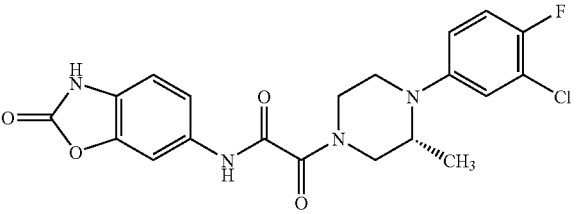 | 107-108 |
| I-207 | 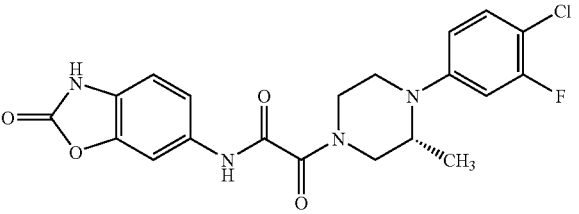 | 202-203 |
| I-208 | 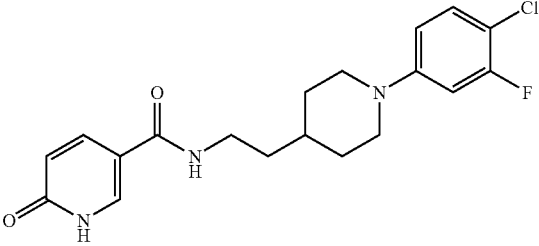 | 230-232 |

TABLE 33-continued

| Compound No. | Structural formula | Melting point |
|---|---|---|
| I-209 | | 197-198 |

TABLE 34

| Compound No. | Structural formula | Melting point |
|---|---|---|
| I-210 | | 195-197 |
| I-211 | | 229-230 |
| I-212 | | 185-187 |
| I-213 | | 253-255 |
| I-214 | | 272-274 |

TABLE 34-continued
I-215 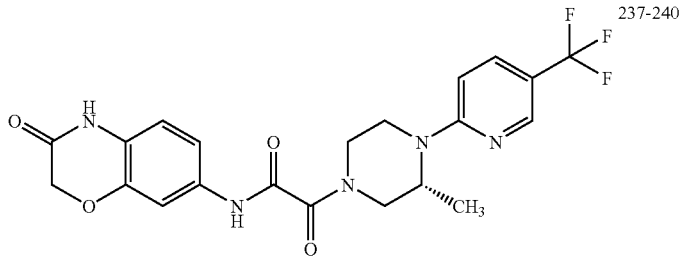 237-240
I-216 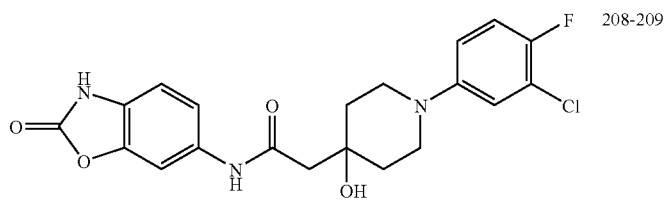 208-209
TABLE 35
I-217 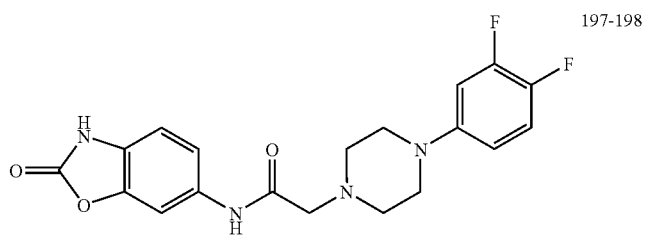 197-198
I-218 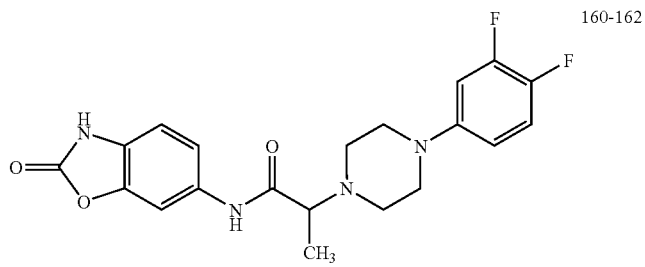 160-162
I-219 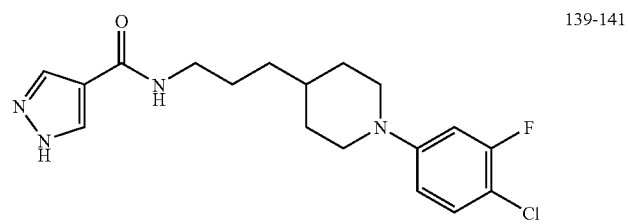 139-141
I-220 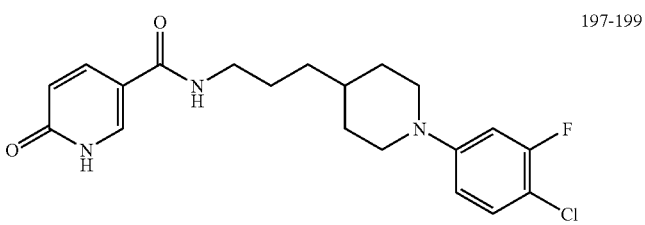 197-199

TABLE 35-continued
I-221 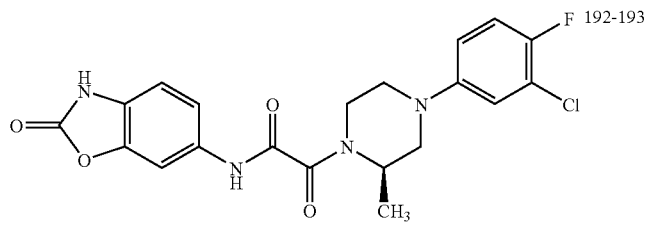 192-193
I-222 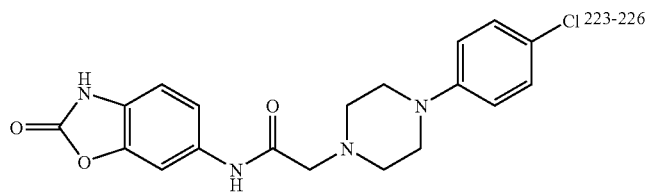 223-226
I-223 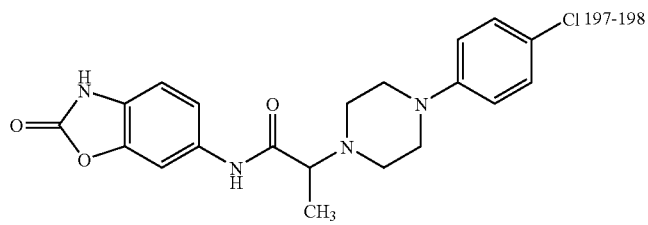 197-198
I-224 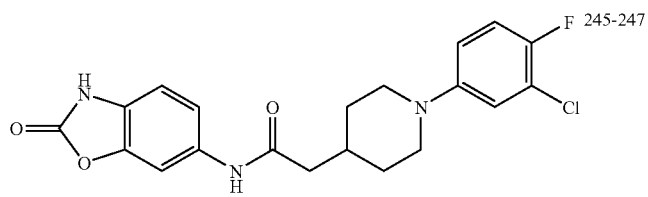 245-247
TABLE 36
I-225 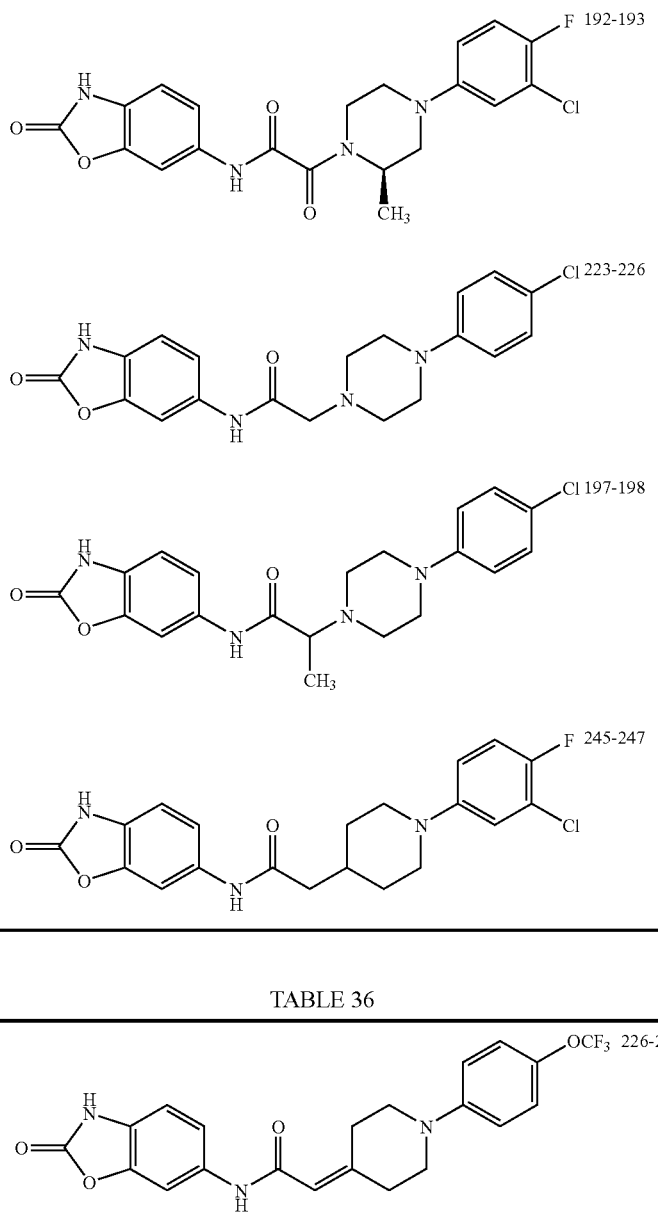 226-228
I-226 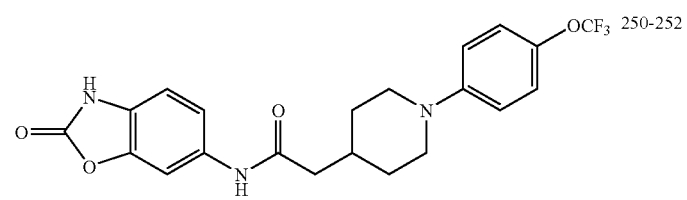 250-252
I-227 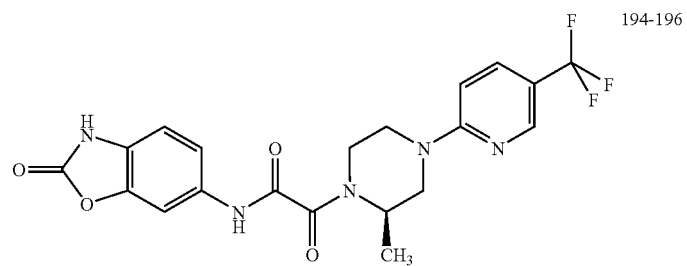 194-196

TABLE 36-continued
I-228 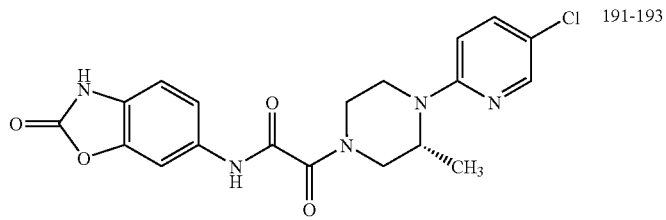 191-193
I-229 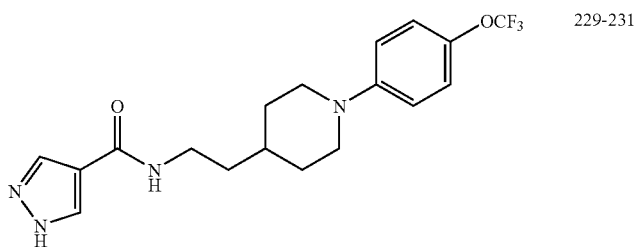 229-231
I-230 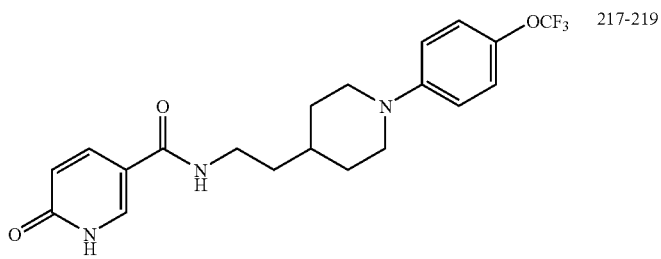 217-219
I-231 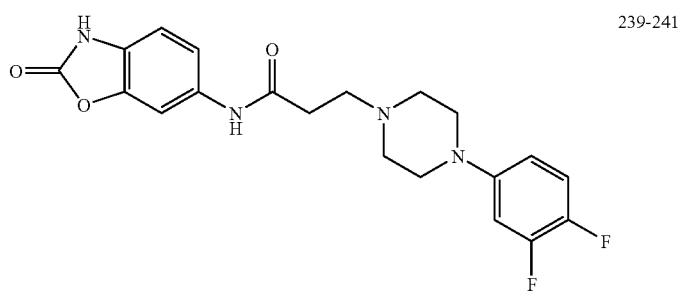 239-241
TABLE 37
I-232 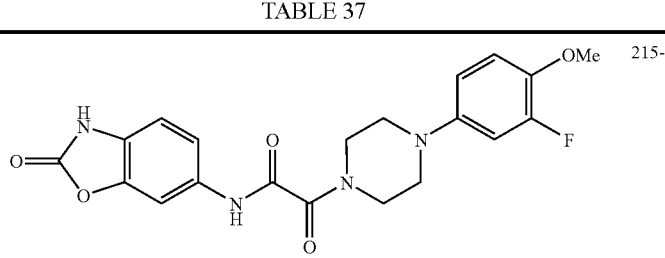 215-126
I-233 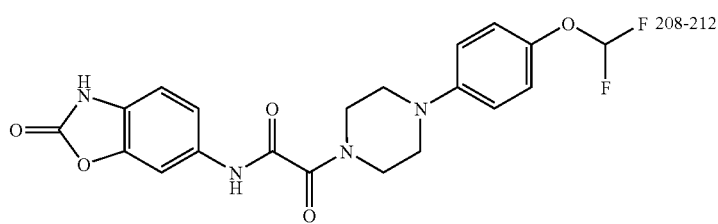 208-212

TABLE 37-continued
I-234 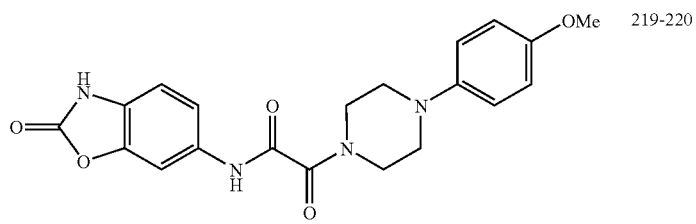 219-220
I-235 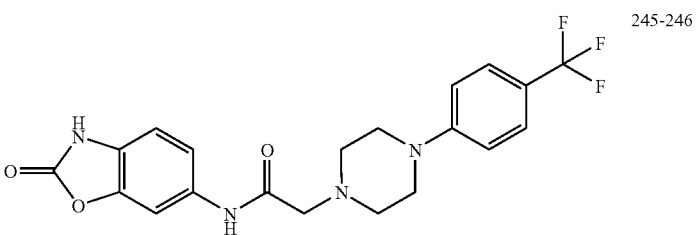 245-246
I-236 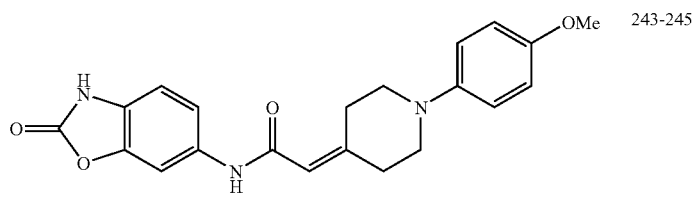 243-245
I-237 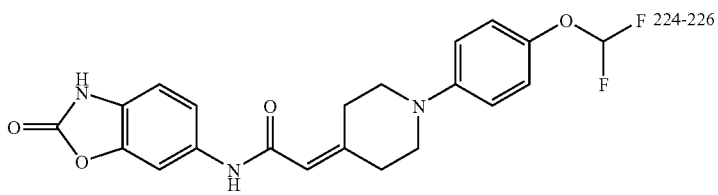 224-226
I-238 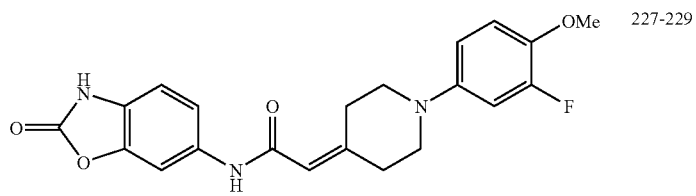 227-229
I-239 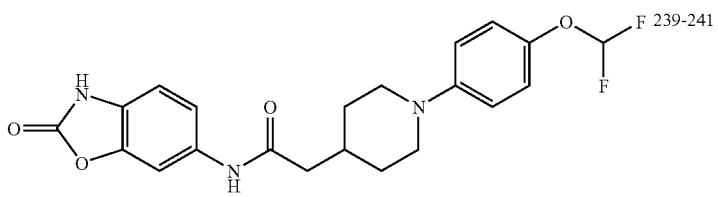 239-241
TABLE 38
I-240 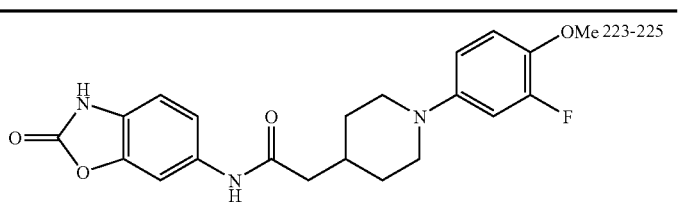 223-225

TABLE 38-continued
I-241 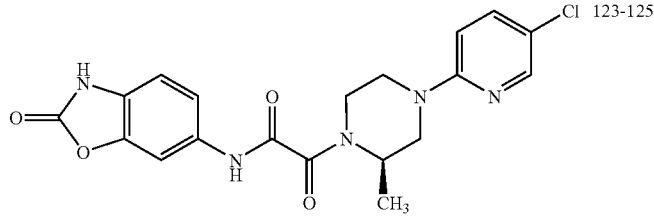 Cl 123-125
I-242 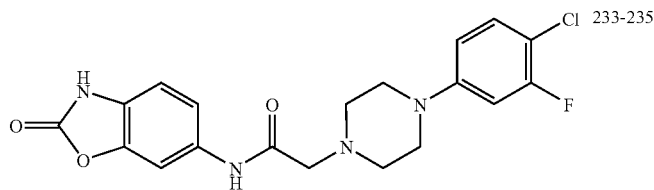 Cl 233-235
I-243 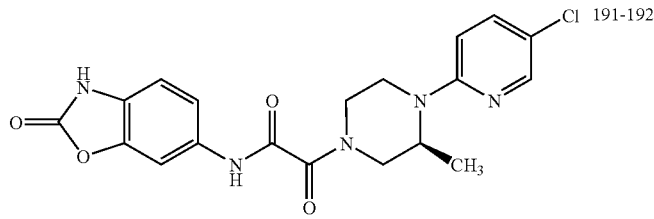 Cl 191-192
I-244 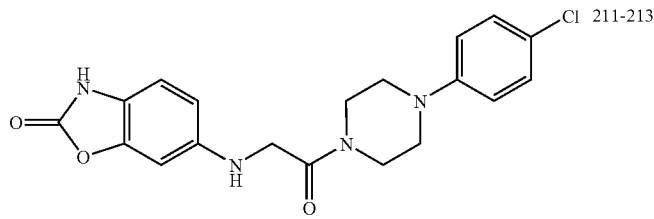 Cl 211-213
I-245 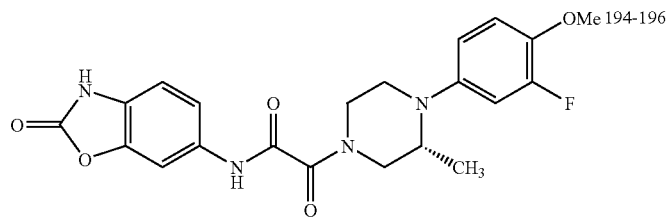 OMe 194-196
I-246 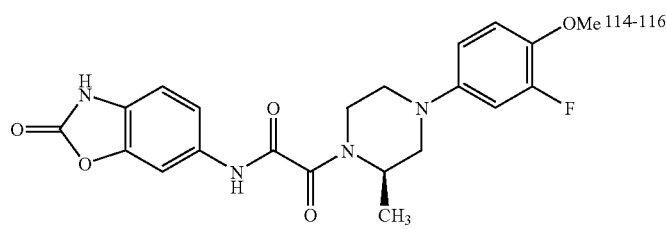 OMe 114-116

TABLE 39

| Compound No. | Structural formula | Melting point |
| --- | --- | --- |
| I-247 | | 224-226 |
| I-248 | | 118-120 |
| I-249 | | 123-125 |
| I-250 | | 201-203 |
| I-251 | | 122-124 |
| I-252 | | |
| I-253 | | 226-228 |

TABLE 40
| | | |
|---|---|---|
| I-254 | 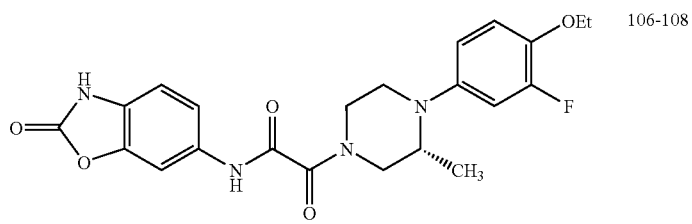 | 106-108 |
| I-255 | 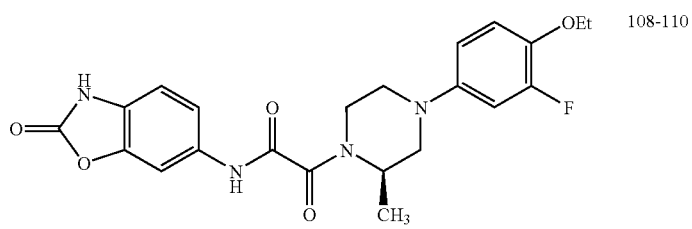 | 108-110 |
| I-256 | 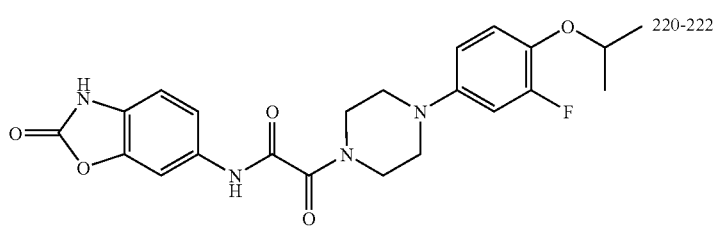 | 220-222 |
| I-257 | 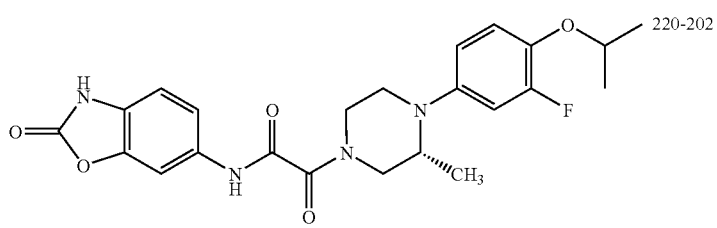 | 220-202 |
| I-258 | 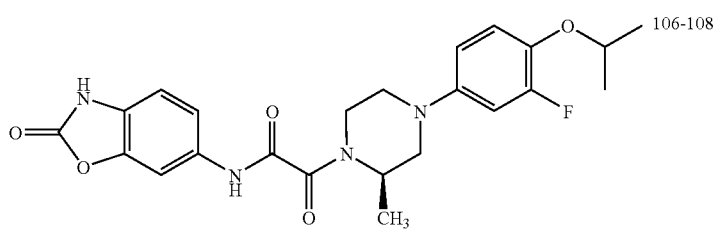 | 106-108 |
| I-259 | 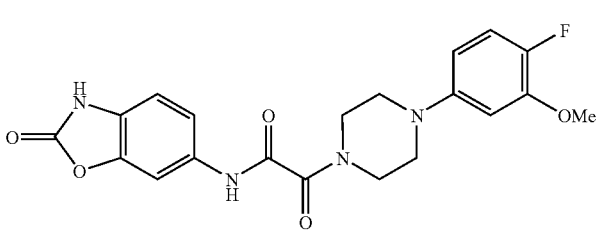 | |
| I-260 | 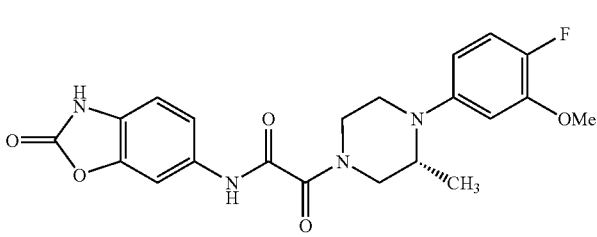 | |

TABLE 41
I-261 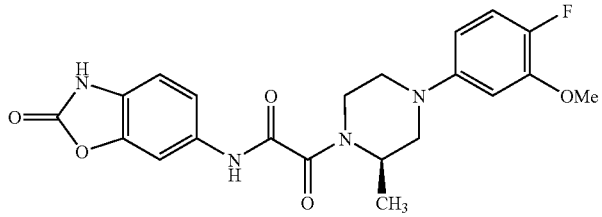
I-262 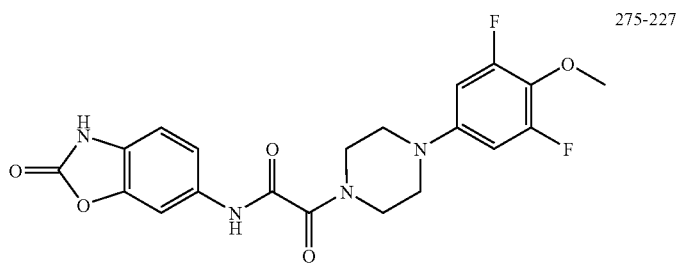 275-227
I-263 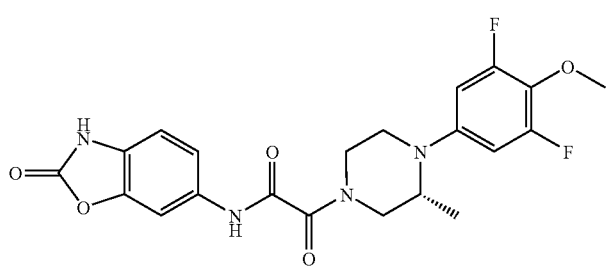 226-228
I-264 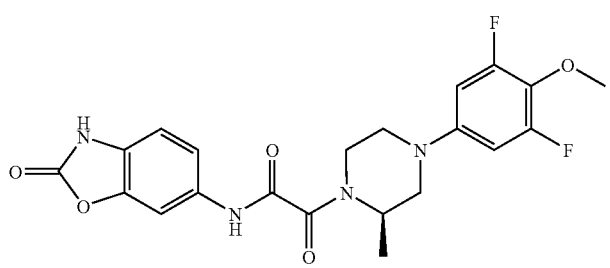 114-116
I-265 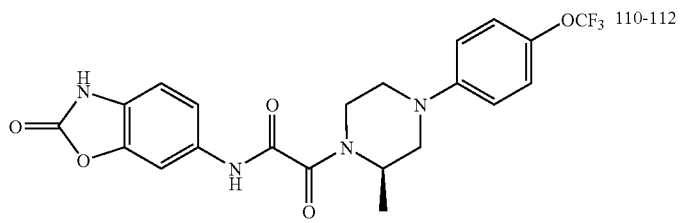 110-112
I-266 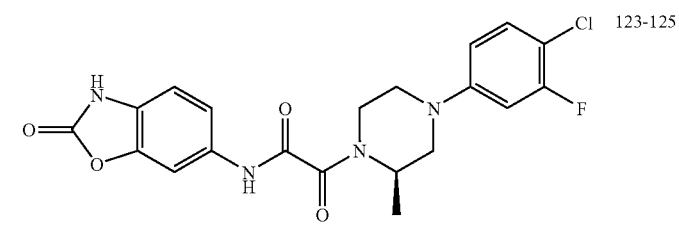 123-125

TEST EXAMPLE 1

Test of Binding with NMDR Receptor (NR1/NR2B Receptor)

Using Ifenprodil which is an antagonist specific for a NR1/NR2B subtype receptor as a ligand, an experiment of competition between a receptor and a test compound was performed.

Using a male Slc: Wistar rat as an animal, a brain was isolated after decapitation, and a cerebral cortex was fractionated. The cerebral cortex was homogenized with a 20-fold amount of an ice-cooled 50 mM Tris/HCl buffer (pH 7.4), and the homogenate was centrifuged at 4° C. and 27,500×g for 10 minutes. The resulting precipitate was suspended in the same buffer, and this was again centrifuged. This operation was repeated for three times, the resulting precipitate was suspended in a buffer, and this was stored at −80° C. Immediately before an experiment, the frozen suspension was thawed at room temperature, this was centrifuged at 4° C. and 27,500×g for 10 minutes, and the resulting precipitate was suspended in a buffer. Further, the suspension was diluted 10-fold with a buffer, and this was used as a membrane specimen in an experiment. In a binding experiment, to 470 μl of the membrane specimen were added 10l of each of test compounds having different concentrations, 10 μl of a labeled ligand [$^3$H]-Ifenprodil and 10 μl GBR-12909, followed by incubation at an ice temperature for 120 minutes. A concentration of [$^3$H]-Ifenprodil of the labeled ligand was finally 5 nM, and a concentration of GBR-12909 was finally 3 μM. For measuring a total binding amount, DMSO as a solvent was used and, for measuring a non-specific binding amount, 100 μM Ifenprodil was used. GBR-12909 was added in order to block binding of [$^3$H]-Ifenprodil to non-polyamine-sensitive site. After incubation, a bound formand a free foramwere separated using Whatman GF/C filter (manufactured by Whatman), and the filter was washed with 2.5 ml ice-cooled buffer four times. The filter was immersed in liquid scintillation (Cryasol I, manufactured by Nacalai tesque), and radioactivity (dpm) was measured with a liquid scintillation counter. From a measured value, a binding inhibition rate (%) was obtained by the following equation, and a dose at which binding is inhibited 50% ($IC_{50}$) was calculated. An $IC_{50}$ value of a test substance is shown in Table 42. A formula of GBR-12909 (vanoxerine) is shown below.

[Chemical formula 65]

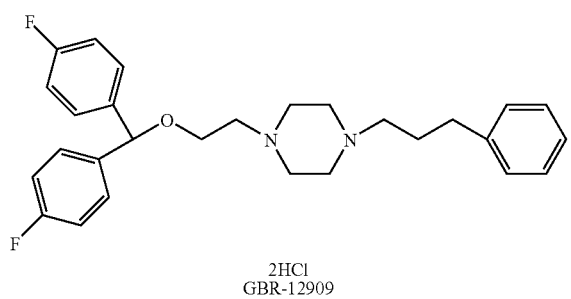

2HCl
GBR-12909

Binding inhibition rate(%)=100−[(binding amount in the presence of test compound−non-specific binding amount)/(total binding amount−non-specific binding amount)]×100

TABLE 42

| Compound No. | NR2B ($IC_{50}$ μM) |
|---|---|
| I-1 | 0.043 |
| I-2 | 0.033 |
| I-5 | 0.043 |
| I-21 | 0.096 |
| I-23 | 0.040 |
| I-30 | 0.077 |
| I-42 | 0.107 |
| I-43 | 0.017 |
| I-55 | 0.025 |
| I-66 | 0.090 |
| I-70 | 0.068 |
| I-73 | 0.015 |
| I-79 | 0.013 |
| I-85 | 0.067 |
| I-87 | 0.012 |
| I-90 | 0.026 |
| I-98 | 0.015 |
| I-100 | 0.074 |
| I-101 | 0.011 |
| I-103 | 0.018 |
| I-104 | 0.016 |
| I-105 | 0.045 |
| I-109 | 0.012 |
| I-113 | 0.034 |
| I-116 | 0.049 |
| I-154 | 0.044 |
| I-177 | 0.059 |
| I-178 | 0.029 |
| I-180 | 0.062 |
| I-184 | 0.041 |
| I-187 | 0.054 |
| I-188 | 0.021 |
| I-192 | 0.052 |
| I-196 | 0.023 |
| I-198 | 0.073 |
| I-200 | 0.081 |
| I-201 | 0.074 |

The following compounds showed $IC_{50}$ of 0.1 μM or lower. I-45, I-99, I-84, I-86, I-107, I-114, I-204, I-205, I-206, I-207, I-208, I-209, I-211, I-221, I-225, I-226, I-227, I-228, I-230, I-232, I-233, I-235, I-237, I-238, I-239, I-241, I-247 and I-249.

From the above result, it was made clear that the present compound exhibits strong binding property on the NR1/NR2B subtype receptor.

TEST EXAMPLE 2

Measurement of Expression of NMDA Receptor and Ca Ion Influx Amount

A complementary DNA (cDNA) of a mouse NMDA receptor subunit was transiently introduced into a HEK293 cell and, after 1 day from introduction, change in a glutamic acid/glycine-induced intracelluar Ca amount was measured using a Ca ion reactive fluorescent coloring matter.

The HEK293 cell was cultured, and passaged using a modified Dulbecco's Eagle medium (DMEM, low glucose). The HEK293 cell (20,000/well) was seeded on a 96-well plate, a NR1 subunit and a NR2B subunit of the NMDA receptor incorporated into the pcDNA3.1 plasmid were transiently introduced into a cell, and the subunits were co-expressed. An introduction amount of a DNA was 0.025 μg in the case of the NR1 subunit, and 0.075 μg in the case of NR2B subunit per well. For the cell after introduction, cell death was inhibited using 50 μM of the NMDA receptor antagonist MK-801.

For adjusting a test compound and washing a cell, Krebs/Ringer/Hepes buffer (KRH, Ca: 5 mM) was used.

After 1 day from introduction, the NMDA receptor antagonist MK-801 was washed out using the KRH buffer, and a Ca ion indication fluorescent coloring matter Fluo-3/AM was made to be taken into the cell. Ca ion influx was induced with 20 μM glutamic acid/2 μM glycine. Change in a fluorescent amount due to Ca ion influx into the cell was measured at excitation of 480 nm using a fluorescent imaging system FDSS 3000.

Usually, if a test compound exhibits the antagonism of the NMDA receptor, Ca ion influx into the cell is reduced, a fluorescent amount is reduced.

From a measured value of the test compound, a Ca ion influx inhibition rate (%) was obtained by the following equation, and a dose at which influx is inhibited 50% ($IC_{50}$) was calculated. An $IC_{50}$ value of the test substance is shown in Table 43.

Ca ion influx inhibition rate(%)=100−[(fluorescent amount in the presence of test compound−background fluorescent amount)/(total fluorescent amount−background fluorescent)]×100

TABLE 43

| Compound No. | Ca2+ IC50 (μM) |
| --- | --- |
| I-2 | 0.014 |
| I-5 | 0.020 |
| I-6 | 0.039 |
| I-8 | 0.048 |
| I-11 | 0.069 |
| I-16 | 0.037 |
| I-21 | 0.037 |
| I-23 | 0.025 |
| I-25 | 0.063 |
| I-26 | 0.048 |
| I-30 | 0.004 |
| I-33 | 0.037 |
| I-34 | 0.020 |
| I-40 | 0.015 |
| I-41 | 0.092 |
| I-42 | 0.013 |
| I-43 | 0.009 |
| I-45 | 0.023 |
| I-53 | 0.067 |
| I-55 | 0.007 |
| I-61 | 0.037 |
| I-62 | 0.092 |
| I-63 | 0.079 |
| I-66 | 0.025 |
| I-70 | 0.015 |
| I-73 | 0.008 |
| I-74 | 0.039 |
| I-78 | 0.031 |
| I-79 | 0.002 |
| I-80 | 0.052 |
| I-81 | 0.062 |
| I-84 | 0.011 |
| I-89 | 0.087 |
| I-94 | 0.051 |
| I-100 | 0.010 |
| I-101 | 0.001 |
| I-104 | 0.001 |
| I-105 | 0.010 |
| I-109 | 0.001 |
| I-110 | 0.009 |
| I-113 | 0.034 |
| I-116 | 0.049 |
| I-122 | 0.024 |
| I-138 | 0.044 |
| I-140 | 0.044 |
| I-154 | 0.004 |
| I-155 | 0.053 |
| I-180 | 0.013 |
| I-184 | 0.011 |
| I-187 | 0.014 |

TABLE 43-continued

| Compound No. | Ca2+ IC50 (μM) |
| --- | --- |
| I-196 | 0.015 |
| I-197 | 0.059 |

The following compounds exhibited $IC_{50}$ of 0.1 μM lower. I-76, I-86, I-87, I-90, I-98, I-99, I-103, I-107, I-111, I-114, 1-176, I-177, I-178, I-207, I-208, I-209, I-211, I-212, I-221, I-225, I-227, I-228, I-230, I-233, I-237, I-238 and I-249.

From the above results, it was made clear that the present compound exhibits the NMDA receptor antagonism.

INDUSTRIAL APPLICABILITY

The present invention is useful as an analgesic and/or nerve protecting agent, which exhibits specific antagonism for a glutamic acid receptor of a central nervous cell, particularly, NR1/NR2B receptor being one kind of NMDA receptors, and has little side effect on motion function (abnormal sensation) and mental symptom (schizophrenia).

The invention claimed is:

1. A compound represented by the formula (I):

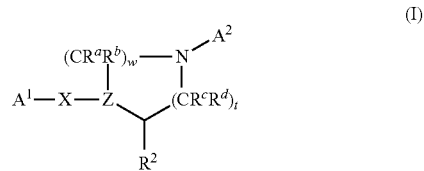

wherein Z is N;

$A^1$ is

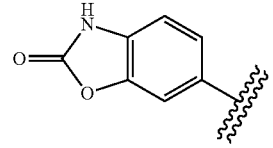

$A^2$ is an aromatic hydrocarbon cyclic group which is optionally substituted, or an aromatic heterocyclic group which is optionally substituted;

$R^2$ is independently hydrogen, hydroxy or lower alkyl;

$R^a$, $R^b$, $R^c$ and $R^d$ are each independently hydrogen or lower alkyl and, when there are a plurality of $R^a$s or a plurality of $R^b$s, they may be different from each other;

w is 2;

t is 1;

X is:
—$NR^5CO(CR^3R^4)n$-,
—$NR^5COCO(CR^3R^4)n$-, or
—$NR^5(CR^3R^4)mCO$—, m is an integer of 1 to 4;

n is an integer of 0 to 4;

$R^3$ and $R^4$ are each independently hydrogen, halogen, hydroxy, optionally substituted lower alkyl, or optionally substituted lower alkoxy, and when there are a plurality of $R^3$s and $R^4$s, respectively, they may be different from each other;

$R^5$ is independently hydrogen or lower alkyl, or a pharmaceutically acceptable salt thereof.

2. The compound according to claim 1, wherein X is NHCOCO(CHR$^3$)n- or a pharmaceutically acceptable salt thereof.

3. The compound according to claim 1, wherein X is —NHCOCHR$^3$—, —NHCO(CHR$^3$)$_2$—, NHCOCO— or —NHCH$_2$CO— or a pharmaceutically acceptable salt thereof.

4. The compound according to claim 1, wherein A$^2$ is phenyl optionally substituted with one or more groups selected from halogen, cyano, lower alkyl, halogeno lower alkyl, lower alkoxy and halogeno lower alkoxy or pyridyl optionally substituted with one or more groups selected from halogen, cyano, lower alkyl, halogeno lower alkyl, lower alkoxy and halogeno lower alkoxy, or a pharmaceutically acceptable salt thereof.

5. The compound according to claim 1, wherein A$^2$ is para-substituted phenyl, meta and para-di-substituted phenyl or meta and para-tri-substituted phenyl, or a pharmaceutically acceptable salt thereof.

6. A pharmaceutical composition containing the compound according to claim 1, or a pharmaceutically acceptable salt thereof along with a pharmaceutically acceptable carrier.

* * * * *